US010106611B2

(12) United States Patent
Wucherpfennig et al.

(10) Patent No.: US 10,106,611 B2
(45) Date of Patent: Oct. 23, 2018

(54) ANTIBODIES THAT BIND TO MHC CLASS I POLYPEPTIDE-RELATED SEQUENCE A

(71) Applicant: Dana-Farber Cancer Institute, Inc., Boston, MA (US)

(72) Inventors: Kai W. Wucherpfennig, Brookline, MA (US); Glenn Dranoff, Sudbury, MA (US); F. Stephen Hodi, Framingham, MA (US); Bettina Franz, Orem, UT (US); Kenneth F. May, Jr., Bozeman, MT (US); Christopher Harvey, Boston, MA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 0 days.

(21) Appl. No.: 15/100,060

(22) PCT Filed: Dec. 5, 2014

(86) PCT No.: PCT/US2014/068862

§ 371 (c)(1),
(2) Date: May 27, 2016

(87) PCT Pub. No.: WO2015/085210

PCT Pub. Date: Jun. 11, 2015

(65) Prior Publication Data

US 2017/0022275 A1 Jan. 26, 2017

Related U.S. Application Data

(60) Provisional application No. 61/953,588, filed on Mar. 14, 2014, provisional application No. 61/913,198, filed on Dec. 6, 2013.

(51) Int. Cl.
*C07K 16/28* (2006.01)
*A61K 39/395* (2006.01)
*A61K 45/06* (2006.01)
*A61K 39/00* (2006.01)

(52) U.S. Cl.
CPC .... *C07K 16/2833* (2013.01); *A61K 39/39558* (2013.01); *A61K 45/06* (2013.01); *A61K 2039/505* (2013.01); *A61K 2039/507* (2013.01); *C07K 2317/21* (2013.01); *C07K 2317/34* (2013.01); *C07K 2317/56* (2013.01); *C07K 2317/565* (2013.01); *C07K 2317/73* (2013.01); *C07K 2317/76* (2013.01); *C07K 2317/92* (2013.01)

(58) Field of Classification Search
CPC ........................................ C07K 16/00–16/468
See application file for complete search history.

(56) References Cited

U.S. PATENT DOCUMENTS

| | | | |
|---|---|---|---|
| 4,816,567 | A | 3/1989 | Cabilly et al. |
| 5,122,464 | A | 6/1992 | Wilson et al. |
| 5,225,539 | A | 7/1993 | Winter |
| 5,530,101 | A | 6/1996 | Queen et al. |
| 5,545,403 | A | 8/1996 | Page |
| 5,545,405 | A | 8/1996 | Page |
| 5,545,806 | A | 8/1996 | Lonberg et al. |
| 5,545,807 | A | 8/1996 | Surani et al. |
| 5,569,825 | A | 10/1996 | Lonberg et al. |
| 5,585,089 | A | 12/1996 | Queen et al. |
| 5,591,639 | A | 1/1997 | Bebbington |
| 5,624,821 | A | 4/1997 | Winter et al. |
| 5,625,126 | A | 4/1997 | Lonberg et al. |
| 5,633,425 | A | 5/1997 | Lonberg et al. |
| 5,648,260 | A | 7/1997 | Winter et al. |
| 5,658,759 | A | 8/1997 | Bebbington |
| 5,661,016 | A | 8/1997 | Lonberg et al. |
| 5,677,425 | A | 10/1997 | Bodmer et al. |
| 5,693,762 | A | 12/1997 | Queen et al. |
| 5,714,350 | A | 2/1998 | Co et al. |
| 5,766,886 | A | 6/1998 | Studnicka et al. |
| 5,869,046 | A | 2/1999 | Presta et al. |
| 5,939,598 | A | 8/1999 | Kucherlapati et al. |
| 5,981,216 | A | 11/1999 | Kenten et al. |
| 5,998,144 | A | 12/1999 | Reff et al. |
| 6,075,181 | A | 6/2000 | Kucherlapati et al. |
| 6,091,001 | A | 6/2000 | Jakobovits et al. |
| 6,114,598 | A | 9/2000 | Kucherlapati et al. |
| 6,121,022 | A | 9/2000 | Presta et al. |
| 6,165,745 | A | 12/2000 | Ward et al. |
| 6,180,370 | B1 | 1/2001 | Queen et al. |
| 6,194,551 | B1 | 2/2001 | Idusogie et al. |
| 6,277,375 | B1 | 8/2001 | Ward |
| 6,344,203 | B1 | 2/2002 | Sandrin |

(Continued)

FOREIGN PATENT DOCUMENTS

| | | |
|---|---|---|
| EP | 0 154 316 | 9/1985 |
| EP | 0 401 384 | 12/1990 |

(Continued)

OTHER PUBLICATIONS

Almagro & Fransson, Frontiers in Bioscience; 13:1619-33 (Year: 2008).*
De Genst et al., Dev Comp Immunol; 30:187-98 (Year: 2006).*
Rudikoff et al., Proc. Nat'l Acad. Sci. USA; 79:1979-83 (Year: 1982).*
Brown et al., J. Immunol.; 156(9):3285-91 (Year: 1996).*
E. A. Padlan, Adv Prot Chem; 49:57-133 (Year: 1996).*
Corada et al., Blood; 97:1679-84 (Year: 2001).*
Balmana et al. Ann Oncol; 20(supp 4):iv19-20 (Year: 2009).*
U.S. Appl. No. 14/776,968, filed Sep. 15, 2015, Kai W. Wucherpfennig.
U.S. Appl. No. 14/025,573, filed Sep. 12, 2013, Kai W. Wucherpfennig.
U.S. Appl. No. 15/211,758, filed Jul. 15, 2016, Kai W. Wucherpfennig.
U.S. Appl. No. 12/442,222, filed Dec. 23, 2009, Glenn Dranoff.
U.S. Appl. No. 14/021,111, filed Sep. 9, 2013, Glenn Dranoff.
U.S. Appl. No. 14/025,573, dated Mar. 31, 2016.
U.S. Appl. No. 14/025,573, dated Dec. 17, 2015.

(Continued)

*Primary Examiner* — Jessica H Roark
(74) *Attorney, Agent, or Firm* — Cooley LLP; Ivor Elrifi; Cynthia A. Kozakiewicz

(57) ABSTRACT

The present disclosure provides, in part, compositions comprising peptides immunospecifically binds to MHC class I polypeptide-related sequence A (MICA).

36 Claims, 53 Drawing Sheets

Specification includes a Sequence Listing.

(56) References Cited

U.S. PATENT DOCUMENTS

| | | | |
|---|---|---|---|
| 6,350,861 | B1 | 2/2002 | Co et al. |
| 6,737,056 | B1 | 5/2004 | Presta |
| 7,317,091 | B2 | 1/2008 | Lazar et al. |
| 7,771,718 | B2 | 8/2010 | Spies et al. |
| 7,959,916 | B2 | 6/2011 | Spies et al. |
| 8,101,720 | B2 | 1/2012 | Lazar et al. |
| 8,182,809 | B1 | 5/2012 | Wu |
| 9,402,905 | B2 | 8/2016 | Wucherpfennig et al. |
| 2003/0022450 | A1 | 1/2003 | Pan et al. |
| 2003/0099647 | A1 | 5/2003 | Deshpande et al. |
| 2003/0118592 | A1 | 6/2003 | Ledbetter et al. |
| 2003/0133939 | A1 | 6/2003 | Ledbetter et al. |
| 2003/0153043 | A1 | 8/2003 | Carr et al. |
| 2003/0165835 | A1 | 9/2003 | Spies et al. |
| 2004/0067503 | A1 | 4/2004 | Tan et al. |
| 2004/0115198 | A1 | 6/2004 | Spies et al. |
| 2005/0053608 | A1 | 3/2005 | Weber et al. |
| 2005/0158307 | A1 | 7/2005 | Spies et al. |
| 2005/0233391 | A1 | 10/2005 | Spies et al. |
| 2006/0024297 | A1 | 2/2006 | Wood et al. |
| 2006/0246071 | A1 | 11/2006 | Green et al. |
| 2007/0248607 | A1 | 10/2007 | Spies et al. |
| 2008/0148432 | A1 | 6/2008 | Abad |
| 2009/0022644 | A1 | 1/2009 | Sweredjuk |
| 2009/0175821 | A1 | 7/2009 | Bridon et al. |
| 2009/0226447 | A1 | 9/2009 | Boone et al. |
| 2009/0252729 | A1 | 10/2009 | Farrington et al. |
| 2010/0111973 | A1 | 5/2010 | Dranoff et al. |
| 2010/0189711 | A1 | 7/2010 | Dranoff et al. |
| 2010/0261269 | A1 | 10/2010 | June et al. |
| 2011/0311561 | A1 | 12/2011 | Martin et al. |
| 2012/0100182 | A1 | 4/2012 | Mooney |
| 2012/0315287 | A1 | 12/2012 | Wu |
| 2013/0202707 | A1 | 8/2013 | Ali et al. |
| 2014/0004112 | A1 | 1/2014 | Wucherpfennig et al. |
| 2014/0027630 | A1 | 1/2014 | Musselman |
| 2014/0037630 | A1 | 2/2014 | Dranoff et al. |
| 2016/0046716 | A1 | 2/2016 | Wucherpfennig et al. |

FOREIGN PATENT DOCUMENTS

| | | | |
|---|---|---|---|
| EP | 1 176 195 | | 1/2002 |
| EP | 2336180 | A1 | 6/2011 |
| WO | WO 88/07054 | | 3/1988 |
| WO | WO 88/08089 | | 10/1988 |
| WO | WO 91/10741 | | 7/1991 |
| WO | WO 94/02602 | | 2/1994 |
| WO | WO 94/29351 | | 12/1994 |
| WO | WO 96/32478 | | 10/1996 |
| WO | WO 96/33735 | | 10/1996 |
| WO | WO 97/34631 | | 9/1997 |
| WO | 98/19167 | A2 | 5/1998 |
| WO | WO 98/24893 | | 6/1998 |
| WO | WO 99/051642 | | 10/1999 |
| WO | WO 99/54342 | | 10/1999 |
| WO | WO 00/42072 | | 7/2000 |
| WO | WO 01/58957 | | 8/2001 |
| WO | WO 02/06919 | | 1/2002 |
| WO | 02/068615 | A2 | 9/2002 |
| WO | WO 03/035835 | | 5/2003 |
| WO | WO 03/041600 | | 5/2003 |
| WO | WO 2003/074679 | | 9/2003 |
| WO | 03/089616 | A2 | 10/2003 |
| WO | WO 04/016750 | | 2/2004 |
| WO | WO 04/035752 | | 4/2004 |
| WO | WO 2004/029207 | | 4/2004 |
| WO | WO 04/063351 | | 7/2004 |
| WO | WO 04/074455 | | 9/2004 |
| WO | WO 2004/099249 | | 11/2004 |
| WO | WO 05/040217 | | 5/2005 |
| WO | WO 05/070963 | | 8/2005 |
| WO | WO 05/092925 | | 10/2005 |
| WO | WO 06/020114 | | 2/2006 |
| WO | 2007/055926 | A1 | 5/2007 |
| WO | 2008/036981 | A1 | 3/2008 |
| WO | WO 2011/063336 | | 5/2011 |
| WO | 2013/049517 | A2 | 4/2013 |
| WO | 2013/117647 | A1 | 8/2013 |
| WO | 2014/144791 | A2 | 9/2014 |

OTHER PUBLICATIONS

U.S. Appl. No. 14/025,573, dated Jun. 23, 2015.
U.S. Appl. No. 14/025,573, dated Jun. 27, 2014.
U.S. Appl. No. 14/025,573, dated Jan. 31, 2014.
U.S. Appl. No. 14/025,573, dated Oct. 31, 2013.
U.S. Appl. No. 12/442,222, dated Jul. 25, 2014.
U.S. Appl. No. 12/442,222, dated May 29, 2013.
U.S. Appl. No. 12/442,222, dated Oct. 6, 2011.
U.S. Appl. No. 14/021,111, dated Sep. 7, 2016.
U.S. Appl. No. 14/021,111, dated Feb. 11, 2016.
U.S. Appl. No. 14/021,111, dated Sep. 29, 2015.
Araya, Carlos L. et al., "Deep mutational scanning: assessing protein function on a massive scale," Trends Biotechnol., vol. 29(9), pp. 435-442 (2011 ).
Barbas, S. et al., "Recognition of DNA by Synthetic Antibodies," J. Am. Chem. Soc., vol. 116(5), pp. 2161-2162 (1994).
Beiboer, S. et al., "Guided Selection of a Pan Carcinoma Specific Antibody Reveals Similar Binding Characteristics yet Structural Divergence Between the Original Murine Antibody and its Human Equivalent," JMB, vol. 296, pp. 833-849 (2000).
Bergers et al., "Extrinsic regulators of epithelial tumor progression: metalloproteinases," Curro Opin. in Genetics and Development, vol. 10, pp. 120-127 (2000).
Bodey, B. et al., "Failure of Cancer Vaccines: The Significant Limitations of this Approach to Immunotherapy," Anticancer Research, vol. 20, pp. 2665-2676 (2000).
Brown, M. et al., "Tolerance to single, but not multiple, amino acid replacements in antibody VH CDR 2: a means of minimizing B cell wastage from somatic hypermutation?," J Immunol., vol. 156(9), pp. 3285-3291 (1996).
Casset, F. et al., "A peptide mimetic of an anti-CD4 monoclonal antibody by rational design," BBRC, vol. 307, pp. 198-205(2003).
Chen, C. et al., "Generation and Analysis of Random Point Mutations in an Antibody CDR2 Sequence: Many Mutated Antibodies Lose Their Ability to Bind Antigen," J. Exp. Med., vol. 176, pp. 855-866 (1992).
Chen, Y. et al, "Selection and analysis of an optimized anti-VEGF antibody: crystal structure of an affinity-matured Fab in complex with antigen," J. Mol. Biol., vol. 293, pp. 865-881 (1999).
Chin et al., "Immune intervention with monoclonal antibodies targeting CD152 (CTLA-4) for autoimmune and malignant diseases," Chang Gung Med J., 31 (1): 1-15 (2008).
Chothia, C. et al., "Conformations of Immunoglobulin hypervariable regions," Nature, vol. 342, pp. 877-883 (1989).
Chothia, C. et al., "Structural Repertoire of the Human VH Segments," J. Mol. Biol., vol. 227, pp. 799-817 (1992).
De Pascalis, R. et al, "Grafting of "abbreviated" complementarity-determining regions containing specificity-determining residues essential for ligand contact to engineer a less immunogenic humanized monoclonal antibody," The Journal of Immunology, vol. 169, pp. 3076-3084 (2002).
Dennis, C. "Off by a whisker", Nature, vol. 442, pp. 739-741 (2006).
Ditzel, H. et al., "Determinants of Polyreactivity in a Large Panel of Recombinant Human Antibodies from HIV-I Infection," The Journal of Immunology, vol. 157, pp. 739-749, (1996).
Doubrovina et al.,"Evasion from NK cell immunity by MHC class I chain-related molecules expressing colon adenocarcinoma," J. Immunol. 171 (12): 6891-6899 (2003).
Duquesnoy, R. et al., "Structurally based epitope analysis of major histocompatibility complex class I-related chain A (MICA) antibody specificity patterns," Human Immunology, vol. 69:826-832 (2008).
Extended European Search Report, EP12835118.6, dated May 4, 2015, 9 pages.

(56) References Cited

OTHER PUBLICATIONS

Fonseca, C. et al., "Protein disulfide isomerases are antibody targets during immune-mediated tumor destruction", Blood, vol. 113, pp. 1681-1688 (2009).

Germain, C. et al., "MHC Class I-Related Chain A Conjugated to Antitumor Antibodies Can Sensitize Tumor Cells to Specific Lysis by Natural Killer Cells," Clinical Cancer Research, The American Association for Cancer Research, US, vol. 11 (20), pp. 7516-7522, Oct. 15, 2005.

Girlanda, S. et al., "MICA Expressed by Multiple Myeloma and Monoclonal Gammopathy of Undetermined Significance Plasma Cells Costimulates Pamidronate-activated Gammadelta Lymphocytes," Cancer Research, vol. 65 (16), pp. 7502-7508 (2005).

Groh, V. et al., "Broad tumor-associated expression and recognition by tumor-derived gammadelta T cells of MICA and MICB," Proc. Natl. Acad. Sci. USA, vol. 96:6879-6884 (1999).

Groh, V. et al., "Cell stress-regulated human major histocompatibility complex class I gene expressed in gastrointestinal epithelium," Proc. Natl. Acad. Sci. USA, vol. 93:12445-12450 (1996).

Groh, V. et al., Efficient cross-priming of tumor anigen-specific T cells by dendritic cells sensistized with diverse anti-MICA opsonized tumor cells. Proc. Nat'l Acad. Sci., May 2005. vol. 102, No. 18 pp. 6461-6466.

Groh, V. et al., "Recognition of Stress-Induced MHC Molecules by Intestinal Epithelial gammadelta T Cells," Science, vol. 279:1737-1740 (1998).

Groh, V. et al., "Tumour-derived soluble MIC ligands impair expression of NKG2D and T-cell activation," Nature, vol. 419:734-738 (2002).

Gura, T. "Systems for Identifying New Drugs are Often Faulty", Science, 278: 1041-1042 (1997).

Hara et al., "Interleukin-2 potentiation of cetuximab antitumor activity for epidermal growth factor receptor-overexpressing gastric cancer xenografts through antibody-dependent cellular cytotoxicity," Cancer Sci., 99 (7): 471-478 (2008).

Holm, P. et al. "Functional mapping and single chain construction of the anti-cytokeratin 8 monoclonal antibody TS1," Mol. Immunol., vol. 44, pp. 1075-1084 (2007).

Hue, S. et al., "Potential Role of NKG2D/MHC Class I-Related Chain A Interaction in Intrathymic Maturation of Single-Positive CD8 T Cells," The Journal of Immunology, vol. 171, pp. 1909-1917 (2003).

International Preliminary Report on Patentability, PCT/US2014/029348, dated Sep. 15, 2015, 7 pages.

International Preliminary Report on Patentability, PCT/US2014/068862, dated Jun. 7, 2016, 7 pages.

International Search Report and Written Opinion, PCT/US2014/029348, dated Oct. 16, 2014, 11 pages.

Jiang, B. et al., "A Novel Peptide Isolated from a Phage Display Peptide Library with Trastuzumab Can Mimic Antigen Epitope of HER-2", J. Biol. Chem., vol. 280 (6), pp. 4656-4662 (2005).

Jinushi, M. et al. "MHC class I chain-related protein A antibodies and shedding are associated with the progression of multiple myeloma", PNAS, vol. 105, pp. 1285-1290 (2008).

Jinushi, M. et al., "Enhancing the clinical activity of granulocyte-macrophage colony stimulating factor-secreting tumor cell vaccines", Immunological Reviews, vol. 222, pp. 287-298 (2008).

Jinushi, M. et al., "Impairment of natural killer cell and dendritic cell functions by the soluble form of MHC class I-related chain A in advanced human hepatocellular carcinomas", J. of Hepatology, vol. 43, pp. 1013-1020 (2005).

Jinushi, M. et al., "Therapy-induced antibodies to MHC class I chain-related protein A antagonize immune suppression and stimulate antitumor cytotoxicity.," Proc. Nat'l Acad. Sci., vol. 103(24) pp. 9190-9195 (Jun. 2006 ).

Jordan, Peter A. et al., "A role for the thiol isomerase protein ERP5 in platelet function," Blood, vol. 105(4), pp. 1500-1507 (2005).

Kaiser et al., "Disulphide-isomerase-enabled shedding of tumour-associated NKG2D ligands.," Nature, 447 (7143): 482-486 (2007).

Kelland, L.R. "Of mice and men: values and liabilities of the athymic nude mouse model in anticancer drug development", Eur. J. Cancer, vol. 40 (6), pp. 827-836 (2004).

Klimka, A., et al., "Human anti-CD30 recombinant antibodies by guided phage antibody selection using cell panning," British Journal of Cancer, vol. 83(2), pp. 252-260 (2000).

Kuo et al.,"Anti-caveolin-1 antibodies as anti-prostate cancer therapeutics," Hybridoma, 31 (2): 77-86 (2012).

LeBlond et al.,"The amphipathic alpha-helical repeats of apolipoprotein A-I are responsible for binding of high density lipoproteins to HepG2 cells," J. Biol. Chem., 266 (10): 6058-6067 (1991).

Liu et al.,"The membrane type matrix metalloproteinase MMP14 mediates constitutive shedding of MHC class I chain-related molecule A independent of a disintegrin and metalloproteinases," J. Immunol. 184 (7): 3346-3350 (2010).

MacCallum, R. et al. , "Antibody-antigen interactions: contact analysis and binding site topography," J. Mol. Biol., vol. 262, pp. 732-745 (1996).

Marten et al., "Soluble MIC is elevated in the serum of patients with pancreatic carcinoma diminishing gammadelta T cell cytotoxicity," Int. J. Cancer. 119 (10): 2359-2365 (2006).

Martin, D., et al., "Symposium on Cancer Immunology and Immunotherapy," Roche/Nature Medicine, Sep. 11-13, 2011 Roche, Nutley, New Jersey, USA, 91 pages (2011).

May, K. et al., "Isolation of human anti-MICA antibody from cancer patients responding to immunotherapies," Journal of Clinical Oncology, vol. 30(15), 2012 ASCO Annual Meeting (Abstract No. 3502, 2 pages (2012).

International Search Report and Written Opinion, PCT/US2014/068862, dated Apr. 10, 2015, 10 pages.

Mei et al., "Expression of NKG2D ligands in multidrug-resistant nasopharyngeal carcinoma cell line CNE2/DDP and their effects on cytotoxicity of natural killer cells," Nan Fang Yi Ke Da Xue Xue Bao.,27 (6):887-889 (2007).

Nausch et al., "NKG2D ligands in tumor immunity," Oncogene, 27: 5944-5958 (2008).

Nelson et al., "Cancer cells engineered to secrete granulocyte-macrophage colony-stimulating factor using ex vivo gene transfer as vaccines for the treatment of genitourinary malignancies," Cancer Chemother. Pharmacol., 46 (Suppl.): S67-72 (2000).

Pantazes, R.J. et al., "OptCDR: a general computational method for the design of antibody complementarity determining regions for targeting epitope binding," Protein Engineering, Design & Selection, vol. 23(11 ), pp. 849-858 (2010).

Pende et al.,"Major histocompatibility complex class I-related chain A and UL16-binding protein expression on tumor cell lines of different histotypes: analysis of tumor susceptibility to NKG2D-dependent natural killer cell cytotoxicity," Cancer Res., 62 (21): 6178-6186 (2002).

Pettersen et al., "CD47 signals T cell death," J. Immunol., 162 (12): 7031-7040 (1999).

Phumyen, A. et al., "Improved Binding Activity of Antibodies Against Major Histocompatibility Complex Class I Chain-Related Gene A by Phage Display Technology for Cancer-Targeted Therapy," Journal of Biomedicine and Biotechnology, vol. 2012(597647) 8 pages, (2012).

Ponsel, Dirk et al., "High Affinity, Developability and Functional Size: The Holy Grail of Combinatorial Antibody Library Generation," Molecules, vol. 16, pp. 3675-3700 (2011).

Rader, C. et al., "A Phage Display Approach for Rapid Antibody Humanization: Designed Combinatorial V Gene Libraries," PNAS, USA, vol. 95, pp. 8910-8915 (1998).

Riemer , A. et al. "Matching of trastuzumab (Herceptin) epitope mimics onto the surface of Her-2/neu—a new method of epitope definition", Mol. Immunol, vol. 42:, pp. 1121-1124 (2005).

Rudikoff, S. et al., "Single amino acid substitution altering antigen-binding specificity," Proc Natl Acad Sci USA, vol. 79, pp. 1979-1983 (1982 ).

Saijo, N., "What are the reasons for negative phase III trials of molecular-target-based drugs?",; Cancer Sci., vol. 95 (10), pp. 772-776 (2004).

(56) References Cited

OTHER PUBLICATIONS

Salih, Helmut R. et al., "Cutting Edge: Down-Regulation of MICA on Human Tumors by Proteolytic Shedding," The Journal of Immunology, vol. 169, pp. 4098-4102 (2002).
Salih, Helmut R. et al., "Functional expression and release of ligands for the activating immunoreceptor NKG2D in leukemia," Blood, vol. 102(4), pp. 1389-1396 (2003).
Schoenfeld. J. et al., "Active Immunotherapy Induces Antibody Responses That Target Tumor Angiogenesis," Microenvironment and Immunology, Cancer Research, vol. 70(24), pp. 10150-10160 (2010).
Sircar, A. et al., "Rosetta Antibody: antibody variable region homology modeling server," Nucleic Acids Research, vol. 37, pp. W474-W479 (2009).
Steinle, A. et al., "Diversification, expression, and gammadelta T cell recognition of evolutionarily distant members of the MIC family of major histocompatibility complex class I-related molecules," Proc. Natl. Acad. Sci. USA, vol. 95, pp. 12510-12515 (1998).
Suarez-Alvarez, B. et al., "Identification of epitopes and immunodominant regions on the MICA protein defined by alloantibodies from kidney transplant patients," Transplantation, Williams and Wilkins, GB, vol. 88 (3) Suppl, pp. S68-S77( Aug. 15, 2009).
Tang, B. et al., "Evaluation of human major histocompatibility complex class I chain-related A as a potential target for tumor imaging," Cancer Letters, New York, NY, US, vol. 263 (1), pp. 99-106 (Jan. 30, 2008).
Thom, George et al., "Probing a protein-protein interaction by in vitro evolution," PNAS, vol. 103(20):7619-7624 (2006).
Vajdos, FF et al., "Comprehensive functional maps of the antigen-binding site of an anti-ErbB2 antibody obtained with shotgun scanning mutagenesis," J Mol Biol. vol. 320(2) pp. 415-428 (2002).
Vitetta, Ellen S. et al., "Monoclonal Antibodies as Agonists: An Expanded Role for Their Use in Cancer Therapy," Cancer Research, vol. 54:5301-5309 (1994).
Weber, "Review: anti-CTLA-4 antibody ipilimumab: case studies of clinical response and immune-related adverse events," Oncologist, 12(7): 864-872 (2007).
Whiteside, T. et al., "Antigen-Processing Machinery in Human Dendritic Cells; Up-regulation by Maturation and Down-Regulation by Tumor Cells," J. Immunol., vol. 173, pp. 1526-1534 (2004).
Wongsena., W. et al., "Production and characterization of monoclonal antibodies against major histocompatibility complex class I chain-related gene A," Tissue Antigens, vol. 72(5), pp. 431-440 (Nov. 2008).
Wu et al., "Prevalent expression of the immunostimulatory MHC class I chain-related molecule is counteracted by shedding in prostate cancer," J. Clin. Invest., 114 (4): 560-568 (2004).
Zou, Yizhou et al., "MICA is a Target for Complement-Dependent Cytotoxicity With Mouse Monoclonal Antibodies and Human Alloantibodies," Human Immunology, vol. 63, pp. 30-39 (2002).
Zwirner, N. et al., "Immunobiology of the human MHC class I chain-related gene A (MICA): from 13 transplantation immunology to tumor immune escape," Immunologia, vol. 25(1), pp. 25-38, (Jan.-Mar. 2006).
Altschul, et al. "Basic Local Alignment Search Tool", *J. Mol. Biol.*, 215:403-10 (1990).
Altschul et al., "Gapped BLAST and PSI-BLAST: a new generation of protein database search programs", *Nucleic Acids Res.* 25(17):3389-3402 (1997).
Amanna et al., "Duration of Humoral Immunity to Common Viral and Vaccine Antigens", N. Engl. J. Med., 357:1903-1915, (2007).
Andrade et al., "Adsorption of complex proteins at interfaces", Pure and Appl. Chem., 64(11):1777-1781 (1992).
Balazs et al., "Antibody-based protection against HIV infection by vectored immunoprophylaxis", *Nature*, 481(7379):81-4 (2011).
Bird et al. "Single-Chain Antigen-Binding Proteins", *Science* 242:423-426 (1988).
Buisman et al., "Long-term presence of memory B-cells specific for different vaccine components", *Vaccine*, 28:179-186 (2009).
Canfield and Morrison, "The Binding Affinity of Human IgG for its High Affinity Fc Receptor is Determined by Multiple Amino Acids in the CH2 Domain and is Modulated by the Hinge Region", *J. Exp. Med.* 173:1483 (1991).
Cao et al., "An optimized assay for the enumeration of antigen-specific memory B cells in different compartments of the human body", *Journal of Immunological Methods*, 358:56-65 (2010).
Champe et al. "Monoclonal Antibodies That Block the Activity of Leukocyte Function-associated Antigen 1 Recognize Three Discrete Epitopes in the Inserted Domain of CD11a", *The Journal of Biological Chemistry*, 270:1388-1394 (1995).
Cheung et al., "Epitope-Specific Antibody Response to the Surface Antigen of Duck Hepatitis B Virus in Infected Ducks", *Virology* 176:546 (1990).
Choi et al., "Evolutionary conservation in multiple faces of protein interaction", *Proteins: Structure, Function, and Bioinformatics*, 77(1):14-25 (2009).
Chothia et al., "Conformations of immunoglobin hypervariable regions", *Nature*, 342:877-883 (1989).
Corti et al., "Analysis of Memory B Cell Responses and Isolation of Novel Monoclonal Antibodies with Neutralizing Breadth from HIV-1-Infected Individuals", *PLoS One*, 5:e8805 (2010).
Cox, J. P. L. et al. "A Directory of Human Germ-line VH Segments Reveals a Strong Bias in their Usage" *Eur. J Immunol.* 24:827-836 (1994).
Cox et al., "Glycan optimization of a human monoclonal antibody in the aquatic plant Lemna minor", *Nat. Biotechnol* 24(12): 1591-7 (2006).
Crotty et al., "Cutting Edge: Long-Term B Cell Memory in Humans after Smallpox Vaccination" *J. Immunol.*, 171:4969-4973 (2003).
Cunningham and Wells, "High-Resolution Epitope Mapping of hGH-Receptor Interactions by Alanine-Scanning Mutagenesis", Science 244: 1081-1085 (1989).
Dall'Acqua et al. "Increasing the Affinity of a Human IgG1 for the Neonatal Fc Receptor: Biological Consequences", *Journal of Immunology*, 169:5171-5180 (2002).
Dall'Acqua et al., "Properties of Human IgG1s Engineered for Enhanced Binding to the Neonatal Fc Receptor (FcRn)", *Journal ofBiological Chemistry* 281:23514-23524 (2006).
Duncan et al., "Localization of the binding site for the human high-affinity Fe receptor on IgG", *Nature* 332:563 (1988).
Fecteau et al., "Peripheral blood CD27+ IgG+ B cells rapidly proliferate and differentiate into immunoglobulin-secreting cells after exposure to low CD154 interaction", *Immunology*, 128:e353-e365 30 (2009).
Fields et al., Chapter 3 Synthetic Peptides: A User's Guide, p. 77(1992).
Franz et al. "Ex vivo characterization and isolation of rare memory B cells with antigen tetramers", *Blood*, 118(2):348-357 (2011).
Gillies S.D. et al., "Improving the Efficacy of Antibody-Interleukin 2 Fusion Proteins by Reducing Their Interaction with Fc Receptors", *Cancer Res.* 59:2159-66 (1999).
Gong et al., "A protein domain interaction interface database: InterPare", *BMC: Bioinformatics*, 6:1471-2105 (2007).
Guo et al., "Protein tolerance to random amino acid change", *Proc. Natl. Acad. Sci.*, USA, 101(25):9205-9210 (2004).
Henn et al., "Modulation of Single-Cell IgG Secretion Frequency and Rates in Human Memory B Cells by CpG DNA, CD40L, IL-21, and Cell Division", *J. Immunol.*, 183:31777-3187 (2009).
Hinton et al., "Engineered Human IgG Antibodies with Longer Serum Half-lives in Primates", *J. Biol. Chem.* 279(8): 6213-6216 (2004).
Hinton et al. "An Engineered Human IgG1 Antibody with Longer Serum Half-Life", *Journal of Immunology* 176:346-356 (2006).
Hofer et al., Adaptation of humoral memory, *Immunological Reviews*, 211:295-302 (2006).
Huggins et al., "CpG DNAactivation and plasma-cell differentiation of CD27_ naïve human B cells", *Blood*, 109:1611-1619 (2007).
Huston et al. "Protein engineering of antibody binding sites: Recovery of specific activity in an anti-digoxin single-chain Fv analogue produced in *Escherichia coli*", *Proc. Natl. Acad. Sci. USA* 85:5879-5883 (1988).

(56) References Cited

OTHER PUBLICATIONS

Jaeger et al., "Improved predictions of secondary structures for RNA", *Proc. Natl. Acad. Sci.* USA 86:7706-10 (1989).
Jaeger et al., "Predicting Optimal and Suboptimal Secondary Structure for RNA", *Methods Enzymol.* 183:281-306 (1989).
Jespers et al., "Guiding the Selection of Human Antibodies from Phage Display Repertoires to a Single Epitope of an Antigen", *Biotechnology* 12:899, (1994).
Jiang et al., "TLR9 stimulation drives na_ve B cells to proliferate and to attain enhanced antigen presenting function", *Eur. J. Immunol.*, 37:2205-2213 (2007).
Jones, P. et al. "Replacing the complementarity-determining regions in a human antibody with those from a mouse", *Nature* 321:522-525 (1986).
Jourdan et al., "An in vitro model of differentiation of memory B cells into plasmablasts and plasma cells including detailed phenotypic and molecular characterization", *Blood*, 114:5173-5181 (2009).
Kalos M, et al., "T Cells with Chimeric Antigen Receptors Have Potent Antitumor Effects and Can Establish Memory in Patients with Advanced Leukemia", Sci Transl Med. Aug. 2010;3 (95), (2011).
Kaneko et al., "Anti-Inflammatory Activity of Immunoglobulin G Resulting from Fc Sialylation", *Science* 313:670-673 (2006).
Kirkland et al., "Analysis of the Fine Specificity and Cross-Reactivity of Monoclonal Anti-Lipid A Antibodies", *J Immunol.* 137:3614 (1986).
Kostelny et al., "Formation of a Bispecific Antibody by the Use of Leucine Zippers", *Journal of Immunol.* 148, 1547-1553 (1992).
Kunkel et al., "Plasma-Cell Homing", *Nat. Rev. Immunol.*, 3:822-829 (2003).
Lanzavecchia et al., "Human B cell memory", *Curr. Opin. Immunol.* 21:298-304 (2009).
Li et al., *Nature Biotechnology* 24(2):210-215 (2006).
Lonberg "Human antibodies from transgenic animals", Nature Biotechnology 23(9): 1117-1125, (2005).
MacCallum, "Antibody-antigen Interactions: Contact Analysis and Binding Site Topography", J. Mol. Biol, 262, 732-745 (1996).
Makabe et al., "Thermodynamic Consequences of Mutations in Vernier Zone Residues of a Humanized Anti-human Epidermal Growth Factor Receptor Murine Antibody, 528", *Journal of Biological Chemistry*, 283:1156-1166 (2008).
Meyers E. and W. Miller "Optimal alignments in linear space", *CABIOS*, 4:11-17 (1989).
Milone et al. "Chimeric Receptors Containing CD137 Signal Transduction Domains Mediate Enhanced Survival of T Cells and Increased Antileukemic Efficacy In Vivo", *Mol. Ther.* 17:1453 (2009).
Moldenhauer et al., "Identity of HML-1 Antigen on Intestinal Intraepithelial T Cells and of B-ly7 Antigen on Hairy Cell Leukaemia", *Scand. J Immunol.* 32:77 (1990).
Morel et al., "Monoclonal Antibodies to Bovine Serum Albumin: Affinity and Specificity Detenninations", *Mol. Immunol.* 25(1):7 (1988).
Nechansky et al., "Compensation of endogenous IgG mediated inhibition of antibody-dependent cellular cytotoxicity by glycoengineering of therapeutic antibodies", *Molecular Immunology* 44(7): 1815-1817 (2007).
Needleman and Wunsch, "A General Method Applicable to the Search for Similarities in the Amino Acid Sequence of Two Proteins", *J. Mol. Biol.* 48:443-453 (1970).
Odendahl et al., "Generation of migratory antigen-specific plasma blasts and mobilization of resident plasma cells in a secondary immune response", *Blood*, 105:1614-1621 (2005).
Park et al., "Prediction of protein-protein interaction types using association rule based classification", *BMC: Bioinformatics*, 10:1471-2105 (2009).
Pearson and Lipman, "Improved tools for biological sequence comparison", *Proc. Natl. Acad. Sci. USA* 85:2444 (1988).
Pluckthun, "Mono- and Bivalent Antibody Fragments Produced in *Escherichia coli*: Engineering, Folding and Antigen Binding", *Immunol. Reviews* 130:151-188 (1992).
Queen, C. et al. "A humanized antibody that binds to the interleukin 2 receptor", *Proc. Natl. Acad. Sci.* USA 86:10029-10033 (1989).
Riechmann, L. et al. "Reshaping human antibodies for therapy", 6*Nature* 332:323-327 (1998).
Sarmay et al. "Mapping and Comparison of the Interaction Sites on the Fc Region of IgG Responsible for Triggering Antibody Dependent Cellular Cytotoxicity (ADCC) through Different Types of Human Fcγ Receptor", *Molec. Immunol.* 29 (5): 633-9 (1992).
Scallon et al., "Higher levels of sialylated Fc glycans in immunoglobulin G molecules can adversely impact functionality", *Mol Immunol.* 44(7): 1524-34 (2007).
Scheid et al., "Broad diversity of neutralizing antibodies isolated from memory B cells in HIV-infected individuals", Nature, 458:636-640 (2009).
Shields, R.L. et al. "High Resolution Mapping of the Binding Site on Human IgG1 for FcgRI, FcgRII, FcgRIII, and FcRn and Design of IgG1 Variants with Improved Binding to the FcgR", *J Biol. Chem.* 276:6591-6604 (2001).
Shields, R.L. et al. "Lack of Fucose on Human IgG1 N-Linked Oligosaccharide Improves Binding to Human Fc_RIII and Antibody-dependent Cellular Toxicity", *J Biol. Chem.* 277:26733-26740 (2002).
Skerra et al., "Bacterial expression of immunoglobulin fragments", *Curr. Opinion in Immunol.*, 5:256-262 (1993).
Smith and Waterman, "Comparison of Biosequences", *Advances in Applied Mathematics*, 2:482 (1981).
Songsivilai & Lachmann, "Bispecific antibody: a tool for diagnosis and treatment of disease", *Clin. Exp. Immunol.* 79:315-321 (1990).
Stahli et al., "Distinction of Epitopes by Monoclonal Antibodies", *Methods in Enzymology* 92:242-253 (1983).
Strohl, "Optimization of Fc-mediated effector functions of monoclonal Antibodies", *Current Opinion in Biotechnology* 20:685-691 (2009).
Tao et al., "Structural Features of Human Immunoglobulin G that Determine Isotype-specitic Differences in Complement Activation", *J. Exp. Med.* 178:661 (1993).
Tao and Morrison "Role of Carbohydrate in the Structure and Effector Functions Mediated by the Human IgG Constant Region", *J. Immunol.* 143:2595-2601 (1989).
Tomlinson, I. M., et al. "The Repertoire of Human Germline VH Sequences Reveals about Fifty Groups ofVH Segments with Different Hypervariable Loops" *J. Mol. Biol.* 227:776-798 ( 1992).
Umana et al. "Engineered glycoforms of an antineuroblastoma IgG1 with optimized antibodydependent cellular cytotoxic activity", *Nat. Biotech.* 17:176-180 (1999).
Wang et al., "Human immunoglobulin variable region gene analysis by single cell RT-PCR", *J. Immunol. Methods*, 244:217-225, (2000).
Ward et al., "Binding activities of a repertoire of single immunoglobulin variable domains secreted from *Escherichia coli*", *Nature* 341:544-546, (1989).
Wu et al., "Rational Design of Envelope Identifies Broadly Neutralizing Human Monoclonal Antibodies to HIV-1", *Science*, 329:856-861 (2010).
Yeung et al., "Engineering Human IgG1 Affinity to Human Neonatal Fc Receptor: Impact of Affinity Improvement on Pharmacokinetics in Primates", *J Immunol*, 182:7663-7671 (2010).
Yoshida et al., "Memory B and memory plasma Cells", *Immunol. Rev.*, 237:117-139 (2010).
Zuker, "On Finding All Suboptimal Foldings of an RNA Molecule", *Science* 244:48-52 (1989).
U.S. Appl. No. 61/792,034, filed Mar. 15, 2013, Wucherpfennig et al.
U.S. Appl. No. 61/913,198, filed Dec. 6, 2013, Wucherpfennig et al.
Ali et al. "In Situ Regulation of DC Subsets and T Cells Mediates Tumor Regression in Mice", Science Translation Medicine, 1, 8ra19, 12 pages (2009).
Ali et al. "Infection-mimicking materials to program dendritic cells in situ", Nature Materials, vol. 8, p. 151-158, (2009).
Balmana et al. "BRCA in breast cancer: ESMO Clinical Recommendations", Annals of Oncology 20(supplement 4):iv19-20 (2009).
Banchereau et al. "Long-Term Human B Cell Lines Dependent on Interleukin-4 and Antibody to CD40", Science, vol. 251, p. 70 (1991).

(56) References Cited

OTHER PUBLICATIONS

Bednsten et al. "Improved Prediction of Signal Peptides: SignalP 3.0", J Mol Biol, vol. 340, No. 4, p. 783-95 (2004).
Benjamin et al. "The Antigenic Structure of Proteins: A Reappraisal", Annual Reviews of Immunology, vol. 2, p. 67-101 (1984).
Boemer et al, "Production of antigen-specific human monoclonal antibodies from in vitro-primed human splenocytes", Journal of Immunology, vol. 147, No. 1, p. 86-95 (1991).
Bordo et al. "Suggestions for "Safe" Residue Substitutions in Site-Directed Mutagenesis", J. Mol. Biol., vol. 217, p. 721-729 (1991).
Caine et al., "Recombinant Human Phenylethanolamine N-Methyltransferase: Overproduction in *Escherichia coli*, Purification, and Characterization", Protein Expression and Purification, vol. 8, No. 2, p. 159-166 (1996).
Chothia et al. "Canonical Structures for the Hypervariable Regions", J Mol Biol, vol. 196, p. 901-917 (1987).
Clackson et al, "Making antibody fragments using phage display libraries", Nature, vol. 352, p. 624-628 (1991).
Cole et al, "The EBV-Hybridoma Technique and its Application to Human Lung Cancer", Monoclonal Antibodies and Cancer Therapy, p. 77-96 (1985).
De Ridder G. et al. "Cell-Surface GRP78 and its Antibodies: Pathologic and Therapeutic Roles in Cancer", 2010. Retrieved from the Internet: //dukespace.lib.duke.edu/dspace/bitstream/handle/10161 /3805/deRidder_duke_0066D_ 10579.pdf?sequence=1.
Emim et al. "Antigenic Conservation and Divergence between the Viral-Specific Proteins of Poliovirus Type 1 and Various Picornaviruses", Virology, vol. 140, p. 13-20 (1985).
Fang et al. "Stable antibody expression at therapeutic levels using the 2A peptide", Nature Biotechnology, vol. 23, p. 584-590 (2005).
Fishwild et al, "High-avidity human IgGk monoclonal antibodies from a novel strain of minilocus transgenic mice", Nature Biotechnology, vol. 14, p. 845-51 (1996).
Getzoff et al. "The Chemistry and Mechanism of Antibody Binding to Protein Antigens", Advances in Immunology, vol. 43, p. 1-98 (1988).
Gonzalez et al. "A novel cancer vaccine composed of human-recombinant epidermal growth factor linked to a carrier protein: Report of a pilot clinical trial", Annals of Oncology, vol. 9, p. 431-435 (1998).
Hofmann et al. "A database of membrane spanning proteins segments", Biol Chem Hoppe-Seyler, vol. 374,166 (1993).
Hoogenboom et al. "Human Antibodies from Synthetic Repertoires of Germline VH Gene Segments Rearranged in Vitro", J Mol Biol, vol. 227, p. 381-388 (1992).
Hopp et al. "A computer program for predicting protein antigenic determinants", Molecular Immunology, vol. 20, p. 483-489 (1983).
Hopp et al. "Prediction of protein antigenic determinants from amino acid sequences", Proc Natl Acad Sci USA, vol. 78, p. 3824-3828 (1981).
Hopp, Methods for identifying antigenic determinants and other interaction sites, Immunol Methods, vol. 88, p. 1-18 (1986).
Huergo-Zapico L. et al. "Expression of ERp5 and GRP78 on the membrane of chronic lymphocytic leukemia cells: association with soluble MICA shedding", Cancer Immunology, Immunotherapy, vol. 61, No. 8, p. 1201-1210 (2012).
Jameson, et al. The antigenic index: a novel algorithm for predicting antigenic determinants, Comput Appl Biosci, vol. 4, No. 1, p. 181-186 (1988).
Johnson et al. A Structural Basis for Sequence Comparisons: An Evaluation of Scoring Methodologies, J. Mol. Biol., vol. 233, p. 716-738 (1993).
Kettleborough et al, "Humanization of a mouse monoclonal antibody by CDR-grafting: the importance of framework residues on loop conformation", Protein Eng, vol. 4, No. 7, p. 773-783 (1991).
Klinman "CpG DNA as a vaccine adjuvant", Expert Review Vaccines, vol. 2, No. 2, p. 305-15 (2003).
Kratz et al. "Native display of complete foreign protein domains on the surface of hepatitis B virus capsids", Proc Natl Acad Sci USA, vol. 96, No. 5, p. 1915-1920 (1999).
Krogh et al. "Predicting transmembrane protein topology with a hidden Markov model Application to complete genomes", Journal of Molecular Biology, vol. 305, No. 3, p. 567-580 (2001).
Kyte et al. "A Simple Method for Displaying the Hydropathic Character of a Protein", J Mol Biol, vol. 157, p. 105-132 (1982).
Liu et al. "Perturbation of NK cell peripheral homeostasis accelerates prostate carcinoma metastasis", The Journal of Clinical Investigation, vol. 123, No. 10, p. 4410-4422 (2013).
Liu R. et al. "Monoclonal Antibody against Cell Surface GRP78 as a Novel Agent in Suppressing PI3K/AKT Signaling, Tumor Growth, and Metastasis", Clinical Cancer Research, vol. 19, No. 24, p. 6802-6811 (2013).
Lonberg et al, "Antigen-specific human antibodies from mice comprising four distinct genetic modifications", Nature, vol. 368, p. 856-859 (1994).
Lonberg et al, "Human Antibodies from Transgenic Mice", International Reviews of Immunology, vol. 13, p. 65-93 (1995).
Marks et al, "By-Passing Immunication: Building High Affinity Human Antibodies by Chain Shuffling", Bio/Technology, vol. 10, p. 779-783 (1992).
Marks et al, "Human Antibodies from V-gene Libraries Displayed on Phage", J Mol Biol, vol. 222, p. 581-597 (1991).
McCafferty et al, "Phage antibodies: filamentous phage displaying antibody variable domains", Nature, vol. 348, p. 552-554 (1990).
Morrison et al., "Genetically Engineered Antibody Molecules", Advances in Immunology, vol. 44, p. 65-92 (1988).
Morrison et al, "Chimeric human antibody molecules: Mouse antigen-binding domains with human constant region domains", Proc Natl Acad Sci USA, vol. 81, p. 6851-6855 (1984).
Morrison, "Success in Specification", Nature, vol. 368, p. 812-813 (1994).
Nassal et al. "Development of hepatitis B virus capsids into a whole-chain protein antigen display platform: New particulate Lyme disease vaccines", International Journal of Medical Microbiology, vol. 298, p. 135-142 (2008).
Neuberger, "Generating high-avidity human Mabs in mice", Nature Biotechnology, vol. 14, p. 826 (1996).
Padlan, "A possible procedure for reducing the immunogenicity of antibody variable domains while preserving their ligand-binding properties", Molecular Immunology, vol. 28, p. 489-498 (1991).
Padlan, "Anatomy of the Antibody Molecule", Molecular Immunology, vol. 31, No. 3, p. 169-217 (1994).
Pashine et al. "Targeting the innate immune response with improved vaccine adjuvants", Nature Med. vol. 11, No. 4, p. S63-S68 (2005).
Pearson, "Rapid and Sensitive Sequence Comparison with FASTP and FASTA", Meth. Enzymology, vol. 183, p. 63-98 (1990).
Qi et al. "Immobilized MICA Could Expand Human Vδ1 γδ T Cells In Vitro that Displayed Major Histocompatibility Complex Class I Chain-Related A-Dependent Cytotoxicity to Human Epithelial Carcinomas", Scandinavian Journal of Immunology, vol. 58, p. 211-220 (2003).
Scatchard, "The attractions of proteins for small molecules and ions", Ann NY Acad Sci, vol. 51, p. 660-672 (1949).
Taylor, The Classification of Amino Acid Conservation, J. Theor. Biol., vol. 119, p. 205-218 (1986).
Vetter et al. "Expression of Stress-induced MHC Class I Related Chain Molecules on Human Melanoma", Journal of Investigative Dermatology, vol. 118, p. 600-605 (2000).
Verhoeyen et al, "Reshaping Human Antibodies: Grafting an Antilysozyme Activity", Science, vol. 239, p. 1534-1536 (1988).
Wang et al. "Role of the Unfolded Protein Response Regulator GRP78/BiP in Development, Cancer, and Neurological Disorders", Antioxidants and Redox Signaling, vol. 11, No. 9, p. 2307-2316 (2009).
Wu et al., "Rational Design of Envelope Identifies Broadly Neutralizing Human Monoclonal Antibodies to HIV-1", Science, vol. 329, p. 856-861 (2010).
Yu et al. "Minimal Lipidation Stabilizes Protein-Like Molecular Architecture", J Am. Chem. Soc., vol. 120, No. 39, p. 9979-9987 (1998).

(56) References Cited

OTHER PUBLICATIONS

Zapata et al , "Engineering linear F(ab')2 fragments for efficient production in *Escherichia coli* and enhanced antiproliferative activity", Protein Engineering, vol. 8, No. 10, p. 1057-1062 (1995).

* cited by examiner

CAGGTGCAGCTACAGCAGTGGGGCGCAGGACTGTTGAAGCCTTCGGAGACCCTGGCCCTCACCTGCGCTGTCTCT
GGTGGGTCCTTCACTGATCATTACTGGAGTTGGATCCGTCAGGCCCCAGGGAAGGGGCTGGAGTGGATTGGAGAA
ATCAATCATAGTGGAGTCACCAACTACAACCCGTCCCTCAAGAGTCGACTCACCATATCAGTAGACACGTCCAAG
AGCCAGTTCTCCCTGAGGCTGACCTCTGTGACCGCCGCGGACACGGCTCTGTACTACTGT GCGAAAACTGGCCTG
TATTATGATGACGTTTGGGGGACTTTTCGTCCACGGGGCGGGTTCGACTCC TGGGGCCAGGGAACCCTGGTCACC
GTCTCCTCA (SEQ ID NO: 1)

FIG. 1

Q V Q L Q Q W G A G L L K P S E T L A L T C A V S
G G S F T D H Y W S W I R Q A P G K G L E W I G E
I N H S G V T N Y N P S L K S R L T I S V D T S K
S Q F S L R L T S V T A A D T A L Y Y C A K T G L
Y Y D D V W G T F R P R G G F D S W G Q G T L V T
V S S (SEQ ID NO: 2)

FIG. 2

GACATCGTGATGACCCAGTCTCCGGACTCCCTGGCTGTGTCTCTGGGCGAGAGGGCCACCATCAACTGCAAGTCC
AGCCAGAGTATTTTATATAGCTCCGACAATAAGAATTAC TTAGCTTGGTACCAGCACAAGCCAGGACAGCCTCCT
AAGCTCCTCTTTTACTGGGCATCT ATCCGGGAATCCGGGGTCCCTGACCGATTCAGTGGCGGCGGGTCTGGGACA
GATTTCACTCTCACCATCAGCAGTCTGCAGGCTGAAGATGTGGCAGTTTATTACTGTCAGCAATATTATAGTCCT
CCTTGCAGTTTTGGCCAGGGGACCAAGCTGGAGATCCAA (SEQ ID NO: 10)

FIG. 3

D I V M T Q S P D S L A V S L G E R A T I N C K S
S Q S I L Y S S D N K N Y L A W Y Q H K P G Q P P
K L L F Y W A S I R E S G V P D R F S G G G S G T
D F T L T I S S L Q A E D V A V Y Y C Q Q Y Y S P
P C S F G Q G T K L E I Q (SEQ ID NO: 11)

FIG. 4

| | Control Tet/ $10^5$ B cells | TTCF Monomer/ $10^4$ B cells | TTCF Tet/# $10^4$ B cells | #Tet/#Mono Foldchange |
|---|---|---|---|---|
| Donor 1 | 3.98 | 2.53 | 18.41 | 7.3 |
| Donor 2 | 15.03 | 38.64 | 117.18 | 3.1 |
| Donor 3 | 4.14 | 48.92 | 77.55 | 1.6 |

CAGGTGCAGCTGCAGGAGTCGGGCCCAGGACTGGTGGAGCCTTCGGGGACCCTGTCCCT
CACCTGCACTGTGTCTGGTGGCTCCATCAGCAGGAGTAACTGGTGGAGTTGGGTCCGCC
AGCCCCCAGGGGAGGGGCTGGAATGGATTGGAGAAATCCATCACATTGGGAGGTCCAGC
TACAATCCGTCCCTCAAGAGTCGAGTCACCATGTCTGTAGACAAGTCCCAGAACCAGTT
CTCCCTGAGGCTGACCTCTGTGACCGCCGCGGACACGGCCGTGTATTACTGTGCGAAAA
ATGGCTACTACGCTATGGACGTCTGGGGCCAAGGGACCACGGTCACCGTCTCCTCG
(SEQ ID NO.76)

FIG. 10

QVQLQESGPGLVEPSGTLSLTCTVSGGSISRSNWWSWVRQPPGEGLEWIGEIHHIGRSS
YNPSLKSRVTMSVDKSQNQFSLRLTSVTAADTAVYYCAKNGYYAMDVWGQGTTVTVSS
(SEQ ID NO.77 )

FIG. 11

GAAATTGTGTTGACGCAGTCTCCAGGCACCCTGTCTTTGTCTCCAGGGGAAAGAGCCAC
CCTCTCCTGCAGGGCCAGTCAGAGTGTTAGCAGCGACTTCCTAGCCTGGTACCAGCAGA
AACCTGGCCAGGCTCCCAGGCTCCTCATCTAC GCTACATCCTTCAGGGCCACTGGCATC
TCAGACAGGTTCAGTGGCAGTGGGTCTGGGACAGACTTCTCTCTCACCATCAACAGACT
GGAACCTGAAGATTTTGCAGTGTATTACTGTCAGCACTATCGTAGTTCACCTCCGTGGT
ACACTTTT GCCCAGGGGACCAAGCTGGACATGAGACGTACGGTGGCTGCACCATCTGTC
(SEQ ID NO. 78)

FIG. 12

EIVLTQSPGTLSLSPGERATLSCRASQSVSSDFLAWYQQKPGQAPRLLIYATSFRATGI
SDRFSGSGSGTDFSLTINRLEPEDFAVYYCQHYRSSPPWYTFAQGTKLDMRRTVAAPSV
(SEQ ID NO. 79)

FIG. 13

CAGGTGCAGCTGCAGGAGTCGGGCCCAGGACTGGTGAAGCCTTCGGGGACCCTGTCCCTC ACCTGCGCTGTCTCT GGTGCCTCCATTACCAATGGT GCCTGGTGGAGTTGGGTCCGCCAG CCCCCAGGGAAGGGGCTGGAGTGGATTGGAGAA ATCTATCTTAATGGGAACACC AACTCC AACCCGTCCCTGAAGAGTCGAGTCATCATATCAGTGGACAAGTCCAAGAACCACTTCTCG CTGACCCTGAACTCTGTGACCGCCGCGGACACGGCCGTGTATTAC TGTGCGAAGAACGCT GCCTACAACCTTGAGTTCTGG GGCCAGGGAGCCCTGGTCACCGTCTCCTCA (SEQ ID NO: 95)

FIG. 14

QVQLQESGPGLVKPSGTLSLTCAVS GASITNGAW WSWVRQPPGKGLEWIGE IYLNGNT NS NPSLKSRVIISVDKSKNHFSLTLNSVTA ADTAVYY CAKNAAYNLEFW GQGALVTVSS (SEQ ID NO:96 )

FIG. 15

GAAATTGTGTTGACGCAGTCTCCAGGCACCCTGTCTTTGTCTCCAGGGGAAAGAGCCACC
CTCTCCTGCAGGGCCAGTCAGACTGTTAGCAGCCCCTAC GTAGCCTGGTACCAGCAGAAA
CGTGGCCAGGCTCCCAGGCTCCTCATCTA TGGTGCATCC ACCAGGGCCACCGGCATCCCAG
ACAGGTTCAGTGGCAGTGGGTCTGGGACAGACTTCACTCTCACCATCAGCAGACTGGAGC
CTGAAGATTTTGCAGTGTATTAC TGTCAGCAGTATGATAGATCATACTATTACACTTT T
GGCCAGGGGACCAAGCTGGAGATCAAA (SEQ ID NO:97 )

FIG. 16

EIVLTQSPGTLSLSPGERATLSCRAS QTVSSPYVAWYQQKRGQAPRLLIY GASTRATGIPDR
FSGSGSGTDFTLTISRLEPEDFAVYYCQQYDRSYYYTFGQGTKLEIK (SEQ ID NO: 98 )

FIG. 17

CAGGTGCAGCTGCAGGAGTCGGGCCCAGGACTGGTGAAGCCTTCGGAGAACCTGTCGCTC
ACCTGCACTGTCTCTGATGCCTCCATGAGTGATTATCAC TGGAGCTGGATCCGGCAGGCC
GCCGGGAAGGGACTGGAGTGGATTGGGCGT ATGTACAGCACTGGGAGTCCC TACTACAA
ACCCTCCCTCAAAGGTCGGGTCACCATGTCAATAGACACGTCCAAGAACCAGTTCTCCCT
GAAGCTGGCCTCTGTGACCGCCGCAGACACGGCCATCTATTAT TGTGCGAGCGGACAACA
TATTGGTGGCTGGGTCCCCCCTGACTTCTGG GGCCAGGGAACCCTGGTCACCGTCTCCTC
A (SEQ ID NO: 112)

FIG. 18

QVQLQESGPGLVKPSENLSLT CTVSDASMSDYHWSWIRQAAGKGLEWIGR MYSTGSPYY
KPSLKGRVTMSIDTSKNQFSLKLASVTAADTAIYY CASGQHIGGWVPPDFWGQGTLVTVS
S (SEQ ID NO:113 )

FIG. 19

GATATTGTGATGACCCAGACTCCACTCTCCTCACCTGTCACCCTTGGACAGCCGGCCTCCA
TCTCCTGCAGGTCTAGT GAAGGCCTCGTATATAGTGATGGAGACACCTAC TTGAGTTGGT
TTCACCAGAGGCCAGGCCAGCCTCCAAGACTCCTGATTTAT AAAATTTCTAACCGGTTCT
CTGGGGTCCCCGACAGATTCAGTGGCAGTGGGGCAGGCACAGATTTCACACTGAAAATCA
GCAGGGTGGAGGCTGAGGATGTCGGGGTTTATTAC TGCATGCAAGCTACACATTTTCCGT
GGACGTTCGGCCAGGGGACCAAAGTGGAAGTCAAACGT (SEQ ID NO: 114)

FIG. 20

DIVMTQTPLSSPVTLGQPASISCRSSEGLVYSDGDTYLSWFHQRPGQPPRLLIYKISNRFSG
VPDRFSGSGAGTDFTLKISRVEAEDVGVYYCMQATHFPWTFGQGTKVEVKR (SEQ ID NO: 115)

FIG. 21

GAGGTGCAGCTGTTGGAGTCTGGGGGAGGCTTGG TACAGCCTGGGGGGTCCCTGAGACTC
TCCTGTGCAGCCTCTGGATTCACCTTTAGTTCATATGGC TTGACCTGGATACGCCAGGCT
CCGGGGAAGGGCCTGGAGTGGGTCTCAAGT ATCAGTGGCAGTGGCAATAACACA TACTA
CGCAGACTCTGTGAAGGGCCGGTTCACCATCTCCAGAGACAAAGTCAAGAAGACACTATA
TCTACAAATGGACAGCCTGACAGTCGGAGACACGGCCGTCTATTAC TGCTTAGGAGTCGG
TCAGGGCCACGGAATTCCGGTCATCGTCTCCT CA (SEQ ID NO. 130)

FIG. 22

EVQLLESGGGLVQPGGSLRLSC AASGFTFSSYGLTWIRQAPGKGLEWVSS ISGSGNNTYYA
DSVKGRFTISRDKVKKTLYLQMDSLTVGDTAVYY CLGVGQGHGIPVIVSS (SEQ ID NO. 131)

FIG. 23

GATATTGTGATGACCCAGACTCCACTCTCCTCACCTGTCACCCTTGGACAGCC GGCCTCCA
TCTCCTGCAGGTCTAGT CAGAGCCTCGTACACCGTGATGGAAACACCTAC TTGAGTTGGT
TTCTGCAGAGGCCAGGCCAGGCTCCAAGACTCCTAATTTAT CGGATTTCTAACCGGTTCT
CTGGGGTCCCAGACAGATTCAGTGGCAGTGGGGCAGGGACGGATTTCACACTGAAAATC
AGCAGGGTGGAAGCTGAGGATGTCGGCGTTTACTAC TGCATGCAAGCTACACAAATCCCC
AACACTTTTGGCCAGGGGACCAAGCTGGAGATCAAG (SEQ ID NO. 132)

FIG. 24

DVVMTQSPLSLPVTLGQPASISCRSS QSLVHSDGNTY LNWFHQRPGQSPRRLIY KVSKR
DSGVPDRFSGSGSGSDFT LKISRVEAEDVGIYY CMQGTHWPTF GQGTKVEIKRTVAA
(SEQ ID NO. 133)

FIG. 25

Secondary Negative Control

Isotype Negative Control

BioLegend Positive Control

CM24002 Ab2

CM24002 Ab4

CM33322 Ab11

CM33322 Ab29

% Max
MICA-FITC
Streptavidin Negative Control
MICA*002
MICA*008
MICA*009
MICB

FIG. 35

CAGGTGCAGCTGCAGGAGTCGGGCCCAGGACTG
GTGAGGCCTTCGGGGACCCTGTCCCTCACTTGCG
CTGTGTCTGGTGGCTCCATCGACTATAGTAATTGGT
GGGGTTGGGTCCGCCAAGTCCCAGGAAAGGGGC
TGGAGTGGATTGGCGAAGTCTATCATACTGGGGC
CACTCATTACAACCCGTCCCTCGAGCGTCGATGCA
TCATTTCAGTGGACAAGTCTAATAACCAGGTCTCC
CTCCAATTGACTTCTGTGACCGCCGCAGACTCGGC
CATCTATTATTGTGCGAGAGAGAGGGGCACGCATT
GTGATGGAAACCGCTGTTATTATGTTTTCTTTGACC
ATTGGGGCCAGGGAATCCCGGTCACCGTCTCCTC
A (SEQ ID NO:149)

FIG. 36

QVQLQESGPGLVRPSGTLSLTCAVSGGSIDYSNWW
GWVRQVPGKGLEWIGEVYHTGATHYNPSLERRCII
SVDKSNNQVSLQLTSVTAADSAIYYCARERGTHCDG
NRCYYVFFDHWGQGIPVTVSS (SEQ ID NO:150)

FIG. 37

GATATTGTGATGACCCAGACTCCACTGTCCTCACC
TGTCACCCTTGGACAACCGGCCTCCATCTCCTGCA
GGTCTAGTGAAAGCCTCGTACATTGGGATGGAAC
CACGTACTTGAGTTGGTTTCACCAGAGGCCAGGC
CAGCCTCCAAGACTCCTAATTTATAAGGTTTCTAAC
CGCTTCTCTGGGGTCCCAGACAGATTCAGTGGCA
GTGGGGCAGGGACAGATTTCACACTGAAAATCAG
CAGGGTGGAAGCTGACGATGTCGGCATTTATTATT
GCATGCAAGCTACACAGTTTCCTCGGACGTTCGG
CCAAGGGACGAAGGTGGAAATCAAACGTAC (SEQ
ID NO:151)

FIG. 38

DIVMTQTPLSSPVTLGQPASISCRSSESLVHWDGTT
YLSWFHQRPGQPPRLLIYKVSNRFSGVPDRFSGSG
AGTDFTLKISRVEADDVGIYYCMQATQFPRTFGQG
TKVEIKR (SEQ ID NO:152)

FIG. 40

| Patient # | Soluble MICA (ng/ml) | Control Serum | Melanoma Serum | Melanoma Serum + Isotype | Melanoma Serum + CM24002 Ab2 | Melanoma Serum + CM33322 Ab29 | Melanoma Serum + CM33322 Ab4 |
|---|---|---|---|---|---|---|---|
| **CM28857** | 25.49 | 63.2 | 41.8 | 39.8 | **57.5** | 62 | 53.3 |
| **CM26953** | 32.36 | 61.3 | 52.9 | 48.3 | **62.1** | 66 | 55.7 |
| **CM26284** | 22.54 | 76.4 | 50 | 50 | 62.5 | 71.4 | 63.6 |
| **CM23023** | 25.69 | 60.4 | 28.9 | 29.7 | 46.4 | 44.9 | 48.3 |
| **CM23094** | 25.27 | 72.8 | 50 | 48.4 | **68.9** | 75.4 | 64.2 |
| **CM29315** | 12.42 | 59.5 | 38.6 | 36.4 | 50 | 60 | **54.3** |
| **CM22714** | 11.76 | 62.7 | 51.5 | 49.1 | **59.7** | **70.8** | 71.1 |
| **CM23367** | 14.39 | 63.9 | 47.1 | 53.3 | **67.9** | 68.1 | **67.7** |
| **CM24836** | 9.8 | 69.8 | 54.5 | 58.1 | **67.2** | 75.6 | **70.2** |
| **CM27819** | 13.76 | 59.3 | 44.2 | 45.8 | 57 | 52.4 | **56.9** |
| **CM25287** | 9.84 | 60.8 | 46.7 | 47.2 | 63.3 | **61** | **58.5** |
| **CM25295** | 7.43 | 60.1 | 46.7 | 47.2 | **60.1** | 60.6 | **58.8** |
| **CM26287** | 15.84 | 67.6 | 56.7 | 51.7 | 74.3 | **72.6** | **72.3** |
| **CM27131** | 8.37 | 72.3 | 57.1 | 62.8 | **73.2** | **75.4** | 75.6 |
| **CM29719** | 8.25 | 64 | 53.4 | 56.7 | 68.9 | **66.9** | **65.4** |

RPMI-8226 cells were cultured in the presence of 10ug/ml isotype control antibody, CM33322 Ab29, or CM24002 Ab2. After 48hrs, cells were washed, and MICA surface expression was determined by flow cytometry.

FIG. 50

CAGGTGCAGCTGGTGCAGTCTGGGGCTGAGGTG
AAGAAGCCTGGGTCCTCGGTGAGANTCTCCTGCA
GGGCCTCTGGAGGCTCCTCCACCACCTATGCTTTC
NACTGGGTGCGTCAGGCCCCTGGCCAAGGGCTT
GAGTGGATGGGAGGCATCGTCCCCATCTTTGGTA
CATTGAAATACGCACAGAAGTTCCAAGACAGAGT
CACACTTACCGCGGATAAGTCCACGGGCACAGCC
TACATGGAACTGAACAGCCTGAGATTAGACGACA
CGGCCGTCTATTATTGTGCGAGAGCGATACAATTG
GAAGGACGCCCCTTTGACCACTGGGGCCAGGGA
ACCCAGGTCACCGTCTCCGCA (SEQ ID NO:167)

FIG. 51

QVQLVQSGAEVKKPGSSVRXSCRASGGSSTTYAFX
WVRQAPGQGLEWMGGIVPIFGTLKYAQKFQDRV
TLTADKSTGTAYMELNSLRLDDTAVYYCARAIQLEGR
PFDHWGQGTQVTVSA (SEQ ID NO:168)

FIG. 52

GACATCCAGTTGACCCAGTCTCCATCCTTCCTGTCT
GCATCTGTTGGAGACAGAGTCACCATCACTTGCC
GGGCCAGTCAGGGCATTACCAGTTATTTAGCCTG
GTATCAGCAAAAACCAGGGAAAGCCCCTAAGCTC
CTGATCTATGCTGCATCCGCTTTGCAAAGTGGGGT
CCCATCAAGATTCAGCGGCCGTGGATCTGGGACA
GAGTTCACTCTCACAATCAGCAGCCTGCAGCCT
GAAGATTTTGCAACTTATTACTGTCAACAGGTGAA
TAGGGGTGCCGCGATCACCTTCGGCCACGGGACA
CGGCTGGACATTAAACGT (SEQ ID NO:169)

FIG. 53

DIQLTQSPSFLSASVGDRVTITCRASQGITSYLAWYQ
QKPGKAPKLLIYAASALQSGVPSRFSGRGSGTEFTLTI
SSLQPEDFATYYCQQVNRGAAITFGHGTRLDIKR
(SEQ ID NO:170)

Epitope of CN33322 Ab29

HSLRYNLTVLSWDGSVQSGFLAEVHLDGQPFLRYDR
QKCRAKPQGQWAEDVLGNKTWDRETRDLTGNGKD
LRMTLAHIKDQKEGLHSLQEIRVCEIHEDNSTRSSQH
FYYDGELFLSQNVETEEWTVPQSSRAQTLAMNVRN
FLKEDAMKTKTHYHAMHADCLQELRRYLESSVVLR
RTVPPMVNVTRSEASEGNITVTCRASSFYPRNITLTW
RQDGVSLSHDTQQWGDVLPDGNGTYQTWVATRIC
QGEEQRFTCYMEHSGNHSTHPVPSGKVLVLQSHWQ
TFHVSAVAAAAAIFVIIIFYVRCCKKKTSAAEGPELV
SLQVLDQHPVGTSDHRDATQLGFQPLMSALGSTGST
EGA

FIG. 60A

Epitope of CM33322 Ab4

FIG. 60B

HSLRYNLTVLSWDGSVQSGFLAEVHLDGQPFLRYDRQKCRAKPQGQWAEDVLGNKTWDRETRDLTGNGKDLRM
TLAHIKDQKEGLHSLQEIRVCEIHEDNSTRSSQHFYYDGELFLSQNVETEEWTVPQSSRAQTLAMNVRNFLKEDAM
KTKTHYHAMHADCLQELRRYLESSVVLRRTVPPMVNVTRSEASEGNITVTCRASSFYPRNITLTWRQDGVSLSHDT
QQWGDVLPDGNGTYQTWVATRICQGEEQRFTCYMEHSGNHSTHPVPSGKVLVLQSHWQTFHVSAVAAAAAIF
VIIIFYVRCCKKKTSAAEGPELVSLQVLDQHPVGTSDHRDATQLGFQPLMSALGSTGSTEGA

Epitope of CM33322 Ab11

FIG. 60C

HSLRYNLTVLSWDGSVQSGFLAEVHLDGQPFLRYDRQKCRAKPQGQWAEDVLGNKTWDRETRDLTGNGKDLR
MTLAHIKDQKEGLHSLQEIRVCEIHEDNSTRSSQHFYYDGELFLSQNVETEEWTVPQSSRAQTLAMNVRNFLKED
AMKTKTHYHAMHADCLQELRRYLESSVVLRRTVPPMVNVTRSEASEGNITVTCRASSFYPRNITLTWRQDGVSLS
HDTQQWGDVLPDGNGTYQTWVATRICQGEEQRFTCYMEHSGNHSTHPVPSGKVLVLQSHWQTFHVSAVAAAA
AAIFVIIIFYVRCCKKKTSAAEGPELVSLQVLDQHPVGTSDHRDATQLGFQPLMSALGSTGSTEGA

Epitope of CM33322 Ab28

FIG. 60D

HSLRYNLTVLSWDGSVQSGFLAEVHLDGQPFLRYDRQKCRAKPQGQWAEDVLGNKTWDRETRDLTGNGKDLR
MTLAHIKDQKEGLHSLQEIRVCEIHEDNSTRSSQHFYYDGELFLSQNVETEEWTVPQSSRAQTLAMNVRNFLKED
AMKTKTHYHAMHADCLQELRRYLESSVVLRRTVPPMVNVTRSEASEGNITVTCRASSFYPRNITLTWRQDGVSLS
HDTQQWGDVLPDGNGTYQTWVATRICQGEEQRFTCYMEHSGNHSTHPVPSGKVLVLQSHWQTFHVSAVAAAA
AAIFVIIIFYVRCCKKKTSAAEGPELVSLQVLDQHPVGTSDHRDATQLGFQPLMSALGSTGSTEGA

SEQUENCE LISTING

```
<160> NUMBER OF SEQ ID NOS: 190

<210> SEQ ID NO 1
<211> LENGTH: 384
<212> TYPE: DNA
<213> ORGANISM: Artificial Sequence
<220> FEATURE:
<223> OTHER INFORMATION: Synthetic

<400> SEQUENCE: 1

caggtgcagc tacagcagtg gggcgcagga ctgttgaagc cttcggagac cctggccctc      60

acctgcgctg tctctggtgg gtccttcact gatcattact ggagttggat ccgtcaggcc     120

ccagggaagg ggctggagtg gattggagaa atcaatcata gtggagtcac caactacaac     180

ccgtccctca agagtcgact caccatatca gtagacacgt ccaagagcca gttctccctg     240

aggctgacct ctgtgaccgc cgcggacacg gctctgtact actgtgcgaa aactggcctg     300

tattatgatg acgtttgggg gacttttcgt ccacggggcg ggttcgactc ctggggccag     360

ggaaccctgg tcaccgtctc ctca                                            384


<210> SEQ ID NO 2
<211> LENGTH: 128
<212> TYPE: PRT
<213> ORGANISM: Artificial Sequence
<220> FEATURE:
<223> OTHER INFORMATION: Synthetic

<400> SEQUENCE: 2

Gln Val Gln Leu Gln Gln Trp Gly Ala Gly Leu Leu Lys Pro Ser Glu
1               5                   10                  15

Thr Leu Ala Leu Thr Cys Ala Val Ser Gly Gly Ser Phe Thr Asp His
            20                  25                  30

Tyr Trp Ser Trp Ile Arg Gln Ala Pro Gly Lys Gly Leu Glu Trp Ile
        35                  40                  45
```

```
Gly Glu Ile Asn His Ser Gly Val Thr Asn Tyr Asn Pro Ser Leu Lys
    50                  55                  60

Ser Arg Leu Thr Ile Ser Val Asp Thr Ser Lys Ser Gln Phe Ser Leu
65                  70                  75                  80

Arg Leu Thr Ser Val Thr Ala Ala Asp Thr Ala Leu Tyr Tyr Cys Ala
                85                  90                  95

Lys Thr Gly Leu Tyr Tyr Asp Asp Val Trp Gly Thr Phe Arg Pro Arg
            100                 105                 110

Gly Gly Phe Asp Ser Trp Gly Gln Gly Thr Leu Val Thr Val Ser Ser
        115                 120                 125


<210> SEQ ID NO 3
<211> LENGTH: 25
<212> TYPE: PRT
<213> ORGANISM: Artificial Sequence
<220> FEATURE:
<223> OTHER INFORMATION: Synthetic

<400> SEQUENCE: 3

Gln Val Gln Leu Gln Gln Trp Gly Ala Gly Leu Leu Lys Pro Ser Glu
1               5                   10                  15

Thr Leu Ala Leu Thr Cys Ala Val Ser
            20                  25


<210> SEQ ID NO 4
<211> LENGTH: 8
<212> TYPE: PRT
<213> ORGANISM: Artificial Sequence
<220> FEATURE:
<223> OTHER INFORMATION: Synthetic

<400> SEQUENCE: 4

Gly Gly Ser Phe Thr Asp His Tyr
1               5


<210> SEQ ID NO 5
<211> LENGTH: 17
<212> TYPE: PRT
<213> ORGANISM: Artificial Sequence
<220> FEATURE:
<223> OTHER INFORMATION: Synthetic

<400> SEQUENCE: 5

Trp Ser Trp Ile Arg Gln Ala Pro Gly Lys Gly Leu Glu Trp Ile Gly
1               5                   10                  15

Glu


<210> SEQ ID NO 6
<211> LENGTH: 7
<212> TYPE: PRT
<213> ORGANISM: Artificial Sequence
<220> FEATURE:
<223> OTHER INFORMATION: Synthetic

<400> SEQUENCE: 6

Ile Asn His Ser Gly Val Thr
1               5


<210> SEQ ID NO 7
<211> LENGTH: 38
<212> TYPE: PRT
<213> ORGANISM: Artificial Sequence
<220> FEATURE:
```

<223> OTHER INFORMATION: Synthetic

<400> SEQUENCE: 7

Asn Tyr Asn Pro Ser Leu Lys Ser Arg Leu Thr Ile Ser Val Asp Thr
1 5 10 15

Ser Lys Ser Gln Phe Ser Leu Arg Leu Thr Ser Val Thr Ala Ala Asp
20 25 30

Thr Ala Leu Tyr Tyr Cys
35

<210> SEQ ID NO 8
<211> LENGTH: 22
<212> TYPE: PRT
<213> ORGANISM: Artificial Sequence
<220> FEATURE:
<223> OTHER INFORMATION: Synthetic

<400> SEQUENCE: 8

Ala Lys Thr Gly Leu Tyr Tyr Asp Asp Val Trp Gly Thr Phe Arg Pro
1 5 10 15

Arg Gly Gly Phe Asp Ser
20

<210> SEQ ID NO 9
<211> LENGTH: 11
<212> TYPE: PRT
<213> ORGANISM: Artificial Sequence
<220> FEATURE:
<223> OTHER INFORMATION: Synthetic

<400> SEQUENCE: 9

Trp Gly Gln Gly Thr Leu Val Thr Val Ser Ser
1 5 10

<210> SEQ ID NO 10
<211> LENGTH: 339
<212> TYPE: DNA
<213> ORGANISM: Artificial Sequence
<220> FEATURE:
<223> OTHER INFORMATION: Synthetic

<400> SEQUENCE: 10
gacatcgtga tgacccagtc tccggactcc ctggctgtgt ctctgggcga gagggccacc 60
atcaactgca agtccagcca gagtatttta tatagctccg acaataagaa ttacttagct 120
tggtaccagc acaagccagg acagcctcct aagctcctct tttactgggc atctatccgg 180
gaatccgggg tccctgaccg attcagtggc ggcgggtctg ggacagattt cactctcacc 240
atcagcagtc tgcaggctga agatgtggca gtttattact gtcagcaata ttatagtcct 300
ccttgcagtt ttggccaggg gaccaagctg gagatccaa 339

<210> SEQ ID NO 11
<211> LENGTH: 113
<212> TYPE: PRT
<213> ORGANISM: Artificial Sequence
<220> FEATURE:
<223> OTHER INFORMATION: Synthetic

<400> SEQUENCE: 11

Asp Ile Val Met Thr Gln Ser Pro Asp Ser Leu Ala Val Ser Leu Gly
1 5 10 15

Glu Arg Ala Thr Ile Asn Cys Lys Ser Ser Gln Ser Ile Leu Tyr Ser
20 25 30

Ser Asp Asn Lys Asn Tyr Leu Ala Trp Tyr Gln His Lys Pro Gly Gln
35 40 45

Pro Pro Lys Leu Leu Phe Tyr Trp Ala Ser Ile Arg Glu Ser Gly Val
50 55 60

Pro Asp Arg Phe Ser Gly Gly Gly Ser Gly Thr Asp Phe Thr Leu Thr
65 70 75 80

Ile Ser Ser Leu Gln Ala Glu Asp Val Ala Val Tyr Tyr Cys Gln Gln
85 90 95

Tyr Tyr Ser Pro Pro Cys Ser Phe Gly Gln Gly Thr Lys Leu Glu Ile
100 105 110

Gln

<210> SEQ ID NO 12
<211> LENGTH: 26
<212> TYPE: PRT
<213> ORGANISM: Artificial Sequence
<220> FEATURE:
<223> OTHER INFORMATION: Synthetic

<400> SEQUENCE: 12

Asp Ile Val Met Thr Gln Ser Pro Asp Ser Leu Ala Val Ser Leu Gly
1 5 10 15

Glu Arg Ala Thr Ile Asn Cys Lys Ser Ser
20 25

<210> SEQ ID NO 13
<211> LENGTH: 12
<212> TYPE: PRT
<213> ORGANISM: Artificial Sequence
<220> FEATURE:
<223> OTHER INFORMATION: Synthetic

<400> SEQUENCE: 13

Gln Ser Ile Leu Tyr Ser Ser Asp Asn Lys Asn Tyr
1 5 10

<210> SEQ ID NO 14
<211> LENGTH: 17
<212> TYPE: PRT
<213> ORGANISM: Artificial Sequence
<220> FEATURE:
<223> OTHER INFORMATION: Synthetic

<400> SEQUENCE: 14

Leu Ala Trp Tyr Gln His Lys Pro Gly Gln Pro Pro Lys Leu Leu Phe
1 5 10 15

Tyr

<210> SEQ ID NO 15
<211> LENGTH: 3
<212> TYPE: PRT
<213> ORGANISM: Artificial Sequence
<220> FEATURE:
<223> OTHER INFORMATION: Synthetic

<400> SEQUENCE: 15

Trp Ala Ser
1

<210> SEQ ID NO 16
<211> LENGTH: 36
<212> TYPE: PRT

<213> ORGANISM: Artificial Sequence
<220> FEATURE:
<223> OTHER INFORMATION: Synthetic

<400> SEQUENCE: 16

```
Ile Arg Glu Ser Gly Val Pro Asp Arg Phe Ser Gly Gly Gly Ser Gly
1               5                   10                  15

Thr Asp Phe Thr Leu Thr Ile Ser Ser Leu Gln Ala Glu Asp Val Ala
            20                  25                  30

Val Tyr Tyr Cys
        35
```

<210> SEQ ID NO 17
<211> LENGTH: 9
<212> TYPE: PRT
<213> ORGANISM: Artificial Sequence
<220> FEATURE:
<223> OTHER INFORMATION: Synthetic

<400> SEQUENCE: 17

```
Gln Gln Tyr Tyr Ser Pro Pro Cys Ser
1               5
```

<210> SEQ ID NO 18
<211> LENGTH: 10
<212> TYPE: PRT
<213> ORGANISM: Artificial Sequence
<220> FEATURE:
<223> OTHER INFORMATION: Synthetic

<400> SEQUENCE: 18

```
Phe Gly Gln Gly Thr Lys Leu Glu Ile Gln
1               5                   10
```

<210> SEQ ID NO 19
<211> LENGTH: 44
<212> TYPE: DNA
<213> ORGANISM: Artificial Sequence
<220> FEATURE:
<223> OTHER INFORMATION: Synthetic

<400> SEQUENCE: 19

```
taatacgact cactataggt tcggggaagt agtccttgac cagg                      44
```

<210> SEQ ID NO 20
<211> LENGTH: 44
<212> TYPE: DNA
<213> ORGANISM: Artificial Sequence
<220> FEATURE:
<223> OTHER INFORMATION: Synthetic

<400> SEQUENCE: 20

```
taatacgact cactataggg atagaagtta ttcagcaggc acac                      44
```

<210> SEQ ID NO 21
<211> LENGTH: 46
<212> TYPE: DNA
<213> ORGANISM: Artificial Sequence
<220> FEATURE:
<223> OTHER INFORMATION: Synthetic

<400> SEQUENCE: 21

```
taatacgact cactataggc gtcaggctca grtagctgct ggccgc                    46
```

<210> SEQ ID NO 22

<211> LENGTH: 43
<212> TYPE: DNA
<213> ORGANISM: Artificial Sequence
<220> FEATURE:
<223> OTHER INFORMATION: Synthetic

<400> SEQUENCE: 22
aatacgactc actataggtt cggggaagta gtccttgacc agg 43

<210> SEQ ID NO 23
<211> LENGTH: 44
<212> TYPE: DNA
<213> ORGANISM: Artificial Sequence
<220> FEATURE:
<223> OTHER INFORMATION: Synthetic

<400> SEQUENCE: 23
taatacgact cactataggg atagaagtta ttcagcaggc acac 44

<210> SEQ ID NO 24
<211> LENGTH: 46
<212> TYPE: DNA
<213> ORGANISM: Artificial Sequence
<220> FEATURE:
<223> OTHER INFORMATION: Synthetic

<400> SEQUENCE: 24
taatacgact cactataggc gtcaggctca grtagctgct ggccgc 46

<210> SEQ ID NO 25
<211> LENGTH: 21
<212> TYPE: DNA
<213> ORGANISM: Artificial Sequence
<220> FEATURE:
<223> OTHER INFORMATION: Synthetic

<400> SEQUENCE: 25
tcaccatgga ctgsacctgg a 21

<210> SEQ ID NO 26
<211> LENGTH: 22
<212> TYPE: DNA
<213> ORGANISM: Artificial Sequence
<220> FEATURE:
<223> OTHER INFORMATION: Synthetic

<400> SEQUENCE: 26
ccatggacac actttgytcc ac 22

<210> SEQ ID NO 27
<211> LENGTH: 23
<212> TYPE: DNA
<213> ORGANISM: Artificial Sequence
<220> FEATURE:
<223> OTHER INFORMATION: Synthetic

<400> SEQUENCE: 27
tcaccatgga gtttgggctg agc 23

<210> SEQ ID NO 28
<211> LENGTH: 25
<212> TYPE: DNA
<213> ORGANISM: Artificial Sequence
<220> FEATURE:
<223> OTHER INFORMATION: Synthetic

<400> SEQUENCE: 28
agaacatgaa acayctgtgg ttctt 25

<210> SEQ ID NO 29
<211> LENGTH: 20
<212> TYPE: DNA
<213> ORGANISM: Artificial Sequence
<220> FEATURE:
<223> OTHER INFORMATION: Synthetic

<400> SEQUENCE: 29
atggggtcaa ccgccatcct 20

<210> SEQ ID NO 30
<211> LENGTH: 23
<212> TYPE: DNA
<213> ORGANISM: Artificial Sequence
<220> FEATURE:
<223> OTHER INFORMATION: Synthetic

<400> SEQUENCE: 30
acaatgtctg tctccttcct cat 23

<210> SEQ ID NO 31
<211> LENGTH: 21
<212> TYPE: DNA
<213> ORGANISM: Artificial Sequence
<220> FEATURE:
<223> OTHER INFORMATION: Synthetic

<400> SEQUENCE: 31
gctcagctcc tggggctcct g 21

<210> SEQ ID NO 32
<211> LENGTH: 21
<212> TYPE: DNA
<213> ORGANISM: Artificial Sequence
<220> FEATURE:
<223> OTHER INFORMATION: Synthetic

<400> SEQUENCE: 32
ctggggctgc taatgctctg g 21

<210> SEQ ID NO 33
<211> LENGTH: 21
<212> TYPE: DNA
<213> ORGANISM: Artificial Sequence
<220> FEATURE:
<223> OTHER INFORMATION: Synthetic

<400> SEQUENCE: 33
ttcctcctgc tactctggct c 21

<210> SEQ ID NO 34
<211> LENGTH: 21
<212> TYPE: DNA
<213> ORGANISM: Artificial Sequence
<220> FEATURE:
<223> OTHER INFORMATION: Synthetic

<400> SEQUENCE: 34
cagacccagg tcttcatttc t 21

<210> SEQ ID NO 35
<211> LENGTH: 20
<212> TYPE: DNA

<213> ORGANISM: Artificial Sequence
<220> FEATURE:
<223> OTHER INFORMATION: Synthetic

<400> SEQUENCE: 35
cctctcctcc tcaccctcct 20

<210> SEQ ID NO 36
<211> LENGTH: 18
<212> TYPE: DNA
<213> ORGANISM: Artificial Sequence
<220> FEATURE:
<223> OTHER INFORMATION: Synthetic

<400> SEQUENCE: 36
ctcctcactc agggcaca 18

<210> SEQ ID NO 37
<211> LENGTH: 19
<212> TYPE: DNA
<213> ORGANISM: Artificial Sequence
<220> FEATURE:
<223> OTHER INFORMATION: Synthetic

<400> SEQUENCE: 37
atggcctgga ycsctctcc 19

<210> SEQ ID NO 38
<211> LENGTH: 19
<212> TYPE: DNA
<213> ORGANISM: Artificial Sequence
<220> FEATURE:
<223> OTHER INFORMATION: Synthetic

<400> SEQUENCE: 38
gccaggggga agacsgatg 19

<210> SEQ ID NO 39
<211> LENGTH: 24
<212> TYPE: DNA
<213> ORGANISM: Artificial Sequence
<220> FEATURE:
<223> OTHER INFORMATION: Synthetic

<400> SEQUENCE: 39
tttcaactgc tcatcagatg gcgg 24

<210> SEQ ID NO 40
<211> LENGTH: 20
<212> TYPE: DNA
<213> ORGANISM: Artificial Sequence
<220> FEATURE:
<223> OTHER INFORMATION: Synthetic

<400> SEQUENCE: 40
agctcctcag aggagggygg 20

<210> SEQ ID NO 41
<211> LENGTH: 20
<212> TYPE: DNA
<213> ORGANISM: Artificial Sequence
<220> FEATURE:
<223> OTHER INFORMATION: Synthetic

<400> SEQUENCE: 41
caggtscagc tggtrcagtc 20

<210> SEQ ID NO 42
<211> LENGTH: 20
<212> TYPE: DNA
<213> ORGANISM: Artificial Sequence
<220> FEATURE:
<223> OTHER INFORMATION: Synthetic

<400> SEQUENCE: 42
cagrtcacct tgaaggagtc 20

<210> SEQ ID NO 43
<211> LENGTH: 20
<212> TYPE: DNA
<213> ORGANISM: Artificial Sequence
<220> FEATURE:
<223> OTHER INFORMATION: Synthetic

<400> SEQUENCE: 43
saggtgcagc tggtggagtc 20

<210> SEQ ID NO 44
<211> LENGTH: 20
<212> TYPE: DNA
<213> ORGANISM: Artificial Sequence
<220> FEATURE:
<223> OTHER INFORMATION: Synthetic

<400> SEQUENCE: 44
caggtgcagc tgcaggagtc 20

<210> SEQ ID NO 45
<211> LENGTH: 20
<212> TYPE: DNA
<213> ORGANISM: Artificial Sequence
<220> FEATURE:
<223> OTHER INFORMATION: Synthetic

<400> SEQUENCE: 45
gargtgcagc tggtgcagtc 20

<210> SEQ ID NO 46
<211> LENGTH: 20
<212> TYPE: DNA
<213> ORGANISM: Artificial Sequence
<220> FEATURE:
<223> OTHER INFORMATION: Synthetic

<400> SEQUENCE: 46
caggtacagc tgcagcagtc 20

<210> SEQ ID NO 47
<211> LENGTH: 20
<212> TYPE: DNA
<213> ORGANISM: Artificial Sequence
<220> FEATURE:
<223> OTHER INFORMATION: Synthetic

<400> SEQUENCE: 47
cgmcatccrg wtgacccagt 20

<210> SEQ ID NO 48
<211> LENGTH: 19
<212> TYPE: DNA
<213> ORGANISM: Artificial Sequence
<220> FEATURE:

<223> OTHER INFORMATION: Synthetic

<400> SEQUENCE: 48
cgatrttgtg atgacycag 19

<210> SEQ ID NO 49
<211> LENGTH: 22
<212> TYPE: DNA
<213> ORGANISM: Artificial Sequence
<220> FEATURE:
<223> OTHER INFORMATION: Synthetic

<400> SEQUENCE: 49
cgaaatwgtg wtgacrcagt ct 22

<210> SEQ ID NO 50
<211> LENGTH: 20
<212> TYPE: DNA
<213> ORGANISM: Artificial Sequence
<220> FEATURE:
<223> OTHER INFORMATION: Synthetic

<400> SEQUENCE: 50
cgacatcgtg atgacccagt 20

<210> SEQ ID NO 51
<211> LENGTH: 20
<212> TYPE: DNA
<213> ORGANISM: Artificial Sequence
<220> FEATURE:
<223> OTHER INFORMATION: Synthetic

<400> SEQUENCE: 51
ccagtctgtg ctgactcagc 20

<210> SEQ ID NO 52
<211> LENGTH: 20
<212> TYPE: DNA
<213> ORGANISM: Artificial Sequence
<220> FEATURE:
<223> OTHER INFORMATION: Synthetic

<400> SEQUENCE: 52
ccagtctgcc ctgactcagc 20

<210> SEQ ID NO 53
<211> LENGTH: 20
<212> TYPE: DNA
<213> ORGANISM: Artificial Sequence
<220> FEATURE:
<223> OTHER INFORMATION: Synthetic

<400> SEQUENCE: 53
ctcctatgag ctgacwcagc 20

<210> SEQ ID NO 54
<211> LENGTH: 21
<212> TYPE: DNA
<213> ORGANISM: Artificial Sequence
<220> FEATURE:
<223> OTHER INFORMATION: Synthetic

<400> SEQUENCE: 54
gacsgatggg cccttggtgg a 21

<210> SEQ ID NO 55
<211> LENGTH: 20
<212> TYPE: DNA
<213> ORGANISM: Artificial Sequence
<220> FEATURE:
<223> OTHER INFORMATION: Synthetic

<400> SEQUENCE: 55
aagatgaaga cagatggtgc 20

<210> SEQ ID NO 56
<211> LENGTH: 16
<212> TYPE: DNA
<213> ORGANISM: Artificial Sequence
<220> FEATURE:
<223> OTHER INFORMATION: Synthetic

<400> SEQUENCE: 56
gggaacagag tgaccg 16

<210> SEQ ID NO 57
<211> LENGTH: 21
<212> TYPE: DNA
<213> ORGANISM: Artificial Sequence
<220> FEATURE:
<223> OTHER INFORMATION: Synthetic

<400> SEQUENCE: 57
tcactatgga ctggatttgg a 21

<210> SEQ ID NO 58
<211> LENGTH: 22
<212> TYPE: DNA
<213> ORGANISM: Artificial Sequence
<220> FEATURE:
<223> OTHER INFORMATION: Synthetic

<400> SEQUENCE: 58
ccatggacay actttgytcc ac 22

<210> SEQ ID NO 59
<211> LENGTH: 23
<212> TYPE: DNA
<213> ORGANISM: Artificial Sequence
<220> FEATURE:
<223> OTHER INFORMATION: Synthetic

<400> SEQUENCE: 59
gtaggagaca tgcaaatagg gcc 23

<210> SEQ ID NO 60
<211> LENGTH: 23
<212> TYPE: DNA
<213> ORGANISM: Artificial Sequence
<220> FEATURE:
<223> OTHER INFORMATION: Synthetic

<400> SEQUENCE: 60
aacaaagcta tgacatatag atc 23

<210> SEQ ID NO 61
<211> LENGTH: 24
<212> TYPE: DNA
<213> ORGANISM: Artificial Sequence
<220> FEATURE:
<223> OTHER INFORMATION: Synthetic

<400> SEQUENCE: 61
atggagttgg ggctgagctg ggtt 24

<210> SEQ ID NO 62
<211> LENGTH: 23
<212> TYPE: DNA
<213> ORGANISM: Artificial Sequence
<220> FEATURE:
<223> OTHER INFORMATION: Synthetic

<400> SEQUENCE: 62
agttgttaaa tgtttatcgc aga 23

<210> SEQ ID NO 63
<211> LENGTH: 23
<212> TYPE: DNA
<213> ORGANISM: Artificial Sequence
<220> FEATURE:
<223> OTHER INFORMATION: Synthetic

<400> SEQUENCE: 63
aggtaattca tggagaaata gaa 23

<210> SEQ ID NO 64
<211> LENGTH: 25
<212> TYPE: DNA
<213> ORGANISM: Artificial Sequence
<220> FEATURE:
<223> OTHER INFORMATION: Synthetic

<400> SEQUENCE: 64
agaacatgaa gcayctgtgg ttctt 25

<210> SEQ ID NO 65
<211> LENGTH: 21
<212> TYPE: DNA
<213> ORGANISM: Artificial Sequence
<220> FEATURE:
<223> OTHER INFORMATION: Synthetic

<400> SEQUENCE: 65
atggactgga cctggagcat c 21

<210> SEQ ID NO 66
<211> LENGTH: 23
<212> TYPE: DNA
<213> ORGANISM: Artificial Sequence
<220> FEATURE:
<223> OTHER INFORMATION: Synthetic

<400> SEQUENCE: 66
cctctgctga tgaaaaccag ccc 23

<210> SEQ ID NO 67
<211> LENGTH: 20
<212> TYPE: DNA
<213> ORGANISM: Artificial Sequence
<220> FEATURE:
<223> OTHER INFORMATION: Synthetic

<400> SEQUENCE: 67
caggtycagc tkgtgcagtc 20

<210> SEQ ID NO 68
<211> LENGTH: 20

<212> TYPE: DNA
<213> ORGANISM: Artificial Sequence
<220> FEATURE:
<223> OTHER INFORMATION: Synthetic

<400> SEQUENCE: 68
caratgcagc tggtgcagtc 20

<210> SEQ ID NO 69
<211> LENGTH: 24
<212> TYPE: DNA
<213> ORGANISM: Artificial Sequence
<220> FEATURE:
<223> OTHER INFORMATION: Synthetic

<400> SEQUENCE: 69
cagrtcacct tgarggagtc tggt 24

<210> SEQ ID NO 70
<211> LENGTH: 20
<212> TYPE: DNA
<213> ORGANISM: Artificial Sequence
<220> FEATURE:
<223> OTHER INFORMATION: Synthetic

<400> SEQUENCE: 70
gargtgcagc tgktggagtc 20

<210> SEQ ID NO 71
<211> LENGTH: 20
<212> TYPE: DNA
<213> ORGANISM: Artificial Sequence
<220> FEATURE:
<223> OTHER INFORMATION: Synthetic

<400> SEQUENCE: 71
gaggtacaac tggtggagtc 20

<210> SEQ ID NO 72
<211> LENGTH: 20
<212> TYPE: DNA
<213> ORGANISM: Artificial Sequence
<220> FEATURE:
<223> OTHER INFORMATION: Synthetic

<400> SEQUENCE: 72
gaggatcagc tggtggagtc 20

<210> SEQ ID NO 73
<211> LENGTH: 20
<212> TYPE: DNA
<213> ORGANISM: Artificial Sequence
<220> FEATURE:
<223> OTHER INFORMATION: Synthetic

<400> SEQUENCE: 73
caggtgcagc tacagcagtg 20

<210> SEQ ID NO 74
<211> LENGTH: 20
<212> TYPE: DNA
<213> ORGANISM: Artificial Sequence
<220> FEATURE:
<223> OTHER INFORMATION: Synthetic

<400> SEQUENCE: 74

```
cagctgcagc tgcaggagtc                                                  20


<210> SEQ ID NO 75
<211> LENGTH: 20
<212> TYPE: DNA
<213> ORGANISM: Artificial Sequence
<220> FEATURE:
<223> OTHER INFORMATION: Synthetic

<400> SEQUENCE: 75

caggtgcagc tggtgcaatc                                                  20


<210> SEQ ID NO 76
<211> LENGTH: 351
<212> TYPE: DNA
<213> ORGANISM: Artificial Sequence
<220> FEATURE:
<223> OTHER INFORMATION: Synthetic

<400> SEQUENCE: 76

caggtgcagc tgcaggagtc gggcccagga ctggtggagc cttcggggac cctgtccctc      60

acctgcactg tgtctggtgg ctccatcagc aggagtaact ggtggagttg ggtccgccag     120

cccccagggg aggggctgga atggattgga gaaatccatc acattgggag gtccagctac     180

aatccgtccc tcaagagtcg agtcaccatg tctgtagaca agtcccagaa ccagttctcc     240

ctgaggctga cctctgtgac cgccgcggac acggccgtgt attactgtgc gaaaaatggc     300

tactacgcta tggacgtctg gggccaaggg accacggtca ccgtctcctc g              351


<210> SEQ ID NO 77
<211> LENGTH: 117
<212> TYPE: PRT
<213> ORGANISM: Artificial Sequence
<220> FEATURE:
<223> OTHER INFORMATION: Synthetic

<400> SEQUENCE: 77

Gln Val Gln Leu Gln Glu Ser Gly Pro Gly Leu Val Glu Pro Ser Gly
1               5                   10                  15

Thr Leu Ser Leu Thr Cys Thr Val Ser Gly Gly Ser Ile Ser Arg Ser
            20                  25                  30

Asn Trp Trp Ser Trp Val Arg Gln Pro Pro Gly Glu Gly Leu Glu Trp
        35                  40                  45

Ile Gly Glu Ile His His Ile Gly Arg Ser Ser Tyr Asn Pro Ser Leu
    50                  55                  60

Lys Ser Arg Val Thr Met Ser Val Asp Lys Ser Gln Asn Gln Phe Ser
65                  70                  75                  80

Leu Arg Leu Thr Ser Val Thr Ala Ala Asp Thr Ala Val Tyr Tyr Cys
                85                  90                  95

Ala Lys Asn Gly Tyr Tyr Ala Met Asp Val Trp Gly Gln Gly Thr Thr
            100                 105                 110

Val Thr Val Ser Ser
        115


<210> SEQ ID NO 78
<211> LENGTH: 353
<212> TYPE: DNA
<213> ORGANISM: Artificial Sequence
<220> FEATURE:
<223> OTHER INFORMATION: Synthetic

<400> SEQUENCE: 78
```

```
gaaattgtgt tgacgcagtc tccaggcacc ctgtctttgt ctccagggga aagagccacc      60

ctctcctgca gggccagtca gagtgttagc agcgacttcc tagcctggta ccagcagaaa     120

cctggccagg ctcccaggct cctcatctag ctacatcctt cagggccact ggcatctcag     180

acaggttcag tggcagtggg tctgggacag acttctctct caccatcaac agactggaac     240

ctgaagattt tgcagtgtat tactgtcagc actatcgtag ttcacctccg tggtacactt     300

ttgcccaggg gaccaagctg gacatgagac gtacggtggc tgcaccatct gtc            353


<210> SEQ ID NO 79
<211> LENGTH: 118
<212> TYPE: PRT
<213> ORGANISM: Artificial Sequence
<220> FEATURE:
<223> OTHER INFORMATION: Synthetic

<400> SEQUENCE: 79

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Asp
            20                  25                  30

Phe Leu Ala Trp Tyr Gln Gln Lys Pro Gly Gln Ala Pro Arg Leu Leu
        35                  40                  45

Ile Tyr Ala Thr Ser Phe Arg Ala Thr Gly Ile Ser Asp Arg Phe Ser
    50                  55                  60

Gly Ser Gly Ser Gly Thr Asp Phe Ser Leu Thr Ile Asn Arg Leu Glu
65                  70                  75                  80

Pro Glu Asp Phe Ala Val Tyr Tyr Cys Gln His Tyr Arg Ser Ser Pro
                85                  90                  95

Pro Trp Tyr Thr Phe Ala Gln Gly Thr Lys Leu Asp Met Arg Arg Thr
            100                 105                 110

Val Ala Ala Pro Ser Val
        115


<210> SEQ ID NO 80
<211> LENGTH: 25
<212> TYPE: PRT
<213> ORGANISM: Artificial Sequence
<220> FEATURE:
<223> OTHER INFORMATION: Synthetic

<400> SEQUENCE: 80

Gln Val Gln Leu Gln Glu Ser Gly Pro Gly Leu Val Glu Pro Ser Gly
1               5                   10                  15

Thr Leu Ser Leu Thr Cys Thr Val Ser
            20                  25


<210> SEQ ID NO 81
<211> LENGTH: 9
<212> TYPE: PRT
<213> ORGANISM: Artificial Sequence
<220> FEATURE:
<223> OTHER INFORMATION: Synthetic

<400> SEQUENCE: 81

Gly Gly Ser Ile Ser Arg Ser Asn Trp
1               5


<210> SEQ ID NO 82
<211> LENGTH: 17
```

<212> TYPE: PRT
<213> ORGANISM: Artificial Sequence
<220> FEATURE:
<223> OTHER INFORMATION: Synthetic

<400> SEQUENCE: 82

Trp Ser Trp Val Arg Gln Pro Pro Gly Glu Gly Leu Glu Trp Ile Gly
1 5 10 15

Glu

<210> SEQ ID NO 83
<211> LENGTH: 10
<212> TYPE: PRT
<213> ORGANISM: Artificial Sequence
<220> FEATURE:
<223> OTHER INFORMATION: Synthetic

<400> SEQUENCE: 83

Gly Gln Gly Thr Thr Val Thr Val Ser Ser
1 5 10

<210> SEQ ID NO 84
<211> LENGTH: 7
<212> TYPE: PRT
<213> ORGANISM: Artificial Sequence
<220> FEATURE:
<223> OTHER INFORMATION: Synthetic

<400> SEQUENCE: 84

Ile His His Ile Gly Arg Ser
1 5

<210> SEQ ID NO 85
<211> LENGTH: 37
<212> TYPE: PRT
<213> ORGANISM: Artificial Sequence
<220> FEATURE:
<223> OTHER INFORMATION: Synthetic

<400> SEQUENCE: 85

Ser Tyr Asn Pro Ser Leu Lys Ser Arg Val Thr Met Ser Val Asp Lys
1 5 10 15

Ser Gln Asn Gln Phe Ser Leu Arg Leu Thr Ser Val Thr Ala Ala Asp
20 25 30

Thr Ala Val Tyr Tyr
35

<210> SEQ ID NO 86
<211> LENGTH: 12
<212> TYPE: PRT
<213> ORGANISM: Artificial Sequence
<220> FEATURE:
<223> OTHER INFORMATION: Synthetic

<400> SEQUENCE: 86

Cys Ala Lys Asn Gly Tyr Tyr Ala Met Asp Val Trp
1 5 10

<210> SEQ ID NO 87
<211> LENGTH: 26
<212> TYPE: PRT
<213> ORGANISM: Artificial Sequence
<220> FEATURE:
<223> OTHER INFORMATION: Synthetic

<400> SEQUENCE: 87

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser
            20                  25


<210> SEQ ID NO 88
<211> LENGTH: 7
<212> TYPE: PRT
<213> ORGANISM: Artificial Sequence
<220> FEATURE:
<223> OTHER INFORMATION: Synthetic

<400> SEQUENCE: 88

Gln Ser Val Ser Ser Asp Phe
1               5


<210> SEQ ID NO 89
<211> LENGTH: 17
<212> TYPE: PRT
<213> ORGANISM: Artificial Sequence
<220> FEATURE:
<223> OTHER INFORMATION: Synthetic

<400> SEQUENCE: 89

Leu Ala Trp Tyr Gln Gln Lys Pro Gly Gln Ala Pro Arg Leu Leu Ile
1               5                   10                  15

Tyr


<210> SEQ ID NO 90
<211> LENGTH: 3
<212> TYPE: PRT
<213> ORGANISM: Artificial Sequence
<220> FEATURE:
<223> OTHER INFORMATION: Synthetic

<400> SEQUENCE: 90

Ala Thr Ser
1


<210> SEQ ID NO 91
<211> LENGTH: 35
<212> TYPE: PRT
<213> ORGANISM: Artificial Sequence
<220> FEATURE:
<223> OTHER INFORMATION: Synthetic

<400> SEQUENCE: 91

Phe Arg Ala Thr Gly Ile Ser Asp Arg Phe Ser Gly Ser Gly Ser Gly
1               5                   10                  15

Thr Asp Phe Ser Leu Thr Ile Asn Arg Leu Glu Pro Glu Asp Phe Ala
            20                  25                  30

Val Tyr Tyr
        35


<210> SEQ ID NO 92
<211> LENGTH: 13
<212> TYPE: PRT
<213> ORGANISM: Artificial Sequence
<220> FEATURE:
<223> OTHER INFORMATION: Synthetic

<400> SEQUENCE: 92

Cys Gln His Tyr Arg Ser Ser Pro Pro Trp Tyr Thr Phe
1               5                   10
```

<210> SEQ ID NO 93
<211> LENGTH: 17
<212> TYPE: PRT
<213> ORGANISM: Artificial Sequence
<220> FEATURE:
<223> OTHER INFORMATION: Synthetic

<400> SEQUENCE: 93

Ala Gln Gly Thr Lys Leu Asp Met Arg Arg Thr Val Ala Ala Pro Ser
1 5 10 15

Val

<210> SEQ ID NO 94
<211> LENGTH: 37
<212> TYPE: PRT
<213> ORGANISM: Artificial Sequence
<220> FEATURE:
<223> OTHER INFORMATION: Synthetic

<400> SEQUENCE: 94

Asn Ser Asn Pro Ser Leu Lys Ser Arg Val Ile Ile Ser Val Asp Lys
1 5 10 15

Ser Lys Asn His Phe Ser Leu Thr Leu Asn Ser Val Thr Ala Ala Asp
20 25 30

Thr Ala Val Tyr Tyr
35

<210> SEQ ID NO 95
<211> LENGTH: 351
<212> TYPE: DNA
<213> ORGANISM: Artificial Sequence
<220> FEATURE:
<223> OTHER INFORMATION: Synthetic

<400> SEQUENCE: 95
caggtgcagc tgcaggagtc gggcccagga ctggtgaagc cttcggggac cctgtccctc 60
acctgcgctg tctctggtgc ctccattacc aatggtgcct ggtggagttg ggtccgccag 120
cccccaggga aggggctgga gtggattgga gaaatctatc ttaatgggaa caccaactcc 180
aacccgtccc tgaagagtcg agtcatcata tcagtggaca agtccaagaa ccacttctcg 240
ctgaccctga actctgtgac cgccgcggac acggccgtgt attactgtgc gaagaacgct 300
gcctacaacc ttgagttctg gggccaggga gccctggtca ccgtctcctc a 351

<210> SEQ ID NO 96
<211> LENGTH: 117
<212> TYPE: PRT
<213> ORGANISM: Artificial Sequence
<220> FEATURE:
<223> OTHER INFORMATION: Synthetic

<400> SEQUENCE: 96

Gln Val Gln Leu Gln Glu Ser Gly Pro Gly Leu Val Lys Pro Ser Gly
1 5 10 15

Thr Leu Ser Leu Thr Cys Ala Val Ser Gly Ala Ser Ile Thr Asn Gly
20 25 30

Ala Trp Trp Ser Trp Val Arg Gln Pro Pro Gly Lys Gly Leu Glu Trp
35 40 45

Ile Gly Glu Ile Tyr Leu Asn Gly Asn Thr Asn Ser Asn Pro Ser Leu
50 55 60

-continued

```
Lys Ser Arg Val Ile Ile Ser Val Asp Lys Ser Lys Asn His Phe Ser
65                  70                  75                  80

Leu Thr Leu Asn Ser Val Thr Ala Ala Asp Thr Ala Val Tyr Tyr Cys
                85                  90                  95

Ala Lys Asn Ala Ala Tyr Asn Leu Glu Phe Trp Gly Gln Gly Ala Leu
            100                 105                 110

Val Thr Val Ser Ser
        115


<210> SEQ ID NO 97
<211> LENGTH: 327
<212> TYPE: DNA
<213> ORGANISM: Artificial Sequence
<220> FEATURE:
<223> OTHER INFORMATION: Synthetic

<400> SEQUENCE: 97

gaaattgtgt tgacgcagtc tccaggcacc ctgtctttgt ctccagggga aagagccacc      60

ctctcctgca gggccagtca gactgttagc agcccctacg tagcctggta ccagcagaaa     120

cgtggccagg ctcccaggct cctcatctat ggtgcatcca ccagggccac cggcatccca     180

gacaggttca gtggcagtgg gtctgggaca gacttcactc tcaccatcag cagactggag     240

cctgaagatt ttgcagtgta ttactgtcag cagtatgata gatcatacta ttacactttt     300

ggccagggga ccaagctgga gatcaaa                                         327


<210> SEQ ID NO 98
<211> LENGTH: 109
<212> TYPE: PRT
<213> ORGANISM: Artificial Sequence
<220> FEATURE:
<223> OTHER INFORMATION: Synthetic

<400> SEQUENCE: 98

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Thr Val Ser Ser Pro
            20                  25                  30

Tyr Val Ala Trp Tyr Gln Gln Lys Arg Gly Gln Ala Pro Arg Leu Leu
        35                  40                  45

Ile Tyr Gly Ala Ser Thr Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Asp Arg Ser Tyr
                85                  90                  95

Tyr Tyr Thr Phe Gly Gln Gly Thr Lys Leu Glu Ile Lys
            100                 105


<210> SEQ ID NO 99
<211> LENGTH: 25
<212> TYPE: PRT
<213> ORGANISM: Artificial Sequence
<220> FEATURE:
<223> OTHER INFORMATION: Synthetic

<400> SEQUENCE: 99

Gln Val Gln Leu Gln Glu Ser Gly Pro Gly Leu Val Lys Pro Ser Gly
1               5                   10                  15

Thr Leu Ser Leu Thr Cys Ala Val Ser
```

20 25

<210> SEQ ID NO 100
<211> LENGTH: 9
<212> TYPE: PRT
<213> ORGANISM: Artificial Sequence
<220> FEATURE:
<223> OTHER INFORMATION: Synthetic

<400> SEQUENCE: 100

Gly Ala Ser Ile Thr Asn Gly Ala Trp
1 5

<210> SEQ ID NO 101
<211> LENGTH: 17
<212> TYPE: PRT
<213> ORGANISM: Artificial Sequence
<220> FEATURE:
<223> OTHER INFORMATION: Synthetic

<400> SEQUENCE: 101

Trp Ser Trp Val Arg Gln Pro Pro Gly Lys Gly Leu Glu Trp Ile Gly
1 5 10 15

Glu

<210> SEQ ID NO 102
<211> LENGTH: 7
<212> TYPE: PRT
<213> ORGANISM: Artificial Sequence
<220> FEATURE:
<223> OTHER INFORMATION: Synthetic

<400> SEQUENCE: 102

Ile Tyr Leu Asn Gly Asn Thr
1 5

<210> SEQ ID NO 103
<211> LENGTH: 12
<212> TYPE: PRT
<213> ORGANISM: Artificial Sequence
<220> FEATURE:
<223> OTHER INFORMATION: Synthetic

<400> SEQUENCE: 103

Cys Ala Lys Asn Ala Ala Tyr Asn Leu Glu Phe Trp
1 5 10

<210> SEQ ID NO 104
<211> LENGTH: 10
<212> TYPE: PRT
<213> ORGANISM: Artificial Sequence
<220> FEATURE:
<223> OTHER INFORMATION: Synthetic

<400> SEQUENCE: 104

Gly Gln Gly Ala Leu Val Thr Val Ser Ser
1 5 10

<210> SEQ ID NO 105
<211> LENGTH: 26
<212> TYPE: PRT
<213> ORGANISM: Artificial Sequence
<220> FEATURE:
<223> OTHER INFORMATION: Synthetic

<400> SEQUENCE: 105

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser
            20                  25


<210> SEQ ID NO 106
<211> LENGTH: 7
<212> TYPE: PRT
<213> ORGANISM: Artificial Sequence
<220> FEATURE:
<223> OTHER INFORMATION: Synthetic

<400> SEQUENCE: 106

Gln Thr Val Ser Ser Pro Tyr
1               5


<210> SEQ ID NO 107
<211> LENGTH: 17
<212> TYPE: PRT
<213> ORGANISM: Artificial Sequence
<220> FEATURE:
<223> OTHER INFORMATION: Synthetic

<400> SEQUENCE: 107

Val Ala Trp Tyr Gln Gln Lys Arg Gly Gln Ala Pro Arg Leu Leu Ile
1               5                   10                  15

Tyr


<210> SEQ ID NO 108
<211> LENGTH: 3
<212> TYPE: PRT
<213> ORGANISM: Artificial Sequence
<220> FEATURE:
<223> OTHER INFORMATION: Synthetic

<400> SEQUENCE: 108

Gly Ala Ser
1


<210> SEQ ID NO 109
<211> LENGTH: 35
<212> TYPE: PRT
<213> ORGANISM: Artificial Sequence
<220> FEATURE:
<223> OTHER INFORMATION: Synthetic

<400> SEQUENCE: 109

Thr Arg Ala Thr Gly Ile Pro Asp Arg Phe Ser Gly Ser Gly Ser Gly
1               5                   10                  15

Thr Asp Phe Thr Leu Thr Ile Ser Arg Leu Glu Pro Glu Asp Phe Ala
            20                  25                  30

Val Tyr Tyr
        35


<210> SEQ ID NO 110
<211> LENGTH: 12
<212> TYPE: PRT
<213> ORGANISM: Artificial Sequence
<220> FEATURE:
<223> OTHER INFORMATION: Synthetic

<400> SEQUENCE: 110

Cys Gln Gln Tyr Asp Arg Ser Tyr Tyr Tyr Thr Phe
1               5                   10
```

<210> SEQ ID NO 111
<211> LENGTH: 9
<212> TYPE: PRT
<213> ORGANISM: Artificial Sequence
<220> FEATURE:
<223> OTHER INFORMATION: Synthetic

<400> SEQUENCE: 111

Gly Gln Gly Thr Lys Leu Glu Ile Lys
1 5

<210> SEQ ID NO 112
<211> LENGTH: 360
<212> TYPE: DNA
<213> ORGANISM: Artificial Sequence
<220> FEATURE:
<223> OTHER INFORMATION: Synthetic

<400> SEQUENCE: 112
caggtgcagc tgcaggagtc gggcccagga ctggtgaagc cttcggagaa cctgtcgctc 60
acctgcactg tctctgatgc ctccatgagt gattatcact ggagctggat ccggcaggcc 120
gccgggaagg gactggagtg gattgggcgt atgtacagca ctgggagtcc ctactacaaa 180
ccctccctca aaggtcgggt caccatgtca atagacacgt ccaagaacca gttctccctg 240
aagctggcct ctgtgaccgc cgcagacacg gccatctatt attgtgcgag cggacaacat 300
attggtggct gggtcccccc tgacttctgg ggccagggaa ccctggtcac cgtctcctca 360

<210> SEQ ID NO 113
<211> LENGTH: 120
<212> TYPE: PRT
<213> ORGANISM: Artificial Sequence
<220> FEATURE:
<223> OTHER INFORMATION: Synthetic

<400> SEQUENCE: 113

Gln Val Gln Leu Gln Glu Ser Gly Pro Gly Leu Val Lys Pro Ser Glu
1 5 10 15

Asn Leu Ser Leu Thr Cys Thr Val Ser Asp Ala Ser Met Ser Asp Tyr
20 25 30

His Trp Ser Trp Ile Arg Gln Ala Ala Gly Lys Gly Leu Glu Trp Ile
35 40 45

Gly Arg Met Tyr Ser Thr Gly Ser Pro Tyr Tyr Lys Pro Ser Leu Lys
50 55 60

Gly Arg Val Thr Met Ser Ile Asp Thr Ser Lys Asn Gln Phe Ser Leu
65 70 75 80

Lys Leu Ala Ser Val Thr Ala Ala Asp Thr Ala Ile Tyr Tyr Cys Ala
85 90 95

Ser Gly Gln His Ile Gly Gly Trp Val Pro Pro Asp Phe Trp Gly Gln
100 105 110

Gly Thr Leu Val Thr Val Ser Ser
115 120

<210> SEQ ID NO 114
<211> LENGTH: 339
<212> TYPE: DNA
<213> ORGANISM: Artificial Sequence
<220> FEATURE:
<223> OTHER INFORMATION: Synthetic

<400> SEQUENCE: 114

-continued

```
gatattgtga tgacccagac tccactctcc tcacctgtca cccttggaca gccggcctcc     60

atctcctgca ggtctagtga aggcctcgta tatagtgatg gagacaccta cttgagttgg    120

tttcaccaga ggccaggcca gcctccaaga ctcctgattt ataaaatttc taaccggttc    180

tctggggtcc ccgacagatt cagtggcagt ggggcaggca cagatttcac actgaaaatc    240

agcagggtgg aggctgagga tgtcggggtt tattactgca tgcaagctac acattttccg    300

tggacgttcg gccaggggac caaagtggaa gtcaaacgt                           339


<210> SEQ ID NO 115
<211> LENGTH: 113
<212> TYPE: PRT
<213> ORGANISM: Artificial Sequence
<220> FEATURE:
<223> OTHER INFORMATION: Synthetic

<400> SEQUENCE: 115

Asp Ile Val Met Thr Gln Thr Pro Leu Ser Ser Pro Val Thr Leu Gly
1               5                   10                  15

Gln Pro Ala Ser Ile Ser Cys Arg Ser Ser Glu Gly Leu Val Tyr Ser
            20                  25                  30

Asp Gly Asp Thr Tyr Leu Ser Trp Phe His Gln Arg Pro Gly Gln Pro
        35                  40                  45

Pro Arg Leu Leu Ile Tyr Lys Ile Ser Asn Arg Phe Ser Gly Val Pro
    50                  55                  60

Asp Arg Phe Ser Gly Ser Gly Ala Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Thr His Phe Pro Trp Thr Phe Gly Gln Gly Thr Lys Val Glu Val Lys
            100                 105                 110

Arg


<210> SEQ ID NO 116
<211> LENGTH: 25
<212> TYPE: PRT
<213> ORGANISM: Artificial Sequence
<220> FEATURE:
<223> OTHER INFORMATION: Synthetic

<400> SEQUENCE: 116

Gln Val Gln Leu Gln Glu Ser Gly Pro Gly Leu Val Lys Pro Ser Glu
1               5                   10                  15

Asn Leu Ser Leu Thr Cys Thr Val Ser
            20                  25


<210> SEQ ID NO 117
<211> LENGTH: 8
<212> TYPE: PRT
<213> ORGANISM: Artificial Sequence
<220> FEATURE:
<223> OTHER INFORMATION: Synthetic

<400> SEQUENCE: 117

Asp Ala Ser Met Ser Asp Tyr His
1               5


<210> SEQ ID NO 118
<211> LENGTH: 17
<212> TYPE: PRT
<213> ORGANISM: Artificial Sequence
```

<220> FEATURE:
<223> OTHER INFORMATION: Synthetic

<400> SEQUENCE: 118

Trp Ser Trp Ile Arg Gln Ala Ala Gly Lys Gly Leu Glu Trp Ile Gly
1 5 10 15

Arg

<210> SEQ ID NO 119
<211> LENGTH: 7
<212> TYPE: PRT
<213> ORGANISM: Artificial Sequence
<220> FEATURE:
<223> OTHER INFORMATION: Synthetic

<400> SEQUENCE: 119

Met Tyr Ser Thr Gly Ser Pro
1 5

<210> SEQ ID NO 120
<211> LENGTH: 37
<212> TYPE: PRT
<213> ORGANISM: Artificial Sequence
<220> FEATURE:
<223> OTHER INFORMATION: Synthetic

<400> SEQUENCE: 120

Tyr Tyr Lys Pro Ser Leu Lys Gly Arg Val Thr Met Ser Ile Asp Thr
1 5 10 15

Ser Lys Asn Gln Phe Ser Leu Lys Leu Ala Ser Val Thr Ala Ala Asp
20 25 30

Thr Ala Ile Tyr Tyr
35

<210> SEQ ID NO 121
<211> LENGTH: 16
<212> TYPE: PRT
<213> ORGANISM: Artificial Sequence
<220> FEATURE:
<223> OTHER INFORMATION: Synthetic

<400> SEQUENCE: 121

Cys Ala Ser Gly Gln His Ile Gly Gly Trp Val Pro Pro Asp Phe Trp
1 5 10 15

<210> SEQ ID NO 122
<211> LENGTH: 10
<212> TYPE: PRT
<213> ORGANISM: Artificial Sequence
<220> FEATURE:
<223> OTHER INFORMATION: Synthetic

<400> SEQUENCE: 122

Gly Gln Gly Thr Leu Val Thr Val Ser Ser
1 5 10

<210> SEQ ID NO 123
<211> LENGTH: 26
<212> TYPE: PRT
<213> ORGANISM: Artificial Sequence
<220> FEATURE:
<223> OTHER INFORMATION: Synthetic

<400> SEQUENCE: 123

Asp Ile Val Met Thr Gln Thr Pro Leu Ser Ser Pro Val Thr Leu Gly

```
1               5                   10                  15

Gln Pro Ala Ser Ile Ser Cys Arg Ser Ser
            20                  25


<210> SEQ ID NO 124
<211> LENGTH: 11
<212> TYPE: PRT
<213> ORGANISM: Artificial Sequence
<220> FEATURE:
<223> OTHER INFORMATION: Synthetic

<400> SEQUENCE: 124

Glu Gly Leu Val Tyr Ser Asp Gly Asp Thr Tyr
1               5                   10


<210> SEQ ID NO 125
<211> LENGTH: 17
<212> TYPE: PRT
<213> ORGANISM: Artificial Sequence
<220> FEATURE:
<223> OTHER INFORMATION: Synthetic

<400> SEQUENCE: 125

Leu Ser Trp Phe His Gln Arg Pro Gly Gln Pro Pro Arg Leu Leu Ile
1               5                   10                  15

Tyr


<210> SEQ ID NO 126
<211> LENGTH: 3
<212> TYPE: PRT
<213> ORGANISM: Artificial Sequence
<220> FEATURE:
<223> OTHER INFORMATION: Synthetic

<400> SEQUENCE: 126

Lys Ile Ser
1


<210> SEQ ID NO 127
<211> LENGTH: 35
<212> TYPE: PRT
<213> ORGANISM: Artificial Sequence
<220> FEATURE:
<223> OTHER INFORMATION: Synthetic

<400> SEQUENCE: 127

Asn Arg Phe Ser Gly Val Pro Asp Arg Phe Ser Gly Ser Gly Ala Gly
1               5                   10                  15

Thr Asp Phe Thr Leu Lys Ile Ser Arg Val Glu Ala Glu Asp Val Gly
            20                  25                  30

Val Tyr Tyr
        35


<210> SEQ ID NO 128
<211> LENGTH: 11
<212> TYPE: PRT
<213> ORGANISM: Artificial Sequence
<220> FEATURE:
<223> OTHER INFORMATION: Synthetic

<400> SEQUENCE: 128

Cys Met Gln Ala Thr His Phe Pro Trp Thr Phe
1               5                   10
```

-continued

<210> SEQ ID NO 129
<211> LENGTH: 10
<212> TYPE: PRT
<213> ORGANISM: Artificial Sequence
<220> FEATURE:
<223> OTHER INFORMATION: Synthetic

<400> SEQUENCE: 129

Gly Gln Gly Thr Lys Val Glu Val Lys Arg
1 5 10

<210> SEQ ID NO 130
<211> LENGTH: 333
<212> TYPE: DNA
<213> ORGANISM: Artificial Sequence
<220> FEATURE:
<223> OTHER INFORMATION: Synthetic

<400> SEQUENCE: 130
gaggtgcagc tgttggagtc tgggggaggc ttggtacagc ctggggggtc cctgagactc 60
tcctgtgcag cctctggatt cacctttagt tcatatggct tgacctggat acgccaggct 120
ccggggaagg gcctggagtg ggtctcaagt atcagtggca gtggcaataa cacatactac 180
gcagactctg tgaagggccg gttcaccatc tccagagaca aagtcaagaa gacactatat 240
ctacaaatgg acagcctgac agtcggagac acggccgtct attactgctt aggagtcggt 300
cagggccacg gaattccggt catcgtctcc tca 333

<210> SEQ ID NO 131
<211> LENGTH: 111
<212> TYPE: PRT
<213> ORGANISM: Artificial Sequence
<220> FEATURE:
<223> OTHER INFORMATION: Synthetic

<400> SEQUENCE: 131

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Gly Leu Thr Trp Ile Arg Gln Ala Pro Gly Lys Gly Leu Glu Trp Val
35 40 45

Ser Ser Ile Ser Gly Ser Gly Asn Asn Thr Tyr Tyr Ala Asp Ser Val
50 55 60

Lys Gly Arg Phe Thr Ile Ser Arg Asp Lys Val Lys Lys Thr Leu Tyr
65 70 75 80

Leu Gln Met Asp Ser Leu Thr Val Gly Asp Thr Ala Val Tyr Tyr Cys
85 90 95

Leu Gly Val Gly Gln Gly His Gly Ile Pro Val Ile Val Ser Ser
100 105 110

<210> SEQ ID NO 132
<211> LENGTH: 336
<212> TYPE: DNA
<213> ORGANISM: Artificial Sequence
<220> FEATURE:
<223> OTHER INFORMATION: Synthetic

<400> SEQUENCE: 132
gatattgtga tgacccagac tccactctcc tcacctgtca cccttggaca gccggcctcc 60
atctcctgca ggtctagtca gagcctcgta caccgtgatg gaaacaccta cttgagttgg 120

```
tttctgcaga ggccaggcca ggctccaaga ctcctaattt atcggatttc taaccggttc    180

tctggggtcc cagacagatt cagtggcagt ggggcaggga cggatttcac actgaaaatc    240

agcagggtgg aagctgagga tgtcggcgtt tactactgca tgcaagctac acaaatcccc    300

aacacttttg gccaggggac caagctggag atcaag                              336


<210> SEQ ID NO 133
<211> LENGTH: 116
<212> TYPE: PRT
<213> ORGANISM: Artificial Sequence
<220> FEATURE:
<223> OTHER INFORMATION: Synthetic

<400> SEQUENCE: 133

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val His Ser
            20                  25                  30

Asp Gly Asn Thr Tyr Leu Asn Trp Phe His Gln Arg Pro Gly Gln Ser
        35                  40                  45

Pro Arg Arg Leu Ile Tyr Lys Val Ser Lys Arg Asp Ser Gly Val Pro
    50                  55                  60

Asp Arg Phe Ser Gly Ser Gly Ser Gly Ser Asp Phe Thr Leu Lys Ile
65                  70                  75                  80

Ser Arg Val Glu Ala Glu Asp Val Gly Ile Tyr Tyr Cys Met Gln Gly
                85                  90                  95

Thr His Trp Pro Thr Phe Gly Gln Gly Thr Lys Val Glu Ile Lys Arg
            100                 105                 110

Thr Val Ala Ala
        115


<210> SEQ ID NO 134
<211> LENGTH: 25
<212> TYPE: PRT
<213> ORGANISM: Artificial Sequence
<220> FEATURE:
<223> OTHER INFORMATION: Synthetic

<400> SEQUENCE: 134

Glu Val Gln Leu Leu Glu Ser Gly Gly Gly Leu Val Gln Pro Gly Gly
1               5                   10                  15

Ser Leu Arg Leu Ser Cys Ala Ala Ser
            20                  25


<210> SEQ ID NO 135
<211> LENGTH: 8
<212> TYPE: PRT
<213> ORGANISM: Artificial Sequence
<220> FEATURE:
<223> OTHER INFORMATION: Synthetic

<400> SEQUENCE: 135

Gly Phe Thr Phe Ser Ser Tyr Gly
1               5


<210> SEQ ID NO 136
<211> LENGTH: 17
<212> TYPE: PRT
<213> ORGANISM: Artificial Sequence
<220> FEATURE:
<223> OTHER INFORMATION: Synthetic
```

<400> SEQUENCE: 136

Leu Thr Trp Ile Arg Gln Ala Pro Gly Lys Gly Leu Glu Trp Val Ser
1               5                   10                  15

Ser

<210> SEQ ID NO 137
<211> LENGTH: 8
<212> TYPE: PRT
<213> ORGANISM: Artificial Sequence
<220> FEATURE:
<223> OTHER INFORMATION: Synthetic

<400> SEQUENCE: 137

Ile Ser Gly Ser Gly Asn Asn Thr
1               5

<210> SEQ ID NO 138
<211> LENGTH: 37
<212> TYPE: PRT
<213> ORGANISM: Artificial Sequence
<220> FEATURE:
<223> OTHER INFORMATION: Synthetic

<400> SEQUENCE: 138

Tyr Tyr Ala Asp Ser Val Lys Gly Arg Phe Thr Ile Ser Arg Asp Lys
1               5                   10                  15

Val Lys Lys Thr Leu Tyr Leu Gln Met Asp Ser Leu Thr Val Gly Asp
            20                  25                  30

Thr Ala Val Tyr Tyr
        35

<210> SEQ ID NO 139
<211> LENGTH: 6
<212> TYPE: PRT
<213> ORGANISM: Artificial Sequence
<220> FEATURE:
<223> OTHER INFORMATION: Synthetic

<400> SEQUENCE: 139

Cys Leu Gly Val Gly Gln
1               5

<210> SEQ ID NO 140
<211> LENGTH: 10
<212> TYPE: PRT
<213> ORGANISM: Artificial Sequence
<220> FEATURE:
<223> OTHER INFORMATION: Synthetic

<400> SEQUENCE: 140

Gly His Gly Ile Pro Val Ile Val Ser Ser
1               5                   10

<210> SEQ ID NO 141
<211> LENGTH: 26
<212> TYPE: PRT
<213> ORGANISM: Artificial Sequence
<220> FEATURE:
<223> OTHER INFORMATION: Synthetic

<400> SEQUENCE: 141

Asp Ile Val Met Thr Gln Thr Pro Leu Ser Ser Pro Val Thr Leu Gly
1               5                   10                  15

Gln Pro Ala Ser Ile Ser Cys Arg Ser Ser 20 25

<210> SEQ ID NO 142
<211> LENGTH: 11
<212> TYPE: PRT
<213> ORGANISM: Artificial Sequence
<220> FEATURE:
<223> OTHER INFORMATION: Synthetic

<400> SEQUENCE: 142

Gln Ser Leu Val His Arg Asp Gly Asn Thr Tyr
1 5 10

<210> SEQ ID NO 143
<211> LENGTH: 17
<212> TYPE: PRT
<213> ORGANISM: Artificial Sequence
<220> FEATURE:
<223> OTHER INFORMATION: Synthetic

<400> SEQUENCE: 143

Leu Ser Trp Phe Leu Gln Arg Pro Gly Gln Ala Pro Arg Leu Leu Ile
1 5 10 15

Tyr

<210> SEQ ID NO 144
<211> LENGTH: 3
<212> TYPE: PRT
<213> ORGANISM: Artificial Sequence
<220> FEATURE:
<223> OTHER INFORMATION: Synthetic

<400> SEQUENCE: 144

Arg Ile Ser
1

<210> SEQ ID NO 145
<211> LENGTH: 35
<212> TYPE: PRT
<213> ORGANISM: Artificial Sequence
<220> FEATURE:
<223> OTHER INFORMATION: Synthetic

<400> SEQUENCE: 145

Asn Arg Phe Ser Gly Val Pro Asp Arg Phe Ser Gly Ser Gly Ala Gly
1 5 10 15

Thr Asp Phe Thr Leu Lys Ile Ser Arg Val Glu Ala Glu Asp Val Gly
20 25 30

Val Tyr Tyr
35

<210> SEQ ID NO 146
<211> LENGTH: 11
<212> TYPE: PRT
<213> ORGANISM: Artificial Sequence
<220> FEATURE:
<223> OTHER INFORMATION: Synthetic

<400> SEQUENCE: 146

Cys Met Gln Ala Thr Gln Ile Pro Asn Thr Phe
1 5 10

<210> SEQ ID NO 147
<211> LENGTH: 9
<212> TYPE: PRT

<213> ORGANISM: Artificial Sequence
<220> FEATURE:
<223> OTHER INFORMATION: Synthetic

<400> SEQUENCE: 147

Gly Gln Gly Thr Lys Leu Glu Ile Lys
1               5

<210> SEQ ID NO 148
<211> LENGTH: 15
<212> TYPE: PRT
<213> ORGANISM: Artificial Sequence
<220> FEATURE:
<223> OTHER INFORMATION: Synthetic

<400> SEQUENCE: 148

Gly Leu Asn Asp Ile Phe Glu Ala Gln Lys Ile Glu Trp His Glu
1               5                   10                  15

<210> SEQ ID NO 149
<211> LENGTH: 381
<212> TYPE: DNA
<213> ORGANISM: Artificial Sequence
<220> FEATURE:
<223> OTHER INFORMATION: Synthetic

<400> SEQUENCE: 149
caggtgcagc tgcaggagtc gggcccagga ctggtgaggc cttcggggac cctgtccctc 60
acttgcgctg tgtctggtgg ctccatcgac tatagtaatt ggtggggttg ggtccgccaa 120
gtcccaggaa aggggctgga gtggattggc gaagtctatc atactggggc cactcattac 180
aacccgtccc tcgagcgtcg atgcatcatt tcagtggaca agtctaataa ccaggtctcc 240
ctccaattga cttctgtgac cgccgcagac tcggccatct attattgtgc gagagagagg 300
ggcacgcatt gtgatggaaa ccgctgttat tatgttttct ttgaccattg gggccaggga 360
atcccggtca ccgtctcctc a 381

<210> SEQ ID NO 150
<211> LENGTH: 127
<212> TYPE: PRT
<213> ORGANISM: Artificial Sequence
<220> FEATURE:
<223> OTHER INFORMATION: Synthetic

<400> SEQUENCE: 150

Gln Val Gln Leu Gln Glu Ser Gly Pro Gly Leu Val Arg Pro Ser Gly
1               5                   10                  15

Thr Leu Ser Leu Thr Cys Ala Val Ser Gly Gly Ser Ile Asp Tyr Ser
            20                  25                  30

Asn Trp Trp Gly Trp Val Arg Gln Val Pro Gly Lys Gly Leu Glu Trp
        35                  40                  45

Ile Gly Glu Val Tyr His Thr Gly Ala Thr His Tyr Asn Pro Ser Leu
    50                  55                  60

Glu Arg Arg Cys Ile Ile Ser Val Asp Lys Ser Asn Asn Gln Val Ser
65                  70                  75                  80

Leu Gln Leu Thr Ser Val Thr Ala Ala Asp Ser Ala Ile Tyr Tyr Cys
                85                  90                  95

Ala Arg Glu Arg Gly Thr His Cys Asp Gly Asn Arg Cys Tyr Tyr Val
            100                 105                 110

Phe Phe Asp His Trp Gly Gln Gly Ile Pro Val Thr Val Ser Ser
        115                 120                 125

<210> SEQ ID NO 151
<211> LENGTH: 341
<212> TYPE: DNA
<213> ORGANISM: Artificial Sequence
<220> FEATURE:
<223> OTHER INFORMATION: Synthetic

<400> SEQUENCE: 151
gatattgtga tgacccagac tccactgtcc tcacctgtca cccttggaca accggcctcc 60
atctcctgca ggtctagtga aagcctcgta cattgggatg gaaccacgta cttgagttgg 120
tttcaccaga ggccaggcca gcctccaaga ctcctaattt ataaggtttc taaccgcttc 180
tctggggtcc cagacagatt cagtggcagt ggggcaggga cagatttcac actgaaaatc 240
agcagggtgg aagctgacga tgtcggcatt tattattgca tgcaagctac acagtttcct 300
cggacgttcg gccaagggac gaaggtggaa atcaaacgta c 341

<210> SEQ ID NO 152
<211> LENGTH: 113
<212> TYPE: PRT
<213> ORGANISM: Artificial Sequence
<220> FEATURE:
<223> OTHER INFORMATION: Synthetic

<400> SEQUENCE: 152

Asp Ile Val Met Thr Gln Thr Pro Leu Ser Ser Pro Val Thr Leu Gly
1 5 10 15

Gln Pro Ala Ser Ile Ser Cys Arg Ser Ser Glu Ser Leu Val His Trp
20 25 30

Asp Gly Thr Thr Tyr Leu Ser Trp Phe His Gln Arg Pro Gly Gln Pro
35 40 45

Pro Arg Leu Leu Ile Tyr Lys Val Ser Asn Arg Phe Ser Gly Val Pro
50 55 60

Asp Arg Phe Ser Gly Ser Gly Ala Gly Thr Asp Phe Thr Leu Lys Ile
65 70 75 80

Ser Arg Val Glu Ala Asp Asp Val Gly Ile Tyr Tyr Cys Met Gln Ala
85 90 95

Thr Gln Phe Pro Arg Thr Phe Gly Gln Gly Thr Lys Val Glu Ile Lys
100 105 110

Arg

<210> SEQ ID NO 153
<211> LENGTH: 24
<212> TYPE: PRT
<213> ORGANISM: Artificial Sequence
<220> FEATURE:
<223> OTHER INFORMATION: Synthetic

<400> SEQUENCE: 153

Gln Val Gln Leu Gln Glu Ser Gly Pro Gly Leu Val Arg Pro Ser Gly
1 5 10 15

Thr Leu Ser Leu Thr Cys Ala Val
20

<210> SEQ ID NO 154
<211> LENGTH: 10
<212> TYPE: PRT
<213> ORGANISM: Artificial Sequence
<220> FEATURE:
<223> OTHER INFORMATION: Synthetic

<400> SEQUENCE: 154

Ser Gly Gly Ser Ile Asp Tyr Ser Asn Trp
1 5 10

<210> SEQ ID NO 155
<211> LENGTH: 16
<212> TYPE: PRT
<213> ORGANISM: Artificial Sequence
<220> FEATURE:
<223> OTHER INFORMATION: Synthetic

<400> SEQUENCE: 155

Trp Gly Trp Val Arg Gln Val Pro Gly Lys Gly Leu Glu Trp Ile Gly
1 5 10 15

<210> SEQ ID NO 156
<211> LENGTH: 8
<212> TYPE: PRT
<213> ORGANISM: Artificial Sequence
<220> FEATURE:
<223> OTHER INFORMATION: Synthetic

<400> SEQUENCE: 156

Glu Val Tyr His Thr Gly Ala Thr
1 5

<210> SEQ ID NO 157
<211> LENGTH: 37
<212> TYPE: PRT
<213> ORGANISM: Artificial Sequence
<220> FEATURE:
<223> OTHER INFORMATION: Synthetic

<400> SEQUENCE: 157

His Tyr Asn Pro Ser Leu Glu Arg Arg Cys Ile Ile Ser Val Asp Lys
1 5 10 15

Ser Asn Asn Gln Val Ser Leu Gln Leu Thr Ser Val Thr Ala Ala Asp
20 25 30

Ser Ala Ile Tyr Tyr
35

<210> SEQ ID NO 158
<211> LENGTH: 22
<212> TYPE: PRT
<213> ORGANISM: Artificial Sequence
<220> FEATURE:
<223> OTHER INFORMATION: Synthetic

<400> SEQUENCE: 158

Cys Ala Arg Glu Arg Gly Thr His Cys Asp Gly Asn Arg Cys Tyr Tyr
1 5 10 15

Val Phe Phe Asp His Trp
20

<210> SEQ ID NO 159
<211> LENGTH: 10
<212> TYPE: PRT
<213> ORGANISM: Artificial Sequence
<220> FEATURE:
<223> OTHER INFORMATION: Synthetic

<400> SEQUENCE: 159

Gly Gln Gly Ile Pro Val Thr Val Ser Ser
1 5 10

<210> SEQ ID NO 160
<211> LENGTH: 25
<212> TYPE: PRT
<213> ORGANISM: Artificial Sequence
<220> FEATURE:
<223> OTHER INFORMATION: Synthetic

<400> SEQUENCE: 160

Asp Ile Val Met Thr Gln Thr Pro Leu Ser Ser Pro Val Thr Leu Gly
1 5 10 15

Gln Pro Ala Ser Ile Ser Cys Arg Ser
20 25

<210> SEQ ID NO 161
<211> LENGTH: 12
<212> TYPE: PRT
<213> ORGANISM: Artificial Sequence
<220> FEATURE:
<223> OTHER INFORMATION: Synthetic

<400> SEQUENCE: 161

Ser Glu Ser Leu Val His Trp Asp Gly Thr Thr Tyr
1 5 10

<210> SEQ ID NO 162
<211> LENGTH: 17
<212> TYPE: PRT
<213> ORGANISM: Artificial Sequence
<220> FEATURE:
<223> OTHER INFORMATION: Synthetic

<400> SEQUENCE: 162

Leu Ser Trp Phe His Gln Arg Pro Gly Gln Pro Pro Arg Leu Leu Ile
1 5 10 15

Tyr

<210> SEQ ID NO 163
<211> LENGTH: 3
<212> TYPE: PRT
<213> ORGANISM: Artificial Sequence
<220> FEATURE:
<223> OTHER INFORMATION: Synthetic

<400> SEQUENCE: 163

Lys Val Ser
1

<210> SEQ ID NO 164
<211> LENGTH: 35
<212> TYPE: PRT
<213> ORGANISM: Artificial Sequence
<220> FEATURE:
<223> OTHER INFORMATION: Synthetic

<400> SEQUENCE: 164

Asn Arg Phe Ser Gly Val Pro Asp Arg Phe Ser Gly Ser Gly Ala Gly
1 5 10 15

Thr Asp Phe Thr Leu Lys Ile Ser Arg Val Glu Ala Asp Asp Val Gly
20 25 30

Ile Tyr Tyr
35

<210> SEQ ID NO 165

<211> LENGTH: 11
<212> TYPE: PRT
<213> ORGANISM: Artificial Sequence
<220> FEATURE:
<223> OTHER INFORMATION: Synthetic

<400> SEQUENCE: 165

Cys Met Gln Ala Thr Gln Phe Pro Arg Thr Phe
1 5 10

<210> SEQ ID NO 166
<211> LENGTH: 10
<212> TYPE: PRT
<213> ORGANISM: Artificial Sequence
<220> FEATURE:
<223> OTHER INFORMATION: Synthetic

<400> SEQUENCE: 166

Gly Gln Gly Thr Lys Val Glu Ile Lys Arg
1 5 10

<210> SEQ ID NO 167
<211> LENGTH: 360
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (58)..(58)
<223> OTHER INFORMATION: n is a, c, g, or t
<220> FEATURE:
<221> NAME/KEY: misc_feature
<222> LOCATION: (103)..(103)
<223> OTHER INFORMATION: n is a, c, g, or t

<400> SEQUENCE: 167
caggtgcagc tggtgcagtc tggggctgag gtgaagaagc ctgggtcctc ggtgagantc 60
tcctgcaggg cctctggagg ctcctccacc acctatgctt tcnactgggt gcgtcaggcc 120
cctggccaag ggcttgagtg gatgggaggc atcgtcccca tctttggtac attgaaatac 180
gcacagaagt tccaagacag agtcacactt accgcggata agtccacggg cacagcctac 240
atggaactga acagcctgag attagacgac acggccgtct attattgtgc gagagcgata 300
caattggaag gacgcccctt tgaccactgg ggccagggaa cccaggtcac cgtctccgca 360

<210> SEQ ID NO 168
<211> LENGTH: 120
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (20)..(20)
<223> OTHER INFORMATION: Xaa can be any naturally occurring amino acid
<220> FEATURE:
<221> NAME/KEY: misc_feature
<222> LOCATION: (35)..(35)
<223> OTHER INFORMATION: Xaa can be any naturally occurring amino acid

<400> SEQUENCE: 168

Gln Val Gln Leu Val Gln Ser Gly Ala Glu Val Lys Lys Pro Gly Ser
1 5 10 15

Ser Val Arg Xaa Ser Cys Arg Ala Ser Gly Gly Ser Ser Thr Thr Tyr
20 25 30

Ala Phe Xaa Trp Val Arg Gln Ala Pro Gly Gln Gly Leu Glu Trp Met

```
        35                  40                  45

Gly Gly Ile Val Pro Ile Phe Gly Thr Leu Lys Tyr Ala Gln Lys Phe
    50                  55                  60

Gln Asp Arg Val Thr Leu Thr Ala Asp Lys Ser Thr Gly Thr Ala Tyr
65                  70                  75                  80

Met Glu Leu Asn Ser Leu Arg Leu Asp Asp Thr Ala Val Tyr Tyr Cys
                85                  90                  95

Ala Arg Ala Ile Gln Leu Glu Gly Arg Pro Phe Asp His Trp Gly Gln
            100                 105                 110

Gly Thr Gln Val Thr Val Ser Ala
        115                 120


<210> SEQ ID NO 169
<211> LENGTH: 327
<212> TYPE: DNA
<213> ORGANISM: Artificial Sequence
<220> FEATURE:
<223> OTHER INFORMATION: Synthetic

<400> SEQUENCE: 169

gacatccagt tgacccagtc tccatccttc ctgtctgcat ctgttggaga cagagtcacc      60

atcacttgcc gggccagtca gggcattacc agttatttag cctggtatca gcaaaaacca     120

gggaaagccc ctaagctcct gatctatgct gcatccgctt tgcaaagtgg ggtcccatca     180

agattcagcg gccgtggatc tgggacagag ttcactctca caatcagcag cctgcagcct     240

gaagattttg caacttatta ctgtcaacag gtgaataggg gtgccgcgat caccttcggc     300

cacgggacac ggctggacat taaacgt                                         327


<210> SEQ ID NO 170
<211> LENGTH: 109
<212> TYPE: PRT
<213> ORGANISM: Artificial Sequence
<220> FEATURE:
<223> OTHER INFORMATION: Synthetic

<400> SEQUENCE: 170

Asp Ile Gln Leu Thr Gln Ser Pro Ser Phe Leu Ser Ala Ser Val Gly
1               5                   10                  15

Asp Arg Val Thr Ile Thr Cys Arg Ala Ser Gln Gly Ile Thr Ser Tyr
            20                  25                  30

Leu Ala Trp Tyr Gln Gln Lys Pro Gly Lys Ala Pro Lys Leu Leu Ile
        35                  40                  45

Tyr Ala Ala Ser Ala Leu Gln Ser Gly Val Pro Ser Arg Phe Ser Gly
    50                  55                  60

Arg Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Val Asn Arg Gly Ala Ala
                85                  90                  95

Ile Thr Phe Gly His Gly Thr Arg Leu Asp Ile Lys Arg
            100                 105


<210> SEQ ID NO 171
<211> LENGTH: 25
<212> TYPE: PRT
<213> ORGANISM: Artificial Sequence
<220> FEATURE:
<223> OTHER INFORMATION: Synthetic
<220> FEATURE:
<221> NAME/KEY: misc_feature
```

<222> LOCATION: (20)..(20)
<223> OTHER INFORMATION: Xaa can be any naturally occurring amino acid

<400> SEQUENCE: 171

```
Gln Val Gln Leu Val Gln Ser Gly Ala Glu Val Lys Lys Pro Gly Ser
1               5                   10                  15

Ser Val Arg Xaa Ser Cys Arg Ala Ser
            20                  25
```

<210> SEQ ID NO 172
<211> LENGTH: 8
<212> TYPE: PRT
<213> ORGANISM: Artificial Sequence
<220> FEATURE:
<223> OTHER INFORMATION: Synthetic

<400> SEQUENCE: 172

```
Gly Gly Ser Ser Thr Thr Tyr Ala
1               5
```

<210> SEQ ID NO 173
<211> LENGTH: 17
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: Xaa can be any naturally occurring amino acid

<400> SEQUENCE: 173

```
Phe Xaa Trp Val Arg Gln Ala Pro Gly Gln Gly Leu Glu Trp Met Gly
1               5                   10                  15

Gly
```

<210> SEQ ID NO 174
<211> LENGTH: 8
<212> TYPE: PRT
<213> ORGANISM: Artificial Sequence
<220> FEATURE:
<223> OTHER INFORMATION: Synthetic

<400> SEQUENCE: 174

```
Ile Val Pro Ile Phe Gly Thr Leu
1               5
```

<210> SEQ ID NO 175
<211> LENGTH: 37
<212> TYPE: PRT
<213> ORGANISM: Artificial Sequence
<220> FEATURE:
<223> OTHER INFORMATION: Synthetic

<400> SEQUENCE: 175

```
Lys Tyr Ala Gln Lys Phe Gln Asp Arg Val Thr Leu Thr Ala Asp Lys
1               5                   10                  15

Ser Thr Gly Thr Ala Tyr Met Glu Leu Asn Ser Leu Arg Leu Asp Asp
            20                  25                  30

Thr Ala Val Tyr Tyr
        35
```

<210> SEQ ID NO 176
<211> LENGTH: 15
<212> TYPE: PRT

<213> ORGANISM: Artificial Sequence
<220> FEATURE:
<223> OTHER INFORMATION: Synthetic

<400> SEQUENCE: 176

Cys Ala Arg Ala Ile Gln Leu Glu Gly Arg Pro Phe Asp His Trp
1 5 10 15

<210> SEQ ID NO 177
<211> LENGTH: 9
<212> TYPE: PRT
<213> ORGANISM: Artificial Sequence
<220> FEATURE:
<223> OTHER INFORMATION: Synthetic

<400> SEQUENCE: 177

Gly Gln Gly Thr Gln Val Thr Val Ser
1 5

<210> SEQ ID NO 178
<211> LENGTH: 26
<212> TYPE: PRT
<213> ORGANISM: Artificial Sequence
<220> FEATURE:
<223> OTHER INFORMATION: Synthetic

<400> SEQUENCE: 178

Asp Ile Gln Leu Thr Gln Ser Pro Ser Phe Leu Ser Ala Ser Val Gly
1 5 10 15

Asp Arg Val Thr Ile Thr Cys Arg Ala Ser
20 25

<210> SEQ ID NO 179
<211> LENGTH: 6
<212> TYPE: PRT
<213> ORGANISM: Artificial Sequence
<220> FEATURE:
<223> OTHER INFORMATION: Synthetic

<400> SEQUENCE: 179

Gln Gly Ile Thr Ser Tyr
1 5

<210> SEQ ID NO 180
<211> LENGTH: 17
<212> TYPE: PRT
<213> ORGANISM: Artificial Sequence
<220> FEATURE:
<223> OTHER INFORMATION: Synthetic

<400> SEQUENCE: 180

Leu Ala Trp Tyr Gln Gln Lys Pro Gly Lys Ala Pro Lys Leu Leu Ile
1 5 10 15

Tyr

<210> SEQ ID NO 181
<211> LENGTH: 3
<212> TYPE: PRT
<213> ORGANISM: Artificial Sequence
<220> FEATURE:
<223> OTHER INFORMATION: Synthetic

<400> SEQUENCE: 181

Ala Ala Ser
1

<210> SEQ ID NO 182
<211> LENGTH: 35
<212> TYPE: PRT
<213> ORGANISM: Artificial Sequence
<220> FEATURE:
<223> OTHER INFORMATION: Synthetic

<400> SEQUENCE: 182

Ala Leu Gln Ser Gly Val Pro Ser Arg Phe Ser Gly Arg Gly Ser Gly
1 5 10 15

Thr Glu Phe Thr Leu Thr Ile Ser Ser Leu Gln Pro Glu Asp Phe Ala
20 25 30

Thr Tyr Tyr
35

<210> SEQ ID NO 183
<211> LENGTH: 12
<212> TYPE: PRT
<213> ORGANISM: Artificial Sequence
<220> FEATURE:
<223> OTHER INFORMATION: Synthetic

<400> SEQUENCE: 183

Cys Gln Gln Val Asn Arg Gly Ala Ala Ile Thr Phe
1 5 10

<210> SEQ ID NO 184
<211> LENGTH: 10
<212> TYPE: PRT
<213> ORGANISM: Artificial Sequence
<220> FEATURE:
<223> OTHER INFORMATION: Synthetic

<400> SEQUENCE: 184

Gly His Gly Thr Arg Leu Asp Ile Lys Arg
1 5 10

<210> SEQ ID NO 185
<211> LENGTH: 360
<212> TYPE: PRT
<213> ORGANISM: Artificial Sequence
<220> FEATURE:
<223> OTHER INFORMATION: Synthetic

<400> SEQUENCE: 185

His Ser Leu Arg Tyr Asn Leu Thr Val Leu Ser Trp Asp Gly Ser Val
1 5 10 15

Gln Ser Gly Phe Leu Ala Glu Val His Leu Asp Gly Gln Pro Phe Leu
20 25 30

Arg Tyr Asp Arg Gln Lys Cys Arg Ala Lys Pro Gln Gly Gln Trp Ala
35 40 45

Glu Asp Val Leu Gly Asn Lys Thr Trp Asp Arg Glu Thr Arg Asp Leu
50 55 60

Thr Gly Asn Gly Lys Asp Leu Arg Met Thr Leu Ala His Ile Lys Asp
65 70 75 80

Gln Lys Glu Gly Leu His Ser Leu Gln Glu Ile Arg Val Cys Glu Ile
85 90 95

His Glu Asp Asn Ser Thr Arg Ser Ser Gln His Phe Tyr Tyr Asp Gly
100 105 110

Glu Leu Phe Leu Ser Gln Asn Val Glu Thr Glu Glu Trp Thr Val Pro
115 120 125

-continued

Gln Ser Ser Arg Ala Gln Thr Leu Ala Met Asn Val Arg Asn Phe Leu
    130                 135                 140

Lys Glu Asp Ala Met Lys Thr Lys Thr His Tyr His Ala Met His Ala
145                 150                 155                 160

Asp Cys Leu Gln Glu Leu Arg Arg Tyr Leu Glu Ser Ser Val Val Leu
                165                 170                 175

Arg Arg Thr Val Pro Pro Met Val Asn Val Thr Arg Ser Glu Ala Ser
            180                 185                 190

Glu Gly Asn Ile Thr Val Thr Cys Arg Ala Ser Ser Phe Tyr Pro Arg
        195                 200                 205

Asn Ile Thr Leu Thr Trp Arg Gln Asp Gly Val Ser Leu Ser His Asp
    210                 215                 220

Thr Gln Gln Trp Gly Asp Val Leu Pro Asp Gly Asn Gly Thr Tyr Gln
225                 230                 235                 240

Thr Trp Val Ala Thr Arg Ile Cys Gln Gly Glu Glu Gln Arg Phe Thr
                245                 250                 255

Cys Tyr Met Glu His Ser Gly Asn His Ser Thr His Pro Val Pro Ser
            260                 265                 270

Gly Lys Val Leu Val Leu Gln Ser His Trp Gln Thr Phe His Val Ser
        275                 280                 285

Ala Val Ala Ala Ala Ala Ala Ala Ile Phe Val Ile Ile Ile Phe Tyr
    290                 295                 300

Val Arg Cys Cys Lys Lys Lys Thr Ser Ala Ala Glu Gly Pro Glu Leu
305                 310                 315                 320

Val Ser Leu Gln Val Leu Asp Gln His Pro Val Gly Thr Ser Asp His
                325                 330                 335

Arg Asp Ala Thr Gln Leu Gly Phe Gln Pro Leu Met Ser Ala Leu Gly
            340                 345                 350

Ser Thr Gly Ser Thr Glu Gly Ala
        355                 360

<210> SEQ ID NO 186
<211> LENGTH: 20
<212> TYPE: PRT
<213> ORGANISM: Artificial Sequence
<220> FEATURE:
<223> OTHER INFORMATION: Synthetic

<400> SEQUENCE: 186

Gly Asp Val Leu Pro Asp Gly Asn Gly Thr Tyr Gln Thr Trp Val Ala
1               5                   10                  15

Thr Arg Ile Cys
            20

<210> SEQ ID NO 187
<211> LENGTH: 10
<212> TYPE: PRT
<213> ORGANISM: Artificial Sequence
<220> FEATURE:
<223> OTHER INFORMATION: Synthetic

<400> SEQUENCE: 187

Asn Val Glu Thr Glu Glu Trp Thr Val Pro
1               5                   10

<210> SEQ ID NO 188
<211> LENGTH: 10
<212> TYPE: PRT
<213> ORGANISM: Artificial Sequence
<220> FEATURE:
<223> OTHER INFORMATION: Synthetic

<400> SEQUENCE: 188

Thr Val Pro Pro Met Val Asn Val Thr Arg
1               5                   10

<210> SEQ ID NO 189
<211> LENGTH: 10
<212> TYPE: PRT
<213> ORGANISM: Artificial Sequence
<220> FEATURE:
<223> OTHER INFORMATION: Synthetic

<400> SEQUENCE: 189

Thr Cys Arg Ala Ser Ser Phe Tyr Pro Arg
1               5                   10

<210> SEQ ID NO 190
<211> LENGTH: 208
<212> TYPE: PRT
<213> ORGANISM: Artificial Sequence
<220> FEATURE:
<223> OTHER INFORMATION: Synthetic

<400> SEQUENCE: 190

Val Phe Leu Phe Pro Pro Lys Pro Lys Asp Thr Leu Met Ile Ser Arg
1               5                   10                  15

Thr Pro Glu Val Thr Cys Val Val Val Asp Val Ser His Glu Asp Pro
            20                  25                  30

Glu Val Lys Phe Asn Trp Tyr Val Asp Gly Val Glu Val His Asn Ala
        35                  40                  45

Lys Thr Lys Pro Arg Glu Glu Gln Tyr Asn Ser Thr Tyr Arg Val Val
    50                  55                  60

Ser Val Leu Thr Val Leu His Gln Asp Trp Leu Asn Gly Lys Glu Tyr
65                  70                  75                  80

Lys Cys Lys Val Ser Asn Lys Ala Leu Pro Ala Pro Ile Glu Lys Thr
                85                  90                  95

Ile Ser Lys Ala Lys Gly Gln Pro Arg Glu Pro Gln Val Tyr Thr Leu
            100                 105                 110

Pro Pro Ser Arg Asp Glu Leu Thr Lys Asn Gln Val Ser Leu Thr Cys
        115                 120                 125

Leu Val Lys Gly Phe Tyr Pro Ser Asp Ile Ala Val Glu Trp Glu Ser
    130                 135                 140

Asn Gly Gln Pro Glu Asn Asn Tyr Lys Thr Thr Pro Pro Val Leu Asp
145                 150                 155                 160

Ser Asp Gly Ser Phe Phe Leu Tyr Ser Lys Leu Thr Val Asp Lys Ser
                165                 170                 175

Arg Trp Gln Gln Gly Asn Val Phe Ser Cys Ser Val Met His Glu Ala
            180                 185                 190

Leu His Asn His Tyr Thr Gln Lys Ser Leu Ser Leu Ser Pro Gly Lys
        195                 200                 205

ANTIBODIES THAT BIND TO MHC CLASS I POLYPEPTIDE-RELATED SEQUENCE A

RELATED APPLICATIONS

This application is the national stage of International Patent Application No. PCT/US2014/068862, filed on Dec. 5, 2014, which claims the benefit of U.S. Provisional Patent Application Ser. No. 61/913,198, filed on Dec. 6, 2013, and U.S. Provisional Patent Application Ser. No. 61/953,588, filed on Mar. 14, 2014, the entire contents each of which are hereby incorporated by reference.

GOVERNMENT SUPPORT

This invention was made with Government support under Grant Nos. P01 AI045757 and P01 CA78378, awarded by the National Institutes of Health. The Government has certain rights in the invention.

TECHNICAL FIELD

This invention relates to therapeutic compositions (e.g., peptides) related to human subjects.

BACKGROUND

Human subjects exposed to a condition or disease offer a source of antibodies with therapeutic potential and general methods for obtaining such antibodies are known in the art. However, methods for specifically obtaining antibodies with therapeutic potential are generally limited by the low frequency, slow proliferation rate, and low antibody secretion levels of B cells that express such antibodies. For example, memory B cells with defined specificity typically account for only one cell per million peripheral blood mononuclear cells or approximately one milliliter of blood (Lanzavecchia et al., Curr. Opin. Immunol., 21:298-304 (2009): Yoshida et al., Immunol. Rev., 237:117-139 (2010)). The frequency of antibodies with therapeutic potential is likely to be even lower in cancer patients, necessitating the development of novel approaches that enable isolation of such cells with high sensitivity and efficiency.

Conventional methods generally rely on conversion of memory B cells into antibody secreting cells by in vitro culture and/or use of immunized animal models (e.g., mice) (Crotty et al., J. Immunol., 171:4969-4973 (2003): Fecteau et al., Immunology, 128:e353-e365 (2009): Buisman et al., Vaccine, 28:179-186 (2009): Corti et al., PLoS One, 5:e8805 (2010)). For example, following in vitro culture for up to one week, antibodies can be measured in culture supernatants and frequencies of antibody secreting cells assessing using enzyme-linked immunosorbent spot (ELISPOT) assay. Limitations of such methods are reported (Henn et al., J. Immunol., 183:31777-3187 (2009): Cao et al., J. Immunol., Methods, 358:56-65 (2010)). For instances, in vitro culture of memory B cells alters the memory B cell phenotype to resemble plasma cells with distinct functional properties (Jiang et al., Eur. J. Immunol., 37:2205-2213 (2007): Huggins et al., Blood, 109:1611-1619 (2007): Jourdan et al., Blood, 114:5173-5181 (2009)). Limitations for fluorescent antigen-based methods are also reported (Hofer et al., Immunol. Rev., 211:295-302 (2006): Odendahl et al., Blood, 105:1614-1621 (2005); Kunkel et al., Nat. Rev. Immunol., 3:822-829 (2003): Scheid et al., Nature, 458:636-640 (2009): Wu et al., Science, 329:856-861 (2010)).

Improved methods for specifically obtaining or targeting antibodies with therapeutic potential are required.

MICA is a ligand for NKG2D, a C-type lectin-like, type II transmembrane receptor expressed on most human NK cells, γδ T cells, and CD8+ T cells. Upon ligation, NKG2D signals through the adaptor protein DAP10 to evoke perforin dependent cytolysis and to provide co-stimulation. In humans, the NKG2D ligands include MHC class I chain-related protein A (MICA), the closely related MICB, UL-16 binding proteins (ULBP) 1-4, and RAE-1G. While NKG2D ligands are not usually found on healthy tissues, various forms of cellular stress, including DNA damage, may upregulate ligand expression, resulting in their frequent detection in multiple solid and hematologic malignancies, including melanoma. NKG2D activation through ligand positive transformed cells contributes to extrinsic tumor suppression, since NKG2D deficient and wild type mice treated with anti-NKG2D blocking antibodies manifest enhanced tumor susceptibility. Immune escape may be achieved in patients, however, by the shedding of NKG2D ligands from tumor cells, which triggers internalization of surface NKG2D and impaired function of cytotoxic lymphocytes. Soluble NKG2D ligands may also stimulate the expansion of regulatory NKG2D+CD4+Foxp3− T cells that may antagonize anti-tumor cytotoxicity through Fas ligand, IL-10, and TGF-β. MICA is a NKG2D ligand shed from tumor cells, i.e., released from the cell surface into the surrounding medium, and sera from cancer patients typically contain elevated levels of the soluble form (sMICA). MICA shedding is accomplished in part through interactions with the protein disulfide isomerase ERp5, which forms a disulfide bond with a critical cysteine that results in unfolding of the α3 domain, rendering it susceptible to proteolysis by ADAM-10/17 and MMP14.

There is a need to identify new agents that specifically recognize and bind cancer targets as immune-based cancer therapy. Such agents would be useful for diagnostic screening and therapeutic intervention in disease states that are associated with tumor development.

SUMMARY

The present disclosure provides compositions and methods related to antibodies with therapeutic potential.

In some embodiments, the disclosure provides compositions comprising peptides that immunospecifically bind to MHC class I polypeptide-related sequence A (MICA), or an epitope thereon. In some aspects, peptides of the compositions include complementarity determining region (CDR) 3 of the $V_H$ of antibody ID 11 or 12 shown in Table 1 having 5 or fewer conservative amino acid substitutions, and CDR3 of the $V_L$ of antibody ID 11 or 12 shown in Table 1 having 5 or fewer conservative amino acid substitutions. In some aspects, such peptides include complementarity determining region (CDR) 3 of the $V_H$ of antibody ID 11 or 12 shown in Table 1, and CDR3 of the $V_L$ of antibody ID 11 or 12 shown in Table 1. In some aspects, peptides further include CDR2 of the $V_H$ of antibody ID 11 or 12 shown in Table 1 having 5 or fewer conservative amino acid substitutions, or CDR2 of the $V_L$ of antibody ID 11 or 12 shown in Table 1 having 5 or fewer conservative amino acid substitutions, or both. In some aspects, such peptides include complementarity determining region CDR2 of the $V_H$ of antibody ID 11 or 12 shown in Table 1, or CDR2 of the $V_L$ of antibody ID 11 or 12 shown in Table 1, or both. In some aspects, peptides further include CDR1 of the $V_H$ of antibody ID 11 or 12 shown in Table 1 having 5 or fewer conservative amino acid substitutions, or CDR1 of the $V_L$ of antibody ID 11 or 12 shown in Table 1 having 5 or fewer conservative amino acid substitutions, or both. In some aspects, such peptides include complementarity determining region CDR1 of the $V_H$ of antibody ID 11 or 12 shown in Table 1, or CDR1 of the $V_L$ of antibody ID 11 or 12 shown in Table 1, or both.

In some aspects, peptides are antibody or antibody fragment that include: a $V_H$ chain with identity to SEQ ID NO:150 or 168, wherein regions corresponding to CDR1, CDR2, and CDR3 comprise CDR1, CDR2, and CDR3 of the $V_H$ of antibody ID 11 or 12 shown in table 1 having 5 or fewer conservative amino acid substitutions, and regions within SEQ ID NO:150 or 168 corresponding to FR1, FR2, FR3, FR4, comprise amino acid sequences with at least 80%, 85%, 90%, 95%, 96%, 97%, 98, 99%, or 100% identity to FR1, FR2, FR3, FR4 of the $V_H$ of antibody ID 11 or 12 shown in table 1; and a VL chain with identity to SEQ ID NO:152 or 170, wherein regions corresponding to CDR1, CDR2, and CDR3 comprise CDR1, CDR2, and CDR3 of the VL of antibody ID 11 or 12 shown in table 1 having 5 or fewer conservative amino acid substitutions, and regions within SEQ ID NO:152 or 170 corresponding to FR1, FR2, FR3, FR4, comprise amino acid sequences with at least 80%, 85%, 90%, 95%, 96%, 97%, 98, 99%, or 100% identity to FR1, FR2, FR3, FR4 of the $V_L$ of antibody ID 11 or 12 shown in table 1. In some aspects, peptides include an antibody or antibody fragment comprising a $V_H$ chain comprising SEQ ID NO:150 or 168 and a VL chain comprising SEQ ID NO:152 or 170.

In some aspects, the disclosure provides peptides that are antibody or antibody fragments which bind to an epitope within MICA which comprises all or a portion of an epitope recognized by the particular antibodies described herein. In some embodiments, the antibody or antigen binding fragment recognizes a region within the MICA α3 domain corresponding to amino acids 181 to 274 of the MICA*009 reference sequence (SEQ ID NO:185). In some embodiments, the antibody or antibody fragment binds to the same epitope as an antibody comprising a $V_H$ chain comprising SEQ ID NO:131 and a VL chain comprising SEQ ID NO:133. In some embodiments, the antibody or antibody fragment recognizes an epitope that includes at least one portion of MICA of at least 5, 6, 7, 8, 9, 10, 11, 12, 13, 14 or 15 amino acids that includes or overlaps with the amino acid sequence GDVLPDGNGTYQTWVATRIC (SEQ ID NO:186). In some embodiments, the antibody or antibody fragment binds to the same epitope as an antibody comprising a $V_H$ chain comprising SEQ ID NO:113 and a VL chain comprising SEQ ID NO:115. In some embodiments, the antibody or antibody fragment recognizes an epitope that includes at least one portion of MICA of at least 5, 6, 7, 8, 9, 10, 11, 12, 13, 14 or 15 amino acids that includes or overlaps with the amino acid sequence NVETEEWTVP (SEQ ID NO:187). In some embodiments, the antibody or antibody fragment binds to the same epitope as an antibody comprising a $V_H$ chain comprising SEQ ID NO:150 and a VL chain comprising SEQ ID NO:152. In some embodiments, the antibody or antibody fragment recognizes an epitope that includes at least one portion of MICA of at least 5, 6, 7, 8, 9, 10, 11, 12, 13, 14 or 15 amino acids that includes or overlaps with the amino acid sequence TVPPMVNVTR (SEQ ID NO:188). In some embodiments, the antibody or antibody fragment binds to the same epitope as an antibody comprising a $V_H$ chain comprising SEQ ID NO:168 and a VL chain comprising SEQ ID NO:170. In some embodiments, the antibody or antibody fragment recognizes an epitope that includes at least one portion of MICA of at least 5, 6, 7, 8, 9, 10, 11, 12, 13, 14 or 15 amino acids that includes or overlaps with the amino acid sequence TCRASSFYPR (SEQ ID NO:189). In some embodiments, the antibody or antibody fragment binds to the same epitope as an antibody comprising a $V_H$ chain comprising SEQ ID NO:77 and a VL chain comprising SEQ ID NO:79. In some embodiments, the antibody or antibody fragment binds to the same epitope as an antibody comprising a $V_H$ chain comprising SEQ ID NO:2 and a VL chain comprising SEQ ID NO:11. In some embodiments, the antibody or antibody fragment binds to the same epitope as an antibody comprising a $V_H$ chain comprising SEQ ID NO:96 and a VL chain comprising SEQ ID NO:98.

In some aspects, in addition to the peptides, compositions further include one or more (e.g., 1 2, 3, 4, 5, 6, 7, 8, 9, 10, or less than 20) anti-cancer therapeutics. In some aspects, compositions are formulated as pharmaceutical compositions (e.g., for administration to a subject).

In some embodiments, the disclosure provides compositions comprising a nucleic acid encoding a peptide that immunospecifically bind to MHC class I polypeptide-related sequence A (MICA), or an epitope thereon. In some aspects, the nucleic acids of the compositions encode the $V_H$ of antibody ID 1, 6, 7, 8, 9, 11 or 12 shown in Table 1 having 5 or fewer conservative amino acid substitutions. In some aspects, the nucleic acids of the compositions encode the $V_L$ of antibody ID 1, 6, 7, 8, 9, 11 or 12 shown in Table 1 having 5 or fewer conservative amino acid substitutions.

In one aspect, the disclosure provides nucleic acids comprising a nucleotide sequence having at least about 75%, 80%, 90%, 95%, 99% or more, or complete (100%) sequence identity to SEQ ID NO: 1. In some aspects, the nucleic acid sequence encodes a peptide comprising an amino acid sequence with at least 80%, 85%, 90%, 95%, 96%, 97%, 98, 99%, or 100% identity SEQ ID NO: 2. In another aspect, the disclosure provides nucleic acids comprising a nucleotide sequence at least about 75%, 80%, 90%, 95%, 99% or more, or complete (100%) sequence identity to SEQ ID NO: 10. In some aspects, the nucleic acid sequence encodes a peptide comprising an amino acid sequences with at least 80%, 85%, 90%, 95%, 96%, 97%, 98, 99%, or 100% identity SEQ ID NO: 11.

In one aspect, the disclosure provides nucleic acids comprising a nucleotide sequence at least about 75%, 80%, 90%, 95%, 99% or more, or complete (100%) sequence identity to SEQ ID NO: 76. In some aspects, the nucleic acid sequence encodes a peptide comprising an amino acid sequence with at least 80%, 85%, 90%, 95%, 96%, 97%, 98, 99%, or 100% identity SEQ ID NO: 77. In another aspect, the disclosure provides nucleic acids comprising a nucleotide sequence at least about 75%, 80%, 90%, 95%, 99% or more, or complete (100%) sequence identity to SEQ ID NO: 78. In some aspects, the nucleic acid sequence encodes a peptide comprising an amino acid sequence with at least 80%, 85%, 90%, 95%, 96%, 97%, 98, 99%, or 100% identity SEQ ID NO: 79.

In one aspect, the disclosure provides nucleic acids comprising a nucleotide sequence at least about 75%, 80%, 90%, 95%, 99% or more, or complete (100%) sequence identity to SEQ ID NO: 95. In some aspects, the nucleic acid sequence encodes a peptide comprising an amino acid sequence with at least 80%, 85%, 90%, 95%, 96%, 97%, 98, 99%, or 100% identity SEQ ID NO: 96. In another aspect, the disclosure provides nucleic acids comprising a nucleotide sequence at least about 75%, 80%, 90%, 95%, 99% or more, or complete (100%) sequence identity to SEQ ID NO: 97. In some aspects, the nucleic acid sequence encodes a peptide comprising an amino acid sequence with at least 80%, 85%, 90%, 95%, 96%, 97%, 98, 99%, or 100% identity SEQ ID NO: 98.

In one aspect, the disclosure provides nucleic acids comprising a nucleotide sequence at least about 75%, 80%, 90%, 95%, 99% or more, or complete (100%) sequence identity to SEQ ID NO: 112. In some aspects, the nucleic acid sequence encodes a peptide comprising an amino acid sequence with at least 80%, 85%, 90%, 95%, 96%, 97%, 98, 99%, or 100% identity SEQ ID NO: 113. In another aspect, the disclosure provides nucleic acids comprising a nucleotide sequence at least about 75%, 80%, 90%, 95%, 99% or more, or complete (100%) sequence identity to SEQ ID NO: 114. In some aspects, the nucleic acid sequence encodes a peptide comprising an amino acid sequence with at least 80%, 85%, 90%, 95%, 96%, 97%, 98, 99%, or 100% identity SEQ ID NO: 115.

In one aspect, the disclosure provides nucleic acids comprising a nucleotide sequence at least about 75%, 80%, 90%, 95%, 99% or more, or complete (100%) sequence identity to SEQ ID NO: 130. In some aspects, the nucleic acid sequence encodes a peptide comprising an amino acid sequence with at least 80%, 85%, 90%, 95%, 96%, 97%, 98, 99%, or 100% identity SEQ ID NO: 131. In another aspect, the disclosure provides nucleic acids comprising a nucleotide sequence at least about 75%, 80%, 90%, 95%, 99% or more, or complete (100%) sequence identity to SEQ ID NO: 132. In some aspects, the nucleic acid sequence encodes a peptide comprising an amino acid sequence with at least 80%, 85%, 90%, 95%, 96%, 97%, 98, 99%, or 100% identity SEQ ID NO: 133.

In one aspect, the disclosure provides nucleic acids comprising a nucleotide sequence at least about 75%, 80%, 90%, 95%, 99% or more, or complete (100%) sequence identity to SEQ ID NO: 149. In some aspects, the nucleic acid sequence encodes a peptide comprising an amino acid sequence with at least 80%, 85%, 90%, 95%, 96%, 97%, 98, 99%, or 100% identity SEQ ID NO: 150. In another aspect, the disclosure provides nucleic acids comprising a nucleotide sequence at least about 75%, 80%, 90%, 95%, 99% or more, or complete (100%) sequence identity to SEQ ID NO: 151. In some aspects, the nucleic acid sequence encodes a peptide comprising an amino acid sequence with at least 80%, 85%, 90%, 95%, 96%, 97%, 98, 99%, or 100% identity SEQ ID NO: 152.

In one aspect, the disclosure provides nucleic acids comprising a nucleotide sequence at least about 75%, 80%, 90%, 95%, 99% or more, or complete (100%) sequence identity to SEQ ID NO: 167. In some aspects, the nucleic acid sequence encodes a peptide comprising an amino acid sequence with at least 80%, 85%, 90%, 95%, 96%, 97%, 98, 99%, or 100% identity SEQ ID NO: 168. In another aspect, the disclosure provides nucleic acids comprising a nucleotide sequence at least about 75%, 80%, 90%, 95%, 99% or more, or complete (100%) sequence identity to SEQ ID NO: 169. In some aspects, the nucleic acid sequence encodes a peptide comprising an amino acid sequence with at least 80%, 85%, 90%, 95%, 96%, 97%, 98, 99%, or 100% identity SEQ ID NO: 170.

In some embodiments, the disclosure provides chimeric antigen receptors (CARs) comprising peptides that immunospecifically bind to MICA and an intracellular T cell domain. In one aspect, the peptides included in the CAR are an antibody or antibody fragment that include: a $V_H$ chain with identity to SEQ ID NO:2, wherein regions corresponding to CDR1, CDR2, and CDR3 comprise CDR1, CDR2, and CDR3 of the $V_H$ of antibody ID 1 shown in table 1 having 5 or fewer conservative amino acid substitutions, and regions within SEQ ID NO:2 corresponding to FR1, FR2, FR3, FR4, comprise amino acid sequences with at least 80%, 85%, 90%, 95%, 96%, 97%, 98, 99%, or 100% identity to FR1, FR2, FR3, FR4 of the $V_H$ of antibody ID 1 shown in table 1; or an antibody or antibody fragment that include a $V_L$ chain with identity to SEQ ID NO:11, wherein regions corresponding to CDR1, CDR2, and CDR3 comprise CDR1, CDR2, and CDR3 of the $V_L$ of antibody ID 1 shown in table 1 having 5 or fewer conservative amino acid substitutions, and regions within SEQ ID NO:11 corresponding to FR1, FR2, FR3, FR4, comprise amino acid sequences with at least 80%, 85%, 90%, 95%, 96%, 97%, 98, 99%, or 100% identity to FR1, FR2, FR3, FR4 of the $V_L$ of antibody ID 1 shown in table 1. In some aspects, peptides include an antibody or antibody fragment comprising a VH chain comprising SEQ ID NO:2 and a $V_L$ chain comprising SEQ ID NO:11.

In one aspect, the peptides included in the CARs are an antibody or antibody fragment that include: a $V_H$ chain with identity to SEQ ID NO:77, wherein regions corresponding to CDR1, CDR2, and CDR3 comprise CDR1, CDR2, and CDR3 of the $V_H$ of antibody ID 6 shown in table 1 having 5 or fewer conservative amino acid substitutions within the CDR1, CDR2, and CDR3 regions, and regions within SEQ ID NO:77 corresponding to FR1, FR2, FR3, FR4, comprise amino acid sequences with at least 80%, 85%, 90%, 95%, 96%, 97%, 98, 99%, or 100% identity to FR1, FR2, FR3, FR4 of the $V_H$ of antibody ID 6 shown in table 1; or antibody or antibody fragment that include a $V_L$ chain with identity to SEQ ID NO:79, wherein regions corresponding to CDR1, CDR2, and CDR3 comprise CDR1, CDR2, and CDR3 of the $V_L$ of antibody ID 6 shown in table 1 having 5 or fewer conservative amino acid substitutions within the CDR1, CDR2, and CDR3 regions, and regions within SEQ ID NO:79 corresponding to FR1, FR2, FR3, FR4, comprise amino acid sequences with at least 80%, 85%, 90%, 95%, 96%, 97%, 98, 99%, or 100% identity to FR1, FR2, FR3, FR4 of the $V_L$ of antibody ID 6 shown in table 1. In some aspects, peptides include an antibody or antibody fragment comprising a $V_H$ chain comprising SEQ ID NO:77 and a $V_L$ chain comprising SEQ ID NO:79.

In one aspect, the peptides that immunospecifically bind to MICA included in the CARs are an antibody or antibody fragment that include: a $V_H$ chain with identity to SEQ ID NO:96, wherein regions corresponding to CDR1, CDR2, and CDR3 comprise CDR1, CDR2, and CDR3 of the $V_H$ of antibody ID 7 shown in table 1 having 5 or fewer conservative amino acid substitutions within the CDR1, CDR2, and CDR3 regions, and regions within SEQ ID NO:96 corresponding to FR1, FR2, FR3, FR4, comprise amino acid sequences with at least 80%, 85%, 90%, 95%, 96%, 97%, 98, 99%, or 100% identity to FR1, FR2, FR3, FR4 of the $V_H$ of antibody ID 7 shown in table 1; and an antibody or antibody fragment that include a $V_L$ chain with identity to SEQ ID NO:98, wherein regions corresponding to CDR1, CDR2, and CDR3 comprise CDR1, CDR2, and CDR3 of the $V_L$ of antibody ID 7 shown in table 1 having 5 or fewer conservative amino acid substitutions within the CDR1, CDR2, and CDR3 regions, and regions within SEQ ID NO:98 corresponding to FR1, FR2, FR3, FR4, comprise amino acid sequences with at least 80%, 85%, 90%, 95%, 96%, 97%, 98, 99%, or 100% identity to FR1, FR2, FR3, FR4 of the $V_L$ of antibody ID 7 shown in table 1. In some aspects, peptides include an antibody or antibody fragment comprising a $V_H$ chain comprising SEQ ID NO:96 and a $V_L$ chain comprising SEQ ID NO:98.

In one aspect, the peptides that immunospecifically bind to MICA included in the CARs are an antibody or antibody fragment that include: a $V_H$ chain with identity to SEQ ID NO:113, wherein regions corresponding to CDR1, CDR2, and CDR3 comprise CDR1, CDR2, and CDR3 of the $V_H$ of antibody ID 8 shown in table 1 having 5 or fewer conservative amino acid substitutions within the CDR1, CDR2, and CDR3 regions, and regions within SEQ ID NO:113 corresponding to FR1, FR2, FR3, FR4, comprise amino acid sequences with at least 80%, 85%, 90%, 95%, 96%, 97%, 98, 99%, or 100% identity to FR1, FR2, FR3, FR4 of the $V_H$ of antibody ID 8 shown in table 1; or an antibody or antibody fragment that include a $V_L$ chain with identity to SEQ ID NO:115, wherein regions corresponding to CDR1, CDR2, and CDR3 comprise CDR1, CDR2, and CDR3 of the $V_L$ of antibody ID 8 shown in table 1 having 5 or fewer conservative amino acid substitutions within the CDR1, CDR2, and CDR3 regions, and regions within SEQ ID NO:115 corresponding to FR1, FR2, FR3, FR4, comprise amino acid sequences with at least 80%, 85%, 90%, 95%, 96%, 97%, 98, 99%, or 100% identity to FR1, FR2, FR3, FR4 of the $V_L$ of antibody ID 8 shown in table 1. In some aspects, peptides include an antibody or antibody fragment comprising a $V_H$ chain comprising SEQ ID NO:113 and a $V_L$ chain comprising SEQ ID NO:115.

In one aspect, the peptides that immunospecifically bind to MICA included in the CARs are an antibody or antibody fragment that include: a $V_H$ chain with identity to SEQ ID NO:131, wherein regions corresponding to CDR1, CDR2, and CDR3 comprise CDR1, CDR2, and CDR3 of the $V_H$ of antibody ID 9 shown in table 1 having 5 or fewer conservative amino acid substitutions within the CDR1, CDR2, and CDR3 regions, and regions within SEQ ID NO:131 corresponding to FR1, FR2, FR3, FR4, comprise amino acid sequences with at least 80%, 85%, 90%, 95%, 96%, 97%, 98, 99%, or 100% identity to FR1, FR2, FR3, FR4 of the $V_H$ of antibody ID 9 shown in table 1; or an antibody or antibody fragment that include a $V_L$ chain with identity to SEQ ID NO:133, wherein regions corresponding to CDR1, CDR2, and CDR3 comprise CDR1, CDR2, and CDR3 of the $V_L$ of antibody ID 9 shown in table 1 having 5 or fewer conservative amino acid substitutions within the CDR1, CDR2, and CDR3 regions, and regions within SEQ ID NO:133 corresponding to FR1, FR2, FR3, FR4, comprise amino acid sequences with at least 80%, 85%, 90%, 95%, 96%, 97%, 98, 99%, or 100% identity to FR1, FR2, FR3, FR4 of the $V_L$ of antibody ID 9 shown in table 1. In some aspects, peptides include an antibody or antibody fragment comprising a $V_H$ chain comprising SEQ ID NO:131 and a $V_L$ chain comprising SEQ ID NO:133.

In one aspect, the peptides that immunospecifically bind to MICA included in the CARs are an antibody or antibody fragment that include: a $V_H$ chain with identity to SEQ ID NO:150, wherein regions corresponding to CDR1, CDR2, and CDR3 comprise CDR1, CDR2, and CDR3 of the $V_H$ of antibody ID 11 shown in table 1 having 5 or fewer conservative amino acid substitutions within the CDR1, CDR2, and CDR3 regions, and regions within SEQ ID NO:150 corresponding to FR1, FR2, FR3, FR4, comprise amino acid sequences with at least 80%, 85%, 90%, 95%, 96%, 97%, 98, 99%, or 100% identity to FR1, FR2, FR3, FR4 of the $V_H$ of antibody ID 11 shown in table 1; or an antibody or antibody fragment that include a $V_L$ chain with identity to SEQ ID NO:152, wherein regions corresponding to CDR1, CDR2, and CDR3 comprise CDR1, CDR2, and CDR3 of the $V_L$ of antibody ID 11 shown in table 1 having 5 or fewer conservative amino acid substitutions within the CDR1, CDR2, and CDR3 regions, and regions within SEQ ID NO:152 corresponding to FR1, FR2, FR3, FR4, comprise amino acid sequences with at least 80%, 85%, 90%, 95%, 96%, 97%, 98, 99%, or 100% identity to FR1, FR2, FR3, FR4 of the $V_L$ of antibody ID 11 shown in table 1. In some aspects, peptides include an antibody or antibody fragment comprising a $V_H$ chain comprising SEQ ID NO:150 and a $V_L$ chain comprising SEQ ID NO:152.

In one aspect, the peptides that immunospecifically bind to MICA included in the CARs are an antibody or antibody fragment that include: a $V_H$ chain with identity to SEQ ID NO:168, wherein regions corresponding to CDR1, CDR2, and CDR3 comprise CDR1, CDR2, and CDR3 of the $V_H$ of antibody ID 12 shown in table 1 having 5 or fewer conservative amino acid substitutions within the CDR1, CDR2, and CDR3 regions, and regions within SEQ ID NO:168 corresponding to FR1, FR2, FR3, FR4, comprise amino acid sequences with at least 80%, 85%, 90%, 95%, 96%, 97%, 98, 99%, or 100% identity to FR1, FR2, FR3, FR4 of the $V_H$ of antibody ID 12 shown in table 1; or an antibody or antibody fragment that include a $V_L$ chain with identity to SEQ ID NO:170, wherein regions corresponding to CDR1, CDR2, and CDR3 comprise CDR1, CDR2, and CDR3 of the $V_L$ of antibody ID 12 shown in table 1 having 5 or fewer conservative amino acid substitutions within the CDR1, CDR2, and CDR3 regions, and regions within SEQ ID NO:170 corresponding to FR1, FR2, FR3, FR4, comprise amino acid sequences with at least 80%, 85%, 90%, 95%, 96%, 97%, 98, 99%, or 100% identity to FR1, FR2, FR3, FR4 of the $V_L$ of antibody ID 12 shown in table 1. In some aspects, peptides include an antibody or antibody fragment comprising a $V_H$ chain comprising SEQ ID NO:168 and a VL chain comprising SEQ ID NO:170.

In other embodiments, the disclosure provides a vector (e.g., an expression vector, a viral vector, a retrovirus vector, an adenovirus vector, an adeno-associated virus (AAV) vector, herpes virus vector, or a poxvirus vector) comprising a nucleic acid encoding a peptide that immunospecifically bind to MICA. In one aspect, the vector comprises a nucleotide sequence having at least about 75%, 80%, 90%, 95%, 99% or more, or complete (100%) sequence identity to SEQ ID NO:10, 78, 97, 114, 132, 151 or 169. In some aspects, the nucleic acid sequence encodes a peptide comprising an amino acid sequences with at least 80%, 85%, 90%, 95%, 96%, 97%, 98, 99%, or 100% identity SEQ ID NO: 11, 79, 98, 115, 133, 152 or 170.

In another aspect, the vector comprises a nucleotide sequence having at least about 75%, 80%, 90%, 95%, 99% or more, or complete (100%) sequence identity to SEQ ID NO: 1, 76, 95, 112, 130, 149 or 167. In some aspects, the nucleic acid sequence encodes a peptide comprising an amino acid sequences with at least 80%, 85%, 90%, 95%, 96%, 97%, 98, 99%, or 100% identity SEQ ID NO: 2, 77, 96, 113, 131, 150 or 168.

In another aspect, the vector comprises a nucleotide sequence having at least about 75%, 80%, 90%, 95%, 99% or more, or complete (100%) sequence identity to SEQ ID NO: 1, 76, 112, 130, or 149. In some aspects, the nucleic acid sequence encodes a peptide comprising an amino acid sequences with at least 80%, 85%, 90%, 95%, 96%, 97%, 98, 99%, or 100% identity SEQ ID NO: 2, 77, 96, 113, 131, or 150.

In one aspect, the vector comprises a nucleotide sequence having at least about 75%, 80%, 90%, 95%, 99% or more, or complete (100%) sequence identity to SEQ ID NO: 1. In some aspects, the nucleic acid sequence encodes a peptide comprising an amino acid sequence with at least 80%, 85%, 90%, 95%, 96%, 97%, 98, 99%, or 100% identity SEQ ID NO: 2. In another aspect, the disclosure provides nucleic acids comprising a nucleotide sequence at least about 75%, 80%, 90%, 95%, 99% or more, or complete (100%) sequence identity to SEQ ID NO: 10. In some aspects, the nucleic acid sequence encodes a peptide comprising an amino acid sequences with at least 80%, 85%, 90%, 95%, 96%, 97%, 98, 99%, or 100% identity SEQ ID NO: 11.

In one aspect, the vector comprises a nucleotide sequence having at least about 75%, 80%, 90%, 95%, 99% or more, or complete (100%) sequence identity to SEQ ID NO: 76. In some aspects, the nucleic acid sequence encodes a peptide comprising an amino acid sequence with at least 80%, 85%, 90%, 95%, 96%, 97%, 98, 99%, or 100% identity SEQ ID NO: 77. In another aspect, the disclosure provides nucleic acids comprising a nucleotide sequence at least about 75%, 80%, 90%, 95%, 99% or more, or complete (100%) sequence identity to SEQ ID NO: 78. In some aspects, the nucleic acid sequence encodes a peptide comprising an amino acid sequences with at least 80%, 85%, 90%, 95%, 96%, 97%, 98, 99%, or 100% identity SEQ ID NO: 79.

In one aspect, the vector comprises a nucleotide sequence having at least about 75%, 80%, 90%, 95%, 99% or more, or complete (100%) sequence identity to SEQ ID NO: 95. In some aspects, the nucleic acid sequence encodes a peptide comprising an amino acid sequence with at least 80%, 85%, 90%, 95%, 96%, 97%, 98, 99%, or 100% identity SEQ ID NO: 96. In another aspect, the disclosure provides nucleic acids comprising a nucleotide sequence at least about 75%, 80%, 90%, 95%, 99% or more, or complete (100%) sequence identity to SEQ ID NO: 97. In some aspects, the nucleic acid sequence encodes a peptide comprising an amino acid sequence with at least 80%, 85%, 90%, 95%, 96%, 97%, 98, 99%, or 100% identity SEQ ID NO: 98.

In one aspect, the vector comprises a nucleotide sequence having at least about 75%, 80%, 90%, 95%, 99% or more, or complete (100%) sequence identity to SEQ ID NO: 112. In some aspects, the nucleic acid sequence encodes a peptide comprising an amino acid sequence with at least 80%, 85%, 90%, 95%, 96%, 97%, 98, 99%, or 100% identity SEQ ID NO: 113. In another aspect, the disclosure provides nucleic acids comprising a nucleotide sequence at least about 75%, 80%, 90%, 95%, 99% or more, or complete (100%) sequence identity to SEQ ID NO: 114. In some aspects, the nucleic acid sequence encodes a peptide comprising an amino acid sequence with at least 80%, 85%, 90%, 95%, 96%, 97%, 98, 99%, or 100% identity SEQ ID NO: 115.

In one aspect, the vector comprises a nucleotide sequence having at least about 75%, 80%, 90%, 95%, 99% or more, or complete (100%) sequence identity to SEQ ID NO: 130. In some aspects, the nucleic acid sequence encodes a peptide comprising an amino acid sequence with at least 80%, 85%, 90%, 95%, 96%, 97%, 98, 99%, or 100% identity SEQ ID NO: 131. In another aspect, the disclosure provides nucleic acids comprising a nucleotide sequence at least about 75%, 80%, 90%, 95%, 99% or more, or complete (100%) sequence identity to SEQ ID NO: 132. In some aspects, the nucleic acid sequence encodes a peptide comprising an amino acid sequence with at least 80%, 85%, 90%, 95%, 96%, 97%, 98, 99%, or 100% identity SEQ ID NO: 133.

In one aspect, the vector comprises a nucleotide sequence having at least about 75%, 80%, 90%, 95%, 99% or more, or complete (100%) sequence identity to SEQ ID NO: 149. In some aspects, the nucleic acid sequence encodes a peptide comprising an amino acid sequence with at least 80%, 85%, 90%, 95%, 96%, 97%, 98, 99%, or 100% identity SEQ ID NO: 150. In another aspect, the disclosure provides nucleic acids comprising a nucleotide sequence at least about 75%, 80%, 90%, 95%, 99% or more, or complete (100%) sequence identity to SEQ ID NO: 151. In some aspects, the nucleic acid sequence encodes a peptide comprising an amino acid sequence with at least 80%, 85%, 90%, 95%, 96%, 97%, 98, 99%, or 100% identity SEQ ID NO: 152.

In one aspect, the vector comprises a nucleotide sequence having at least about 75%, 80%, 90%, 95%, 99% or more, or complete (100%) sequence identity to SEQ ID NO: 167. In some aspects, the nucleic acid sequence encodes a peptide comprising an amino acid sequence with at least 80%, 85%, 90%, 95%, 96%, 97%, 98, 99%, or 100% identity SEQ ID NO: 168. In another aspect, the disclosure provides nucleic acids comprising a nucleotide sequence at least about 75%, 80%, 90%, 95%, 99% or more, or complete (100%) sequence identity to SEQ ID NO: 169. In some aspects, the nucleic acid sequence encodes a peptide comprising an amino acid sequence with at least 80%, 85%, 90%, 95%, 96%, 97%, 98, 99%, or 100% identity SEQ ID NO: 170.

In some embodiments, the disclosure includes methods of treating cancer in a subject. In some aspects, methods include administering to a subject a composition comprising one or more of the peptides and/or nucleic acids disclosed herein.

The present disclosure also provides methods of isolating human antibodies from cancer patients following immunotherapy.

In some embodiments, the disclosure includes method of obtaining immune cells directed against a self antigen from a subject, the method comprising identifying a subject exhibiting a positive immune response towards the self antigen, providing a multimeric form of the self antigen, contacting the multimeric form of the self antigen with a sample from the subject exhibiting a positive immune response towards the self antigen, and obtaining immune cells bound to the multimeric form of the self antigen.

In some embodiments, the disclosure includes method of obtaining immune cells from a cancer patient directed against a self antigen, the method comprising identifying a subject exhibiting a positive immune response towards the self antigen; providing a multimeric form of the self antigen; contacting the multimeric form of the self antigen with a sample from the subject exhibiting a positive immune response towards the self antigen; and obtaining immune cells bound to the multimeric form of the self antigen.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIG. 1| Nucleic acid sequence of the variable heavy ($V_H$) chain of antibody ID 1 (anti-MHC class I polypeptide-related sequence A (MICA) antibody) (SEQ ID NO:1).

FIG. 2| Amino acid sequence of $V_H$ chain of antibody ID 1 (anti-MICA antibody) (SEQ ID NO:2).

FIG. 3| Nucleic acid sequence of the variable light ($V_L$) chain of antibody ID 1 (anti-MICA antibody) (SEQ ID NO:10).

FIG. 4| Amino acid sequence of $V_L$ chain of antibody ID 1 (anti-MICA antibody) (SEQ ID NO:11).

FIG. 10| Nucleic acid sequence of the variable heavy ($V_H$) chain of antibody ID 6 (anti-MHC class I polypeptide-related sequence A (MICA) antibody) (SEQ ID NO:76).

FIG. 11| Amino acid sequence of $V_H$ chain of antibody 6 (anti-MICA antibody) (SEQ ID NO:77).

FIG. 12| Nucleic acid sequence of the variable light ($V_L$) chain of antibody ID 6 (anti-MICA antibody) (SEQ ID NO:78).

FIG. 13| Amino acid sequence of $V_L$ chain of antibody ID 6 (anti-MICA antibody) (SEQ ID NO: 79).

FIG. 14| Nucleic acid sequence of the variable heavy ($V_H$) chain of antibody ID 7 (anti-MHC class I polypeptide-related sequence A (MICA) antibody) (SEQ ID NO:95).

FIG. 15| Amino acid sequence of $V_H$ chain of antibody ID 7 (anti-MICA antibody) (SEQ ID NO:96).

FIG. 16| Nucleic acid sequence of the variable light ($V_L$) chain of antibody ID 7 (anti-MICA antibody) (SEQ ID NO:97).

FIG. 17| Amino acid sequence of $V_L$ chain of antibody ID 7 (anti-MICA antibody) (SEQ ID NO: 98).

FIG. 18| Nucleic acid sequence of the variable heavy ($V_H$) chain of antibody ID 8 (anti-MHC class I polypeptide-related sequence A (MICA) antibody) (SEQ ID NO:112).

FIG. 19| Amino acid sequence of $V_H$ chain of antibody ID 8 (anti-MICA antibody) (SEQ ID NO:113).

FIG. 20| Nucleic acid sequence of the variable light ($V_L$) chain of antibody ID 8 (anti-MICA antibody) (SEQ ID NO:114).

FIG. 21| Amino acid sequence of $V_L$ chain of antibody ID 8 (anti-MICA antibody) (SEQ ID NO: 115).

FIG. 22| Nucleic acid sequence of the variable heavy ($V_H$) chain of antibody ID 9 (anti-MHC class I polypeptide-related sequence A (MICA) antibody) (SEQ ID NO:130).

FIG. 23| Amino acid sequence of $V_H$ chain of antibody ID 9 (anti-MICA antibody) (SEQ ID NO:131).

FIG. 24| Nucleic acid sequence of the variable light ($V_L$) chain of antibody ID 9 (anti-MICA antibody) (SEQ ID NO:132).

FIG. 25| Amino acid sequence of $V_L$ chain of antibody ID 9 (anti-MICA antibody) (SEQ ID NO: 133).

FIG. 35| Nucleic acid sequence of the variable heavy ($V_H$) chain of antibody ID 11 (anti-MHC class I polypeptide-related sequence A (MICA) antibody) (SEQ ID NO:149).

FIG. 36| Amino acid sequence of $V_H$ chain of antibody 11 (anti-MICA antibody) (SEQ ID NO:150).

FIG. 37| Nucleic acid sequence of the variable light ($V_L$) chain of antibody ID 11 (anti-MICA antibody) (SEQ ID NO:151).

FIG. 38| Amino acid sequence of $V_L$ chain of antibody ID 11 (anti-MICA antibody) (SEQ ID NO:152).

FIG. 40| Table showing anti-MICA antibodies block NKG2D down-regulation on NK cells incubated with melanoma patient serum. PBMCs were incubated with control serum or melanoma patient samples containing soluble MICA alone or in the presence of the indicated antibodies at 100 ug/ml for 48 hrs. At 48 hrs, NKG2D expression was determined on NK cells (CD3−, CD8−, CD56+) by flow cytometry. Data are presented as % of NK cells that are NKG2D positive.

FIG. 50| Nucleic acid sequence of the variable heavy ($V_H$) chain of antibody ID 12 (CM33322 Ab28)(anti-MICA antibody) (SEQ ID NO:167).

FIG. 51| Amino acid sequence of $V_H$ chain of antibody ID 12 (CM33322 Ab28) (anti-MICA antibody) (SEQ ID NO:168).

FIG. 52| Nucleic acid sequence of the variable light ($V_L$) chain of antibody ID 12 (CM33322 Ab28)(anti-MICA antibody) (SEQ ID NO:169).

FIG. 53| Amino acid sequence of $V_L$ chain of antibody ID 12 (CM33322 Ab28)(anti-MICA antibody) (SEQ ID NO:170).

FIG. 60A-60D| A. The epitope of CM33322 Ab29 is shown within the amino acid sequence of MICA*009 (SEQ ID NO: 185); B. The epitope of CM33322 Ab4 is shown within the amino acid sequence of MICA*009 (SEQ ID NO: 185); C. The epitope of CM33322 Ab11 is shown within the amino acid sequence of MICA*009(SEQ ID NO: 185); D. The epitope of CM33322 Ab23 is shown within the amino acid sequence of MICA*009(SEQ ID NO: 185).

DETAILED DESCRIPTION

Figures 5A, 5B, 5C, 5D, 5E, 5F:
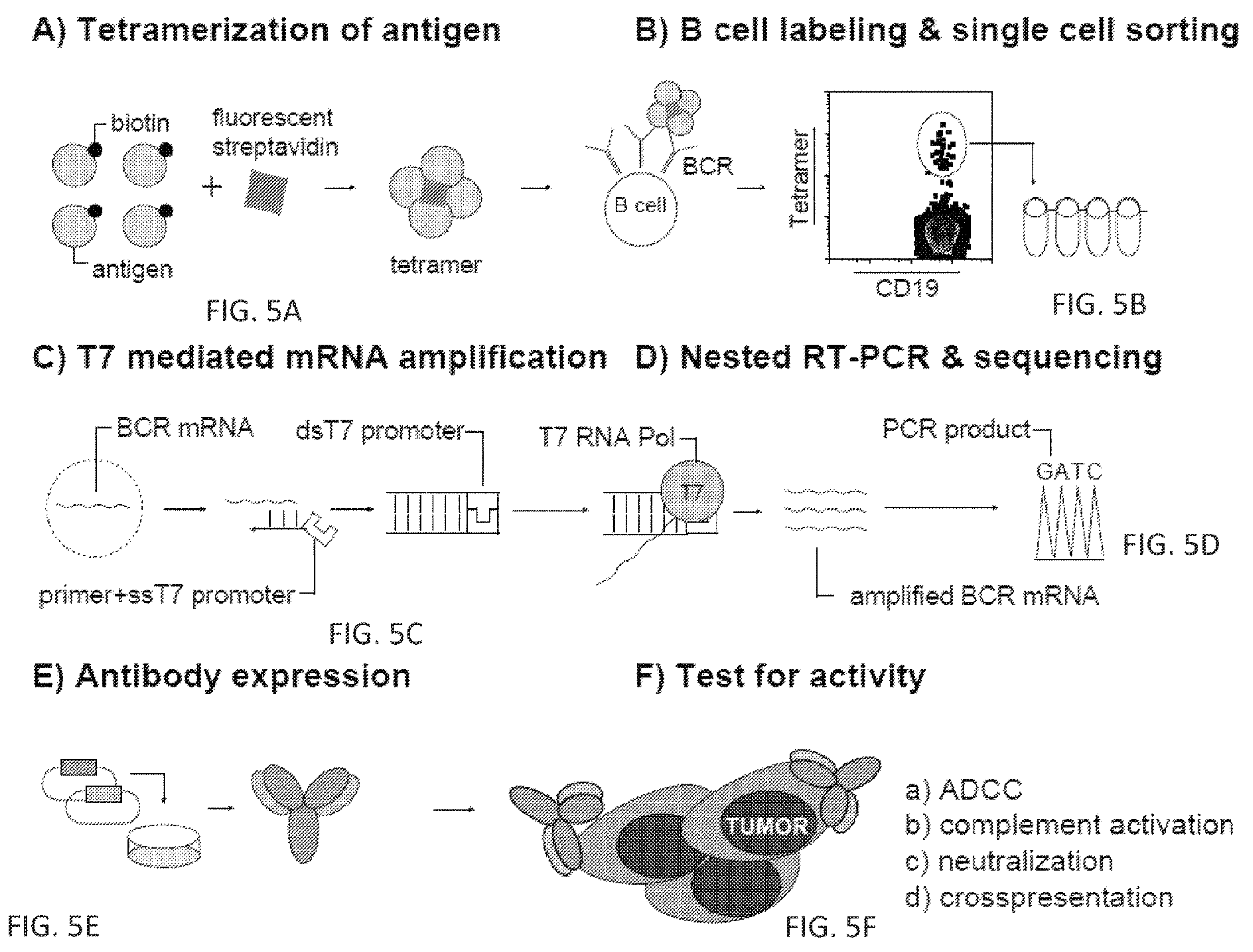
FIG. 5A-5F| Illustrates exemplary methods for making antibodies from B-cells. (A) Antigen is expressed with a BirA tag for site-specific biotinylation and tetramerization with fluorescently-labeled streptavidin. (B) B cells are stained with tetramer and a panel of monoclonal antibodies. Tetramer$^+$, class-switched memory B cells are single-cell sorted into PCR strips. (C) mRNA amplification is performed with T7 RNA polymerase. (D) Sequencing of PCR products is carried out using 300-400 bp PCR products. (E) Overlap PCR is used for construction of full-length IgG1 heavy chain and kappa/lambda light sequences which are cloned into separate vectors. Vectors are transiently transfected into CHO-S cells for expression of fully human recombinant antibodies. (F) Antibodies are tested for antigen binding and assessed for potential therapeutic properties.

The present disclosure is based, in part, on the observation that antibodies directed against therapeutic targets important in a disease can be obtained from human subjects exposed to the disease by labeling of B cells with a tetrameric form of the antigen of interest. As described in the background section above, prior methods are limited at least in that they are inefficient at identifying appropriate B cells in human subjects and/or because they induce any captured B cells to undergo phenotypic changes, thus reducing their value. In contrast, methods are described herein that allow capture of rare memory B cells directed against specific disease-related antigens. As described below, the methods require tetramerization of the disease-related antigen, which process, as demonstrated in the Examples below, enhances the identification of appropriate memory B cells. Specifically, methods herein permit more efficient capture of appropriate memory B cells for increased periods of time following initial exposure of a subject to the antigen. Methods herein also include antibodies (and peptides generated from the sequences of such antibodies) generated using genetic material obtained from memory B cells captured using the methods disclosed herein.

Described herein are human antibodies against MHC class I polypeptide-related sequence A (MICA). These human antibodies against MICA were identified from patients who had received a cell-based cancer vaccine (GM-CSF transduced autologous tumor cells) by methods that entail the use of tetrameric antigens.

In some instances, the disclosure provides methods for specifically obtaining or targeting antibodies with therapeutic potential from select human subjects and therapeutic compositions resulting therefrom. These methods can include: obtaining or targeting immune cells in a human subject, wherein immune cells include but are not limited to, for example, B cells and/or memory B cells, isolating or purifying genetic material (e.g., DNA and/or mRNA) from the obtained or targeted immune cells, and using the isolated or purified genetic material to produce therapeutic compositions, e.g., therapeutic compositions disclosed herein. Further description of the methods is provided under the section entitled "Methods," below.

In some instances, the disclosure provides therapeutic compositions (e.g., including therapeutic peptides, including antibodies, antibody fragments, antibody derivatives, and/or antibody conjugates) related to antibodies present in subjects that have or had a condition or disease and that exhibited a positive immune response towards the condition or disease.

Therapeutic Compositions

In some instances, therapeutic compositions herein can interact with (e.g., bind, bind specifically and/or bind immunospecifically) binding partners (e.g., an immunogen(s), antigen(s), and/or epitope(s)) related to a disease or condition, wherein interaction between the therapeutic composition and the binding partners results in a positive immune response towards the condition or disease (e.g., a decrease in the level of disease or symptoms thereof in a subject).

In some instances, therapeutic compositions can include peptides that include (e.g., comprise, consist essentially of, or consist of) at least one (e.g., one, two, three, four, five, and/or six) complementarity determining region (CDR) of the variable heavy chain ($V_H$) and/or variable light chain ($V_L$) of antibody ID 1, 6, 7, 8, 9 11 or 12, shown in Table 1.

In some instances, therapeutic compositions can include peptides that include (e.g., comprise, consist essentially of, or consist of) at least one (e.g., one, two, three, four, five, and/or six) complementarity determining region (CDR) of the variable heavy chain ($V_H$) and/or variable light chain ($V_L$) of antibody ID 1, 6, 7, 8, 9 11 or 12, shown in Table 1, and that interact with (e.g., bind, bind specifically and/or bind immunospecifically) to MHC class I polypeptide-related sequence A (MICA (e.g., UniGene Hs.130838)) (e.g., soluble MICA (sMICA)), including epitopes thereof.

In some instances, therapeutic compositions can include peptides that include at least one CDR of the $V_H$ and/or $V_L$ of antibody ID 1, 6, 7, 8, 9, 11 or 12 shown in Table 1, wherein the peptide binds (e.g., binds specifically and/or binds immunospecifically) to MICA (e.g., human MICA (e.g., soluble MICA (sMICA))). In some instances, peptides can include at least two CDRs, wherein the at least two CDRs are CDRs shown in Table 1 for different antibodies. In other words, CDRs (and FRs and/or AA sequences) shown in Table 1 for antibodies IDs 1, 6, 7, 8, 9, 11 or 12 are interchangeable and can be combined to generate peptides, so long as the peptides bind (e.g., bind specifically and/or bind immunospecifically) to MICA (e.g., human MICA (e.g., soluble MICA (sMICA))). In some instances, such peptides include CDR3 of the $V_H$ and/or $V_L$ of antibody ID 1, 6, 7, 8, 9, 11 or 12 shown in Table 1. In some instances, such peptides include CDR3 of the $V_H$ and $V_L$ of antibody ID 1, 6, 7, 8, 9 and/or 11 and CDR1 and/or CDR2 of the $V_H$ and/or $V_L$ of antibody ID 1, 6, 7, 8, 9, 11 or 12 shown in Table 1. In some instances, such peptides include CDR1, CDR2, and CDR3 of the $V_H$ and/or $V_L$ of antibody ID 1, 6, 7, 8, 9, 11 or 12. In some instances, such peptides include CDR1, CDR2, and CDR3 of the $V_H$ and/or $V_L$ of antibody ID 1, 6, 7, 8, 9, 11 or 12 and at least one of FR1 FR2 FR3, and/or FR4 of the $V_H$ and/or $V_L$ of antibody ID 1, 6, 7, 8, 9, 11 or 12, shown in Table 1. In some instances, such peptides include one of SEQ ID NO: 2, 77, 96, 113, 131, 150 or 168 and/or one of SEQ ID NO: 11, 79, 98, 115, 133, 152 or 170. In each instance, the peptide can bind (e.g., bind specifically and/or bind immunospecifically) to MICA (e.g., human MICA (e.g., soluble MICA (sMICA))). In some instances, the affinity of binding between the peptides and MICA can be between about 0.1 nM to 1 μM, for example, about 10 nM.

In some instances, therapeutic compositions can include peptides that include at least one CDR of the $V_H$ and/or $V_L$ of antibody ID 1 shown in Table 1, wherein the peptide binds (e.g., binds specifically and/or binds immunospecifically) to MICA (e.g., human MICA (e.g., soluble MICA (sMICA))). In some instances, such peptides include CDR3 of the $V_H$ and/or $V_L$ of antibody ID 1 shown in Table 1. In some instances, such peptides include CDR3 of the $V_H$ and $V_L$ of antibody ID 1 and CDR1 and/or CDR2 of the $V_H$ and/or $V_L$ of antibody ID 1 shown in Table 1. In some instances, such peptides include CDR1, CDR2, and CDR3 of the $V_H$ and/or $V_L$ of antibody ID 1. In some instances, such peptides include CDR1, CDR2, and CDR3 of the $V_H$ and/or $V_L$ of antibody ID 1 and at least one of FR1 FR2 FR3, and/or FR4 of the $V_H$ and/or $V_L$ of antibody ID 1, shown in Table 1. In some instances, such peptides include SEQ ID NO:2 and/or SEQ ID NO:11. In each instance, the peptide can bind (e.g., bind specifically and/or bind immunospecifically) to MICA (e.g., human MICA (e.g., soluble MICA (sMICA))). In some instances, the affinity of binding between the peptides and MICA can be between about 0.1 nM to 1 μM, for example, about 10 nM.

In some instances, therapeutic compositions can include peptides that include at least one CDR of the $V_H$ and/or $V_L$ of antibody ID 6 shown in Table 1, wherein the peptide binds (e.g., binds specifically and/or binds immunospecifically) to MICA (e.g., human MICA (e.g., soluble MICA (sMICA))). In some instances, such peptides include CDR3 of the $V_H$ and/or $V_L$ of antibody ID 6 shown in Table 1. In some instances, such peptides include CDR3 of the $V_H$ and $V_L$ of antibody ID 6 and CDR1 and/or CDR2 of the $V_H$ and/or $V_L$ of antibody ID 6 shown in Table 1. In some instances, such peptides include CDR1, CDR2, and CDR3 of the $V_H$ and/or $V_L$ of antibody ID 6. In some instances, such peptides include CDR1, CDR2, and CDR3 of the $V_H$ and/or $V_L$ of antibody ID 6 and at least one of FR1, FR2, FR3, and/or FR4 of the $V_H$ and/or $V_L$ of antibody ID 6, shown in Table 1. In some instances, such peptides include SEQ ID NO:77 and/or SEQ ID NO:79. In each instance, the peptide can bind (e.g., bind specifically and/or bind immunospecifically) to MICA (e.g., human MICA (e.g., soluble MICA (sMICA))). In some instances, the affinity of binding between the peptides and MICA can be between about 0.1 nM to 1 μM, between about 50 nM and 200 nM, or between 1 nM and 20 nM, for example, 500 nM or less, 400 nM or less, 300 nM or less, 200 nM or less, 100 nM or less, 50 nM or less, 10 nM or less, 5 nM or less, 1 nM, 0.5 nM or less, 0.4 nM or less, 0.3 nM or less, 0.2 nM or less, or 0.10 nM or less.

In some instances, therapeutic compositions can include peptides that include at least one CDR of the $V_H$ and/or $V_L$ of antibody ID 7 shown in Table 1, wherein the peptide binds (e.g., binds specifically and/or binds immunospecifically) to MICA (e.g., human MICA (e.g., soluble MICA (sMICA))). In some instances, such peptides include CDR3 of the $V_H$ and/or $V_L$ of antibody ID 7 shown in Table 1. In some instances, such peptides include CDR3 of the $V_H$ and $V_L$ of antibody ID 7 and CDR1 and/or CDR2 of the $V_H$ and/or $V_L$ of antibody ID 7 shown in Table 1. In some instances, such peptides include CDR1, CDR2, and CDR3 of the $V_H$ and/or $V_L$ of antibody ID 7. In some instances, such peptides include CDR1, CDR2, and CDR3 of the $V_H$ and/or $V_L$ of antibody ID 7 and at least one of FR1, FR2, FR3, and/or FR4 of the $V_H$ and/or $V_L$ of antibody ID 7, shown in Table 1. In some instances, such peptides include SEQ ID NO:96 and/or SEQ ID NO:98. In each instance, the peptide can bind (e.g., bind specifically and/or bind immunospecifically) to MICA (e.g., human MICA (e.g., soluble MICA (sMICA))). In some instances, the affinity of binding between the peptides and MICA can be between about 0.1 nM to 1 μM, between about 50 nM and 200 nM, or between 1 nM and 20 nM, for example, 500 nM or less, 400 nM or less, 300 nM or less, 200 nM or less, 100 nM or less, 50 nM or less, 10 nM or less, 5 nM or less, 1 nM, 0.5 nM or less, 0.4 nM or less, 0.3 nM or less, 0.2 nM or less, or 0.10 nM or less.

In some instances, therapeutic compositions can include peptides that include at least one CDR of the $V_H$ and/or $V_L$ of antibody ID 8 shown in Table 1, wherein the peptide binds (e.g., binds specifically and/or binds immunospecifically) to MICA (e.g., human MICA (e.g., soluble MICA (sMICA))). In some instances, such peptides include CDR3 of the $V_H$ and/or $V_L$ of antibody ID 8 shown in Table 1. In some instances, such peptides include CDR3 of the $V_H$ and $V_L$ of antibody ID 8 and CDR1 and/or CDR2 of the $V_H$ and/or $V_L$ of antibody ID 8 shown in Table 1. In some instances, such peptides include CDR1, CDR2, and CDR3 of the $V_H$ and/or $V_L$ of antibody ID 8. In some instances, such peptides include CDR1, CDR2, and CDR3 of the $V_H$ and/or $V_L$ of antibody ID 8 and at least one of FR1, FR2, FR3, and/or FR4 of the $V_H$ and/or $V_L$ of antibody ID 8, shown in Table 1. In some instances, such peptides include SEQ ID NO:113 and/or SEQ ID NO:115. In each instance, the peptide can bind (e.g., bind specifically and/or bind immunospecifically) to MICA (e.g., human MICA (e.g., soluble MICA (sMICA))). In some instances, the affinity of binding between the peptides and MICA can be between about 0.1 nM to 1 μM, between about 50 nM and 200 nM, or between 1 nM and 20 nM, for example, 500 nM or less, 400 nM or less, 300 nM or less, 200 nM or less, 100 nM or less, 50 nM or less, 10 nM or less, 5 nM or less, 1 nM, 0.5 nM or less, 0.4 nM or less, 0.3 nM or less, 0.2 nM or less, or 0.10 nM or less.

In some instances, therapeutic compositions can include peptides that include at least one CDR of the $V_H$ and/or $V_L$ of antibody ID 9 shown in Table 1, wherein the peptide binds (e.g., binds specifically and/or binds immunospecifically) to MICA (e.g., human MICA (e.g., soluble MICA (sMICA))). In some instances, such peptides include CDR3 of the $V_H$ and/or $V_L$ of antibody ID 9 shown in Table 1. In some instances, such peptides include CDR3 of the $V_H$ and $V_L$ of antibody ID 9 and CDR1 and/or CDR2 of the $V_H$ and/or $V_L$ of antibody ID 9 shown in Table 1. In some instances, such peptides include CDR1, CDR2, and CDR3 of the $V_H$ and/or $V_L$ of antibody ID 9. In some instances, such peptides include CDR1, CDR2, and CDR3 of the $V_H$ and/or $V_L$ of antibody ID 9 and at least one of FR1, FR2, FR3, and/or FR4 of the $V_H$ and/or $V_L$ of antibody ID 9, shown in Table 1. In some instances, such peptides include SEQ ID NO:131 and/or SEQ ID NO:133. In each instance, the peptide can bind (e.g., bind specifically and/or bind immunospecifically) to MICA (e.g., human MICA (e.g., soluble MICA (sMICA))). In some instances, the affinity of binding between the peptides and MICA can be between about 0.1 nM to 1 μM, between about 50 nM and 200 nM, or between 1 nM and 20 nM, for example, 500 nM or less, 400 nM or less, 300 nM or less, 200 nM or less, 100 nM or less, 50 nM or less, 10 nM or less, 5 nM or less, 1 nM, 0.5 nM or less, 0.4 nM or less, 0.3 nM or less, 0.2 nM or less, or 0.10 nM or less.

In some instances, therapeutic compositions can include peptides that include at least one CDR of the $V_H$ and/or $V_L$ of antibody ID 11 shown in Table 1, wherein the peptide binds (e.g., binds specifically and/or binds immunospecifically) to MICA (e.g., human MICA (e.g., soluble MICA (sMICA))). In some instances, such peptides include CDR3 of the VH and/or $V_L$ of antibody ID 11 shown in Table 1. In some instances, such peptides include CDR3 of the $V_H$ and $V_L$ of antibody ID 11 and CDR1 and/or CDR2 of the $V_H$ and/or $V_L$ of antibody ID 11 shown in Table 1. In some instances, such peptides include CDR1, CDR2, and CDR3 of the $V_H$ and/or $V_L$ of antibody ID 11. In some instances, such peptides include CDR1, CDR2, and CDR3 of the $V_H$ and/or $V_L$ of antibody ID 11 and at least one of FR1, FR2, FR3, and/or FR4 of the $V_H$ and/or $V_L$ of antibody ID 11, shown in Table 1. In some instances, such peptides include SEQ ID NO:150 and/or SEQ ID NO:152. In each instance, the peptide can bind (e.g., bind specifically and/or bind immunospecifically) to MICA (e.g., human MICA (e.g., soluble MICA (sMICA))). In some instances, the affinity of binding between the peptides and MICA can be between about 0.1 nM to 1 μM, between about 50 nM and 200 nM, or between 1 nM and 20 nM, for example, 500 nM or less, 400 nM or less, 300 nM or less, 200 nM or less, 100 nM or less, 50 nM or less, 10 nM or less, 5 nM or less, 1 nM, 0.5 nM or less, 0.4 nM or less, 0.3 nM or less, 0.2 nM or less, or 0.10 nM or less.

In some instances, therapeutic compositions can include peptides that include at least one CDR of the $V_H$ and/or $V_L$ of antibody ID 12 shown in Table 1, wherein the peptide binds (e.g., binds specifically and/or binds immunospecifically) to MICA (e.g., human MICA (e.g., soluble MICA (sMICA)). In some instances, such peptides include CDR3 of the $V_H$ and/or $V_L$ of antibody ID 12 shown in Table 1. In some instances, such peptides include CDR3 of the $V_H$ and $V_L$ of antibody ID 12 and CDR1 and/or CDR2 of the $V_H$ and/or $V_L$ of antibody ID 12 shown in Table 1. In some instances, such peptides include CDR1, CDR2, and CDR3 of the $V_H$ and/or $V_L$ of antibody ID 12. In some instances, such peptides include CDR1, CDR2, and CDR3 of the $V_H$ and/or $V_L$ of antibody ID 12 and at least one of FR1, FR2, FR3, and/or FR4 of the $V_H$ and/or $V_L$ of antibody ID 12, shown in Table 1. In some instances, such peptides include SEQ ID NO:168 and/or SEQ ID NO:170. In each instance, the peptide can bind (e.g., bind specifically and/or bind immunospecifically) to MICA (e.g., human MICA (e.g., soluble MICA (sMICA))). In some instances, the affinity of binding between the peptides and MICA can be between about 0.1 nM to 1 μM, between about 50 nM and 200 nM, or between 1 nM and 20 nM, for example, 500 nM or less, 400 nM or less, 300 nM or less, 200 nM or less, 100 nM or less, 50 nM or less, 10 nM or less, 5 nM or less, 1 nM, 0.5 nM or less, 0.4 nM or less, 0.3 nM or less, 0.2 nM or less, or 0.10 nM or less.

In some instances, therapeutic compositions can include peptides that include: SEQ ID NO: 2 and/or SEQ ID NO:11; SEQ ID NO: 77 and/or SEQ ID NO:79; SEQ ID NO: 96 and/or SEQ ID NO:98; SEQ ID NO: 113 and/or SEQ ID NO:115; SEQ ID NO: 131 and/or SEQ ID NO:133; SEQ ID NO: 150 and/or SEQ ID NO:152; and SEQ ID NO: 168 and/or 170.

TABLE 1

| ID | Target | $V_H$\|$V_L$ | FR1* | CDR1** | FR2* | CDR2** | FR3* | CDR3** | FR4* | A.A.[#] | Nuc. Acid [##] |
|---|---|---|---|---|---|---|---|---|---|---|---|
| 1 | Human MICA | $V_H$ | QVQLQQW GAGLLKP SETLAL TCAVS (SEQ ID NO: 3) | GGSFTD HY (SEQ ID NO: 4) | WSWIR QAPGK GLEWIG E (SEQ ID NO: 5) | INHSGV T (SEQ ID NO: 6) | NYNPS LKSRLT ISVDTS KSQFSL RLTSVT AADTA LYYC (SEQ ID NO: 7) | AKTG LYYD DVW GTFR PRGG FDS (SEQ ID NO: 8) | WGQGT LVTVSS (SEQ ID NO: 9) | SEQ ID NO: 2 (see FIG. 2) | SEQ ID NO: 1 (see FIG. 1) |
| | | $V_L$ | DIVMTQ SPD SLAVSL GERATI NCKSS (SEQ ID NO: 12) | QSILYSS D NKNY (SEQ ID NO: 13) | LAWYQ HKPGQP P KLLFY (SEQ ID NO: 14) | WAS (SEQ ID NO: 15) | IRESG VPDRF SGGGSG T DFTLT ISSLQA EDVAV YYC (SEQ ID NO: 16) | QQYYSP PCS (SEQ ID NO: 17) | FGQGTK LEIQ (SEQ ID NO: 18) | SEQ ID NO: 11 (see FIG. 4) | SEQ ID NO: 10 (see FIG. 3) |

TABLE 1-continued

| ID | Target | $V_H$\|$V_L$ | FR1* | CDR1** | FR2* | CDR2** | FR3* | CDR3** | FR4* | A.A.# | Nuc. Acid ## |
|---|---|---|---|---|---|---|---|---|---|---|---|
| 6 | Human MICA | $V_H$ | QVQLQESGPGLVEPSGTLSLTCTVS (SEQ ID NO: 80) | GGSISRSNW (SEQ ID NO: 81) | WSWVRQPPGEGLEWIGE (SEQ ID NO: 82) | IHHIGRS (SEQ ID NO: 84) | SYNPSLKSRVTMSVDKSQNQFSLRLTSVTAADTAVYY (SEQ ID NO: 85) | CAKNGYYAMDVW (SEQ ID NO: 86) | GQGTTVTVSS (SEQ ID NO: 83) | SEQ ID NO: 77 (see FIG. 10) | SEQ ID NO: 76 (see FIG. 11) |
| | | $V_L$ | EIVLTQSPGTLSLSPGERATLSCRAS (SEQ ID NO: 87) | QSVSSDF (SEQ ID NO: 88) | LAWYQQKPGQAPRLLIY (SEQ ID NO: 89) | ATS (SEQ ID NO: 90) | FRATGISDRFSGSGSGTDFSLTINRLEPEDFAVYY (SEQ ID NO: 91) | CQHYRSSPPWYTF (SEQ ID NO: 92) | AQGTKLDMRRTVAAPSV (SEQ ID NO: 93) | SEQ ID NO: 79 (see FIG. 13) | SEQ ID NO: 78 (see FIG. 12) |
| 7 | Human MICA | $V_H$ | QVQLQESGPGLVKPSGTLSLTCAVS (SEQ ID NO: 99) | GASITNGAW (SEQ ID NO: 100) | WSWVRQPPGKGLEWIGE (SEQ ID NO: 101) | IYLNGNT (SEQ ID NO: 102) | NSNPSLKSRVIISVDKSKNHFSLTLNSVTAADTAVYY (SEQ ID NO: 94) | CAKNAAYNLEFW (SEQ ID NO: 103) | GQGALVTVSS (SEQ ID NO: 104) | SEQ ID NO: 96 (see FIG. 15) | SEQ ID NO: 95 (see FIG. 14) |
| | | $V_L$ | EIVLTQSPGTLSLSPGERATLSCRAS (SEQ ID NO: 105) | QTVSSPY (SEQ ID NO: 106) | VAWYQQKRGQAPRLLIY (SEQ ID NO: 107) | GAS (SEQ ID NO: 108) | TRATGIPDRFSGSGSGTDFTLTISRLEPEDFAVYY (SEQ ID NO: 109) | CQQYDRSYYTF (SEQ ID NO: 110) | GQGTKLEIK (SEQ ID NO: 111) | SEQ ID NO: 98 (see FIG. 17) | SEQ ID NO: 97 (see FIG. 16) |
| 8 | Human MICA | $V_H$ | QVQLQESGPGLVKPSENLSLTCTVS (SEQ ID NO: 116) | DASMSDYH (SEQ ID NO: 117) | WSWIRQAAGKGLEWIGR (SEQ ID NO: 118) | MYSTGSP (SEQ ID NO: 119) | YYKPSLKGRVTMSIDTSKNQFSLKLASVTAADTAIYY (SEQ ID NO: 120) | CASGQHIGGWVPPDFW (SEQ ID NO: 121) | GQGTLVTVSS (SEQ ID NO: 122) | SEQ ID NO: 113 (see FIG. 19) | SEQ ID NO: 112 (see FIG. 18) |
| | | $V_L$ | DIVMTQTPLSSPVTLGQPASISCRSS (SEQ ID NO: 123) | EGLVYSDGDTY (SEQ ID NO: 124) | LSWFHQRPGQPPRLLIY (SEQ ID NO: 125) | KIS (SEQ ID NO: 126) | NRFSGVPDRFSGSGAGTDFTLKISRVEAEDVGVYY (SEQ ID NO: 127) | CMQATHFPWTF (SEQ ID NO: 128) | GQGTKVEVKR (SEQ ID NO: 129) | SEQ ID NO: 115 (see FIG. 21) | SEQ ID NO: 114 (see FIG. 20) |
| 9 | Human MICA | $V_H$ | EVQLLESGGGLVQPGGSLRLSCAAS (SEQ ID NO: 134) | GFTFSSYG (SEQ ID NO: 135) | LTWIRQAPGKGLEWVSS (SEQ ID NO: 136) | ISGSGNNT (SEQ ID NO: 137) | YYADSVKGRFTISRDKVKKTLYLQMDSLTVGDTAVYY (SEQ ID NO: 138) | CLGVGQ (SEQ ID NO: 139) | GHGIPVIVSS (SEQ ID NO: 140) | SEQ ID NO: 131 (see FIG. 23) | SEQ ID NO: 130 (see FIG. 22) |
| | | $V_L$ | DIVMTQTPLSSPVTLGQPASISCRSS (SEQ ID NO: 141) | QSLVHRDGNTY (SEQ ID NO: 142) | LSWFLQRPGQAPRLLIY (SEQ ID NO: 143) | RIS (SEQ ID NO: 144) | NRFSGVPDRFSGSGAGTDFTLKISRVEAEDVGVYY (SEQ ID NO: 145) | CMQATQIPNTF (SEQ ID NO: 146) | GQGTKLEIK (SEQ ID NO: 147) | SEQ ID NO: 133 (see FIG. 25) | SEQ ID NO: 132 (see FIG. 24) |

TABLE 1-continued

| ID | Target | $V_H$\|$V_L$ | FR1* | CDR1** | FR2* | CDR2** | FR3* | CDR3** | FR4* | A.A.# | Nuc. Acid ## |
|---|---|---|---|---|---|---|---|---|---|---|---|
| 11 | Human MICA | $V_H$ | QVQLQE SGPGLV RPSGTLS LTCAV (SEQ ID NO: 153) | SGGSID YSNW (SEQ ID NO: 154) | WGWVR QVPGKG LEWIG (SEQ ID NO: 155) | EVYHTG AT (SEQ ID NO: 156) | HYNPSL ERRCIIS VDKSN NQVSLQ LTSVTA ADSAIY Y (SEQ ID NO: 157) | CARERG THCDGN RCYYVF FDHW (SEQ ID NO: 158) | GQGIPV TVSS (SEQ ID NO: 159) | SEQ ID NO: 150 (see FIG. 37) | SEQ ID NO: 149 (see FIG. 36) |
| | | $V_L$ | DIVMTQ TPLSSPV TLGQPA SISCRS (SEQ ID NO: 160) | SESLVH WDGTT Y (SEQ ID NO: 161) | LSWFHQ RPGQPP RLLIY (SEQ ID NO: 162) | KVS (SEQ ID NO: 163) | NRFSGV PDRFSG SGAGTD FTLKISR VEADD VGIYY (SEQ ID NO: 164) | CMQATQ FPRTF (SEQ ID NO: 165) | GQGTKV EIKR (SEQ ID NO: 166) | SEQ ID NO: 152 (see FIG. 38) | SEQ ID NO: 151 (see FIG. 37) |
| 12 | Human MICA | $V_H$ | QVQLVQ SGAEVK KPGSSV RXSCRA S (SEQ ID NO: 171) | GGSSTT YA (SEQ ID NO: 172) | FXWVR QAPGQG LEWMG G (SEQ ID NO: 173) | IVPIFGT L (SEQ ID NO: 174) | KYAQK FQDRVT LTADKS TGTAY MELNSL RLDDTA VYY (SEQ ID NO: 175) | CARAIQ LEGRPF DHW (SEQ ID NO: 176) | GQGTQV TVS (SEQ ID NO: 177) | SEQ ID NO: 168 (see FIG. 51) | SEQ ID NO: 167 (see FIG. 50) |
| | | $V_L$ | DIQLTQS PSFLSAS VGDRVT ITCRAS (SEQ ID NO: 178) | QGITSY (SEQ ID NO: 179) | LAWYQ QKPGKA PKLLIY (SEQ ID NO: 180) | AAS (SEQ ID NO: 181) | ALQSGV PSRFSGR GSGTEF TLTISSL QPEDFA TYY (SEQ ID NO: 182) | CQQVNR GAAITF (SEQ ID NO: 183) | GHGTRL DIKR (SEQ ID NO: 184) | SEQ ID NO: 170 (see FIG. 53) | SEQ ID NO: 169 (see FIG. 52) |

*Sequences include sequences or variants with (e.g., with at least) 80%, 85%, 90%, 95%, 96%, 97%, 98, 99%, and/or 100% sequence identity to the sequences shown.
**Sequences can include one, two, three, four, five, less than five, or less than ten conservative amino acid modifications.
#Sequences include sequences or variants with (e.g., with at least) 80%, 85%, 90%, 95%, 96%, 97%, 98, 99%, and/or 100% sequence identity to the sequences shown, e.g., within regions corresponding to FR1, FR2, FR3, and/or FR4, and/or one, two, three, four, five, less than 5, or less than ten conservative amino acid modifications within regions corresponding to CDRs 1, 2, and/or 3.
Sequences include sequences or variants with (e.g., with at least) 80%, 85%, 90%, 95%, 96%, 97%, 98, 99%, and/or 100% sequence identity to the sequences shown, wherein the sequences encode the corresponding AA.
A.A.# shows the $V_H$ or $V_L$ amino acid sequence.
Nuc. Acid## shows the $V_H$ or $V_L$ nucleic acid sequence.
While CDR and FR regions are shown above, such regions can also be defined according to Kabat (Sequences of Proteins of Immunological Interest (National Institutes of Health, Bethesda, Md., 1987 and 1991)). Amino acid numbering of antibodies or antigen binding fragments is also according to that of Kabat.

A "peptide" refers to a chain comprising at least two consecutively linked amino acid residues, with no upper limit on the length of the chain. One or more amino acid residues in the protein may contain a modification such as, but not limited to, glycosylation, phosphorylation or disulfide bond formation. The term "peptide" is used interchangeabley herein with "polypeptide" and "protein".

In some instances, therapeutic compositions can include peptides, including for example, antibodies, including full length and/or intact antibodies, or antibody fragments. An "antibody" is an immunoglobulin molecule capable of specific binding to a target, such as a carbohydrate, polynucleotide, lipid, polypeptide, etc., through at least one antigen recognition site, located in the variable region of the immunoglobulin molecule. As used herein, the term "antibody" encompasses not only intact polyclonal or monoclonal antibodies, but also any antigen binding fragment (i.e., "antigen-binding portion") or single chain thereof, fusion proteins comprising an antibody, and any other modified configuration of the immunoglobulin molecule that comprises an antigen recognition site. An antibody includes an antibody of any class, such as IgG, IgA, or IgM (or sub-class thereof), and the antibody need not be of any particular class. Depending on the antibody amino acid sequence of the constant region of its heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA1 and IgA2. The heavy-chain constant regions that correspond to the different classes of immunoglobulins are called alpha, delta, epsilon, gamma, and mu, respectively. The subunit structures and three-dimensional configurations of different classes of immunoglobulins are well known.

Exemplary antibodies and antibody fragments include, but are not limited to, monoclonal antibodies (including full-length monoclonal antibodies), polyclonal antibodies, multispecific antibodies formed from at least two different epitope binding fragments (e.g., bispecific antibodies), camelised antibodies, chimeric antibodies, single-chain Fvs (scFv), single-chain antibodies, single domain antibodies, domain antibodies, Fab fragments, F(ab')2 fragments, antibody fragments that exhibit the desired biological activity (e.g. the antigen binding portion), disulfide-linked Fvs (dsFv), and anti-idiotypic (anti-Id) antibodies (including, e.g., anti-Id antibodies to antibodies of the invention), intrabodies, and epitope-binding fragments of any of the above. Antibodies or antibody fragments can be human or humanized. In certain embodiments, an antibody is a non-naturally occurring antibody, such as an antibody that comprises at most 1, 2, 3, 4, 5, 6, 7, 8, 9 or 10 amino acid differences (e.g., substitutions, additions, or deletions) relative to a naturally occurring antibody. The one or more amino acid differences may be in the light chain and/or in the heavy chain, and may be in one or more of the CDRs, in a framework region or in a constant region, e.g., in CL, CH1, hinge, CH2 or CH3.

Antibodies typically bind specifically to their cognate antigen with high affinity, reflected by a dissociation constant ($K_D$) of $10^{-5}$ to $10^{-11}$ M or less. Any $K_D$ greater than about $10^{-4}$ M is generally considered to indicate nonspecific binding. As used herein, an antibody that "binds specifically" to an antigen refers to an antibody that binds to the antigen and substantially identical antigens with high affinity, which means having a $K_D$ of $10^{-7}$ M or less, preferably $10^{-8}$ M or less, even more preferably $5\times10^{-9}$ M or less, and most preferably between $10^{-8}$ M and $10^{-10}$ M or less, but does not bind with high affinity to unrelated antigens. An antigen is "substantially identical" to a given antigen if it exhibits a high degree of sequence identity to the given antigen, for example, if it exhibits at least 80%, at least 90%, preferably at least 95%, more preferably at least 97%, or even more preferably at least 99% sequence identity to the sequence of the given antigen. By way of example, an antibody that binds specifically to human MICA may also have cross-reactivity with MICA antigens from certain primate species (e.g., cynomolgus MICA), but may not cross-react with MICA antigens from other species or with an antigen other than MICA.

Fragments of antibodies are suitable for use in the methods provided so long as they contain an antigen-binding portion of and retain the desired affinity and specificity of the full-length antibody. The term "antigen-binding portion" of an antibody (or simply "antibody portion"), as used herein, refers to one or more fragments of an antibody that retain the ability to specifically bind to an antigen (e.g., human MICA). Such "fragments" are, for example between about 8 and about 1500 amino acids in length, suitably between about 8 and about 745 amino acids in length, suitably about 8 to about 300, for example about 8 to about 200 amino acids, or about 10 to about 50 or 100 amino acids in length. Thus, a fragment of an anti-MICA antibody will retain an ability to bind to MICA, respectively, in the Fv portion and the ability to bind the Fc receptor on dendritic cells, macrophages, neutrophils, B-cells, and NK cells in the FC portion. Such fragments are characterized by properties similar to the corresponding full-length anti-MICA antibody, that is, the fragments will specifically bind a human MICA antigen, respectively, expressed on the surface of a human cell or the corresponding sMICA antigen that has been shed into the media.

It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the $V_L$, $V_H$, CL and CH1 domains; (ii) a $F(ab')_2$ fragment, a bivalent fragment comprising two Fab fragments linked by a disulfide bridge at the hinge region; (iii) a Fd fragment consisting of the $V_H$ and CH1 domains; (iv) a Fv fragment consisting of the $V_L$ and $V_H$ domains of a single arm of an antibody, (v) a dAb fragment (Ward et al., (1989) *Nature* 341:544-546), which consists of a $V_H$ domain; and (vi) an isolated complementarity determining region (CDR) or (vii) a combination of two or more isolated CDRs which may optionally be joined by a synthetic linker. Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al. (1988) *Science* 242:423-426; and Huston et al. (1988) *Proc. Natl. Acad. Sci. USA* 85:5879-5883). Such single chain antibodies are also intended to be encompassed within the term "antigen-binding portion" of an antibody. These antibody fragments are obtained using conventional techniques known to those with skill in the art, and the fragments are screened for utility in the same manner as are intact antibodies. Antigen-binding portions can be produced by recombinant DNA techniques, or by enzymatic or chemical cleavage of intact immunoglobulins.

An Fv fragment is an antibody fragment which contains a complete antigen recognition and binding site. This region consists of a dimer of one heavy and one light chain variable domain in tight association, which can be covalent in nature, for example in scFv. It is in this configuration that the three CDRs of each variable domain interact to define an antigen binding site on the surface of the $V_H$-$V_L$ dimer. Collectively, the six CDRs or a subset thereof confer antigen binding specificity to the antibody. However, even a single variable domain (or half of an Fv comprising only three CDRs specific for an antigen) can have the ability to recognize and bind antigen, although usually at a lower affinity than the entire binding site.

Single-chain Fv or (scFv) antibody fragments comprise the $V_H$ and $V_L$ domains of antibody, wherein these domains are present in a single polypeptide chain. Generally the Fv polypeptide further comprises a polypeptide linker between the $V_H$ and $V_L$ domains, which enables the scFv to form the desired structure for antigen binding.

The Fab fragment contains a variable and constant domain of the light chain and a variable domain and the first constant domain (CH1) of the heavy chain. F(ab')2 antibody fragments comprise a pair of Fab fragments which are generally covalently linked near their carboxy termini by hinge cysteines between them. Other chemical couplings of antibody fragments are also known in the art.

A "bispecific" or "bifunctional antibody" is an artificial hybrid antibody having two different heavy/light chain pairs and two different binding sites. Bispecific antibodies can be produced by a variety of methods including fusion of hybridomas or linking of Fab' fragments. See, e.g., Songsivilai & Lachmann, *Clin. Exp. Immunol.* 79:315-321 (1990); Kostelny et al., *J. Immunol.* 148, 1547-1553 (1992).

Diabodies are small antibody fragments with two antigen-binding sites, which fragments comprise a $V_H$ connected to a $V_L$ in the same polypeptide chain ($V_H$ and $V_L$). By using a linker that is too short to allow pairing between the two domains on the same chain, the domains are forced to pair with the complementary domains of another chain and create two antigen-binding sites.

Linear antibodies comprise a pair of tandem Fd segments ($V_H$-CH1-$V_H$-CH1) which, together with complementary light chain polypeptides, form a pair of antigen binding regions. Linear antibodies can be bispecific or monospecific.

Antibodies and antibody fragments of the present disclosure can be modified in the Fc region to provide desired effector functions or serum half-life. In some instances, the Fc region can be conjugated to PEG or albumin to increase the serum half-life, or some other conjugation that results in the desired effect. Alternatively, where it is desirable to eliminate or reduce effector function, so as to minimize side effects or therapeutic complications, certain other Fc regions may be used.

Human and humanized antibodies include antibodies having variable and constant regions derived from (or having the same amino acid sequence as those derived from) human germline immunoglobulin sequences. Human antibodies may include amino acid residues not encoded by human germline immunoglobulin sequences (e.g., mutations introduced by random or site-specific mutagenesis in vitro or by somatic mutation in vivo), for example in the CDRs and in particular CDR3. The term "recombinant human antibody," as used herein, includes all human antibodies that are prepared, expressed, created or isolated by recombinant means, such as (a) antibodies isolated from an animal (e.g., a mouse) that is transgenic or transchromosomal for human immunoglobulin genes or a hybridoma prepared therefrom, (b) antibodies isolated from a host cell transformed to express the antibody, e.g., from a transfectoma, (c) antibodies isolated from a recombinant, combinatorial human antibody library, and (d) antibodies prepared, expressed, created or isolated by any other means that involve splicing of human immunoglobulin gene sequences to other DNA sequences. Such recombinant human antibodies comprise variable and constant regions that utilize particular human germline immunoglobulin sequences are encoded by the germline genes, but include subsequent rearrangements and mutations which occur, for example, during antibody maturation. As known in the art (see, e.g., Lonberg (2005) Nature Biotech. 23(9):1117-1125), the variable region contains the antigen binding domain, which is encoded by various genes that rearrange to form an antibody specific for a foreign antigen. In addition to rearrangement, the variable region can be further modified by multiple single amino acid changes (referred to as somatic mutation or hypermutation) to increase the affinity of the antibody to the foreign antigen. The constant region will change in further response to an antigen (i.e., isotype switch). Therefore, the rearranged and somatically mutated nucleic acid molecules that encode the light chain and heavy chain immunoglobulin polypeptides in response to an antigen may not have sequence identity with the original nucleic acid molecules, but instead will be substantially identical or similar (i.e., have at least 80% identity).

A "human" antibody (HuMAb) refers to an antibody having variable regions in which both the framework and CDR regions are derived from human germline immunoglobulin sequences. Furthermore, if the antibody contains a constant region, the constant region also is derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences. The terms "human" antibodies and "fully human" antibodies and are used synonymously.

A "humanized" antibody refers to an antibody in which some, most or all of the amino acids outside the CDR domains of a non-human antibody are replaced with corresponding amino acids derived from human immunoglobulins. In one embodiment of a humanized form of an antibody, some, most or all of the amino acids outside the CDR domains have been replaced with amino acids from human immunoglobulins, whereas some, most or all amino acids within one or more CDR regions are unchanged. Small additions, deletions, insertions, substitutions or modifications of amino acids are permissible as long as they do not abrogate the ability of the antibody to bind to a particular antigen. A "humanized" antibody retains an antigenic specificity similar to that of the original antibody.

A "chimeric antibody" refers to an antibody in which the variable regions are derived from one species and the constant regions are derived from another species, such as an antibody in which the variable regions are derived from a mouse antibody and the constant regions are derived from a human antibody.

The term "epitope" as used herein refers to a protein determinant capable of binding to an antibody. Epitopes usually consist of chemically active surface groupings of molecules such as amino acids or sugar side chains and usually have specific three dimensional structural characteristics, as well as specific charge characteristics. Epitopes can be formed both from non-contiguous amino acids juxtaposed by tertiary folding of a protein (e.g., conformational epitopes) or from contiguous amino acids (e.g., non-conformational epitopes). Conformational and non-conformational epitopes are distinguished in that the binding to the former but not the latter is lost in the presence of denaturing solvents. An epitope typically includes at least 3, 4, 5, 6, 7, 8, 9, 10, 11, 12, 13, 14 or 15 amino acids in a unique spatial conformation. Methods for determining what epitopes are bound by a given antibody (i.e., epitope mapping) are well known in the art and include, for example, immunoblotting and immunoprecipitation assays, wherein overlapping or contiguous peptides from (e.g., from MICA) are tested for reactivity with a given antibody (e.g., anti-MICA antibody). Methods of determining spatial conformation of epitopes include techniques in the art and those described herein, for example, x-ray crystallography and 2-dimensional nuclear magnetic resonance (see, e.g., *Epitope Mapping Protocols in Methods in Molecular Biology*, Vol. 66, G. E. Morris, Ed. (1996)).

The term "epitope mapping" refers to the process of identification of the molecular determinants for antibody-antigen recognition.

The term "binds to an epitope" or "recognizes an epitope" with reference to an antibody or antibody fragment refers to continuous or discontinuous segments of amino acids within an antigen. Those of skill in the art understand that the terms do not necessarily mean that the antibody or antibody fragment is in direct contact with every amino acid within an epitope sequence.

The term "binds to the same epitope" with reference to two or more antibodies means that the antibodies bind to the same, overlapping or encompassing continuous or discontinuous segments of amino acids. Those of skill in the art understand that the phrase "binds to the same epitope" does not necessarily mean that the antibodies bind to or contact exactly the same amino acids. The precise amino acids which the antibodies contact can differ. For example, a first antibody can bind to a segment of amino acids that is completely encompassed by the segment of amino acids bound by a second antibody. In another example, a first antibody binds one or more segments of amino acids that significantly overlap the one or more segments bound by the second antibody. For the purposes herein, such antibodies are considered to "bind to the same epitope."

Accordingly, also, encompassed by the present invention are antibodies that bind to an epitope on MICA which comprises all or a portion (e.g., 3, 4, 5, 6, 7, 8, 9, or 10 amino acids, continuous or discontinuous) of an epitope recognized by the particular antibodies described herein (e.g., the same or an overlapping region or a region between or spanning the region).

Techniques for determining antibodies that bind to the "same epitope on MICA" with the antibodies described herein include, for example, epitope mapping methods, such as, x-ray analyses of crystals of antigen: antibody complexes which provides atomic resolution of the epitope. Other methods monitor the binding of the antibody to antigen fragments or mutated variations of the antigen where loss of binding due to a modification of an amino acid residue within the antigen sequence is often considered an indication of an epitope component. In addition, computational combinatorial methods for epitope mapping can also be used. These methods rely on the ability of the antibody of interest to affinity isolate specific short peptides from combinatorial phage display peptide libraries. The peptides are then regarded as leads for the definition of the epitope corresponding to the antibody used to screen the peptide library. For epitope mapping, computational algorithms have also been developed which have been shown to map conformational discontinuous epitopes.

Also encompassed by the present invention are antibodies that compete for binding to MICA with the antibodies described herein. Antibodies that recognize the same epitope or compete for binding can be identified using routine techniques. Such techniques include, for example, an immunoassay, which shows the ability of one antibody to block the binding of another antibody to a target antigen, i.e., a competitive binding assay. Competitive binding is determined in an assay in which the immunoglobulin under test inhibits specific binding of a reference antibody to a common antigen, such as MICA. Numerous types of competitive binding assays are known, for example: solid phase direct or indirect radioimmunoassay (RIA), solid phase direct or indirect enzyme immunoassay (EIA), sandwich competition assay (see Stahli et al., *Methods in Enzymology* 9:242 (1983)); solid phase direct biotin-avidin EIA (see Kirkland et al., *J. Immunol.* 137:3614 (1986)); solid phase direct labeled assay, solid phase direct labeled sandwich assay (see Harlow and Lane, *Antibodies: A Laboratory Manual*, Cold Spring Harbor Press (1988)); solid phase direct label RIA using I-125 label (see Morel et al., *Mol. Immunol.* 25(1):7 (1988)); solid phase direct biotin-avidin EIA (Cheung et al., *Virology* 176:546 (1990)); and direct labeled RIA. (Moldenhauer et al., *Scand. J. Immunol.* 32:77 (1990)). Typically, such an assay involves the use of purified antigen bound to a solid surface or cells bearing either of these, an unlabeled test immunoglobulin and a labeled reference immunoglobulin. Competitive inhibition is measured by determining the amount of label bound to the solid surface or cells in the presence of the test immunoglobulin. Usually the test immunoglobulin is present in excess. Usually, when a competing antibody is present in excess, it will inhibit specific binding of a reference antibody to a common antigen by at least 50-55%, 55-60%, 60-65%, 65-70% 70-75% or more.

As used herein, the terms "specific binding," "selective binding," "selectively binds," and "specifically binds," refer to antibody binding to an epitope on a predetermined antigen. Typically, the antibody binds with an equilibrium dissociation constant ($K_D$) of approximately less than $10^{-7}$ M, such as approximately less than $10^{-8}$ M, $10^{-9}$ M or $10^{-10}$ M or even lower when determined by surface plasmon resonance (SPR) technology in a BIACORE 2000 instrument using recombinant MICA as the analyte and the antibody as the ligand and binds to the predetermined antigen with an affinity that is at least two-fold greater than its affinity for binding to a non-specific antigen (e.g., BSA, casein) other than the predetermined antigen or a closely-related antigen. Accordingly, an antibody that "specifically binds to human MICA" refers to an antibody that binds to human MICA with a $K_D$ of $10^{-7}$ M or less, such as approximately less than $10^{-8}$ M, $10^{-9}$ M or $10^{-10}$ M or even lower. An antibody that "cross-reacts with cynomolgus MICA" refers to an antibody that binds to cynomolgus MICA with a $K_D$ of $10^{-7}$ M or less, such as approximately less than $10^{-8}$ M, $10^{-9}$ M or $10^{-10}$ M or even lower. In certain embodiments, such antibodies that do not cross-react with MICA from a non-human species exhibit essentially undetectable binding against these proteins in standard binding assays.

The term "$k_{assoc}$" or "$k_a$", as used herein, is intended to refer to the association rate of a particular antibody-antigen interaction, whereas the term "$k_{dis}$" or "$k_d$," as used herein, is intended to refer to the dissociation rate of a particular antibody-antigen interaction. The term "$K_D$", as used herein, is intended to refer to the dissociation constant, which is obtained from the ratio of $k_d$ to $k_a$ (i.e., $k_d/k_a$) and is expressed as a molar concentration (M). $K_D$ values for antibodies can be determined using methods well established in the art. A preferred method for determining the $K_D$ of an antibody is by using surface plasmon resonance, preferably using a biosensor system such as a Biacore® system.

As used herein, the term "high affinity" for an IgG antibody refers to an antibody having a $K_D$ of $10^{-8}$ M or less, more preferably $10^{-9}$ M or less and even more preferably $10^{-10}$ M or less for a target antigen. However, "high affinity" binding can vary for other antibody isotypes. For example, "high affinity" binding for an IgM isotype refers to an antibody having a $K_D$ of $10^{-7}$ M or less, more preferably $10^{-8}$ M or less.

The term "EC50," as used herein, refers to the concentration of an antibody or an antigen-binding portion thereof, which induces a response, either in an in vitro or an in vivo assay, which is 50% of the maximal response, i.e., halfway between the maximal response and the baseline.

The term "binds to immobilized MICA," refers to the ability of an antibody of the invention to bind to MICA, for example, expressed on the surface of a cell or which is attached to a solid support.

The term "cross-reacts," as used herein, refers to the ability of an antibody of the invention to bind to MICA from a different species. For example, an antibody of the present invention which binds human MICA may also bind another species of MICA (e.g., cynomolgus MICA). As used herein, cross-reactivity is measured by detecting a specific reactivity with purified antigen in binding assays (e.g., SPR, ELISA) or binding to, or otherwise functionally interacting with, cells physiologically expressing MICA. Methods for determining cross-reactivity include standard binding assays as described herein, for example, by Biacore™ surface plasmon resonance (SPR) analysis using a Biacore™ 2000 SPR instrument (Biacore AB, Uppsala, Sweden), or flow cytometric techniques.

A "CDR" of a variable domain are amino acid residues within the hypervariable region that are identified in accordance with the definitions of the Kabat, Chothia, the cumulation of both Kabat and Chothia, AbM, contact, and/or conformational definitions or any method of CDR determination well known in the art. Antibody CDRs may be identified as the hypervariable regions originally defined by Kabat et al. See, e.g., Kabat et al., 1992, Sequences of Proteins of Immunological Interest, 5th ed., Public Health Service, NIH, Washington D.C. The positions of the CDRs may also be identified as the structural loop structures originally described by Chothia and others. See, e.g., Chothia et al., 1989, Nature 342:877-883. Other approaches to CDR identification include the "AbM definition," which is a compromise between Kabat and Chothia and is derived using Oxford Molecular's AbM antibody modeling software (now Accelrys®), or the "contact definition" of CDRs based on observed antigen contacts, set forth in MacCallum et al., 1996, J. Mol. Biol., 262:732-745. In another approach, referred to herein as the "conformational definition" of CDRs, the positions of the CDRs may be identified as the residues that make enthalpic contributions to antigen binding. See, e.g., Makabe et al., 2008, Journal of Biological Chemistry, 283:1156-1166. Still other CDR boundary definitions may not strictly follow one of the above approaches, but will nonetheless overlap with at least a portion of the Kabat CDRs, although they may be shortened or lengthened in light of prediction or experimental findings that particular residues or groups of residues or even entire CDRs do not significantly impact antigen binding. As used herein, a CDR may refer to CDRs defined by any approach known in the art, including combinations of approaches. The methods used herein may utilize CDRs defined according to any of these approaches. For any given embodiment containing more than one CDR, the CDRs may be defined in accordance with any of Kabat, Chothia, extended, AbM, contact, and/or conformational definitions.

In some instances, amino acid sequences of the peptides disclosed herein can be modified and varied to create peptide variants (e.g., peptides with a defined sequence homology to the peptides disclosed herein), for example, so long as the antigen binding property of the peptide variant is maintained or improved relative to the unmodified peptide (antigen binding properties of any modified peptide can be assessed using the in vitro and/or in vivo assays described herein and/or techniques known in the art).

While peptide variants are generally observed and discussed at the amino acid level, the actual modifications are typically introduced or performed at the nucleic acid level. For example, variants with 80%, 85%, 90%, 95%, 96%, 97%, 98, or 99% amino acid sequence identity to the peptides shown in Table 1 can be generated by modifying the nucleic acids encoding SEQ ID NOs:1, 10, 76, 78, 95, 97, 112, 114, 130, 132, 149, 151, 167 and/or 169 or portions/fragments thereof, using techniques (e.g., cloning techniques) known in the art and/or that are disclosed herein.

Amino acid sequence modifications typically fall into one or more of three classes: substitutional, insertional, or deletional modifications. Insertions include amino and/or terminal fusions as well as intra-sequence insertions of single or multiple amino acid residues. Insertions ordinarily will be smaller insertions than those of amino or carboxyl terminal fusions, for example, on the order of one to four residues. Deletions are characterized by the removal of one or more amino acid residues from the protein sequence. Typically, no more than about from 2 to 6 residues are deleted at any one site within the protein molecule. Amino acid substitutions are typically of single residues, but can occur at a number of different locations at once; insertions usually will be on the order of about from 1 to 10 amino acid residues; and deletions will range about from 1 to 30 residues. Deletions or insertions can be made in adjacent pairs, i.e., a deletion of 2 residues or insertion of 2 residues. Substitutions, deletions, insertions or any combination thereof may be combined to arrive at a final construct. The mutations must not place the sequence out of reading frame and preferably will not create complementary regions that could produce secondary mRNA structure. Substitutional modifications are those in which at least one residue has been removed and a different residue inserted in its place. In some instances, substitutions can be conservative amino acid substitutions. In some instances, peptides herein can include one or more conservative amino acid substitutions relative to a peptide shown in Table 1. For example, variants can include 1, 2, 3, 4, 5, 6, 7, 8, 9, 10, 11, 12, 13, 14, 15, 16, 17, 18, 19, 20, 20-30, 30-40, or 40-50 conservative amino acid substitutions relative to a peptide shown in Table 1. Alternatively, variants can include 50 or fewer, 40 or fewer, 30 or fewer, 20 or fewer, 10 or fewer, 9 or fewer, 8 or fewer, 7 or fewer, 6 or fewer, 5 or fewer, 4 or fewer, 3 or fewer, or 2 or fewer conservative amino acid substitutions relative to a peptide shown in Table 1. Such substitutions generally are made in accordance with the following Table 2 and are referred to as conservative substitutions. Methods for predicting tolerance to protein modification are known in the art (see, e.g., Guo et al., Proc. Natl. Acad. Sci., USA, 101(25):9205-9210 (2004)).

TABLE 2

Conservative Amino Acid Substitutions

| Amino Acid | Substitutions (others are known in the art) |
|---|---|
| Ala | Ser, Gly, Cys |
| Arg | Lys, Gln, His |
| Asn | Gln, His, Glu, Asp |
| Asp | Glu, Asn, Gln |
| Cys | Ser, Met, Thr |
| Gln | Asn, Lys, Glu, Asp, Arg |
| Glu | Asp, Asn, Gln |
| Gly | Pro, Ala, Ser |
| His | Asn, Gln, Lys |
| Ile | Leu, Val, Met, Ala |
| Leu | Ile, Val, Met, Ala |
| Lys | Arg, Gln, His |
| Met | Leu, Ile, Val, Ala, Phe |
| Phe | Met, Leu, Tyr, Trp, His |
| Ser | Thr, Cys, Ala |
| Thr | Ser, Val, Ala |
| Trp | Tyr, Phe |
| Tyr | Trp, Phe, His |
| Val | Ile, Leu, Met, Ala, Thr |

In some instances, substitutions are not conservative. For example, an amino acid in a peptide shown in Table 1 can be replaced with an amino acid that can alter some property or aspect of the peptide. In some instances, non-conservative amino acid substitutions can be made, e.g., to change the structure of a peptide, to change the binding properties of a peptide (e.g., to increase or decrease the affinity of binding of the peptide to an antigen and/or to alter increase or decrease the binding specificity of the peptide to the antigen).

In some instances, peptides and/or peptide variants can include or can be fragments of the peptides shown in Table 1. Such fragments can include, for example, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36 37, 38, 39, 40, 41, 42, 43, 44, 45, 46, 47, 48, 49, 50, 50-100, 101-150, fewer amino acids than the CDRs, FRs, and/or AAs shown in Table 1, e.g., so long as the fragments retain at least at portion of the binding properties of the full-length peptide (e.g., at least 50%, 60%, 70%, 80%, 90%, or 100% of the binding properties of the full-length peptide). Truncations can be made at the amino-terminus, the carboxy-terminus, and/or within the peptides herein.

In some instances, the interacting face of a peptide variant can be the same (e.g., substantially the same) as an unmodified peptide, e.g., to alter (e.g., increase or decrease), preserve, or maintain the binding properties of the peptide variant relative to the unmodified peptide. Methods for identifying the interacting face of a peptide are known in the art (Gong et al., BMC: Bioinformatics, 6:1471-2105 (2007); Andrade and Wei et al., Pure and Appl. Chem., 64(11):1777-1781 (1992); Choi et al., Proteins: Structure, Function, and Bioinformatics, 77(1):14-25 (2009); Park et al., BMC: and Bioinformatics, 10:1471-2105 (2009).

Those of skill in the art readily understand how to determine the identity of two polypeptides (e.g., an unmodified peptide and a peptide variant). For example, identity can be calculated after aligning the two sequences so that the identity is at its highest level. Another way of calculating identity can be performed by published algorithms. Optimal alignment of sequences for comparison may be conducted by the local identity algorithm of Smith and Waterman, Adv. Appl. Math, 2:482 (1981), by the identity alignment algorithm of Needleman and Wunsch, J. Mol. Biol. 48:443 (1970), by the search for similarity method of Pearson and Lipman, Proc. Natl. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by inspection.

The same types of identity can be obtained for nucleic acids by, for example, the algorithms disclosed in Zuker, Science 244:48-52 (1989); Jaeger et al., Proc. Natl. Acad. Sci. USA 86:7706-10 (1989); Jaeger et al., Methods Enzymol. 183:281-306 (1989), which are herein incorporated by reference for at least material related to nucleic acid alignment. It is understood that any of the methods typically can be used and that in certain instances the results of these various methods may differ, but the skilled artisan understands if identity is found with at least one of these methods, the sequences would be said to have the stated identity and to be disclosed herein.

The percent identity between two sequences is a function of the number of identical positions shared by the sequences (i.e., % homology=# of identical positions/total # of positions×100), taking into account the number of gaps, and the length of each gap, which need to be introduced for optimal alignment of the two sequences. The comparison of sequences and determination of percent identity between two sequences can be accomplished using a mathematical algorithm, as described in the non-limiting examples below.

The percent identity between two nucleotide sequences can be determined using the GAP program in the GCG software package (available at www.gcg.com), using a NWSgapdna.CMP matrix and a gap weight of 40, 50, 60, 70, or 80 and a length weight of 1, 2, 3, 4, 5, or 6. The percent identity between two nucleotide or amino acid sequences can also be determined using the algorithm of E. Meyers and W. Miller (CABIOS, 4:11-17 (1989)) which has been incorporated into the ALIGN program (version 2.0), using a PAM120 weight residue table, a gap length penalty of 12 and a gap penalty of4. In addition, the percent identity between two amino acid sequences can be determined using the Needleman and Wunsch (J. Mol. Biol. (48):444-453 (1970)) algorithm which has been incorporated into the GAP program in the GCG software package (available at www.gcg.com), using either a Blossum 62 matrix or a PAM250 matrix, and a gap weight of 16, 14, 12, 10, 8, 6, or 4 and a length weight of 1, 2, 3, 4, 5, or 6.

The nucleic acid and protein sequences of the present invention can further be used as a "query sequence" to perform a search against public databases to, for example, identify related sequences. Such searches can be performed using the NBLAST and XBLAST programs (version 2.0) of Altschul, et al. (1990) *J. Mol. Biol.* 215:403-10. BLAST nucleotide searches can be performed with the NBLAST program, score=100, wordlength=12 to obtain nucleotide sequences homologous to the nucleic acid molecules of the invention. BLAST protein searches can be performed with the XBLAST program, score=50, wordlength=3 to obtain amino acid sequences homologous to the protein molecules of the invention. To obtain gapped alignments for comparison purposes, Gapped BLAST can be utilized as described in Altschul et al., (1997) *Nucleic Acids Res.* 25(17):3389-3402. When utilizing BLAST and Gapped BLAST programs, the default parameters of the respective programs (e.g., XBLAST and NBLAST) can be used. See www.ncbi.nlm.nih.gov.

In some instances, as described in more detail under the methods section below, therapeutic compositions disclosed herein can be produced using genetic material (e.g., DNA and/or mRNA) isolated and/or purified from immune cells (e.g., B cells, including memory B cells) obtained using the methods disclosed herein. Once such genetic material has been obtained, methods for using it to produce the therapeutic compositions disclosed herein are known in the art and/or are summarized below.

In some instances, peptides can include a detectable label. As used herein, a "label" refers to a moiety that has at least one element, isotope, or functional group incorporated into the moiety which enables detection of the peptide to which the label is attached. Labels can be directly attached (i.e., via a bond) or can be attached by a linker (e.g., such as, for example, a cyclic or acyclic, branched or unbranched, substituted or unsubstituted alkylene; cyclic or acyclic, branched or unbranched, substituted or unsubstituted alkenylene; cyclic or acyclic, branched or unbranched, substituted or unsubstituted alkynylene; cyclic or acyclic, branched or unbranched, substituted or unsubstituted heteroalkylene; cyclic or acyclic, branched or unbranched, substituted or unsubstituted heteroalkenylene; cyclic or acyclic, branched or unbranched, substituted or unsubstituted heteroalkynylene; substituted or unsubstituted arylene; substituted or unsubstituted heteroarylene; or substituted or unsubstituted acylene, or any combination thereof, which can make up a linker). Labels can be attached to a peptide at any position that does not interfere with the biological activity or characteristic of the inventive polypeptide that is being detected.

Labels can include: labels that contain isotopic moieties, which may be radioactive or heavy isotopes, including, but not limited to, $^{2}H$, $^{3}H$, $^{13}C$, $^{14}C$, $^{15}N$, $^{31}P$, $^{32}P$, $^{35}S$, $^{67}Ga$, $^{99m}Tc$ (Tc-99m), $^{111}In$, $^{123}I$, $^{125}I$, $^{169}Yb$, and $^{186}Re$; labels that include immune or immunoreactive moieties, which may be antibodies or antigens, which may be bound to enzymes {e.g., such as horseradish peroxidase); labels that are colored, luminescent, phosphorescent, or include fluorescent moieties (e.g., such as the fluorescent label FITC); labels that have one or more photoaffinity moieties; labels that have ligand moieties with one or more known binding partners (such as biotin-streptavidin, FK506-FKBP, etc.).

In some instances, labels can include one or more photoaffinity moieties for the direct elucidation of intermolecular interactions in biological systems. A variety of known photophores can be employed, most relying on photoconversion of diazo compounds, azides, or diazirines to nitrenes or carbenes (see, e.g., Bayley, H., Photogenerated Reagents in Biochemistry and Molecular Biology (1983), Elsevier, Amsterdam, the entire contents of which are incorporated herein by reference). In certain embodiments of the invention, the photoaffinity labels employed are o-, m- and p-azidobenzoyls, substituted with one or more halogen moieties, including, but not limited to 4-azido-2,3,5,6-tetrafluorobenzoic acid.

Labels can also be or can serve as imaging agents. Exemplary imaging agents include, but are not limited to, those used in positron emissions tomography (PET), computer assisted tomography (CAT), single photon emission computerized tomography, x-ray, fluoroscopy, and magnetic resonance imaging (MRI); anti-emetics; and contrast agents. Exemplary diagnostic agents include but are not limited to, fluorescent moieties, luminescent moieties, magnetic moieties; gadolinium chelates (e.g., gadolinium chelates with DTPA, DTPA-BMA, DOTA and HP-DO3A), iron chelates, magnesium chelates, manganese chelates, copper chelates, chromium chelates, iodine-based materials useful for CAT and x-ray imaging, and radionuclides. Suitable radionuclides include, but are not limited to, $^{123}I$, $^{125}I$, $^{130}I$, $^{131}I$, $^{133}I$, $^{135}I$, $^{47}Sc$, $^{72}As$, $^{72}Se$, $^{90}Y$ $^{88}Y$ $^{97}Ru$, $^{100}Pd$, $^{101}mRh$, $^{119}Sb$, $^{128}Ba$, $^{197}Hg$, $^{211}At$, $^{212}Bi$, $^{212}Pb$, $^{109}Pd$, $^{111}In$, $^{67}Ga$, $^{68}Ga$, $^{67}Cu$, $^{75}Br$, $^{77}Br$, $^{99}mTc$, $^{14}C$, $^{13}N$, $^{15}0$, $^{32}P$, $^{33}P$, and $^{18}F$.

Fluorescent and luminescent moieties include, but are not limited to, a variety of different organic or inorganic small molecules commonly referred to as "dyes," "labels," or "indicators." Examples include, but are not limited to, fluorescein, rhodamine, acridine dyes, Alexa dyes, cyanine dyes, etc. Fluorescent and luminescent moieties may include a variety of naturally occurring proteins and derivatives thereof, e.g., genetically engineered variants. For example, fluorescent proteins include green fluorescent protein (GFP), enhanced GFP, red, blue, yellow, cyan, and sapphire fluorescent proteins, reef coral fluorescent protein, etc. Luminescent proteins include luciferase, aequorin and derivatives thereof. Numerous fluorescent and luminescent dyes and proteins are known in the art (see, e.g., U.S. Patent Publication 2004/0067503; Valeur, B., "Molecular Fluorescence: Principles and Applications," John Wiley and Sons, 2002; and Handbook of Fluorescent Probes and Research Products, Molecular Probes, 9th edition, 2002).

The term "purified" or "isolated" as used herein, refers to other molecules, e.g. polypeptide, nucleic acid molecule that have been identified and separated and/or recovered from a component of its natural environment. Thus, in one embodiment the antibodies of the invention are purified antibodies wherein they have been separated from one or more components of their natural environment.

Nucleic Acid Compositions

In some instances, the disclosure provides nucleotide sequences corresponding to (e.g., encoding) the disclosed peptides (e.g., disclosed in Table 1). These sequences include all degenerate sequences related to the disclosed peptides, i.e., all nucleic acids having a sequence that encodes one particular peptide and variants and derivatives thereof. Thus, while each particular nucleic acid sequence may not be written out herein, it is understood that each and every sequence is in fact disclosed and described herein through the disclosed polypeptide sequences.

In some instances, nucleic acids of the disclosed can include expression vectors. Examples of suitable vectors include, but are not limited to, plasmids, artificial chromosomes, such as BACs, YACs, or PACs, and viral vectors.

The provided vectors also can include, for example, origins of replication and/or markers. A marker gene can confer a selectable phenotype, e.g., antibiotic resistance, on a cell. The marker product is used to determine if the vector has been delivered to the cell and once delivered is being expressed. Examples of selectable markers for mammalian cells are dihydrofolate reductase (DHFR), thymidine kinase, neomycin, neomycin analog G418, hygromycin, puromycin, and blasticidin. When such selectable markers are successfully transferred into a mammalian host cell, the transformed mammalian host cell can survive if placed under selective pressure. Examples of other markers include, for example, the *E. coli* lacZ gene, green fluorescent protein (GFP), and luciferase. In addition, an expression vector can include a tag sequence designed to facilitate manipulation or detection (e.g., purification or localization) of the expressed polypeptide. Tag sequences, such as GFP, glutathione S-transferase (GST), polyhistidine, c-myc, hemagglutinin, or FLAG™ tag (Kodak; New Haven, Conn.) sequences typically are expressed as a fusion with the encoded polypeptide. Such tags can be inserted anywhere within the polypeptide including at either the carboxyl or amino terminus.

In some instances, the disclosure includes cells comprising the nucleic acids (e.g., vectors) and/or peptides disclosed herein. Cells can include, for example, eukaryotic and/or prokaryotic cells. In general, cells that can be used herein are commercially available from, for example, the American Type Culture Collection (ATCC), P.O. Box 1549, Manassas, Va. 20108. See also F. Ausubel et al., Current Protocols in Molecular Biology, John Wiley & Sons, New York, N.Y., (1998). Transformation and transfection methods useful in the generation of the cells disclosed herein are described, e.g., in F. Ausubel et al., Current Protocols in Molecular Biology, John Wiley & Sons, New York, N.Y., (1998).

Vector-mediated gene transfer has been shown to engineer targeted delivery of antibodies. (Balazs et al., *Nature.* 2011 Nov. 30; 481(7379):81-4) Accordingly, in one aspect, this disclosure provides methods and compositions are provided for delivering a polynucleotide encoding a peptide that immunospecifically bind to MICA of interest to a target cell using a virus. In the context of gene therapy, nucleic acid sequences encoding the peptide that immunospecifically bind to MICA may be delivered into cells via a vector (e.g., a viral vector, including but not limited to adenovirus, vaccinia virus or adeno-associated virus). For example, a protein such as an antibody or antibody fragment having specificity for a particular cell surface molecule may be attached to the surface of the virus, allowing the virus to target specific cells. Further, the virus may be engineered to contain nucleic acid sequences, such as promoters, which allow the virus to function in only particular cells, such as cancer cells.

In some instances, the disclosed therapeutic compositions can include a vector (e.g., expression vector, a viral vector, an adeno-associated virus vector) comprising a nucleic acid encoding a peptide that immunospecifically bind to MICA. In one aspect, the peptide that immunospecifically bind to MICA is an antibody or antibody fragment that immunospecifically bind to MICA. As described herein, antibodies and antibody fragments include, but are not limited to, monoclonal antibodies (including full-length monoclonal antibodies), polyclonal antibodies, multispecific antibodies formed from at least two different epitope binding fragments (e.g., bispecific antibodies), camelised antibodies, chimeric antibodies, single-chain Fvs (scFv), single-chain antibodies, single domain antibodies, domain antibodies, Fab fragments, F(ab')2 fragments, antibody fragments that exhibit the desired biological activity (e.g. the antigen binding portion), disulfide-linked Fvs (dsFv), and anti-idiotypic (anti-Id) antibodies (including, e.g., anti-Id antibodies to antibodies of the invention), intrabodies, and epitope-binding fragments of any of the above.

Accordingly, in one aspect, the disclosure provides vectors and cells which comprise a nucleotide sequence having at least about 75%, 80%, 90%, 95%, 99% or more, or complete (100%) sequence identity to SEQ ID NO: 1, 76, 95, 112, 130, 149 or 167. In some aspects, the nucleic acid sequence encodes a peptide comprising an amino acid sequences with at least 80%, 85%, 90%, 95%, 96%, 97%, 98, 99%, or 100% identity SEQ ID NO: 2, 77, 96, 113, 131, 150 or 167.

In one aspect, the vector can comprise a nucleotide sequence having at least about 75%, 80%, 90%, 95%, 99% or more, or complete (100%) sequence identity to SEQ ID NO:10, 78, 97, 114, 132, 151 or 169. In some aspects, the nucleic acid sequence encodes a peptide comprising an amino acid sequences with at least 80%, 85%, 90%, 95%, 96%, 97%, 98, 99%, or 100% identity SEQ ID NO11, 79, 98, 115, 133, 152 or 169.

In some embodiments, the disclosure provides compositions comprising nucleic acids encoding peptides that immunospecifically bind to MHC class I polypeptide-related sequence A (MICA), or an epitope thereon. In some aspects, the nucleic acids of the compositions encode the $V_H$ of antibody ID 1, 6, 7, 8, 9, 11 or 12 shown in Table 1 having 5 or fewer conservative amino acid substitutions. In some aspects, the nucleic acids of the compositions encode the $V_L$ of antibody ID 1, 6, 7, 8, 9, 11 or 12 shown in Table 1 having 5 or fewer conservative amino acid substitutions.

In some embodiments, a nucleic acid encoding a peptide described herein, e.g., a heavy or light chain of an antibody, is not a naturally occurring nucleic acid. A non-naturally occurring nucleic acid may comprise, e.g., at most 1, 2, 3, 4, 5, 6, 7, 8, 9 or 10 nucleotide differences (e.g., substitutions, additions, or deletions) relative to a naturally occurring nucleic acid.

In one aspect, the disclosure provides isolated nucleic acids comprising a nucleotide sequence at least about 75%, 80%, 90%, 95%, 99% or more, or complete (100%) sequence identity to SEQ ID NO: 1. In some aspects, the isolated nucleic acid sequence encodes a peptide comprising an amino acid sequences with at least 80%, 85%, 90%, 95%, 96%, 97%, 98, 99%, or 100% identity SEQ ID NO: 2. In another aspect, the disclosure provides isolated nucleic acids comprising a nucleotide sequence at least about 75%, 80%, 90%, 95%, 99% or more, or complete (100%) sequence identity to SEQ ID NO:10. In some aspects, the isolated nucleic acid sequence encodes a peptide comprising an amino acid sequence with at least 80%, 85%, 90%, 95%, 96%, 97%, 98, 99%, or 100% identity SEQ ID NO:11.

In one aspect, the disclosure provides isolated nucleic acids comprising a nucleotide sequence at least about 75%, 80%, 90%, 95%, 99% or more, or complete (100%) sequence identity to SEQ ID NO:76. In some aspects, the isolated nucleic acid sequence encodes a peptide comprising an amino acid sequences with at least 80%, 85%, 90%, 95%, 96%, 97%, 98, 99%, or 100% identity SEQ ID NO:77. In another aspect, the disclosure provides isolated nucleic acids comprising a nucleotide sequence at least about 75%, 80%, 90%, 95%, 99% or more, or complete (100%) sequence identity to SEQ ID NO:78. In some aspects, the isolated nucleic acid sequence encodes a peptide comprising an amino acid sequence with at least 80%, 85%, 90%, 95%, 96%, 97%, 98, 99%, or 100% identity SEQ ID NO:79.

In one aspect, the disclosure provides isolated nucleic acids comprising a nucleotide sequence at least about 75%, 80%, 90%, 95%, 99% or more, or complete (100%) sequence identity to SEQ ID NO:95. In some aspects, the isolated nucleic acid sequence encodes a peptide comprising an amino acid sequences with at least 80%, 85%, 90%, 95%, 96%, 97%, 98, 99%, or 100% identity SEQ ID NO:96. In another aspect, the disclosure provides isolated nucleic acids comprising a nucleotide sequence at least about 75%, 80%, 90%, 95%, 99% or more, or complete (100%) sequence identity to SEQ ID NO:97. In some aspects, the isolated nucleic acid sequence encodes a peptide comprising an amino acid sequence with at least 80%, 85%, 90%, 95%, 96%, 97%, 98, 99%, or 100% identity SEQ ID NO:98.

In one aspect, the disclosure provides isolated nucleic acids comprising a nucleotide sequence at least about 75%, 80%, 90%, 95%, 99% or more, or complete (100%) sequence identity to SEQ ID NO:112. In some aspects, the isolated nucleic acid sequence encodes a peptide comprising an amino acid sequences with at least 80%, 85%, 90%, 95%, 96%, 97%, 98, 99%, or 100% identity SEQ ID NO:113. In another aspect, the disclosure provides isolated nucleic acids comprising a nucleotide sequence at least about 75%, 80%, 90%, 95%, 99% or more, or complete (100%) sequence identity to SEQ ID NO:114. In some aspects, the isolated nucleic acid sequence encodes a peptide comprising an amino acid sequence with at least 80%, 85%, 90%, 95%, 96%, 97%, 98, 99%, or 100% identity SEQ ID NO:115.

In one aspect, the disclosure provides isolated nucleic acids comprising a nucleotide sequence at least about 75%, 80%, 90%, 95%, 99% or more, or complete (100%) sequence identity to SEQ ID NO:130. In some aspects, the isolated nucleic acid sequence encodes a peptide comprising an amino acid sequences with at least 80%, 85%, 90%, 95%, 96%, 97%, 98, 99%, or 100% identity SEQ ID NO:131. In another aspect, the disclosure provides isolated nucleic acids comprising a nucleotide sequence at least about 75%, 80%, 90%, 95%, 99% or more, or complete (100%) sequence identity to SEQ ID NO:132. In some aspects, the isolated nucleic acid sequence encodes a peptide comprising an amino acid sequence with at least 80%, 85%, 90%, 95%, 96%, 97%, 98, 99%, or 100% identity SEQ ID NO:133.

In one aspect, the disclosure provides isolated nucleic acids comprising a nucleotide sequence at least about 75%, 80%, 90%, 95%, 99% or more, or complete (100%) sequence identity to SEQ ID NO:149. In some aspects, the isolated nucleic acid sequence encodes a peptide comprising an amino acid sequences with at least 80%, 85%, 90%, 95%, 96%, 97%, 98, 99%, or 100% identity SEQ ID NO:150. In another aspect, the disclosure provides isolated nucleic acids comprising a nucleotide sequence at least about 75%, 80%, 90%, 95%, 99% or more, or complete (100%) sequence identity to SEQ ID NO:151. In some aspects, the isolated nucleic acid sequence encodes a peptide comprising an amino acid sequence with at least 80%, 85%, 90%, 95%, 96%, 97%, 98, 99%, or 100% identity SEQ ID NO:152.

In one aspect, the disclosure provides isolated nucleic acids comprising a nucleotide sequence at least about 75%, 80%, 90%, 95%, 99% or more, or complete (100%) sequence identity to SEQ ID NO:167. In some aspects, the isolated nucleic acid sequence encodes a peptide comprising an amino acid sequences with at least 80%, 85%, 90%, 95%, 96%, 97%, 98, 99%, or 100% identity SEQ ID NO:168. In another aspect, the disclosure provides isolated nucleic acids comprising a nucleotide sequence at least about 75%, 80%, 90%, 95%, 99% or more, or complete (100%) sequence identity to SEQ ID NO:169. In some aspects, the isolated nucleic acid sequence encodes a peptide comprising an amino acid sequence with at least 80%, 85%, 90%, 95%, 96%, 97%, 98, 99%, or 100% identity SEQ ID NO:170.

The term "nucleic acid" or "nucleic acid molecule", as used herein, is intended to include DNA molecules and RNA molecules. A nucleic acid molecule may be single-stranded or double-stranded, but preferably is double-stranded DNA.

An isolated nucleic acid can be, for example, a DNA molecule, provided one of the nucleic acid sequences normally found immediately flanking that DNA molecule in a naturally-occurring genome is removed or absent. Thus, an isolated nucleic acid includes, without limitation, a DNA molecule that exists as a separate molecule (e.g., a chemically synthesized nucleic acid, cDNA, or genomic DNA fragment produced by PCR or restriction endonuclease treatment) independent of other sequences as well as DNA that is incorporated into a vector, an autonomously replicating plasmid, a virus (e.g., a retrovirus, lentivirus, adenovirus, or herpes virus), or into the genomic DNA of a prokaryote or eukaryote. In addition, an isolated nucleic acid can include an engineered nucleic acid such as a recombinant DNA molecule that is part of a hybrid or fusion nucleic acid. A nucleic acid existing among hundreds to millions of other nucleic acids within, for example, cDNA libraries or genomic libraries, or gel slices containing a genomic DNA restriction digest, is not to be considered an isolated nucleic acid.

In calculating percent sequence identity, two sequences are aligned and the number of identical matches of nucleotides or amino acid residues between the two sequences is determined. The number of identical matches is divided by the length of the aligned region (i.e., the number of aligned nucleotides or amino acid residues) and multiplied by 100 to arrive at a percent sequence identity value. It will be appreciated that the length of the aligned region can be a portion of one or both sequences up to the full-length size of the shortest sequence. It also will be appreciated that a single sequence can align with more than one other sequence and hence, can have different percent sequence identity values over each aligned region. It is noted that the percent identity value is usually rounded to the nearest integer. For example, 78.1%, 78.2%, 78.3%, and 78.4% are rounded down to 78%, while 78.5%, 78.6%, 78.7%, 78.8%, and 78.9% are rounded up to 79%. It is also noted that the length of the aligned region is always an integer.

As used herein, the term "percent sequence identity" refers to the degree of identity between any given query sequence and a subject sequence. A percent identity for any query nucleic acid or amino acid sequence, e.g., a transcription factor, relative to another subject nucleic acid or amino acid sequence can be determined as follows.

The nucleic acids may be present in whole cells, in a cell lysate, or in a partially purified or substantially pure form. A nucleic acid is "isolated" or "rendered substantially pure" when purified away from other cellular components or other contaminants, e.g., other cellular nucleic acids or proteins, by standard techniques, including alkaline/SDS treatment, CsCl banding, column chromatography, agarose gel electrophoresis and others well known in the art. See, F. Ausubel, et al., ed. Current Protocols in Molecular Biology, Greene Publishing and Wiley Interscience, New York (1987).

The nucleic acid compositions of the present invention, while often in a native sequence (except for modified restriction sites and the like), from either cDNA, genomic or mixtures thereof may be mutated, in accordance with standard techniques to provide gene sequences. For coding sequences, these mutations, may affect amino acid sequence as desired. In particular, DNA sequences substantially homologous to or derived from native V, D, J, constant, switches and other such sequences described herein are contemplated (where "derived" indicates that a sequence is identical or modified from another sequence).

A nucleic acid is "operably linked" when it is placed into a functional relationship with another nucleic acid sequence. For instance, a promoter or enhancer is operably linked to a coding sequence if it affects the transcription of the sequence. With respect to transcription regulatory sequences, operably linked means that the DNA sequences being linked are contiguous and, where necessary to join two protein coding regions, contiguous and in reading frame. For switch sequences, operably linked indicates that the sequences are capable of effecting switch recombination.

The term "vector" as used herein refers to any molecule used to transfer a nucleic acid sequence to a host cell. In some aspects, an expression vector is utilized. An expression vector is a nucleic acid molecule that is suitable for transformation of a host cell and contains nucleic acid sequences that direct and/or control the expression of the transferred nucleic acid sequences. Expression includes, but is not limited to, processes such as transcription, translation, and splicing, if introns are present. In some aspects, a viral vector is utilized (e.g., a retrovirus, adenovirus, adeno-associated virus (AAV), herpes virus, and poxvirus, among others). It is understood in the art that many such viral vectors are available in the art. In yet other aspects, a non-viral plasmid vector may also be suitable in practicing the present invention. The vectors of the present invention may be constructed using standard recombinant techniques widely available to one skilled in the art. Such techniques may be found in common molecular biology references such as Sambrook et al., Molecular Cloning: A Laboratory Manual (2nd Edition, 1989).

The term "recombinant host cell" (or simply "host cell"), as used herein, is intended to refer to a cell into which a recombinant expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein.

Chimeric Antigen Receptors

In some instances, the invention provides chimeric antigen receptors (CARs) comprising peptides that immunospecifically bind to MICA and an intracellular T cell receptor signaling domain. (Kalos M, et al., Sci Transl Med. 2011 Aug. 10; 3 (95)) In some aspects, the CARs comprising peptides that immunospecifically bind to MICA, an extracellular hinge domain, a T cell receptor transmembrane domain, and an intracellular T cell receptor signaling domain. Further embodiments of the invention provide related nucleic acids, recombinant expression vectors, host cells, populations of cells, antibodies, or antigen binding portions thereof, and pharmaceutical compositions relating to the CARs of the invention.

A chimeric antigen receptor (CAR) is an artificially constructed hybrid protein or polypeptide containing the antigen binding domains of an antibody (scFv) linked to T-cell signaling domains. (Kalos M, et al., Sci Transl Med. 2011 Aug. 10; 3 (95)) Kalos et al. describes the generation of CAR T cells that target CD19 and demonstrates the CAR modified T-cells mediated potent antitumor effect in chronic lymphocytic leukemia patients. The engineered T-cells Characteristics of CARs include their ability to redirect T-cell specificity and reactivity toward a selected target in a non-MHC-restricted manner, exploiting the antigen-binding properties of monoclonal antibodies. The CAR-modified T-cells have the potential to replicate in vivo and long term persistence allows for sustained tumor control and obviate the need for repeated infusions of antibody. (Kalos M, et al., Sci Transl Med. 2011 Aug. 10; 3 (95)) The non-MHC-restricted antigen recognition gives T cells expressing CARs the ability to recognize antigen independent of antigen processing, thus bypassing a major mechanism of tumor escape. Moreover, when expressed in T-cells, CARs advantageously do not dimerize with endogenous T cell receptor (TCR) alpha and beta chains. CAR-modified T cells are described in detail in US2003/022450 and US2010/0261269 and in Milone et al. 2009 *Mol. Ther.* 17:1453

Pharmaceutical Formulations

In some instances, therapeutic compositions disclosed herein can include other compounds, drugs, and/or agents used for the treatment of cancer. Such compounds, drugs, and/or agents can include, for example, chemotherapy drugs, small molecule drugs or antibodies that stimulate the immune response to a given cancer. In some instances, therapeutic compositions can include, for example, one or more peptides disclosed herein and one or more of an anti-CTLA-4 antibody or peptide, an anti-PD-1 antibody or peptide, an anti-PDL-1 antibody or peptide, an anti-OX40 (also known as CD134, TNFRSF4, ACT35 and/or TXGP1L) antibody or peptide, an anti-GITR (also known as TNFRSF18, AITR, and/or CD357) antibody or peptide, an anti-LAG-3 antibody or peptide, and/or an anti-TIM-3 antibody or peptide. For example, in some instances, therapeutic compositions disclosed herein can be combined with one or more (e.g., one, two, three, four, five, or less than ten) compounds.

In some instances, therapeutic compositions disclosed herein can include other compounds including histone deacetylase inhibitors ("HDAC") inhibitors. Examples of HDAC inhibitors include, for example, hydroxamic acid, Vorinostat (Zolinza); suberoylanilide hydroxamic acid (SAHA)(Merck), Trichostatin A (TSA), LAQ824 (Novartis), Panobinostat (LBH589) (Novartis), Belinostat (PXD101)(CuraGen), ITF2357 Italfarmaco SpA (Cinisello), Cyclic tetrapeptide; Depsipeptide (romidepsin, FK228) (Gloucester Pharmaceuticals), Benzamide; Entinostat (SNDX-275/MS-275)(Syndax Pharmaceuticals), MGCD0103 (Celgene), Short-chain aliphatic acids, Valproic acid, Phenyl butyrate, AN-9, pivanex (Titan Pharmaceutical), CHR-3996 (Chroma Therapeutics), and CHR-2845 (Chroma Therapeutics).

In some instances, therapeutic compositions disclosed herein can include other compounds including proteasome inhibitors, including, for example, Bortezomib, (Millennium Pharmaceuticals), NPI-0052 (Nereus Pharmaceuticals), Carfilzomib (PR-171)(Onyx Pharmaceuticals), CEP 18770, and MLN9708.

In some instances, the therapeutic compositions disclosed herein can include alkylating agents such as mephalan and topoisomerase inhibitors such as Adriamycin (doxorubicin) have been shown to increase MICA expression, which could enhance efficacy of an anti-MICA monoclonal antibody.

In some instances, therapeutic compositions can include, for example, one or more peptides disclosed herein and a one or more other agents, such as chemotherapy, radiation therapy, cytokines, chemokines and other biologic signaling molecules, tumor specific vaccines, cellular cancer vaccines (e.g., GM-CSF transduced cancer cells), tumor specific monoclonal antibodies, autologous and allogeneic stem cell rescue (e.g., to augment graft versus tumor effects), other therapeutic antibodies, molecular targeted therapies, anti-angiogenic therapy, infectious agents with therapeutic intent (such as tumor localizing bacteria) and gene therapy.

In some instances, therapeutic compositions can include one or a combination of anti-MICA antibodies, or antigen-binding portion(s) thereof, as described herein, formulated together with a pharmaceutically acceptable carrier. Such compositions may include one or a combination of (e.g., two or more different) peptides, antibodies, antigen-binding portions, immunoconjugates or bispecific molecules which bind to MICA.

For example, a pharmaceutical composition can comprise a combination of antibodies (or immunoconjugates or bispecifics) that bind to different epitopes on the target antigen or that have complementary activities. In some instances, such compositions may include one or more antibody or antibody fragment that interacts with an epitope involving or overlapping with amino acids 229 to 248 within the MICA*009 sequence (SEQ ID NO: 185), an antibody or antibody fragment that interacts with an epitope involving or overlapping with amino acids 179 to 188 within the MICA*009 amino acid sequence (SEQ ID NO: 185), an antibody or antibody fragment that interacts with an epitope involving or overlapping with amino acids 119 to 128 within the MICA*009 amino acid sequence (SEQ ID NO: 185), and/or and antibody or antibody fragment that interacts with an epitope involving or overlapping with amino acids 199 to 208 within the MICA*009 amino acid sequence (SEQ ID NO: 185).

In some instances, therapeutic compositions can include a peptide, antibody or antibody fragment which binds to MICA and which comprises CDR1, CDR2 and CDR3 of the $V_H$ CM33322 mAb4 and/or CDR1, CDR2 and CDR3 of the $V_L$ of CM33322 mAb4, in combination with one or more peptides, antibodies or antigen-binding fragments that comprise the CDR1, CDR2 and CDR3 of a $V_H$ of antibody ID 1, 6, 7, 8 9, or 12 and/or the CDR1, CDR2 and CDR3 of a $V_L$ of antibody ID 1, 6, 7, 8, 9 or 12. In some instances, therapeutic compositions can include a peptide, antibody or antibody fragment which binds to MICA and which comprises CDR1, CDR2 and CDR3 of the $V_H$ CM33322 mAb28 and/or CDR1, CDR2 and CDR3 of the $V_L$ of CM33322 mAb28, in combination with one or more peptides, antibodies or antigen-binding fragments that comprise the CDR1, CDR2 and CDR3 of a $V_H$ of antibody ID 1, 6, 7, 8 9, 11 or 12 and/or the CDR1, CDR2 and CDR3 of a $V_L$ of antibody ID 1, 6, 7, 8, 9, 11 or 12.

In some instances, therapeutic compositions disclosed herein can be formulated for use as or in pharmaceutical compositions. Such compositions can be formulated or adapted for administration to a subject via any route, e.g., any route approved by the Food and Drug Administration (FDA). Exemplary methods are described in the FDA's CDER Data Standards Manual, version number 004 (which is available at fda.give/cder/dsm/DRG/drg00301.htm).

The amount of active ingredient which can be combined with a carrier material to produce a single dosage form will vary depending upon the subject being treated, and the particular mode of administration. The amount of active ingredient which can be combined with a carrier material to produce a single dosage form will generally be that amount of the composition which produces a therapeutic effect. Generally, out of one hundred percent, this amount will range from about 0.01 percent to about ninety-nine percent of active ingredient, preferably from about 0.1 percent to about 70 percent, most preferably from about 1 percent to about 30 percent of active ingredient in combination with a pharmaceutically acceptable carrier.

In some instances, pharmaceutical compositions can include an effective amount of one or more peptides. The terms "effective amount" and "effective to treat," as used herein, refer to an amount or a concentration of one or more peptides disclosed herein (e.g., antibody or antibody fragment which binds MICA) for a period of time (including acute or chronic administration and periodic or continuous administration) that is effective within the context of its administration for causing an intended effect or physiological outcome.

In some instances, pharmaceutical compositions can include one or more peptides and any pharmaceutically acceptable carrier, adjuvant and/or vehicle. In some instances, pharmaceuticals can further include one or more additional therapeutic agents in amounts effective for achieving a modulation of disease or disease symptoms.

The term "pharmaceutically acceptable carrier or adjuvant" refers to a carrier or adjuvant that may be administered to a patient, together with a peptide of this invention, and which does not destroy the pharmacological activity thereof and is nontoxic when administered in doses sufficient to deliver a therapeutic amount of the compound.

Pharmaceutically acceptable carriers, adjuvants and vehicles that may be used in the pharmaceutical compositions of this invention include, but are not limited to, ion exchangers, alumina, aluminum stearate, lecithin, self-emulsifying drug delivery systems (SEDDS) such as d-I-tocopherol polyethyleneglycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as I-, ϑ-, and K-cyclodextrin, may also be advantageously used to enhance delivery of compounds of the formulae described herein.

The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intra-articular, intraarterial, intrasynovial, intrasternal, intrathecal, intralesional and intracranial injection or infusion techniques.

Pharmaceutical compositions can be in the form of a solution or powder for inhalation and/or nasal administration. Such compositions may be formulated according to techniques known in the art using suitable dispersing or wetting agents (such as, for example, Tween 80) and suspending agents. The sterile injectable preparation may also be a sterile injectable solution or suspension in a non-toxic parenterally acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, or carboxymethyl cellulose or similar dispersing agents which are commonly used in the formulation of pharmaceutically acceptable dosage forms such as emulsions and or suspensions. Other commonly used surfactants such as Tweens or Spans and/or other similar emulsifying agents or bioavailability enhancers which are commonly used in the manufacture of pharmaceutically acceptable solid, liquid, or other dosage forms may also be used for the purposes of formulation.

Pharmaceutical compositions can be orally administered in any orally acceptable dosage form including, but not limited to, capsules, tablets, emulsions and aqueous suspensions, dispersions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions and/or emulsions are administered orally, the active ingredient may be suspended or dissolved in an oily phase is combined with emulsifying and/or suspending agents. If desired, certain sweetening and/or flavoring and/or coloring agents may be added.

Alternatively or in addition, pharmaceutical compositions can be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

In some embodiments, the present disclosure provides methods for using any one or more of the peptides or pharmaceutical compositions (indicated below as 'X') disclosed herein in the following methods:

Substance X for use as a medicament in the treatment of one or more diseases or conditions disclosed herein (e.g., cancer, referred to in the following examples as 'Y'). Use of substance X for the manufacture of a medicament for the treatment of Y; and substance X for use in the treatment of Y.

In some instances, therapeutic compositions disclosed herein can be formulated for sale in the US, import into the US, and/or export from the US.

Methods

In some instances, methods can include selection of a human subject who has or had a condition or disease and who exhibits or exhibited a positive immune response towards the condition or disease. In some instances, suitable subjects include, for example, subjects who have or had a condition or disease but that resolved the disease or an aspect thereof, present reduced symptoms of disease (e.g., relative to other subjects (e.g., the majority of subjects) with the same condition or disease), and/or that survive for extended periods of time with the condition or disease (e.g., relative to other subjects (e.g., the majority of subjects) with the same condition or disease), e.g., in an asymptomatic state (e.g., relative to other subjects (e.g., the majority of subjects) with the same condition or disease). In some instances, subjects can be selected if they have been vaccinated (e.g., previously vaccinated and/or vaccinated and re-vaccinated (e.g., received a booster vaccine)) against a condition or disease.

The term "subject," as used herein, refers to any animal. In some instances, the subject is a mammal. In some instances, the term "subject", as used herein, refers to a human (e.g., a man, a woman, or a child). Samples for use in the methods can include serum samples, e.g., obtained from the selected subject.

In some instances, subject selection can include obtaining a sample from a subject (e.g., a candidate subject) and testing the sample for an indication that the subject is suitable for selection. In some instances, the subject can be confirmed or identified, e.g. by a health care professional, as having had or having a condition or disease. In some instances, exhibition of a positive immune response towards a condition or disease can be made from patient records, family history, and/or detecting an indication of a positive immune response. In some instances multiple parties can be included in subject selection. For example, a first party can obtain a sample from a candidate subject and a second party can test the sample. In some instances, subjects can be selected and/or referred by a medical practitioner (e.g., a general practitioner). In some instances, subject selection can include obtaining a sample from a selected subject and storing the sample and/or using the in the methods disclosed herein. Samples can include, for example, cells or populations of cells.

In some instances, obtaining or targeting immune cells can include one or more and/or combinations of, for example: obtaining or providing a tetrameric immunogen that can bind (e.g., bind specifically) to a target immune cell; contacting the tetrameric immunogen with a sample; detecting the tetrameric immunogen; determining whether the tetrameric immunogen is bound to a target immune cell; and, if the tetrameric immunogen is bound to a target immune cell, then obtaining the target immune cell.

Tetrameric immunogens can include immunogens related to a condition or disease and/or that bind (e.g., bind specifically) to a target immune cell, e.g., wherein the target immune cell is related to a selected condition or disease. Immunogens and target immune cells related to a condition or disease include, for example, immunogens or immune cells present in subjects with a certain condition or disease, but not subjects without the condition or disease; and/or immunogens or immune cells present at altered levels (e.g., increased) in subjects with a certain condition or disease relative to subjects without the condition or disease. In some instances, immunogens or immune cells can be cancer specific. Immunogens can be soluble. Tetrameric immunogen can include tetrameric (including, e.g., tetramerized monomeric, dimeric, and/or trimeric antigen immunogen (e.g., antigen and/or epitope). In some instances, a tetrameric immunogen has increased binding to a cell relative to the level of binding between a non-tetrameric form of the immunogen to the cell under similar conditions. In some instances, a tetrameric antigen includes a detectable moiety, e.g., a streptavidin moiety. Tetramerization methods are known in the art and are disclosed herein.

Detecting tetrameric immunogen and/or determining whether tetrameric immunogen is bound to a target cell can be performed using methods known in the art and/or disclosed herein. For example, methods can include flow cytometry. Optimization methods for flow cytometry, including sorting and gating methods, are known in the art and/or are disclosed herein. In some instances, methods can include analysis of the level of binding, binding affinity, and/or binding specificity between a tetrameric immunogen bound to a target immune cell. For example, a target immune cell can be obtained if (e.g., only if) a pre-determined level of binding between a tetrameric immunogen and a target immune cell is determined. Pre-determined levels of binding can be specific levels and/or can be relative levels. Obtaining target immune cells can include obtaining, providing, identifying, selecting, purifying, and/or isolating the target immune cells. Such methods can include, for example, cell sorting methods, cell enrichment, and/or background reduction.

In some instances, obtaining immune cells directed against a self antigen can include one or more and/or combinations of, for example, identifying a subject exhibiting a positive immune response towards the self antigen; obtaining or providing a multimeric form of the self antigen; contacting the multimeric form of the self antigen with a sample from the subject exhibiting a positive immune response towards the self antigen; obtaining immune cells bound to the multimeric form of the self antigen.

In some instances, methods can include obtaining immune cells directed against a self antigen from a cancer patient, can include one or more and/or combinations of, for example, identifying a subject exhibiting a positive immune response towards the self antigen; providing a multimeric form of the self antigen; contacting the multimeric form of the self antigen with a sample from the subject exhibiting a positive immune response towards the self antigen; and obtaining immune cells bound to the multimeric form of the self antigen.

Multimeric forms of a self antigen can include self antigens related to a condition or disease and/or that bind (e.g., bind specifically) to a target immune cell, e.g., wherein the target immune cell is related to a selected condition or disease. Self antigens and target immune cells related to a condition or disease include, for example, antigens or immune cells present in subjects with a certain condition or disease, but not subjects without the condition or disease; and/or immunogens or immune cells present at altered levels (e.g., increased) in subjects with a certain condition or disease relative to subjects without the condition or disease. In some instances, the condition or disease can be a cancer. In some embodiments, the cancer is melanoma, lung, breast, kidney, ovarian, prostate, pancreatic, gastric, glioblastoma, liver cancer, and colon carcinoma, lymphoma or leukemia. In some instances, the self antigens or immune cells can be cancer specific. The self antigens can be soluble. Multimeric form of the self antigen can include a tetrameric form (including, e.g., tetramerized monomeric, dimeric, and/or trimeric antigen) of the self-antigen (e.g., antigen and/or epitope). In some instances, a multimeric form of the self antigen includes a detectable moiety, e.g., a streptavidin moiety. Multimerization methods are known in the art and are disclosed herein.

Methods for isolating or purifying genetic material (e.g., DNA and/or mRNA) from the obtained target immune cell are known in the art and are exemplified herein. Once such genetic material has been obtained, methods for using it to produce the therapeutic compositions disclosed herein are known in the art and/or are summarized below. As discussed above, genetic material can be varied, using techniques known in the art to create peptide variants disclosed herein.

Generating peptides from nucleic acids (e.g., cDNA) contained within or obtained from the target cell can include, for example, analysis, e.g., sequencing of heavy and light chain variable domains from target immune cells (e.g., single or isolated identified target immune cells). In some instances, methods can include generating fully human antibodies, or fragments thereof (e.g., as disclosed above), and humanization of non-human antibodies. DNA can be readily isolated and/or sequenced from the obtained immune cells using conventional procedures (e.g., by using oligonucleotide probes that are capable of binding specifically to genes encoding the heavy and light chains of murine antibodies).

Once isolated, DNA can be placed into expression vectors, which are then transfected into host cells such as *Escherichia coli* cells, simian COS cells, Chinese Hamster Ovary (CHO) cells, or myeloma cells that do not otherwise produce antibody protein, to obtain the synthesis of monoclonal antibodies in the recombinant host cells. Review articles on recombinant expression in bacteria of DNA encoding the antibody include Skerra et al., Curr. Opinion in Immunol., 5:256-262 (1993) and Pluckthun, Immunol. Revs., 130:151-188 (1992).

Recombinant expression of an antibody or variant thereof generally requires construction of an expression vector containing a polynucleotide that encodes the antibody. The invention, thus, provides replicable vectors comprising a nucleotide sequence encoding an antibody molecule, a heavy or light chain of an antibody, a heavy or light chain variable domain of an antibody or a portion thereof, or a heavy or light chain CDR, operably linked to a promoter. Such vectors may include the nucleotide sequence encoding the constant region of the antibody molecule (see, e.g., U.S. Pat. Nos. 5,981,216; 5,591,639; 5,658,759 and 5,122,464) and the variable domain of the antibody may be cloned into such a vector for expression of the entire heavy, the entire light chain, or both the entire heavy and light chains. Once the expression vector is transferred to a host cell by conventional techniques, the transfected cells are then cultured by conventional techniques to produce an antibody. Thus, the invention includes host cells containing a polynucleotide encoding an antibody of the invention or fragments thereof, or a heavy or light chain thereof, or portion thereof, or a single-chain antibody of the invention, operably linked to a heterologous promoter. In certain embodiments for the expression of double-chained antibodies, vectors encoding both the heavy and light chains may be co-expressed in the host cell for expression of the entire immunoglobulin molecule, as detailed below.

Mammalian cell lines available as hosts for expression of recombinant antibodies are well known in the art and include many immortalized cell lines available from the American Type Culture Collection (ATCC), including but not limited to Chinese hamster ovary (CHO) cells, HeLa cells, baby hamster kidney (BHK) cells, monkey kidney cells (COS), human hepatocellular carcinoma cells (e.g., Hep G2), human epithelial kidney 293 cells, and a number of other cell lines. Different host cells have characteristic and specific mechanisms for the post-translational processing and modification of proteins and gene products. Appropriate cell lines or host systems can be chosen to ensure the correct modification and processing of the antibody or portion thereof expressed. To this end, eukaryotic host cells which possess the cellular machinery for proper processing of the primary transcript, glycosylation, and phosphorylation of the gene product may be used. Such mammalian host cells include but are not limited to CHO, VERY, BHK, Hela, COS, MDCK, 293, 3T3, W138, BT483, Hs578T, HTB2, BT2O and T47D, NS0 (a murine myeloma cell line that does not endogenously produce any functional immunoglobulin chains), SP20, CRL7O3O and HsS78Bst cells. In one embodiment, human cell lines developed by immortalizing human lymphocytes can be used to recombinantly produce monoclonal antibodies. In one embodiment, the human cell line PER.C6. (Crucell, Netherlands) can be used to recombinantly produce monoclonal antibodies.

In some instances, peptides disclosed herein can be generated synthetically. Synthetic chemistry transformations and protecting group methodologies (protection and deprotection) useful in synthesizing peptides described herein are known in the art and include, for example, those such as described in R. Larock, Comprehensive Organic Transformations, VCH Publishers (1989); T. W. Greene and P.G.M. Wuts, Protective Groups in Organic Synthesis, 3d. Ed., John Wiley and Sons (1999); L. Fieser and M. Fieser, Fieser and Fieser's Reagents for Organic Synthesis, John Wiley and Sons (1994); and L. Paquette, ed., Encyclopedia of Reagents for Organic Synthesis, John Wiley and Sons (1995), and subsequent editions thereof.

Peptides can also be made by chemical synthesis methods, which are well known to the ordinarily skilled artisan. See, for example, Fields et al., Chapter 3 in Synthetic Peptides: A User's Guide, ed. Grant, W. H. Freeman & Co., New York, N.Y., 1992, p. 77. Hence, peptides can be synthesized using the automated Merrifield techniques of solid phase synthesis with the $\alpha$-$NH_2$ protected by either t-Boc or Fmoc chemistry using side chain protected amino acids on, for example, an Applied Biosystems Peptide Synthesizer Model 430A or 431.

One manner of making of the peptides described herein is using solid phase peptide synthesis (SPPS). The C-terminal amino acid is attached to a cross-linked polystyrene resin via an acid labile bond with a linker molecule. This resin is insoluble in the solvents used for synthesis, making it relatively simple and fast to wash away excess reagents and by-products. The N-terminus is protected with the Fmoc group, which is stable in acid, but removable by base. Any side chain functional groups are protected with base stable, acid labile groups.

Longer peptides could be made by conjoining individual synthetic peptides using native chemical ligation. Alternatively, the longer synthetic peptides can be synthesized by well-known recombinant DNA techniques. Such techniques are provided in well-known standard manuals with detailed protocols. To construct a gene encoding a peptide of this invention, the amino acid sequence is reverse translated to obtain a nucleic acid sequence encoding the amino acid sequence, preferably with codons that are optimum for the organism in which the gene is to be expressed. Next, a synthetic gene is made, typically by synthesizing oligonucleotides which encode the peptide and any regulatory elements, if necessary. The synthetic gene is inserted in a suitable cloning vector and transfected into a host cell. The peptide is then expressed under suitable conditions appropriate for the selected expression system and host. The peptide is purified and characterized by standard methods.

The peptides can be made in a high-throughput, combinatorial fashion, e.g., using a high-throughput multiple channel combinatorial synthesizer available from Advanced Chemtech.

Peptide bonds can be replaced, e.g., to increase physiological stability of the peptide, by: a retro-inverso bonds (C(O)—NH); a reduced amide bond ($NH—CH_2$); a thiomethylene bond ($S—CH_2$ or $CH_2—S$); an oxomethylene bond ($O—CH_2$ or $CH_2—O$); an ethylene bond ($CH_2—CH_2$); a thioamide bond (C(S)—NH); a trans-olefin bond (CH═CH); a fluoro substituted trans-olefin bond (CF═CH); a ketomethylene bond (C(O)—CHR) or CHR—C(O) wherein R is H or $CH_3$; and a fluoro-ketomethylene bond (C(O)—CFR or CFR—C(O) wherein R is H or F or $CH_3$.

Peptides can be further modified by: acetylation, amidation, biotinylation, cinnamoylation, farnesylation, fluoresceination, formylation, myristoylation, palmitoylation, phosphorylation (Ser, Tyr or Thr), stearoylation, succinylation and sulfurylation. As indicated above, peptides can be conjugated to, for example, polyethylene glycol (PEG); alkyl groups (e.g., C1-C20 straight or branched alkyl groups); fatty acid radicals; and combinations thereof.

In some instances, peptides can be purified by any method known in the art for purification of an immunoglobulin molecule, for example, by chromatography (e.g., ion exchange, affinity, particularly by affinity for the specific antigens Protein A or Protein G, and sizing column chromatography), centrifugation, differential solubility, or by any other standard technique for the purification of proteins. Further, the antibodies of the present invention or fragments thereof may be fused to heterologous polypeptide sequences (referred to herein as "tags") described above or otherwise known in the art to facilitate purification.

An exemplary, non-limiting, overview of the methods is shown in FIG. 5A-5F. Ordering is not implied.

In some instances, the disclosure also provides antibody or antibody fragments having heavy chain variable and/or light chain regions comprising amino acid sequences that are homologous to the amino acid sequences of the antibodies described herein which retain the desired functional MICA binding properties. For example, in some embodiments the antibody or antibody fragment can contain $V_H$ and/or $V_L$ amino acid sequences that are 85%, 90%, 95%, 96%, 97%, 98% or 99% identical to the sequences set forth above. An antibody or antibody fragment having $V_H$ and $V_L$ regions having high (i.e., 80% or greater) homology to the $V_H$ and $V_L$ regions of SEQ ID NOs: 2, 77, 96, 113, 131, 150 or 168 and 11, 79, 98, 115, 133, 152 or 170, respectively, can be obtained by mutagenesis (e.g., site-directed or PCR-mediated mutagenesis) of nucleic acid molecules encoding SEQ ID NOs: 77, 96, 113, 131, 150 or 168 and/or 79, 98, 115, 133 152 or 170, followed by testing of the encoded altered antibody for retained function (i.e., one of more functions such as binding to alpha 3 domain of MICA; blocking of MICA shedding; do not inhibit binding of NGKD binding to MICA; block soluble MICA induced NGKD downregulation and diminished NK cell cytotoxicity) using the functional assays described herein.

Also provided are antibodies and antibody fragments that compete (e.g., cross-compete) for binding to MICA the particular anti-MICA antibodies described herein (e.g., antibody ID 1, 6, 7, 8, 9, 11 and 12). Such competing antibodies can be identified based on their ability to competitively inhibit binding of MICA to the antibody in standard MICA binding assays. For example, standard ELISA assays can be used in which a recombinant human MICA protein is immobilized on the plate, one of the antibodies is fluorescently labeled and the ability of non-labeled antibodies to compete off the binding of the labeled antibody is evaluated. Additionally or alternatively, BIAcore analysis can be used to assess the ability of the antibodies to cross-compete. The ability of a test antibody to inhibit the binding of an anti-MICA antibody to MICA demonstrates that the test antibody can compete with the antibody for binding to MICA.

Accordingly, in one embodiment, the disclosure provides anti-MICA antibodies which inhibits the binding of the anti-MICA antibodies described herein to MICA on activated T cells by at least 50%, for example, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, as measured by FACS. For example, inhibition of binding of the anti-MICA antibodies by candidate competing anti-MICA antibodies can be assessed under the conditions as described in the Examples.

In some instances, the disclosure provides anti-MICA antibodies which bind to the same epitope as the anti-MICA antibodies described herein (e.g., antibody ID 8, 9, 11 and 12). As discussed further in Example 14, antibody ID 8 (CM33322 mAb11) binds to an epitope involving residues 119 to 128 within the MICA*009 amino acid sequence (SEQ ID NO: 185); antibody ID 9 (CM33322 mAb29) binds to an epitope involving residues 229 to 248 within the MICA*009 amino acid sequence (SEQ ID NO: 185); antibody ID 11 (CM33322 mAb4) binds to an epitope involving residues 179 to 188 within the MICA*009 amino acid sequence (SEQ ID NO: 185); and antibody ID 12 (CM33322 mAb28) binds to an epitope involving residues 199 to 208 within the MICA*009 amino acid sequence (SEQ ID NO: 185). Accordingly, in some embodiments, the disclosure provides an anti-MICA antibody or antibody fragment that binds to amino acid residues within the α3 region corresponding to amino acids 181 to 274 of MICA*009.

Techniques for determining antibodies that bind to the "same epitope on MICA" with the antibodies described herein include, for example, epitope mapping methods, such as, x-ray analyses of crystals of antigen:antibody complexes which provides atomic resolution of the epitope. Other methods monitor the binding of the antibody to antigen fragments or mutated variations of the antigen where loss of binding due to a modification of an amino acid residue within the antigen sequence is often considered an indication of an epitope component. In addition, computational combinatorial methods for epitope mapping can also be used. These methods rely on the ability of the antibody of interest to affinity isolate specific short peptides from combinatorial phage display peptide libraries. The peptides are then regarded as leads for the definition of the epitope corresponding to the antibody used to screen the peptide library. For epitope mapping, computational algorithms have also been developed which have been shown to map conformational discontinuous epitopes.

For example, mice may be immunized with human MICA as described herein, hybridomas produced, and the resulting monoclonal antibodies screened for the ability to compete with mAb4 or mAb28 for binding to MICA. Mice can also be immunized with a smaller fragment of MICA containing the epitope to which the mAb4 monoclonal antibody binds. For example, the method of Jespers et al., Biotechnology 12:899, 1994 may be used to guide the selection of monoclonal antibodies having the same epitope and therefore similar properties to the archetypal monoclonal antibody. Using phage display, first the heavy chain of the archetypal antibody is paired with a repertoire of (preferably human) light chains to select a MICA-binding monoclonal antibody, and then the new light chain is paired with a repertoire of (preferably human) heavy chains to select a (preferably human) MICA-binding monoclonal antibody having the same epitope as the archetypal monoclonal antibody. Alternatively variants of the archetypal monoclonal antibody (e.g., mAb4, ID 11 or mAb28, ID 12) can be obtained by mutagenesis of cDNA encoding the heavy and light chains of the antibody.

Epitope mapping, e.g., as described in Champe et al. (1995) J. Biol. Chem. 270:1388-1394, can be performed to determine whether the antibody binds an epitope of interest. "Alanine scanning mutagenesis," as described by Cunningham and Wells (1989) Science 244: 1081-1085, or some other form of point mutagenesis of amino acid residues in MICA or MICB may also be used to determine the functional epitope for an anti-MICA or MICB antibody of the present invention. Mutagenesis studies, however, may also reveal amino acid residues that are crucial to the overall three-dimensional structure of MICA or MICB but that are not directly involved in antibody-antigen contacts, and thus other methods may be necessary to confirm a functional epitope determined using this method.

Antibody competition assays, as described herein, can also be used to determine whether an antibody "binds to the same epitope" as another antibody. Typically, competition of 50% or more, 60% or more, 70% or more, such as 70%, 71%, 72%, 73%, 74%, 75%, 80%, 85%, 90%, 95% or more, of an antibody known to interact with the epitope by a second antibody under conditions in which the second antibody is in excess and the first saturates all sites, is indicative that the antibodies "bind to the same epitope." To assess the level of competition between two antibodies, for example, radioimmunoassays or assays using other labels for the antibodies, can be used. For example, a MICA or MICB antigen can be incubated with a saturating amount of a first anti-MICA antibody or antigen-binding fragment thereof conjugated to a labeled compound (e.g., $^{3}H$, $^{125}I$, biotin, or rubidium) in the presence the same amount of a second unlabeled anti-MICA antibody. The amount of labeled antibody that is bound to the antigen in the presence of the unlabeled blocking antibody is then assessed and compared to binding in the absence of the unlabeled blocking antibody. Competition is determined by the percentage change in binding signals in the presence of the unlabeled blocking antibody compared to the absence of the blocking antibody. Thus, if there is a 50% inhibition of binding of the labeled antibody in the presence of the blocking antibody compared to binding in the absence of the blocking antibody, then there is competition between the two antibodies of 50%. Thus, reference to competition between a first and second antibody of 50% or more, 60% or more, 70% or more, such as 70%, 75%, 80%, 85%, 90%, 95% or more, means that the first antibody inhibits binding of the second antibody (or vice versa) to the antigen by 50%, 60%, 70%, 75%, 80%, 85%, 90%, 95% or more (compared to binding of the antigen by the second antibody in the absence of the first antibody). Thus, inhibition of binding of a first antibody to an antigen by a second antibody of 50%, 60%, 70%, 75%, 80%, 85%, 90%, 95% or more indicates that the two antibodies bind to the same epitope.

Also provided are engineered and recombinant antibodies that comprise at most 1, 2, 3, 4, 5, 6, 7, 8, 9 or 10 amino acid differences (e.g., substitutions, additions, or deletions) relative to a naturally occurring antibody. The one or more amino acid differences may be in the light chain and/or in the heavy chain, and may be in one or more of the CDRs, in a framework region or in a constant region, e.g., in CL, CH1, hinge, CH2 or CH3. For example engineered and recombinant antibodies are provided that comprise (1) a $V_H$ sequence comprising one or more of the $V_H$ CDR regions described herein and a $V_L$ sequence comprising one or more of the $V_L$ CDR regions described herein, and (2) a heterologous framework region. The heterologous framework region may be derived from an antibody, cell, or human that is not the native source of the CDR regions. For example, in some embodiments, an antibody may comprise CDR1, CDR2 and CDR3 of a $V_H$ of antibody ID 1, 6, 7, 8, 9, 11 or 12 and/or CDR1, CDR2 and CDR3 of a $V_L$ of antibody ID 1, 6, 7, 8, 9, 11 or 12 shown in Table 1, and a framework region that is not from antibody ID 1, 6, 7, 8, 9, 11 or 12 that comprise the same CDRs. In some embodiments, an antibody may comprise CDR1, CDR2 and CDR3 of $V_H$ of antibody ID 1 and/or CDR1, CDR2 and CDR3 of a $V_L$ of antibody ID 1 shown in Table 1, and a framework region that is not from antibody ID1. In some embodiments, an antibody may comprise CDR1, CDR2 and CDR3 of $V_H$ of antibody ID 6 and/or CDR1, CDR2 and CDR3 of a $V_L$ of antibody ID 6 shown in Table 1, and a framework region that is not from antibody ID 6. In some embodiments, an antibody may comprise CDR1, CDR2 and CDR3 of $V_H$ of antibody ID 7 and/or CDR1, CDR2 and CDR3 of a $V_L$ of antibody ID 7 shown in Table 1, and a framework region that is not from antibody ID 7. In some embodiments, an antibody may comprise CDR1, CDR2 and CDR3 of $V_H$ of antibody ID 8 and/or CDR1, CDR2 and CDR3 of a $V_L$ of antibody ID 8 shown in Table 1, and a framework region that is not from antibody ID 8. In some embodiments, an antibody may comprise CDR1, CDR2 and CDR3 of $V_H$ of antibody ID 9 and/or CDR1, CDR2 and CDR3 of a $V_L$ of antibody ID 9 shown in Table 1, and a framework region that is not from antibody ID 9. In some embodiments, an antibody may comprise CDR1, CDR2 and CDR3 of $V_H$ of antibody ID 11 and/or CDR1, CDR2 and CDR3 of a $V_L$ of antibody ID 11 shown in Table 1, and a framework region that is not from antibody ID 11. In some embodiments, an antibody may comprise CDR1, CDR2 and CDR3 of $V_H$ of antibody ID 12 and/or CDR1, CDR2 and CDR3 of a $V_L$ of antibody ID 12 shown in Table 1, and a framework region that is not from antibody ID 12.

Also provided are engineered and recombinant antibodies that comprise (1) a $V_H$ sequence comprising one or more of the $V_H$ CDR regions described herein and a $V_L$ sequence comprising one or more of the $V_L$ CDR regions described herein, and (2) a heterologous constant region. The heterologous constant region may be derived from an antibody, cell, or human that is not the native source of the CDR regions. For example, in some embodiments, an antibody may comprise CDR1, CDR2 and CDR3 of a $V_H$ of antibody ID 1, 6, 7, 8, 9, 11 or 12 and/or CDR1, CDR2 and CDR3 of a $V_L$ of antibody ID 1, 6, 7, 8, 9, 11 or 12 shown in Table 1, and a constant region from a human that is not the human from whom the CDRs were obtained from. In some embodiments, an antibody may comprise CDR1, CDR2 and CDR3 of $V_H$ of antibody ID 1 and/or CDR1, CDR2 and CDR3 of a $V_L$ of antibody ID 1 shown in Table 1, and a constant region that is not from antibody ID1. In some embodiments, an antibody may comprise CDR1, CDR2 and CDR3 of $V_H$ of antibody ID 6 and/or CDR1, CDR2 and CDR3 of a $V_L$ of antibody ID 6 shown in Table 1, and a constant region that is not from antibody ID 6. In some embodiments, an antibody may comprise CDR1, CDR2 and CDR3 of $V_H$ of antibody ID 7 and/or CDR1, CDR2 and CDR3 of a $V_L$ of antibody ID 7 shown in Table 1, and a constant region that is not from antibody ID 7. In some embodiments, an antibody may comprise CDR1, CDR2 and CDR3 of $V_H$ of antibody ID 8 and/or CDR1, CDR2 and CDR3 of a $V_L$ of antibody ID 8 shown in Table 1, and a constant region that is not from antibody ID 8. In some embodiments, an antibody may comprise CDR1, CDR2 and CDR3 of $V_H$ of antibody ID 9 and/or CDR1, CDR2 and CDR3 of a $V_L$ of antibody ID 9 shown in Table 1, and a constant region that is not from antibody ID 9. In some embodiments, an antibody may comprise CDR1, CDR2 and CDR3 of $V_H$ of antibody ID 11 and/or CDR1, CDR2 and CDR3 of a $V_L$ of antibody ID 11 shown in Table 1, and a constant region that is not from antibody ID 11. In some embodiments, an antibody may comprise CDR1, CDR2 and CDR3 of $V_H$ of antibody ID 12 and/or CDR1, CDR2 and CDR3 of a $V_L$ of antibody ID 12 shown in Table 1, and a constant region that is not from antibody ID 12.

Also provided are engineered and recombinant antibodies that comprise (1) a $V_H$ sequence comprising one or more of the $V_H$ CDR regions described herein and a $V_L$ sequence comprising one or more of the $V_L$ CDR regions described herein, and (2) a heterologous Fc region. The heterologous Fc region may be derived from an antibody, cell, or human that is not the native source of the CDR regions.

Also provided are engineered and modified antibodies that can be prepared using an antibody having one or more of the $V_H$ and/or $V_L$ sequences disclosed herein as starting material to engineer a modified antibody, which modified antibody may have altered properties from the starting antibody. An antibody can be engineered by modifying one or more residues within one or both variable regions (i.e., $V_H$ and/or $V_L$), for example within one or more CDR regions and/or within one or more framework regions. Additionally or alternatively, an antibody can be engineered by modifying residues within the constant region(s), for example to alter the effector function(s) of the antibody.

One type of variable region engineering that can be performed is CDR grafting. Antibodies interact with target antigens predominantly through amino acid residues that are located in the six heavy and light chain complementarity determining regions (CDRs). For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties (see, e.g., Riechmann, L. et al. (1998) *Nature* 332:323-327; Jones, P. et al. (1986) *Nature* 321:522-525; Queen, C. et al. (1989) *Proc. Natl. Acad. See. U.S.A.* 86:10029-10033; U.S. Pat. No. 5,225,539 to Winter, and U.S. Pat. Nos. 5,530,101; 5,585,089; 5,693,762 and 6,180,370 to Queen et al.)

Accordingly, another embodiment of the invention pertains to an isolated monoclonal antibody, or antigen binding portion thereof, comprising a heavy chain variable region comprising CDR1, CDR2, and CDR3 sequences comprising an amino acid sequence selected from the group consisting of SEQ ID NOs: 4, 81, 100, 117, 135, 154 and 172, SEQ ID NOs: 84, 102, 119, 137, 156 and 174 and SEQ ID NOs: 8, 86, 103, 121, 139, 158 and 176, respectively, and a light chain variable region comprising CDR1, CDR2, and CDR3 sequences comprising an amino acid sequence selected from the group consisting of SEQ ID NOs: 13, 88, 106, 124, 142, 161 and 179, SEQ ID NOs: 90, 108, 126, 144, 163 and 181, and SEQ ID NOs: 17, 92, 110, 128, 146, 165 and 183, respectively. Thus, such antibodies contain the $V_H$ and $V_L$ CDR sequences of monoclonal antibodies ID 1, 6, 7, 8, 9, 11 or 12 shown in Table 1, yet may contain different framework sequences from these antibodies.

Such framework sequences can be obtained from public DNA databases or published references that include germline antibody gene sequences. For example, germline DNA sequences for human heavy and light chain variable region genes can be found in the "VBase" human germline sequence database (available on the Internet at www.mrc-cpe.cam.ac.uk/vbase), as well as in Kabat, E. A., et al. (1991) Sequences of Proteins of Immunological Interest, Fifth Edition, U.S. Department of Health and Human Services, NIH Publication No. 91-3242; Tomlinson, I. M., et al. (1992) "The Repertoire of Human Germline $V_H$ Sequences Reveals about Fifty Groups of $V_H$ Segments with Different Hypervariable Loops" *J. Mol. Biol.* 227:776-798; and Cox, J. P. L. et al. (1994) "A Directory of Human Germ-line $V_H$ Segments Reveals a Strong Bias in their Usage" *Eur. J. Immunol.* 24:827-836; the contents of each of which are expressly incorporated herein by reference.

Exemplified framework sequences for use in the antibodies of the invention include those that are structurally similar to the framework sequences used by antibodies described herein. The $V_H$ CDR1, 2 and 3 sequences, and the $V_L$ CDR1, 2 and 3 sequences, can be grafted onto framework regions that have the identical sequence as that found in the germline immunoglobulin gene from which the framework sequence derive, or the CDR sequences can be grafted onto framework regions that contain one or more mutations as compared to the germline sequences. For example, it has been found that in certain instances it is beneficial to mutate residues within the framework regions to maintain or enhance the antigen binding ability of the antibody (see e.g., U.S. Pat. Nos. 5,530,101; 5,585,089; 5,693,762 and 6,180,370 to Queen et al).

Another type of variable region modification is to mutate amino acid residues within the $V_H$ and/or $V_L$ CDR1, CDR2 and/or CDR3 regions to thereby improve one or more binding properties (e.g., affinity) of the antibody of interest. Site-directed mutagenesis or PCR-mediated mutagenesis can be performed to introduce the mutation(s) and the effect on antibody binding, or other functional property of interest, can be evaluated in in vitro or in vivo assays as described herein and provided in the Examples. Preferably conservative modifications (as discussed above) are introduced. The mutations may be amino acid substitutions, additions or deletions, but are preferably substitutions. Moreover, typically no more than one, two, three, four or five residues within a CDR region are altered.

Accordingly, in another embodiment, the invention provides isolated anti-MICA monoclonal antibodies, or antigen binding portions thereof, comprising a heavy chain variable region comprising: (a) a $V_H$ CDR1 region comprising an amino acid sequence selected from the group consisting of SEQ ID NOs: 4, 81, 100, 117, 135, 154 and 172, or an amino acid sequence having one, two, three, four or five amino acid substitutions, deletions or additions as compared to SEQ ID NOs: 4, 81, 100, 117, 135, 154 and 172; (b) a $V_H$ CDR2 region comprising an amino acid sequence selected from the group consisting of SEQ ID NOs: 6, 84, 102, 119, 137, 156 and 174, or an amino acid sequence having one, two, three, four or five amino acid substitutions, deletions or additions as compared to SEQ ID NOs: 6, 84, 102, 119, 137, 156 and 174; (c) a $V_H$ CDR3 region comprising an amino acid sequence selected from the group consisting of SEQ ID NOs: 8, 86, 103, 121, 139, 158 and 176, or an amino acid sequence having one, two, three, four or five amino acid substitutions, deletions or additions as compared to SEQ ID NOs: 8, 86, 103, 121, 139, 158 and 176; (d) a $V_L$ CDR1 region comprising an amino acid sequence selected from the group consisting of SEQ ID NOs: 13, 88, 106, 124, 142, 161 and 179, or an amino acid sequence having one, two, three, four or five amino acid substitutions, deletions or additions as compared to SEQ ID NOs: 13, 88, 106, 124, 142, 161 and 179; (e) a $V_L$ CDR2 region comprising an amino acid sequence selected from the group consisting of SEQ ID NOs: 15, 90, 108, 126, 144, 163 and 181, or an amino acid sequence having one, two, three, four or five amino acid substitutions, deletions or additions as compared to SEQ ID NOs: 15, 90, 108, 126, 144, 163 and 181; and (f) a $V_L$ CDR3 region comprising an amino acid sequence selected from the group consisting of SEQ ID NOs: 17, 92, 110, 128, 146, 165 and 183, or an amino acid sequence having one, two, three, four or five amino acid substitutions, deletions or additions as compared to SEQ ID NOs: 17, 92, 110, 128, 146, 165 and 183.

Methionine residues in CDRs of antibodies can be oxidized, resulting in potential chemical degradation and consequent reduction in potency of the antibody. Accordingly, the invention also provides anti-MICA antibodies which have one or more methionine residues in the heavy and/or light chain CDRs replaced with amino acid residues which do not undergo oxidative degradation. In one embodiment, the methionine residues in the CDRs of antibodies ID 1, 6, 7, 8, 9, 11 or 12 shown in Table 1 are replaced with amino acid residues which do not undergo oxidative degradation.

Engineered antibodies of the invention include those in which modifications have been made to framework residues within $V_H$ and/or $V_L$, e.g. to improve the properties of the antibody. Typically such framework modifications are made to decrease the immunogenicity of the antibody. For example, one approach is to "backmutate" one or more framework residues to the corresponding germline sequence. More specifically, an antibody that has undergone somatic mutation may contain framework residues that differ from the germline sequence from which the antibody is derived. Such residues can be identified by comparing the antibody framework sequences to the germline sequences from which the antibody is derived. To return the framework region sequences to their germline configuration, the somatic mutations can be "backmutated" to the germline sequence by, for example, site-directed mutagenesis or PCR-mediated mutagenesis. Such "backmutated" antibodies are also intended to be encompassed by the invention.

Another type of framework modification involves mutating one or more residues within the framework region, or even within one or more CDR regions, to remove T cell epitopes to thereby reduce the potential immunogenicity of the antibody. This approach is also referred to as "deimmunization" and is described in further detail in U.S. Patent Publication No. 20030153043 by Carr et al.

In addition or alternative to modifications made within the framework or CDR regions, antibodies of the invention may be engineered to include modifications within the Fc region, typically to alter one or more functional properties of the antibody, such as serum half-life, complement fixation, Fc receptor binding, and/or antigen-dependent cellular cytotoxicity. Furthermore, an antibody of the invention may be chemically modified (e.g., one or more chemical moieties can be attached to the antibody) or be modified to alter its glycosylation, again to alter one or more functional properties of the antibody. Each of these embodiments is described in further detail below. The numbering of residues in the Fc region is that of the EU index of Kabat.

An Fc encompasses domains derived from the constant region of an immunoglobulin, preferably a human immunoglobulin, including a fragment, analog, variant, mutant or derivative of the constant region. Suitable immunoglobulins include IgG1, IgG2, IgG3, IgG4, and other classes such as IgA, IgD, IgE and IgM. The constant region of an immunoglobulin may be a naturally-occurring or synthetically-produced polypeptide, and may include a CH1 domain, a hinge, a CH2 domain, a CH3 domain, or a CH4 domain, separately or in combination.

The constant region of an immunoglobulin is responsible for many important antibody functions including Fc receptor (FcR) binding and complement fixation. There are five major classes of heavy chain constant region, classified as IgA, IgG, IgD, IgE, IgM, each with characteristic effector functions designated by isotype. For example, IgG is separated into four subclasses known as IgG1, IgG2, IgG3, and IgG4. An Fc referred to herein may comprise any class or subclass of heavy chain constant region.

Ig molecules interact with multiple classes of cellular receptors. For example IgG molecules interact with three classes of Fcγ receptors (FcγR) specific for the IgG class of antibody, namely FcγRI, FcγRII, and FcγRIII. The important sequences for the binding of IgG to the FcγR receptors have been reported to be located in the CH2 and CH3 domains. The serum half-life of an antibody is influenced by the ability of that antibody to bind to an Fc receptor (FcR). Similarly, the serum half-life of IgFc is also influenced by the ability to bind to such receptors (Gillies S D et al., (1999) *Cancer Res.* 59:2159-66). An Fc referred to herein may bind to one or more of these receptors.

The antibodies disclosed herein may comprise an Fc that includes at least a portion of the carboxy-terminus of an immunoglobulin heavy chain. For example, the Fc may comprise: a CH2 domain, a CH3 domain, a CH4 domain, a CH2-CH3 domain, a CH2-CH4 domain, a CH2-CH3-CH4 domain, a hinge-CH2 domain, a hinge-CH2-CH3 domain, a hing-CH2-CH4 domain, or a hinge-CH2-CH3-CH4 domain. The Fc domain may be derived from antibodies belonging any of the immunoglobulin classes, i.e., IgA, IgD, IgE, IgG, or IgM or any of the IgG antibody subclasses, i.e., IgG1, IgG2, IgG3, and IgG4. The Fc domain may be a naturally occurring Fc sequence, including natural allelic or splice variants. The Fc domain may be a hybrid domain comprising a portion of an Fc domain from two or more different Ig isotypes, for example, an IgG2/IgG4 hybrid Fc domain. In exemplary embodiments, the Fc domain is derived from a human immunoglobulin molecule. The Fc domain may be a humanized or deimmunized version of an Fc domain from a non-human animal, including but not limited to mouse, rat, rabbit, camel, llama, dromedary and monkey.

In certain embodiments, the Fc domain is a variant Fc sequence, e.g., an Fc sequence that has been modified (e.g., by amino acid substitution, deletion and/or insertion) relative to a parent Fc sequence (e.g., an unmodified Fc polypeptide that is subsequently modified to generate a variant), to provide desirable structural features and/or biological activity.

For example, one may make modifications in the Fc region in order to generate an Fc variant that (a) has increased or decreased antibody-dependent cell-mediated cytotoxicity (ADCC), (b) increased or decreased complement mediated cytotoxicity (CDC), (c) has increased or decreased affinity for C1q and/or (d) has increased or decreased affinity for a Fc receptor relative to the parent Fc. Such Fc region variants will generally comprise at least one amino acid modification in the Fc region. Combining amino acid modifications is thought to be particularly desirable. For example, the variant Fc region may include two, three, four, five, etc substitutions therein, e.g. of the specific Fc region positions identified herein (including the figures).

A variant Fc domain may comprise a sequence alteration wherein sites involved in disulfide bond formation are removed. Such removal may avoid reaction with other cysteine-containing proteins present in the host cell used to produce the molecules of the invention. For this purpose, the cysteine-containing segment at the N-terminus may be truncated or cysteine residues may be deleted or substituted with other amino acids (e.g., alanyl, seryl). Even when cysteine residues are removed, the single chain Fc domains can still form a dimeric Fc domain that is held together non-covalently. In other embodiments, a native Fc domain may be modified to make it more compatible with a selected host cell. For example, one may remove the PA sequence near the N-terminus of a typical native Fc, which may be recognized by a digestive enzyme in *E. coli* such as proline iminopeptidase. In other embodiments, one or more glycosylation sites within the Fc domain may be removed. Residues that are typically glycosylated (e.g., asparagine) may confer cytolytic response. Such residues may be deleted or substituted with unglycosylated residues (e.g., alanine). In other embodiments, sites involved in interaction with complement, such as the C1q binding site, may be removed from the Fc domain. For example, one may delete or substitute the EKK sequence of human IgG1. In certain embodiments, sites that affect binding to Fc receptors may be removed, preferably sites other than salvage receptor binding sites. In other embodiments, an Fc domain may be modified to remove an ADCC site. ADCC sites are known in the art; see, for example, Molec. Immunol. 29 (5): 633-9 (1992) with regard to ADCC sites in IgG1. Specific examples of variant Fc domains are disclosed for example, in WO 97/34631 and WO 96/32478.

In one embodiment, the hinge region of CH1 is modified such that the number of cysteine residues in the hinge region is altered, e.g., increased or decreased. This approach is described further in U.S. Pat. No. 5,677,425 by Bodmer et al. The number of cysteine residues in the hinge region of CH1 is altered to, for example, facilitate assembly of the light and heavy chains or to increase or decrease the stability of the antibody.

In another embodiment, the Fc hinge region of an antibody is mutated to decrease the biological half-life of the antibody. More specifically, one or more amino acid mutations are introduced into the CH2-CH3 domain interface region of the Fc-hinge fragment such that the antibody has impaired Staphylococcyl protein A (SpA) binding relative to native Fc-hinge domain SpA binding. This approach is described in further detail in U.S. Pat. No. 6,165,745 by Ward et al.

In another embodiment, the antibody is modified to increase its biological half-life. Various approaches are possible. For example, one or more of the following mutations can be introduced: T252L, T254S, T256F, as described in U.S. Pat. No. 6,277,375 to Ward. Alternatively, to increase the biological half life, the antibody can be altered within the CH1 or CL region to contain a salvage receptor binding epitope taken from two loops of a CH2 domain of an Fc region of an IgG, as described in U.S. Pat. Nos. 5,869,046 and 6,121,022 by Presta et al.

In certain embodiments, an Fc comprises the CH2 and CH3 regions of a human IgG1 as shown below: VFLFPPKPKDTLMISRTPEVTCVVVDVSHEDPEVKFNWYVDGVEVHNAKTKPREEQ YNSTYRVVSVLTVLHQDWLNGKEYKCKVSNKALPAPIEKTISKAKGQPR EPQVYTLPPSRDELTKNQVSLTCLVKGFYPSDIAVEWESNGQPENNYKTTPPVLDSDGSFFLYSKL TVDKSRWQQGNVFSCSVMHEALHNHYTQKSLSLSPGK (SEQ ID NO: 171). It should be understood that the glycine and lysine at the end of are optional. In certain embodiments, an Fc comprises an amino acid sequence that is at least 50%, 60%, 75%, 80%, 85%, 90%, 95%, 96%, 97%, 98%, or 99% identical to (SEQ ID NO: 171). In certain embodiments, an Fc comprises an amino acid sequence having at least 50, 100, or 150 contiguous amino acids of (SEQ ID NO: 171). In certain embodiments, an Fc comprises an amino acid sequence having from 50-100, 50-150, or 100-150 contiguous amino acids of (SEQ ID NO: 171). In certain embodiments, an Fc comprises an amino acid sequence comprising (SEQ ID NO: 171) with from 1-5, 1-10, 1-15, 1-20, or 1-25 substitutions or conservative substitutions. The human wild type γ1 constant region sequence was first described by Leroy Hood's group in Ellison et al., Nucl. Acids Res. 10:4071 (1982). EU Index positions 356, 358, and 431 define the G1m γ1 haplotype.

Additional Fc variants are described below. It is understood that the Fc regions of the disclosure comprise the numbering scheme according to the EU index as in Kabat et al. (1991, NIH Publication 91-3242, National Technical Information Service, Springfield, Va.).

The present disclosure encompasses peptides having an Fc region that is altered by replacing at least one amino acid residue with a different amino acid residue to alter the effector function(s) of the antibody. For example, one or more amino acids selected from amino acid residues 234, 235, 236, 237, 297, 318, 320 and 322 can be replaced with a different amino acid residue such that the antibody has an altered affinity for an effector ligand but retains the antigen-binding ability of the parent antibody. The effector ligand to which affinity is altered can be, for example, an Fc receptor or the C1 component of complement. This approach is described in further detail in U.S. Pat. Nos. 5,624,821 and 5,648,260, both by Winter et al.

In another example, one or more amino acids selected from amino acid residues 329, 331 and 322 can be replaced with a different amino acid residue such that the antibody has altered C1q binding and/or reduced or abolished complement dependent cytotoxicity (CDC). This approach is described in further detail in U.S. Pat. No. 6,194,551 by Idusogie et al.

In another example, one or more amino acid residues within amino acid positions 231 and 239 are altered to thereby alter the ability of the antibody to fix complement. This approach is described further in PCT Publication WO 94/29351 by Bodmer et al.

In yet another example, the Fc region is modified to increase the ability of the antibody to mediate antibody dependent cellular cytotoxicity (ADCC) and/or to increase the affinity of the antibody for an Fcγ receptor by modifying one or more amino acids at the following positions: 238, 239, 248, 249, 252, 254, 255, 256, 258, 265, 267, 268, 269, 270, 272, 276, 278, 280, 283, 285, 286, 289, 290, 292, 293, 294, 295, 296, 298, 301, 303, 305, 307, 309, 312, 315, 320, 322, 324, 326, 327, 329, 330, 331, 333, 334, 335, 337, 338, 340, 360, 373, 376, 378, 382, 388, 389, 398, 414, 416, 419, 430, 434, 435, 437, 438 or 439. This approach is described further in PCT Publication WO 00/42072 by Presta. Moreover, the binding sites on human IgG1 for FcγR1, FcγRII, FcγRIII and FcRn have been mapped and variants with improved binding have been described (see Shields, R. L. et al. (2001) *J. Biol. Chem.* 276:6591-6604). Specific mutations at positions 256, 290, 298, 333, 334 and 339 were shown to improve binding to FcγRIII. Additionally, the following combination mutants were shown to improve FcγRIII binding: T256A/S298A, S298A/E333A, S298A/K224A and S298A/E333A/K334A. Exemplary substitutions include 236A, 239D, 239E, 268D, 267E, 268E, 268F, 324T, 332D, and 332E. Exemplary variants include 239D/332E, 236A/332E, 236A/239D/332E, 268F/324T, 267E/268F, 267E/324T, and 267E/268F/324T. Other modifications for enhancing FcyR and complement interactions include but are not limited to substitutions 298A, 333A, 334A, 326A, 2471, 339D, 339Q, 280H, 290S, 298D, 298V, 243L, 292P, 300L, 396L, 3051, and 396L. These and other modifications are reviewed in Strohl, 2009, Current Opinion in Biotechnology 20:685-691.

Fc modifications that increase binding to an Fc gamma receptor include amino acid modifications at any one or more of amino acid positions 238, 239, 248, 249, 252, 254, 255, 256, 258, 265, 267, 268, 269, 270, 272, 279, 280, 283, 285, 298, 289, 290, 292, 293, 294, 295, 296, 298, 301, 303, 305, 307, 312, 315, 324, 327, 329, 330, 335, 337, 3338, 340, 360, 373, 376, 379, 382, 388, 389, 398, 414, 416, 419, 430, 434, region, wherein the numbering of the residues in the Fc region is that of the EU index as in Kabat (WO00/42072).

Other Fc modifications that can be made to Fcs are those for reducing or ablating binding to FcyRs and/or complement proteins, thereby reducing or ablating Fc-mediated effector functions such as ADCC, ADCP, and CDC. Exemplary modifications include but are not limited substitutions, insertions, and deletions at positions 234, 235, 236, 237, 267, 269, 325, and 328, wherein numbering is according to the EU index. Exemplary substitutions include but are not limited to 234G, 235G, 236R, 237K, 267R, 269R, 325L, and 328R, wherein numbering is according to the EU index. An Fc variant may comprise 236R/328R. Other modifications for reducing FcyR and complement interactions include substitutions 297A, 234A, 235A, 237A, 318A, 228P, 236E, 268Q, 309L, 330S, 331S, 220S, 226S, 229S, 238S, 233P, and 234V, as well as removal of the glycosylation at position 297 by mutational or enzymatic means or by production in organisms such as bacteria that do not glycosylate proteins. These and other modifications are reviewed in Strohl, 2009, Current Opinion in Biotechnology 20:685-691.

Optionally, the Fc region may comprise a non-naturally occurring amino acid residue at additional and/or alternative positions known to one skilled in the art (see, e.g., U.S. Pat. Nos. 5,624,821; 6,277,375; 6,737,056; 6,194,551; 7,317,091; 8,101,720; PCT Patent Publications WO 00/42072; WO 01/58957; WO 02/06919; WO 04/016750; WO 04/029207; WO 04/035752; WO 04/074455; WO 04/099249; WO 04/063351; WO 05/070963; WO 05/040217, WO 05/092925 and WO 06/020114).

Fc variants that enhance affinity for an inhibitory receptor FcyR11b may also be used. Such variants may provide an Fc with immunomodulatory activities related to FcyR11b+ cells, including for example B cells and monocytes. In one embodiment, the Fc variants provide selectively enhanced affinity to FcyR11b relative to one or more activating receptors. Modifications for altering binding to FcyR11b include one or more modifications at a position selected from the group consisting of 234, 235, 236, 237, 239, 266, 267, 268, 325, 326, 327, 328, and 332, according to the EU index. Exemplary substitutions for enhancing FcyR11b affinity include but are not limited to 234D, 234E, 234W, 235D, 235F, 235R, 235Y, 236D, 236N, 237D, 237N, 239D, 239E, 266M, 267D, 267E, 268D, 268E, 327D, 327E, 328F, 328W, 328Y, and 332E. Exemplary substitutions include 235Y, 236D, 239D, 266M, 267E, 268D, 268E, 328F, 328W, and 328Y. Other Fc variants for enhancing binding to FcyR11b include 235Y/267E, 236D/267E, 239D/268D, 239D/267E, 267E/268D, 267E/268E, and 267E/328F.

The affinities and binding properties of an Fc region for its ligand may be determined by a variety of in vitro assay methods (biochemical or immunological based assays) known in the art including but not limited to, equilibrium methods (e.g., enzyme-linked immunoabsorbent assay (ELISA), or radioimmunoassay (RIA)), or kinetics (e.g., BIACORE analysis), and other methods such as indirect binding assays, competitive inhibition assays, fluorescence resonance energy transfer (FRET), gel electrophoresis and chromatography (e.g., gel filtration). These and other methods may utilize a label on one or more of the components being examined and/or employ a variety of detection methods including but not limited to chromogenic, fluorescent, luminescent, or isotopic labels. A detailed description of binding affinities and kinetics can be found in Paul, W. E., ed., Fundamental Immunology, 4th Ed., Lippincott-Raven, Philadelphia (1999), which focuses on antibody-immunogen interactions.

An Fc may also increase the serum half-life of an antibody. For example, this may be done by increasing the binding affinity of the Fc region for FcRn. For example, one or more of more of following residues can be mutated: 252, 254, 256, 433, 435, 436, as described in U.S. Pat. No. 6,277,375.

Other exemplary Fc variants that increase binding to FcRn and/or improve pharmacokinetic properties include substitutions at positions 259, 308, 428, and 434, including for example 2591, 308F, 428L, 428M, 434S, 434H, 434F, 434Y, and 434M. Other variants that increase Fc binding to FcRn include: 250E, 250Q, 428L, 428F, 250Q/428L (Hinton et al., 2004, J. Biol. Chem. 279(8): 6213-6216, Hinton et al. 2006 Journal of Immunology 176:346-356), 256A, 272A, 286A, 305A, 307A, 307Q, 311A, 312A, 376A, 378Q, 380A, 382A, 434A (Shields et al, Journal of Biological Chemistry, 2001, 276(9):6591-6604), 252F, 252T, 252Y, 252W, 254T, 256S, 256R, 256Q, 256E, 256D, 256T, 309P, 311S, 433R, 433S, 433I, 433P, 433Q, 434H, 434F, 434Y, 252Y/254T/256E, 433K/434F/436H, 308T/309P/311S (Dall Acqua et al. Journal of Immunology, 2002, 169:5171-5180, Dall'Acqua et al., 2006, Journal of Biological Chemistry 281:23514-23524). Other modifications for modulating FcRn binding are described in Yeung et al., 2010, J Immunol, 182:7663-7671.

In certain embodiments, hybrid IgG isotypes with particular biological characteristics may be used. For example, an lgG1/lgG3 hybrid variant may be constructed by substituting lgG1 positions in the CH2 and/or CH3 region with the amino acids from lgG3 at positions where the two isotypes differ. Thus a hybrid variant IgG antibody may be constructed that comprises one or more substitutions, e.g., 274Q, 276K, 300F, 339T, 356E, 358M, 384S, 392N, 397M, 422I, 435R, and 436F. In other embodiments of the invention, an lgG1/lgG2 hybrid variant may be constructed by substituting lgG2 positions in the CH2 and/or CH3 region with amino acids from lgG1 at positions where the two isotypes differ. Thus a hybrid variant IgG antibody may be constructed that comprises one or more substitutions, e.g., one or more of the following amino acid substitutions: 233E, 234L, 235L, -236G (referring to an insertion of a glycine at position 236), and 327A.

In still another embodiment, the glycosylation of an antibody is modified. For example, an aglycoslated antibody can be made (i.e., the antibody lacks glycosylation). Glycosylation can be altered to, for example, increase the affinity of the antibody for antigen. Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen. Such an approach is described in further detail in U.S. Pat. Nos. 5,714,350 and 6,350,861 by Co et al. Alternatively, oligosaccharides that are covalently attached to the Fc region can be changed, for example by expressing an IgG in various organisms or cell lines, engineered or otherwise (for example Lec-13 CHO cells or rat hybridoma YB2/0 cells), by regulating enzymes involved in the glycosylation pathway (for example FUT8 [a1,6-fucosyltranserase] and/or β1-4-N-acetylglucosaminyltransferase III [GnTIII]), by modifying carbohydrate(s) after the IgG has been expressed, or by expressing an Fc fusion protein in the presence of fucose analogs as enzymatic inhibitors. Other methods for modifying glycoforms of Fc include using glycoengineered strains of yeast (Li et al., 2006, Nature Biotechnology 24(2):210-215), moss (Nechansky et al., 2007, Mol Immunjol 44(7): 1826-8), and plants (Cox et al., 2006, Nat Biotechnol 24(12):1591-7).

In one embodiment, Fc fusions are glycoengineered to alter the level of sialylation. Higher levels of sialylated Fc glycans in Fc molecules can adversely impact functionality (Scallon et al., 2007, Mol Immunol. 44(7): 1524-34), and differences in levels of Fc sialylation can result in modified anti-inflammatory activity (Kaneko et al., 2006, Science 313:670-673).

The level of glycosylation of an Fc molecule may also be modified by specific mutations. For example, a mutation at amino acid position 297 or 299 removes the glycosyation at position 297. Other Fc modifications that may be used include those described in WO88/07054, WO88/07089, U.S. Pat. No. 6,277,375, WO99/051642, WO01/058957, WO2003/074679, WO2004/029207, U.S. Pat. No. 7,317, 091 and WO2004/099249.

Additionally or alternatively, an antibody can be made that has an altered type of glycosylation, such as a hypofucosylated antibody having reduced amounts of fucosyl residues or an antibody having increased bisecting GlcNac structures. Such altered glycosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies of the invention to thereby produce an antibody with altered glycosylation. For example, EP 1,176,195 by Hanai et al. describes a cell line with a functionally disrupted FUT8 gene, which encodes a fucosyl transferase, such that antibodies expressed in such a cell line exhibit hypofucosylation. PCT Publication WO 03/035835 by Presta describes a variant CHO cell line, Lec13 cells, with reduced ability to attach fucose to Asn(297)-linked carbohydrates, also resulting in hypofucosylation of antibodies expressed in that host cell (see also Shields, R. L. et al. (2002) *J. Biol. Chem.* 277:26733-26740). PCT Publication WO 99/54342 by Umana et al. describes cell lines engineered to express glycoprotein-modifying glycosyl transferases (e.g., beta(1, 4)-N-acetylglucosaminyltransferase III (GnTIII)) such that antibodies expressed in the engineered cell lines exhibit increased bisecting GlcNac structures which results in increased ADCC activity of the antibodies (see also Umana et al. (1999) *Nat. Biotech.* 17:176-180).

Moreover, particular Fc variants include the Fc4 variant which contains a γ1 hinge region, but Arg 218 has been introduced in the hinge region to include a Bg1II restriction enzyme recognition sequence to facilitate cloning, and includes a Ser for Cys residue substitution to prevent deleterious effects due to the potential presence of an unpaired sulfhydral group. The CH2 region of Fc4 is based on the γ1 CH2 and contains three amino acid substitutions that reduce Fc γ receptor I (FcγRI) binding. These are the substitutions at EU index positions 234, 235, and 237. These substitutions were described by Greg Winter's group in Duncan et al., Nature 332:563 (1988) and were shown in that paper to reduce binding to the Fc γ RI. In addition, two amino acid substitutions in the complement C1q binding site were introduced to reduce complement fixation. These are the substitutions at EU index positions 330 and 331. The importance, or relevance, of positions 330 and 331 in complement C1q binding (or lack of complement fixation or activation) is described by Sherie Morrison's group in Tao et al., J. Exp. Med. 178:661 (1993) and Canfield and Morrison, J. Exp. Med. 173:1483 (1991). The CH3 region in the Fc4 variant remains identical to the wild type γ1 Fc.

Fc5 is a variant of Fc4 in which the Arg 218 substitution in the hinge region was returned to the wild type Lys 218 residue. Fc5 also contains the same Cys 220 to Ser substitution as Fc4 as well as the same CH2 substitutions with a CH2 region that is identical to the wild type γ1 Fc. The Fc6 variant contains the same hinge region substitutions as Fc5 and contains the same CH2 substitutions as Fc4. The Fc6 CH3 region does not contain a carboxyl terminal lysine residue. This particular Lys residue does not have an assigned EU index number. This lysine is removed to a varying degree from mature immunoglobulins and therefore predominantly not found on circulating antibodies. The absence of this residue on recombinant Fc may result in a more homogeneous product. The Fc7 variant is identical to the wild type γ1 Fc in the hinge region. Its CH2 region is based on γ1 CH2, but the N-linked carbohydrate attachment site at residue Asn-297 is changed to Gln to produce a deglycosylated Fc. (See e.g., Tao and Morrison (1989) J. Immunol. 143:2595-2601). The CH3 region is identical to the wild type γ1 Fc. The Fc8 variant has a hinge region that is identical to Fc4, and both the CH2 region and the CH3 region are identical to the corresponding wild type γ1 Fc regions. The Fc9 variant contains a shortened γ1 hinge starting at the Asp residue just carboxy-terminal to the Cys residue involved in disulfide linkage to the light chain. The remaining hinge sequence is identical to the wild type γ1 hinge. Both the CH2 region sequence and the CH3 region sequence are identical to the corresponding regions for the wild-type γ1 Fc. The Fc10 variant-contains the same hinge region substitution as Fc5. Both the CH2 region sequence and the CH3 region sequence are identical to the corresponding regions for the wild-type γ1 Fc. The Fc11 variant contains the same hinge region substitutions as Fc5. Its CH2 domain is based on γ1 CH2, but contains the substitutions to decrease Fcγ Receptor binding (substitutions at EU index positions 234, 235, and 237). Fc11 is wild type for C1q binding and complement fixation. The CH3 domain of Fc11 is identical to the wild type γ1 CH3. The Fc12 variant contains a γ1 hinge with Cys 220 Ser, Cys 226 Ser, and Cys 229 Ser substitutions, has a CH2 domain that is identical to that of Fc5, and has wild-type γ1 CH3 domain. The Fc13 variant contains a γ1 hinge with Cys 220 Ser, Cys 226 Ser, and Cys 229 Ser substitutions, has CH2 domain that is identical to that of Fc5, and has a wild-type γ1 CH3 with Tyr 407 Gly substitution. The Fc14 variant contains a γ1 hinge with Cys 220 Ser, Cys 226 Ser, and Cys 229 Ser substitutions, has a wild-type γ1 CH2, and has a wild-type γ1 CH3 with Tyr 407 Gly substitution. The Fc15 variant contains a γ1 hinge with a Ser 228 Pro substitution to decrease IgG4 "Fab exchange", and has a wild-type γ4 CH2 and CH3 domains. The Fc16 variant contains a γ1 hinge that contains a Cys 220 Ser substitution, has a CH2 domain identical to the γ1 CH2, and has a CH3 domain identical to the wild type γ4 CH3. The Fc17 variant contains a γ1 hinge with a Cys 220 Ser substitution, has a γ1 CH2 domain with a Phe 243 Ala substitution, and has a CH3 domain identical to the wild type γ1 CH3. The Fc18 variant contains a γ1 hinge with a Cys 220 Ser substitution, has a γ1 CH2 domain identical to the wild type γ1 CH2, and contains a γ1 CH3 with a His 435 Ala substitution. The Fc19 variant contains a hinge identical to Fc5, has a CH2 domain identical to Fc5, except N-linked carbohydrate attachment site at residue Asn-297 is changed to Gln to produce a deglycosylated Fc, and has a CH3 domain identical to the wild type γ1 CH3. The Fc21 variant contains a γ1 hinge with Cys 220 Ser, Cys 226 Ser, and Cys 229 Ser substitutions, has a CH2 domain identical to Fc5, and has a γ1 CH3 with Phe 405 Ala and Tyr 407 Gly substitutions. The Fc22 variant contains a γ1 hinge with Cys 220 Ser, Cys 226 Ser, and Cys 229 Ser substitutions, has a CH2 domain identical to Fc1, and has a γ1 CH3 with Phe 405 Ala and Tyr 407 Gly substitutions. The Fc23 variant contains a γ1 hinge with Cys 220 Ser substitution, has a γ1 CH2 domain with Leu 234 Ala, Leu 235 Glu, Pro 331 Ser substitutions, and a CH3 domain identical to the wild type γ1 Fc.

Another modification of the antibodies herein that is contemplated by the invention is pegylation. An antibody can be pegylated to, for example, increase the biological (e.g., serum) half-life of the antibody. To pegylate an antibody, the antibody, or fragment thereof, typically is reacted with polyethylene glycol (PEG), such as a reactive ester or aldehyde derivative of PEG, under conditions in which one or more PEG groups become attached to the antibody or antibody fragment. Preferably, the pegylation is carried out via an acylation reaction or an alkylation reaction with a reactive PEG molecule (or an analogous reactive water-soluble polymer). As used herein, the term "polyethylene glycol" is intended to encompass any of the forms of PEG that have been used to derivatize other proteins, such as mono (C1-C10) alkoxy- or aryloxy-polyethylene glycol or polyethylene glycol-maleimide. In certain embodiments, the antibody to be pegylated is an aglycosylated antibody. Methods for pegylating proteins are known in the art and can be applied to the antibodies of the invention. See for example, EP 0 154 316 by Nishimura et al. and EP 0 401 384 by Ishikawa et al.

Methods of Use

In some instances, the disclosure provides methods of treatment that include administering to a subject a composition disclosed herein.

Provided herein are methods for treating and/or preventing cancer or symptoms of cancer in a subject comprising administering to the subject a therapeutically effective amount of a composition comprising a peptide that immunospecifically binds to MHC class I polypeptide-related sequence A (MICA), wherein the peptide comprises complementarity determining region (CDR) 3 of the $V_H$ of antibody ID 1, 6, 7, 8, 9, 11 or 12 shown in Table 1 having 5 or fewer conservative amino acid substitutions, and CDR3 of the $V_L$ of antibody ID 1, 6, 7, 8, 9, 11 or 12 shown in Table 1 having 5 or fewer conservative amino acid substitutions. In some embodiments the cancer is a cancer associated with overexpression of MICA. In some embodiments, the cancer is melanoma, lung, breast, kidney, ovarian, prostate, pancreatic, gastric, and colon carcinoma, lymphoma or leukemia. In some embodiments, the cancer is melanoma. In some embodiments, the cancer is a plasma cell malignancy, for example, multiple myeloma (MM) or pre-malignant condition of plasma cells. In some embodiments the subject has been diagnosed as having a cancer or as being predisposed to cancer.

In some instances, the disclosure provides methods for treating and/or preventing cancer or symptoms of cancer in a subject comprising administering to the subject a therapeutically effective amount of a composition comprising an isolated antibody which specifically binds to MHC class I polypeptide-related sequence A (MICA), wherein the antibody comprises a heavy chain variable region $V_H$) comprising the $V_H$ CDR1, $V_H$ CDR2, and $V_H$ CDR3 as shown in the $V_H$ sequence of SEQ ID NO: 2, 77, 96, 113, 131, 150 or 168 and a light chain variable region ($V_L$) sequence of SEQ ID NO: 11, 79, 98, 113, 133, 152 or 170.

Symptoms of cancer are well-known to those of skill in the art and include, without limitation, unusual mole features, a change in the appearance of a mole, including asymmetry, border, color and/or diameter, a newly pigmented skin area, an abnormal mole, darkened area under nail, breast lumps, nipple changes, breast cysts, breast pain, death, weight loss, weakness, excessive fatigue, difficulty eating, loss of appetite, chronic cough, worsening breathlessness, coughing up blood, blood in the urine, blood in stool, nausea, vomiting, liver metastases, lung metastases, bone metastases, abdominal fullness, bloating, fluid in peritoneal cavity, vaginal bleeding, constipation, abdominal distension, perforation of colon, acute peritonitis (infection, fever, pain), pain, vomiting blood, heavy sweating, fever, high blood pressure, anemia, diarrhea, jaundice, dizziness, chills, muscle spasms, colon metastases, lung metastases, bladder metastases, liver metastases, bone metastases, kidney metastases, and pancreatic metastases, difficulty swallowing, and the like.

The methods disclosed herein can be applied to a wide range of species, e.g., humans, non-human primates (e.g., monkeys), horses, cattle, pigs, sheep, deer, elk, goats, dogs, cats, mustelids, rabbits, guinea pigs, hamsters, rats, and mice.

The terms "treat" or "treating," as used herein, refers to partially or completely alleviating, inhibiting, ameliorating, and/or relieving the onset, progression or recurrence of at least one symptom or biological indicia of the disease or condition from which the subject is suffering. In some instances, treatment can result in the continued absence of the disease or condition from which the subject is suffering.

The term "effective dose" or "effective dosage" is defined as an amount sufficient to achieve or at least partially achieve the desired effect. The term "therapeutically effective dose" is defined as an amount sufficient to cure or at least partially arrest the disease and its complications in a patient already suffering from the disease. Amounts effective for this use will depend upon the severity of the disorder being treated and the general state of the patient's own immune system.

A "therapeutically effective amount" or "therapeutically effective dosage" of a drug or therapeutic agent, such as an Fc fusion protein of the invention, is any amount of the drug that, when used alone or in combination with another therapeutic agent, promotes disease regression evidenced by a decrease in severity of disease symptoms, an increase in frequency and duration of disease symptom-free periods, or a prevention of impairment or disability due to the disease affliction. A therapeutically effective amount or dosage of a drug includes a "prophylactically effective amount" or a "prophylactically effective dosage", which is any amount of the drug that, when administered alone or in combination with another therapeutic agent to a subject at risk of developing a disease or of suffering a recurrence of disease, inhibits the development or recurrence of the disease. The ability of a therapeutic agent to promote disease regression or inhibit the development or recurrence of the disease can be evaluated using a variety of methods known to the skilled practitioner, such as in human subjects during clinical trials, in animal model systems predictive of efficacy in humans, or by assaying the activity of the agent in in vitro assays.

By way of example, an anti-cancer agent promotes cancer regression in a subject. In preferred embodiments, a therapeutically effective amount of the drug promotes cancer regression to the point of eliminating the cancer. "Promoting cancer regression" means that administering an effective amount of the drug, alone or in combination with an anti-neoplastic agent, results in a reduction in tumor growth or size, necrosis of the tumor, a decrease in severity of at least one disease symptom, an increase in frequency and duration of disease symptom-free periods, a prevention of impairment or disability due to the disease affliction, or otherwise amelioration of disease symptoms in the patient. In addition, the terms "effective" and "effectiveness" with regard to a treatment includes both pharmacological effectiveness and physiological safety. Pharmacological effectiveness refers to the ability of the drug to promote cancer regression in the patient. Physiological safety refers to the level of toxicity, or other adverse physiological effects at the cellular, organ and/or organism level (adverse effects) resulting from administration of the drug.

By way of example for the treatment of tumors, a therapeutically effective amount or dosage of the drug preferably inhibits cell growth or tumor growth by at least about 20%, more preferably by at least about 40%, even more preferably by at least about 60%, and still more preferably by at least about 80% relative to untreated subjects. In the most preferred embodiments, a therapeutically effective amount or dosage of the drug completely inhibits cell growth or tumor growth, i.e., preferably inhibits cell growth or tumor growth by 100%. The ability of a compound to inhibit tumor growth can be evaluated using the assays described infra. Alternatively, this property of a composition can be evaluated by examining the ability of the compound to inhibit cell growth, such inhibition can be measured in vitro by assays known to the skilled practitioner. In other preferred embodiments of the invention, tumor regression may be observed and continue for a period of at least about 20 days, more preferably at least about 40 days, or even more preferably at least about 60 days.

In general, methods include selecting a subject at risk for or with a condition or disease. In some instances, the subject's condition or disease can be treated with a pharmaceutical composition disclosed herein. For example, in some instances, methods include selecting a subject with cancer, e.g., wherein the subject's cancer can be treated by targeting one or both of MICA and/or angiopoetin-2.

In some instances, treatments methods can include a single administration, multiple administrations, and repeating administration as required for the prophylaxis or treatment of the disease or condition from which the subject is suffering. In some instances treatment methods can include assessing a level of disease in the subject prior to treatment, during treatment, and/or after treatment. In some instances, treatment can continue until a decrease in the level of disease in the subject is detected.

The terms "administer," "administering," or "administration," as used herein refers to implanting, absorbing, ingesting, injecting, or inhaling, the inventive peptide, regardless of form. In some instances, one or more of the peptides disclosed herein can be administered to a subject topically (e.g., nasally) and/or orally. For example, the methods herein include administration of an effective amount of compound or compound composition to achieve the desired or stated effect. Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

For example, dosage regimens are adjusted to provide the optimum desired response (e.g., a therapeutic response). A single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. "Dosage unit form" as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

For administration of an anti-MICA antibody or antibody fragment, the dosage ranges from about 0.0001 to 100 mg/kg, and more usually 0.01 to 5 mg/kg, of the host body weight. For example dosages can be 0.3 mg/kg body weight, 1 mg/kg body weight, 3 mg/kg body weight, 5 mg/kg body weight or 10 mg/kg body weight or within the range of 1-10 mg/kg. An exemplary treatment regime entails administration once per week, once every two weeks, once every three weeks, once every four weeks, once a month, once every 3 months or once every three to 6 months. Preferred dosage regimens for an anti-MICA antibody of the invention include 1 mg/kg body weight or 3 mg/kg body weight via intravenous administration, with the antibody being given using one of the following dosing schedules: (i) every four weeks for six dosages, then every three months; (ii) every three weeks; (iii) 3 mg/kg body weight once followed by 1 mg/kg body weight every three weeks.

In some methods, two or more monoclonal antibodies with different binding specificities are administered simultaneously, in which case the dosage of each antibody administered falls within the ranges indicated. Antibody is usually administered on multiple occasions. Intervals between single dosages can be, for example, weekly, monthly, every three months or yearly. Intervals can also be irregular as indicated by measuring blood levels of antibody to the target antigen in the patient. In some methods, dosage is adjusted to achieve a plasma antibody concentration of about 1-1000 μg/ml and in some methods about 25-300 μg/ml.

Alternatively, pharmaceutical compositions can be administered as a sustained release formulation, in which case less frequent administration is required. Dosage and frequency vary depending on the half-life of the antibody in the patient. In general, human antibodies show the longest half-life, followed by humanized antibodies, chimeric antibodies, and nonhuman antibodies. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patient can be administered a prophylactic regime.

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

Following administration, the subject can be evaluated to detect, assess, or determine their level of disease. In some instances, treatment can continue until a change (e.g., reduction) in the level of disease in the subject is detected.

Upon improvement of a patient's condition (e.g., a change (e.g., decrease) in the level of disease in the subject), a maintenance dose of a compound, composition or combination of this invention may be administered, if necessary. Subsequently, the dosage or frequency of administration, or both, may be reduced, as a function of the symptoms, to a level at which the improved condition is retained. Patients may, however, require intermittent treatment on a long-term basis upon any recurrence of disease symptoms.

In some instances, the disclosure provides methods for detecting immune cells e.g., B cells and/or memory B cells, from a human subject. Such methods can be used, for example, to monitor the levels of immune cells e.g., B cells and/or memory B cells, in a human subject, e.g., following an event. Exemplary events can include, but are not limited to, detection of diseases, infection; administration of a therapeutic composition disclosed herein, administration of a therapeutic agent or treatment regimen, administration of a vaccine, induction of an immune response. Such methods can be used clinically and/or for research.

EXAMPLES

The invention is further described in the following examples, which do not limit the scope of the invention described in the claims.

Methods are described herein that allow sensitive, specific, and reliable detection of rare memory B cells, with defined antigen specificity, from limited quantities of peripheral blood. Methods allowed visualization and isolation of memory B cells months to years after antigen had been cleared.

Proof of principle for the methods disclosed herein was established using tetramers of tetanus toxin C-fragment (TTCF), as reported in detail in Franz et al. (Blood, 118(2): 348-357 (2011)), which reference is hereby incorporated by reference in its entirety.

TTCF (i.e., the 52 kDa, non-toxic, C-terminal fragment of TTCF) was selected as a model antigen because the majority of individuals have been vaccinated with tetanus toxoid and persistent IgG antibody titers are induced by the vaccine (Amanna et al., N. Engl. J. Med., 357:1903-1915, 2007). Accordingly, use of TTCF afforded a large pool of subjects in which the methods disclosed herein could be verified. One of skill in the art will appreciate, however, that the present methods can be adapted to include any disease-related antigen using routine skill. As demonstrated in the examples below, such adaption has been shown through the acquisition of antibodies directed against MICA and angiopoietin-2, which are cancer-related antigens.

Example 1

Antigen Expression and Tetramer Formation

As described in further detail below, TTCF was expressed in *Eschericia coli* and a BirA site was attached to the N-terminus for site-specific mono-biotinylation by BirA enzyme. A flexible linker was placed between the protein and the biotinylation site to prevent steric hindrance of antibody binding. TTCF was purified by anion-exchange chromatography, biotinylated with BirA, and separated from free biotin and BirA by gel filtration chromatography. TTCF tetramers were generated by incubating fluorescently tagged streptavidin with biotinylated TTCF antigen at a molar ratio of 1:4. These tetramers were then used along with a panel of mAbs for the identification of tetanus toxoid specific memory B cells.

TTCF was cloned in pET-15b (Novagen). Protein expression was induced in BL21(DE3) *Eschericia coli* with 1 mM isopropyl β-D-1-thiogalactopyranoside (IPTG) for 4 hours at 28° C. Cells were washed, lysed, and resulting supernatant was collected. TTCF was purified using a HIS-Select affinity column (Sigma). The His-tag was removed proteolytically. Murine CD80 membrane proximal domain was produced using similar methods. Proteins were mono-biotinylated. For certain experiments, Alexa-488 dye molecules (Molecular probes) were linked to primary amines on biotinylated TTCF or CD80.

Antigen tetramers were prepared by incubating biotinyated antigen with premium grade PE labeled streptavidin (Molecular Probes) for at least 20 minutes on ice at a molar ratio of 4:1. Prior to use, tetramer preparations were centrifuged to remove aggregates. In some experiments, tetramers were formed with Alexa-fluor-488 tagged antigens and non-fluorescent streptavidin at a 4:1 ratio.

Example 2

Identification Methods

Methods were performed as described in Franz et al., Blood, 118(2):348-357 (2011). Cells were sorted on a BD FACS Aria II cell sorter. Cells were single-cell sorted. Samples were first gated on $CD19^+$ cells that were negative for a panel of exclusion markers (CD3, CD14, CD16, 7AAD) then gated on plasmablasts, identified by high levels of CD27 and an immediate level of CD19 expression, and finally on tetramer$^+$ CD19$^+$ cells.

Due to the low frequency of memory B cells, it was necessary to carefully reduce background as much as possible. B cells were first enriched by negative selection (cocktail of antibodies to CD2, CD3, CD14, CD16, CD56 and glycophorin A) to remove most cells that could non-specifically bind the tetramer. Enriched cells were split evenly and stained with TTCF or a control tetramer followed by labeling with CD19, CD27 and IgM to specifically select class-switched memory B cells. The gating strategy considered expression of CD19, lack of labeling with a panel of exclusion markers (CD3, CD14, CD16, 7AAD), expression of the memory marker CD27 and lack of IgM expression as evidence of class switching. Tetramer staining was plotted versus CD27 staining for visualization of memory B cells with the antigen specificity of interest. Tetramer-positive B cells were directly sorted into PCR strips containing 3 μl mRNA extraction buffer.

Tubes were kept cold during sorting and sorted cells were frozen and stored at −80° C. CD19+ CD27+ IgM-B cells were used as positive controls.

A previously reported nest PCR protocol was used to amplify heavy and light chain variable segments (Wang et al., J. Immunol. Methods., 244:217-225, 2000). mRNA amplification was carried out under conditions suitable to minimize contamination. Primers used included:

(SEQ ID NO: 19)
TAATACGACTCACTATAGGTTCGGGGAAGTAGTCCTTGACCAGG;

(SEQ ID NO: 20)
TAATACGACTCACTATAGGGATAGAAGTTATTCAGCAGGCACAC;

(SEQ ID NO: 21)
TAATACGACTCACTATAGGCGTCAGGCTCAGRTAGCTGCTGGCCGC.

Nested RT-PCR was performed as described in Franz et al., Blood, 118(2):348-357 (2011).

Negative controls were included to monitor and guard against contamination. From a total of 35 single cells labeled with the TTCF tetramer, 32 heavy and 30 light chain segments were amplified and directly sequence from gel-purified PCR products, corresponding to an overall PCR efficiency of 89%. Sequence analysis revealed that TTCF tetramer$^+$ cells employed a variety of different $V_H$D-$J_H$ gene segments, without dominance of one particular gene segment. Sequences observed supported that clones represented cells diversified by somatic hypermutation.

Antibody production and purification included cloning heavy and light variable domain DNA into separate pcDNA3.3 expression vectors containing the bovine prolactin signal peptide sequence as well as full length IgG1 heavy or kappa light chain constant domains. Antibodies were expressed in CHO-S media (Invitrogen) supplemented with 8 mM Glutamax (Gibco) in 100 ml sinner flasks at 37° C. with 8% $CO_2$. One day prior to transfection, cells were split to 6×10$^5$ cells/ml. On the day of transfection, cells were adjusted, were necessary, to 1×10$^6$ cells/ml. 25 μg of heavy and light chain plasmid DNA were co-transfected using MAX transfection reagent (Invitrogen) and transfected cells were cultured for 6-8 days. Protein was obtained using Protein G sepharose beads and antibody was eluted using 100 mM glycine pH2.5 and separated from beads using Spin-X centrifuge tubes. Purified antibody was exchanged into phosphate buffered saline (PBS) using Micro Bio-Spin columns (BioRad). Protein concentration was assessed by absorbance at 280 nm.

For saturation binding assay, non-biotinylated, MonoQ purified TTCF was labeled with europium and free europium was removed. 96-well flat bottom plates were coated overnight with 20 ng of antibody per well in 100 mM $NaHCO_3$ buffer at pH 9.6. Blocking was performed with assay buffer supplemented with bovine serum albumin (BSA) and bovine gamma globulins. TTCF-europium was diluted in assay buffer (100 nM to 4 pM) and 200 μl was added per well in triplicate. Plates were incubated for 2 hours at 37° C. and washed three times with 200 μl wash buffer (50 mM Tris pH 8, 150 mM NaCl, 20 μM EDTA, 0.05% Tween). 100 μl enhancement solution was added to each well and fluorescence counts measured using a Victor$^3$ plate reader at 615 nm.

Heavy and light chain variable domain sequences were analyzed using IMGT/V-Quest and JIONSOLVER software. Flow cytometry data were evaluated using FlowJo analysis software. Statistical analyses were carried out using GraphPad Prism 5 software using unpaired t-test. To determine antibody $K_D$ values, saturation binding data were fitted using GraphPad Prism 5 software using non-linear regression analysis.

Example 3

Multimerization Enhances Identification of Memory B Cells

Tetrameric and monomeric TTCF were compared. TTCF was fluorescently labeled with Alexa-488 and then used in monomeric form or was converted to a tetramer using unlabeled streptavidin (see above). Enriched B cells were then incubated with tetrameric or monomeric TTCF-Alexa-488 at the same concentration. Control protein (CD80 membrane proximal domain) was labeled in the same way and also used as a tetramer.

Figures 6A, 6B:
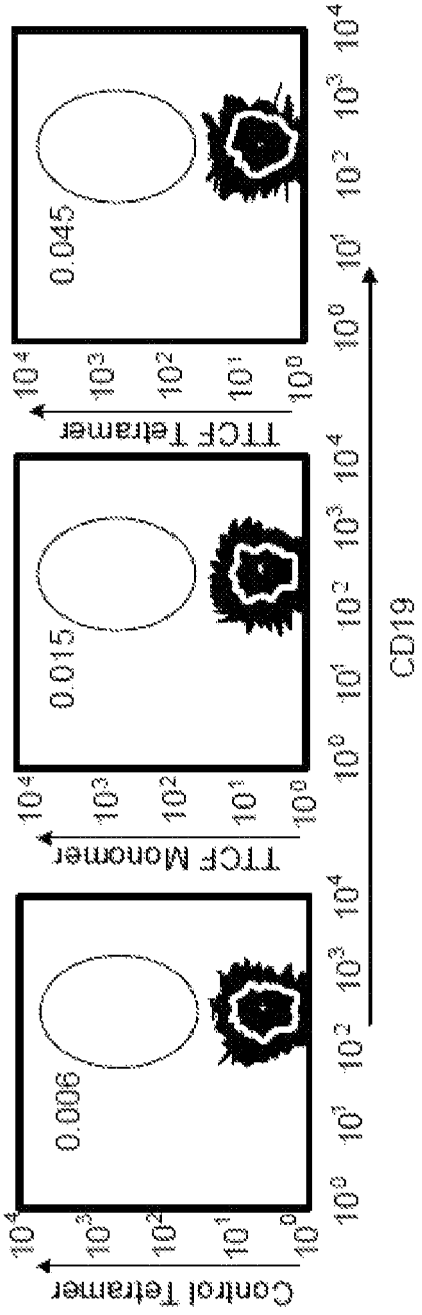
FIGS. 6A-6B| Graphs showing comparison of monomeric and tetrameric antigen for identification of memory B cells. (A) Mono-biotinylated TTCF or CD80 antigens were directly labeled with Alexa-488 fluorophore; tetramers were generated with unlabeled streptavidin. Enriched B cells from each donor were split into three fractions and stained with control CD80 tetramer, TTCF monomer, or TTCF tetramer at the same total antigen concentration of 0.125 μg/mL. FACS plots depict CD19$^+$ CD27$^-$ IgM$^-$ class-switched memory B cells; numbers adjacent to the gate represent the percentage of the parental gate. (B) Frequencies of tetramer$^+$ memory B cells detected in three different donors. Numbers are calculated as tetramer$^+$ cells per $1\times10^6$ CD19$^+$ memory B cells.

As shown in FIGS. 6A and 6B, TTCF labeled some memory B cells, but frequencies identified with tetramer were substantially larger (1.6-7.3 fold) using cells from three donors. In one of the three donors TTCF specific memory B cells could be detected with the tetramer but not with the monomer.

These results demonstrate that antigen tetramers enable sensitive detection of memory B cells based on the antigen specificity of their BCR, despite such cells being very rare in peripheral blood. Class-switched memory B cells specific for TTCF were brightly labeled by the appropriate tetrameric TTCF antigen, while background labeling with control tetramer was consistently low.

Example 4

Method/Antibody Validation

Fully human antibodies were generated by joining constant regions of IgG heavy and kappa chains to isolated variable segments via overlap PCR. Antibodies were expressed in a transient, serum free mammalian expression system using CHO-S cells for a period of 6-8 days. Antibodies were purified using protein G and gel filtration chromatography.

Figure 7A:
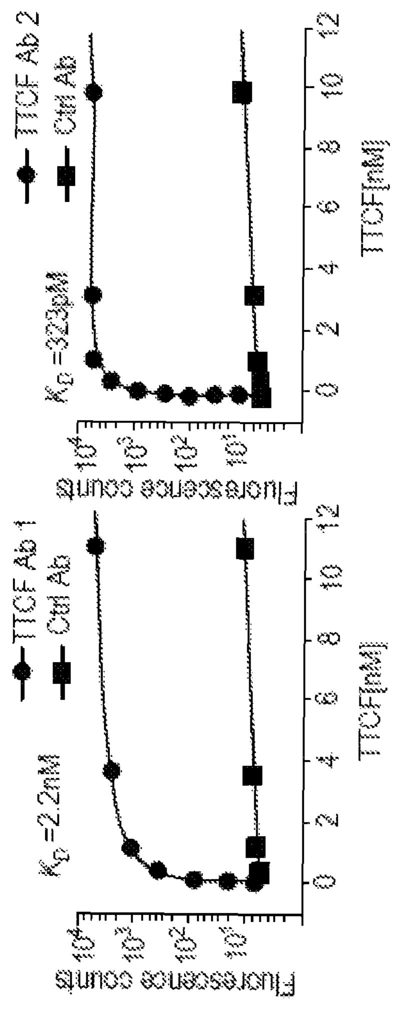
FIGS. 7A-7B| Line graphs showing high affinity binding of TTCF by antibodies generated from plasmablasts and memory B cells. Saturation binding experiments were carried out to determine the affinities of recombinant antibodies. TTCF antigen was labeled with europium, which emits a strong fluorescent signal at 615 nm upon incubation with a chelating reagent. Antibodies were immobilized in a 96-well plate and incubated with TTCF-europium (100 nM to 4 pM) for two hours at 37° C. Fluorescent counts at 615 nm were recorded and $K_D$ calculated using non-linear regression analysis. Control antibody (clone 8.18.C5) that was also produced in CHO-S cells was included in all experiments. (A) Recombinant TTCF Abs 1 and 2 were generated from TTCF tetramer$^+$ plasmablasts (donor 1). (B) TTCF antibodies 3, 4, and 5 originated from TTCF tetramer$^+$ memory B cells of three different donors.
Figure 7B:
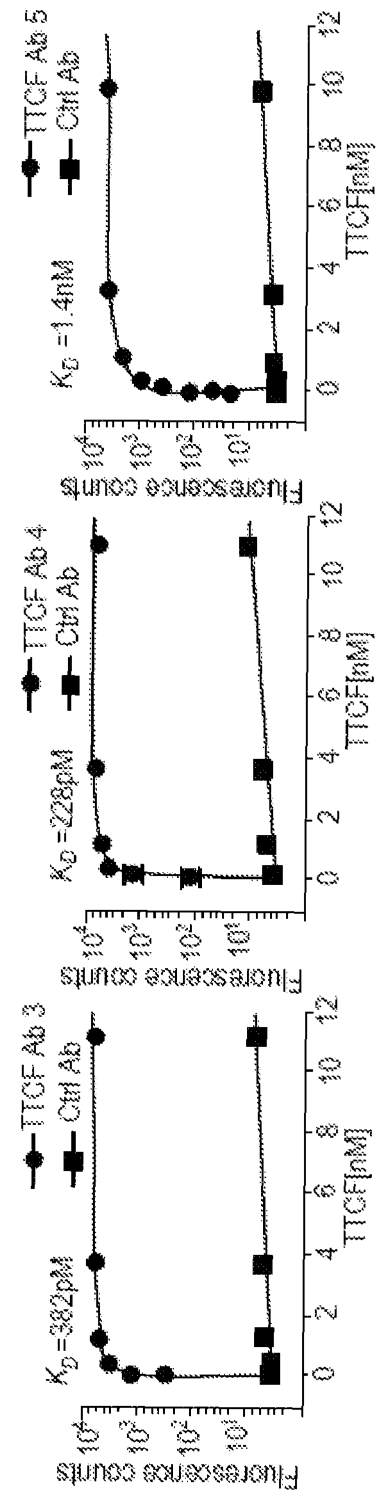

As shown in FIG. 7A-7B, antibodies isolated from TTCF-specific plasmablasts showed high binding affinities to TTCF antigen, with a $K_D$ of 2.2 nM (TTCF Ab 1) and 323 pM (TTCF Ab 2)(FIG. 7B). Antibodies isolated from memory B cells also exhibited high binding affinities, with $K_D$ of 382 pM, 228 pM, and 1.4 nM, for other antibodies (TTCF Abs 3, 4, and 5)(FIG. 7B).

These data support the specificity of the methods disclosed herein. Moreover, the specificity of the methods herein was demonstrated by the construction of five anti-TTCF antibodies from three different donors, all of which bound to TTCF with high affinities.

Data herein also demonstrate that antigen tetramers enable sensitive detection of memory B cells long after clearance of the antigen from the host.

Example 5

Obtaining Anti-MICA Antibodies

Antibodies that immunospecifically bind to MICA were developed using the methods herein.

Briefly, MICA antigen (UniGene Hs.130838) was expressed with a C-terminal BirA tag (GLNDIFEAQKIEWHE (SEQ ID NO: 148)), which enables mono-biotinylation of the antigen. Antigen was tetramerized with streptavidin (SA) labeled with R-Phycoerythrin (PE) at a molar ratio of 4 MICA: 1 SA. Peripheral blood mononuclear cells were obtained from advanced stage melanoma patients who had been vaccinated with autologous tumor cells transduced with a GM-CSF expression vector (GVAX) (PNAS 103: 9190, 2006), and subsequently treated with the anti-CTLA-4 monoclonal antibody ipilimumab (YERVOY™ (available from Bristol Myers Squib)) Peripheral blood mononuclear cells were quickly thawed, washed and resuspended at $5\times10^6$ in phosphate buffered saline (pH 7.2) supplemented with 2% fetal calf serum and stained with approximately 0.1 μg/ml tetramer for 30 minutes on ice. Antibodies were added to identify class-switched, memory B-cells ($CD19^+$, $CD27^+$, and $IgM^-$). A panel of exclusion antibodies labeling T-cells, natural killer-cells, marcrophages, and dead cells were included to reduce background tetramer staining (CD3, CD14, CD16, 7-AAD). Single B-cells that bound to the MICA tetramer were sorted into 8-tube-PCR strips using the BD FACS Aria II. The B-cell receptor (BCR) mRNA was amplified using a commercial kit from Epicentre Biotechnologies (catalog number: MBCL90310) using gene specific primers shown below:

```
mRNA Amplification
IgG-T7:
                                        (SEQ ID NO: 22)
AATACGACTCACTATAGGTTCGGGGAAGTAGTCCTTGACCAGG

Kappa-T7:
                                        (SEQ ID NO: 23)
TAATACGACTCACTATAGGGATAGAAGTTATTCAGCAGGCACAC

Lambda-T7:
                                        (SEQ ID NO: 24)
TAATACGACTCACTATAGGCGTCAGGCTCAGRTAGCTGCTGGCCGC

PCR One
VHL-1:
                                        (SEQ ID NO: 25)
TCACCATGGACTG(C/G)ACCTGGA

VHL-2:
                                        (SEQ ID NO: 26)
CCATGGACACACTTTG(C/T)TCCAC
```

-continued

```
VHL-3:
                                        (SEQ ID NO: 27)
TCACCATGGAGTTTGGGCTGAGC

VHL-4:
                                        (SEQ ID NO: 28)
AGAACATGAAACA(C/T)CTGTGGTTCTT

VHL-5:
                                        (SEQ ID NO: 29)
ATGGGGTCAACCGCCATCCT

VHL-6:
                                        (SEQ ID NO: 30)
ACAATGTCTGTCTCCTTCCTCAT

VkL-1:
                                        (SEQ ID NO: 31)
GCTCAGCTCCTGGGGCTCCTG

VkL-2:
                                        (SEQ ID NO: 32)
CTGGGGCTGCTAATGCTCTGG

VkL-3:
                                        (SEQ ID NO: 33)
TTCCTCCTGCTACTCTGGCTC

VkL-4:
                                        (SEQ ID NO: 34)
CAGACCCAGGTCTTCATTTCT

VlL-1:
                                        (SEQ ID NO: 35)
CCTCTCCTCCTCACCCTCCT

VlL-2:
                                        (SEQ ID NO: 36)
CTCCTCACTCAGGGCACA

VlL-3:
                                        (SEQ ID NO: 37)
ATGGCCTGGA(T/C)C(C/G)CTCTCC

CgII:
                                        (SEQ ID NO: 38)
GCCAGGGGGAAGAC(C/G)GATG

CkII:
                                        (SEQ ID NO: 39)
TTTCAACTGCTCATCAGATGGCGG

ClII:
                                        (SEQ ID NO: 40)
AGCTCCTCAGAGGAGGG(C/T)GG

PCR Two
VH-1:
                                        (SEQ ID NO: 41)
CAGGT(G/C)CAGCTGGT(G/A)CAGTC

VH-2:
                                        (SEQ ID NO: 42)
CAG(A/G)TCACCTTGAAGGAGTC

VH-3:
                                        (SEQ ID NO: 43)
(G/C)AGGTGCAGCTGGTGGAGTC

VH-4:
                                        (SEQ ID NO: 44)
CAGGTGCAGCTGCAGGAGTC

VH-5:
                                        (SEQ ID NO: 45)
GA(G/A)GTGCAGCTGGTGCAGTC

VH-6:
                                        (SEQ ID NO: 46)
CAGGTACAGCTGCAGCAGTC
```

-continued

Vk-1:
(SEQ ID NO: 47)
CG(A/C)CATCC(A/G)G(A/T)TGACCCAGT

Vk-2:
(SEQ ID NO: 48)
CGAT(A/G)TTGTGATGAC(C/T)CAG

Vk-3:
(SEQ ID NO: 49)
CGAAAT(T/A)GTG(T/A)TGAC(G/A)CAGTCT

Vk-4:
(SEQ ID NO: 50)
CGACATCGTGATGACCCAGT

Vl-1:
(SEQ ID NO: 51)
CCAGTCTGTGCTGACTCAGC

Vl-2:
(SEQ ID NO: 52)
CCAGTCTGCCCTGACTCAGC

Vl-3:
(SEQ ID NO: 53)
CTCCTATGAGCTGAC(T/A)CAGC

CgIII:
(SEQ ID NO: 53)
GAC(C/G)GATGGGCCCTTGGTGGA

CkIII:
(SEQ ID NO: 55)
AAGATGAAGACAGATGGTGC

ClIII:
(SEQ ID NO: 56)
GGGAACAGAGTGACCG

The primers and PCR cycling conditions used in PCR one and PCR two are adapted from Wang and Stollar et al. (journal of immunological methods, 2000).

An alternate heavy chain variable region forward primer set was developed to cover heavy chain variable region sequences potentially not adequately covered by the above primer set. The following alternate primers were generated:

PCR One
VHL1-58:
(SEQ ID NO: 57)
TCACTATGGACTGGATTTGGA

VHL2-5:
(SEQ ID NO: 58)
CCATGGACA(C/T)ACTTTG(C/T)TCCAC

VHL3-7:
(SEQ ID NO: 59)
GTAGGAGACATGCAAATAGGGCC

VHL3-11:
(SEQ ID NO: 60)
AACAAAGCTATGACATATAGATC

VHL3-13.1:
(SEQ ID NO: 61)
ATGGAGTTGGGGCTGAGCTGGGTT

VHL3-13.2:
(SEQ ID NO: 62)
AGTTGTTAAATGTTTATCGCAGA

VHL3-23:
(SEQ ID NO: 63)
AGGTAATTCATGGAGAAATAGAA

-continued

VHL4-39:
(SEQ ID NO: 64)
AGAACATGAAGCA(C/T)CTGTGGTTCTT

VHL4-61:
(SEQ ID NO: 65)
ATGGACTGGACCTGGAGCATC

VHL-9:
(SEQ ID NO: 66)
CCTCTGCTGATGAAAACCAGCCC

PCR Two
VH1-3/18:
(SEQ ID NO: 67)
CAGGT(C/T)CAGCT(T/G)GTGCAGTC

VH1-45/58:
(SEQ ID NO: 68)
CA(A/G)ATGCAGCTGGTGCAGTC

VH2-5:
(SEQ ID NO: 69)
CAG(A/G)TCACCTTGA(A/G)GGAGTCTGGT

VH3-9/23/43:
(SEQ ID NO: 70)
GA(A/G)GTGCAGCTG(T/G)TGGAGTC

VH3-16:
(SEQ ID NO: 71)
GAGGTACAACTGGTGGAGTC

VH3-47:
(SEQ ID NO: 72)
GAGGATCAGCTGGTGGAGTC

V4-34:
(SEQ ID NO: 72)
CAGGTGCAGCTACAGCAGTG

V4-30-2/39:
(SEQ ID NO: 74)
CAGCTGCAGCTGCAGGAGTC

VH7-4-1:
(SEQ ID NO: 75)
CAGGTGCAGCTGGTGCAATC

Briefly, 2 ul cDNA generated via mRNA amplification was used as a template for first-round PCR, with the following cycling conditions: 3 cycles of preamplification (94° C./45 seconds, 45° C./45 seconds, 72° C./105 seconds); 30 cycles of amplification (94° C./45 seconds, 50° C./45 seconds, 72° C./105 seconds); 10 minutes of final extension at 72° C.

3 ul of first-round PCR product served as a template for the second round of nested PCR. The same cycling conditions were used for the first round of PCR, but the 3 cycles of preamplification were omitted. Both PCR steps were performed by the use of cloned Pfu polymerase AD (Agilent Technologies). PCR products were separated on 1% agarose gels and products of 300-400 nucleotides in size isolated with the use of Zymoclean DNA gel recovery kit (Zymo Research). Sequencing was performed by the use of forward and reverse primers used for the second-round nested PCR. A two-step nested PCR amplifies the BCR variable domains of heavy and light chains (see above). Peripheral blood mononuclear cells were obtained from advanced stage melanoma patients who had been vaccinated with autologous tumor cells transduced with a GM-CSF expression vector (GVAX) (PNAS 103: 9190, 2006). The antibodies were expressed as full-length IgG1 antibodies in a transient CHO-S expression system.

Validation of anti-MICA antibody binding to MICA was performed using two independent bead-based assays. The first assay used a commercially available solution-based bead assay kit designed for detection of anti-MICA antibodies reactive to a variety of MICA alleles (One Lambda, catalog number LSMICA001). Varying concentrations of the MICA antibody were incubated with beads, then washed, and incubated with an anti-human IgG antibody conjugated with phycoerythrin. Following a second wash step, beads were analyzed on a Luminex machine. A negative control consisted of incubation of beads with anti-human IgG antibody conjugated with phycoerythrin alone (no anti-MICA antibody). A positive control consisted of incubation of beads with a commercially available anti-MICA/MICB monoclonal antibody (clone 6D4) directly conjugated to phycoerythrin (BioLegend catalog #320906). The second assay was developed internally using polystyrene beads conjugated with streptavidin. Beads were coated with mono-biotinylated MICA protein, and incubated with varying concentrations of anti-MICA antibody, anti-TTCF antibody (isotype negative control), or BioLegend anti-MICA/MICB antibody directly conjugated to phycoerythrin (positive control). Beads incubated with anti-MICA antibody or anti-TTCF antibody were washed and then incubated with anti-human IgG antibody conjugated with Alexa488. To determine background binding to the beads, the same incubation was performed using streptavidin-conjugated beads not coated with MICA protein for comparison. Beads were analyzed for binding to antibodies on a FACS Caliber flow cytometer.

Figure 8:
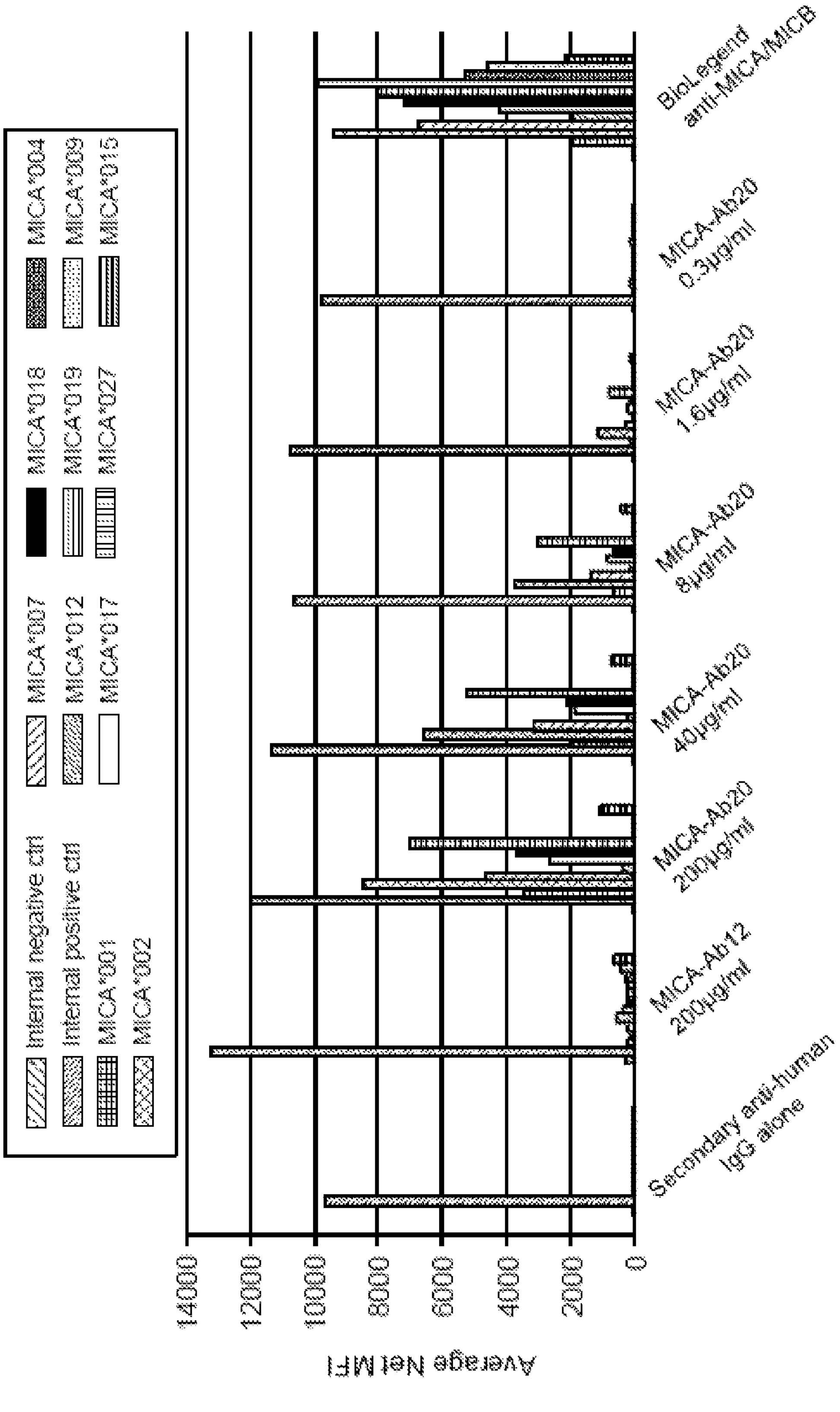
FIG. 8| Bar chart showing binding of anti-MICA antibodies to MICA-coated luminex beads.
Figures 9A, 9B, 9C, 9D, 9E:
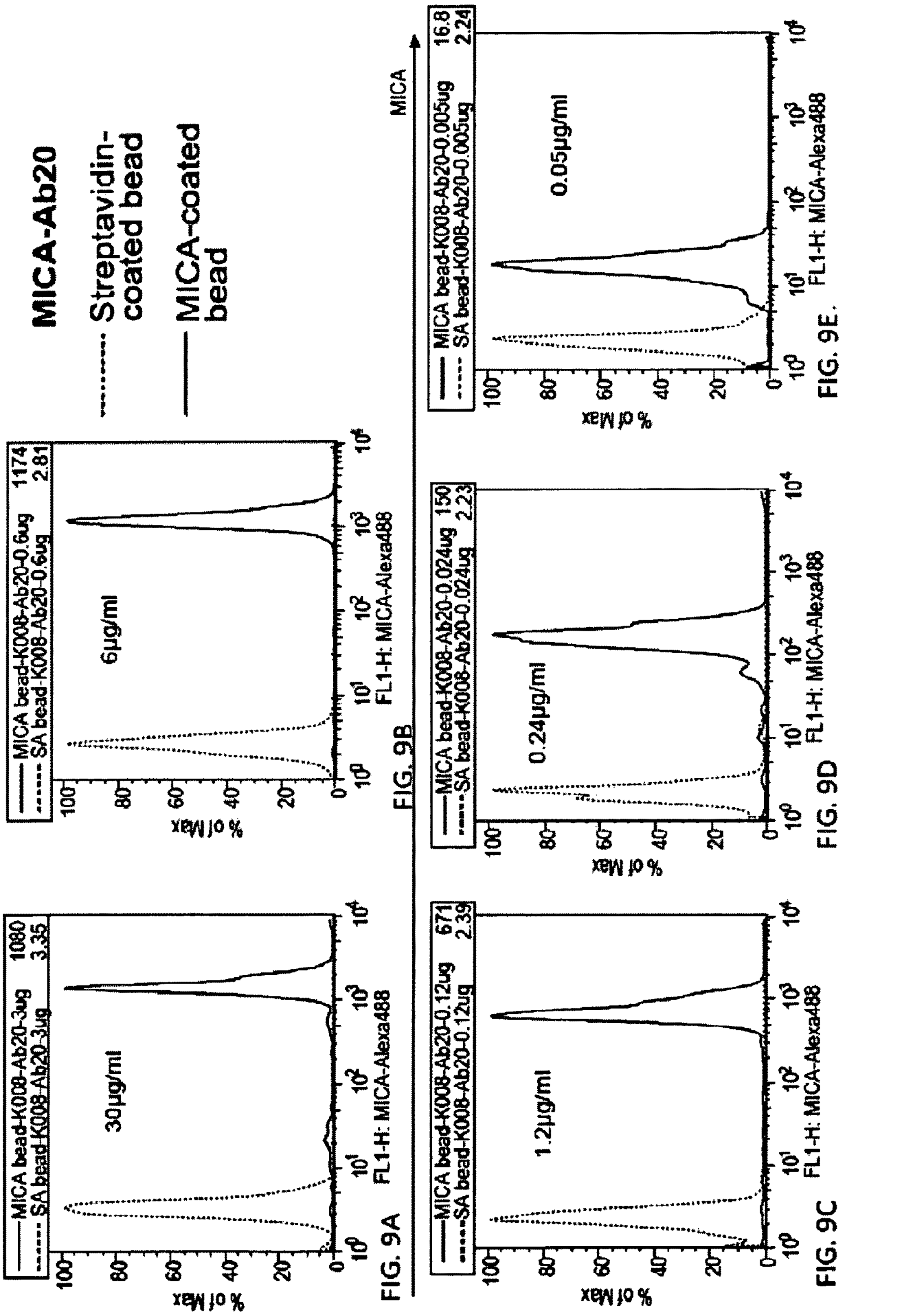
FIGS. 9A-9O| Line graphs showing binding of anti-MICA antibodies to MICA-coated beads.
Figures 9F, 9G, 9H, 9I, 9J:
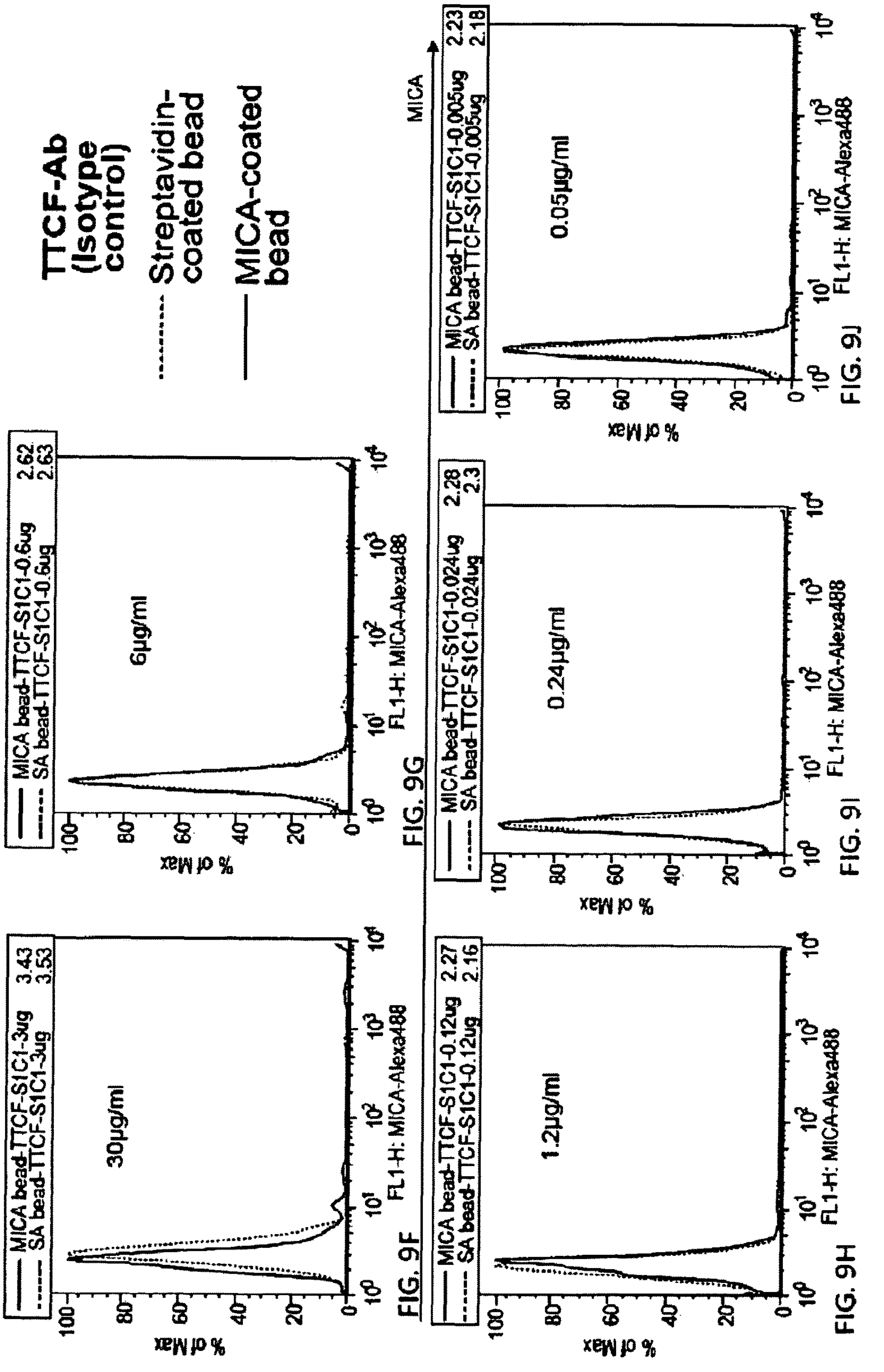
Figures 9K, 9L, 9M, 9N, 9O:
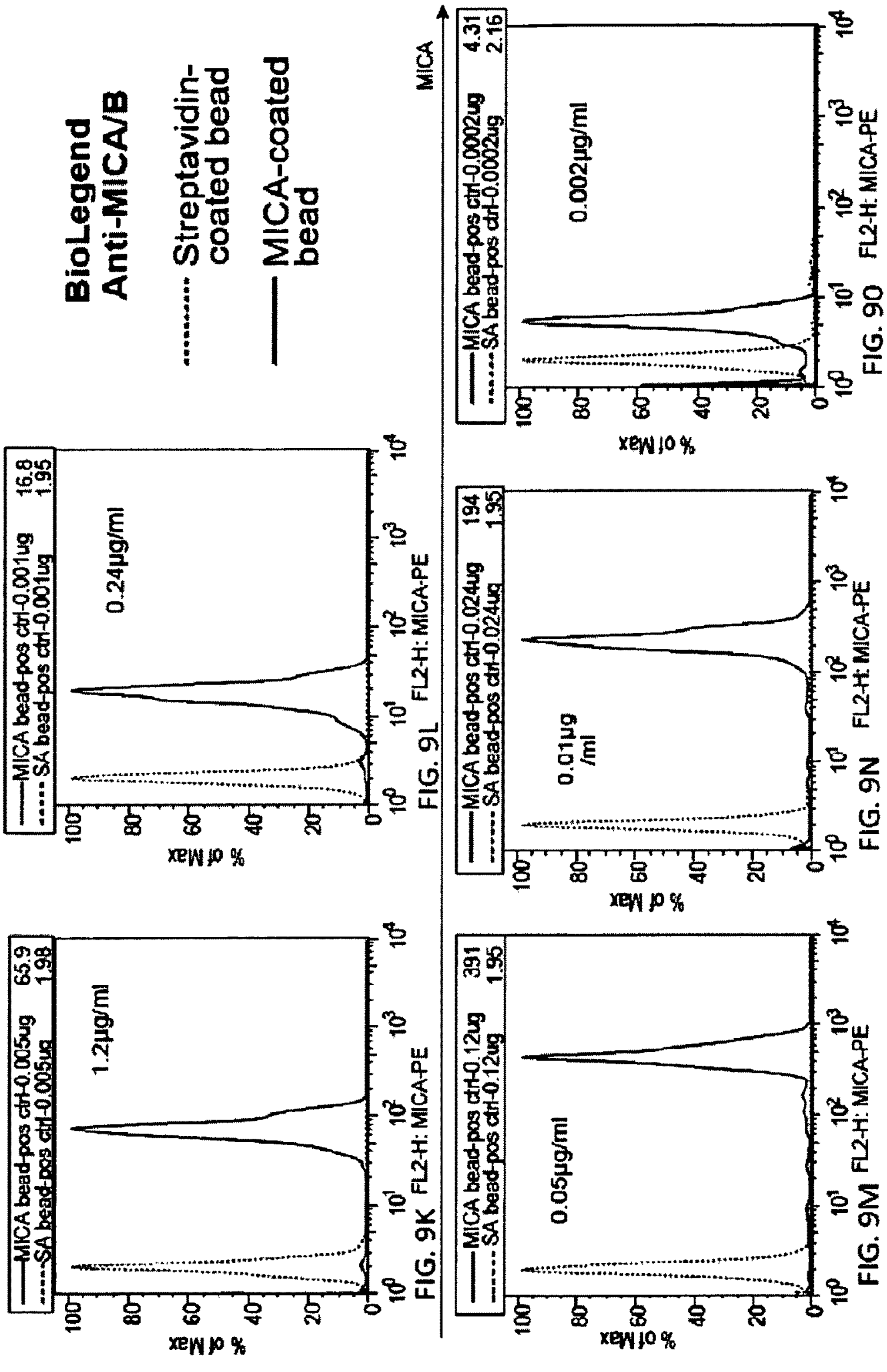
Figures 26A, 26B, 26C, 26D, 26E, 26F, 26G:
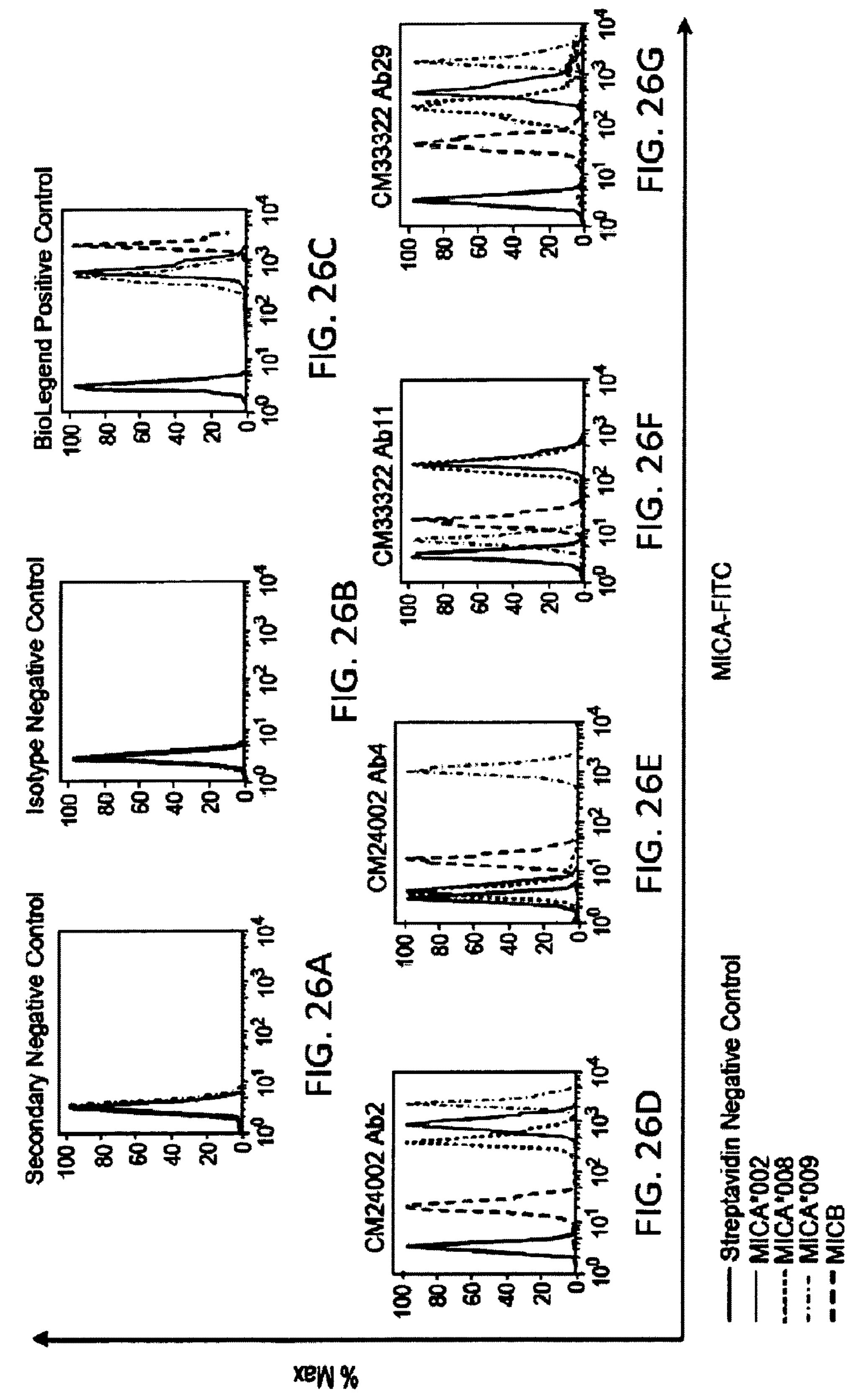
FIG. 26A-G| Line graphs showing assessment of MICA allele-specific binding by recombinant anti-MICA antibodies.

As shown in FIGS. 8 and 9A-9O, anti-MICA antibodies (MICA-Ab12 and MICA-Ab20) bind with high affinity to MICA. MICA-Ab20 corresponds to the anti-MICA antibody ID-1 described in Table 1.

Example 6

Anti-MICA Antibodies

Additional anti-MICA antibodies with clinically relevant biological properties were developed using the methods herein. MICA-specific antibodies reactive to common alleles were identified in patients who had received a cellular cancer vaccine (GM-CSF transduced cancer cells, referred to as GVAX) and an antibody that blocks the inhibitory CTLA-4 receptor on T cells ipilimumab (YERVOY™ (available from Bristol Myers Squib)). MICA tetramers were then used to isolate B cells from peripheral blood mononuclear cells of patients with the highest serum MICA reactivity. Heavy and light chain sequences were determined from these B cells by single cell PCR, as outlined in the in Example 5. This effort led to the identification of antibodies that recognize alleles common in the North American population.

CM24002 Ab2 (anti-MICA antibody ID-6 described in Table 1) is an antibody isolated from a patient with acute myeloid leukemia (AML) who demonstrated a significant clinical response to the GVAX+Ipilimumab combination therapy and whose plasma reacted strongly with MICA. The CM24002 Ab2 light chain (FIGS. 12 and 13) and heavy chain (FIGS. 10 and 11) nucleotide and amino acid sequences are shown, with CDR1, CDR2 and CDR3 sequences underlined. An additional antibody with strong binding was obtained from the same patient and is labeled as CM24002 Ab4 (anti-MICA antibody ID-7 described in Table 1) The CM24002 Ab4 light chain (FIGS. 16 and 17) and heavy chain (FIGS. 15 and 14) nucleotide and amino acid sequences are shown, with CDR1, CDR2 and CDR3 sequences underlined.

CM33322 Ab11 (anti-MICA antibody ID-8 described in Table 1), CM33322 Ab4 (anti-MICA antibody ID-11 described in Table 1) and CM33322 Ab28 (anti-MICA antibody ID-12 described in Table 1) are antibodies isolated from a patient with metastatic melanoma who is a long-term responder to the GVAX+Ipilimumab combination therapy. The CM33322 Ab11 light chain (FIGS. 20 and 21) and heavy chain (FIGS. 18 and 19) nucleotide and amino acid sequences are shown, with CDR1, CDR2 and CDR3 sequences underlined. The CM33322 Ab29 light chain (FIGS. 24 and 25) and heavy chain (FIGS. 22 and 23) nucleotide and amino acid sequences are shown, with CDR1, CDR2 and CDR3 sequences underlined. The CM33322 Ab4 light chain (FIGS. 37 and 38) and heavy chain (FIGS. 35 and 36) nucleotide and amino acid sequences are shown, with CDR1, CDR2 and CDR3 sequences underlined. The CM33322 Ab28 light chain ((FIGS. 52 and 53) and heavy chain (FIGS. 50 and 51) nucleotide and amino acid sequences are shown, with CDR1, CDR2 and CDR3 sequences underlined. Due to the long-term clinical response of this patient, these antibodies are of particular interest.

After initial identification, cloning, and expression of the antibodies of interest, the specificity of these antibodies for different MICA alleles was determined with a cytometric bead assay. Briefly, soluble, recombinant MICA alleles 002, 008, 009 and MICB with a single BirA biotinylation site were expressed, purified, and captured on streptavidin beads. Indicated anti-MICA antibodies were then incubated with the beads coated with recombinant MICA at different concentrations for one hour, then washed, and incubated with a FITC-labeled anti-human IgG secondary antibody. Following a second wash step, quantification of bead-bound FITC fluorescence was completed by flow cytometry. MICA alleles 002, 008, 009 as well as the related MICB protein were chosen based on their prevalence in the North American population (FIGS. 26A-G). Importantly, CM24002 Ab2 and CM33322 Ab29 bound strongly to all MICA alleles as well as to MICB. The other two antibodies bound to a subset of alleles: CM24002 Ab4 bound highly to MICA*009 and MICB, and CM33322 Ab11 bound highly to MICA*002, MICA*008, and MICB. (FIG. 26A-G) Specificity was documented by use of a negative human control antibody generated with the same technology (specific for tetanus toxoid C-terminal fragment, TTCF) and a positive control antibody to MICA (a commercial murine antibody from BioLegend directed against MICA). These studies identified CM24002 Ab2 and CM33322 Ab29 as potential candidates for clinical application.

Binding of CM33322 Ab28 was tested at two antibody concentrations (500 ng/ml and 1 μg/ml) against recombinant MICA encoded by three common alleles (MICA*002, MICA*008, MICA*009) by ELISA (HRP readout). The results demonstrated that CM33322 Ab28 bound to all three alleles, indicating that this antibody is also a candidate for clinical application.

Example 7

Binding of Anti-MICA Antibody to Autologous Tumor Cells

Figure 27:
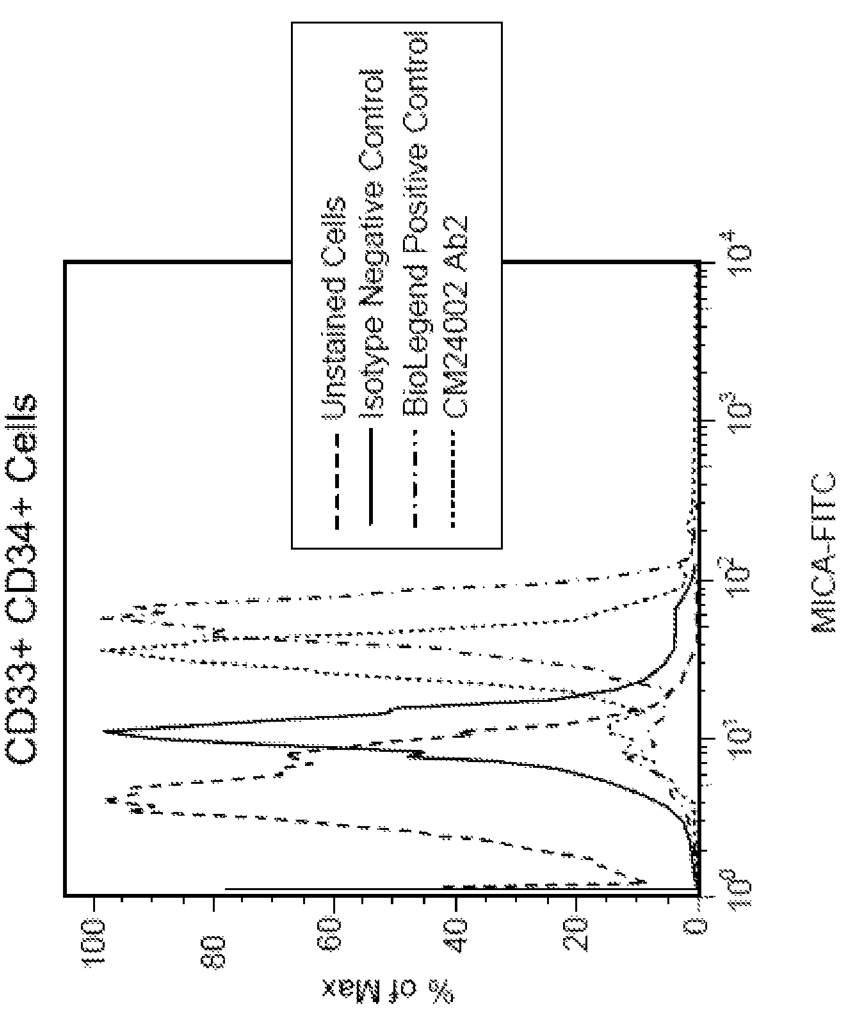
FIG. 27| Line graph showing labeling of autologous tumor cells by anti-MICA antibody CM24002 Ab2.

The ability of isolated anti-MICA antibody CM24002 Ab2 to bind to autologous tumor cells was examined by flow cytometry (FIG. 27). Bone marrow obtained from patient CM24002 and tested binding to tumor cells by CM24002 Ab2. Tumor cells were then identified from the bone marrow sample as CD33+ CD34+ cells. The tumor cells were then stained with 10 μg/ml with anti-MICA antibody CM24002 Ab2, positive control commercial MICA antibody (BioLegend) or a negative control antibody (TTCF specific). As shown in FIG. 27, CM24002 Ab2 strongly bound to these cells. CM24002 Ab2 did not display binding to non-tumor cells (CD16+ and CD3+ cells) and only background binding to CD14+ cells, demonstrating anti-tumor specificity (data not shown).

Example 8

Anti-MICA Antibody Inhibition of NKG2D Receptor on NK Cells

Figure 28:
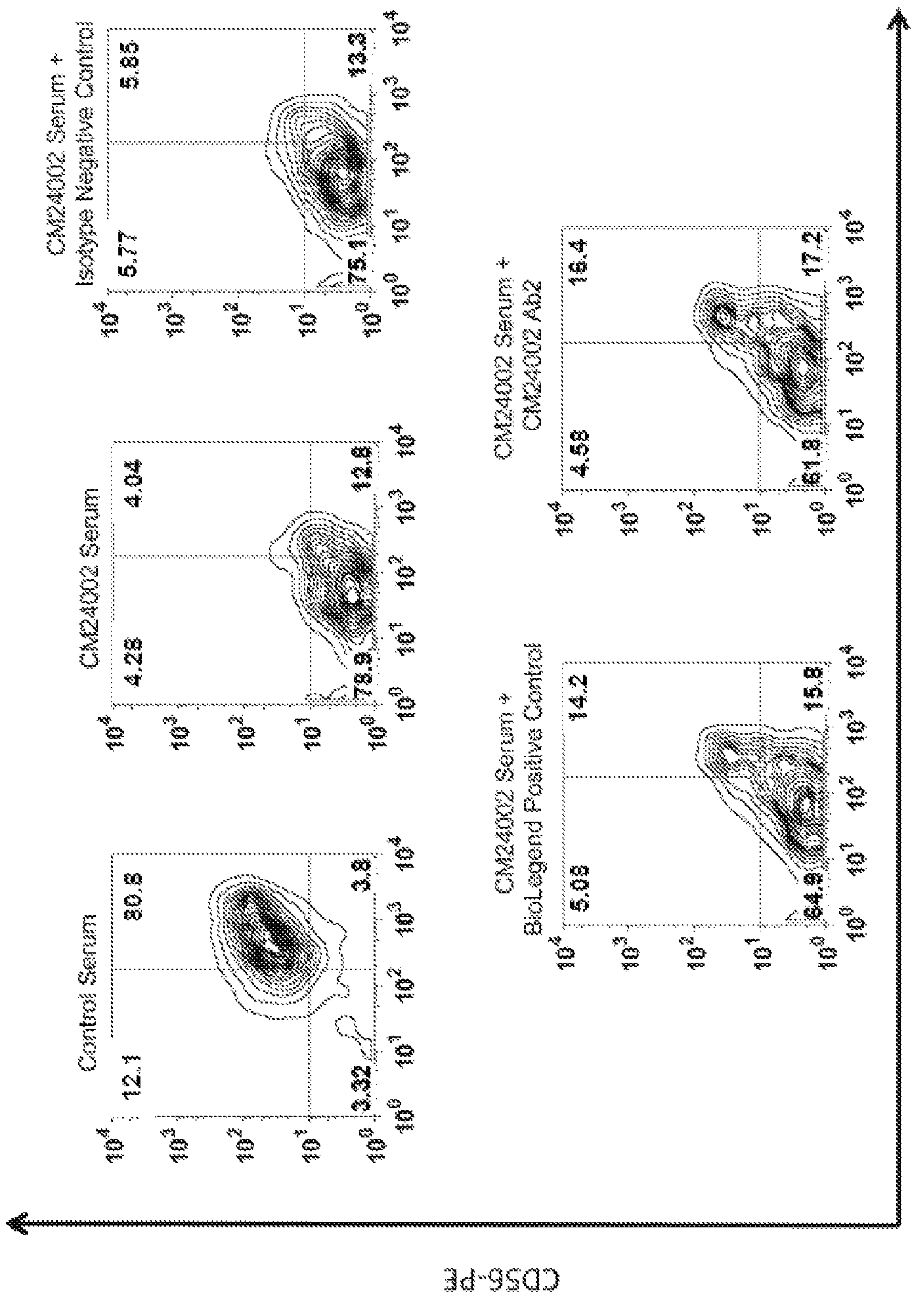
FIG. 28| A series of FACS plots showing regulation of NKG2D by serum MICA. Human NK cells were incubated with control serum from patient CM24002 at a 1:10 dilution for 48 hours. Indicated antibodies were added at the start of the incubation at a concentration of 10 μg/ml. NKG2D expression was assessed on CD56+ NK cells by flow cytometry.
Figure 29:
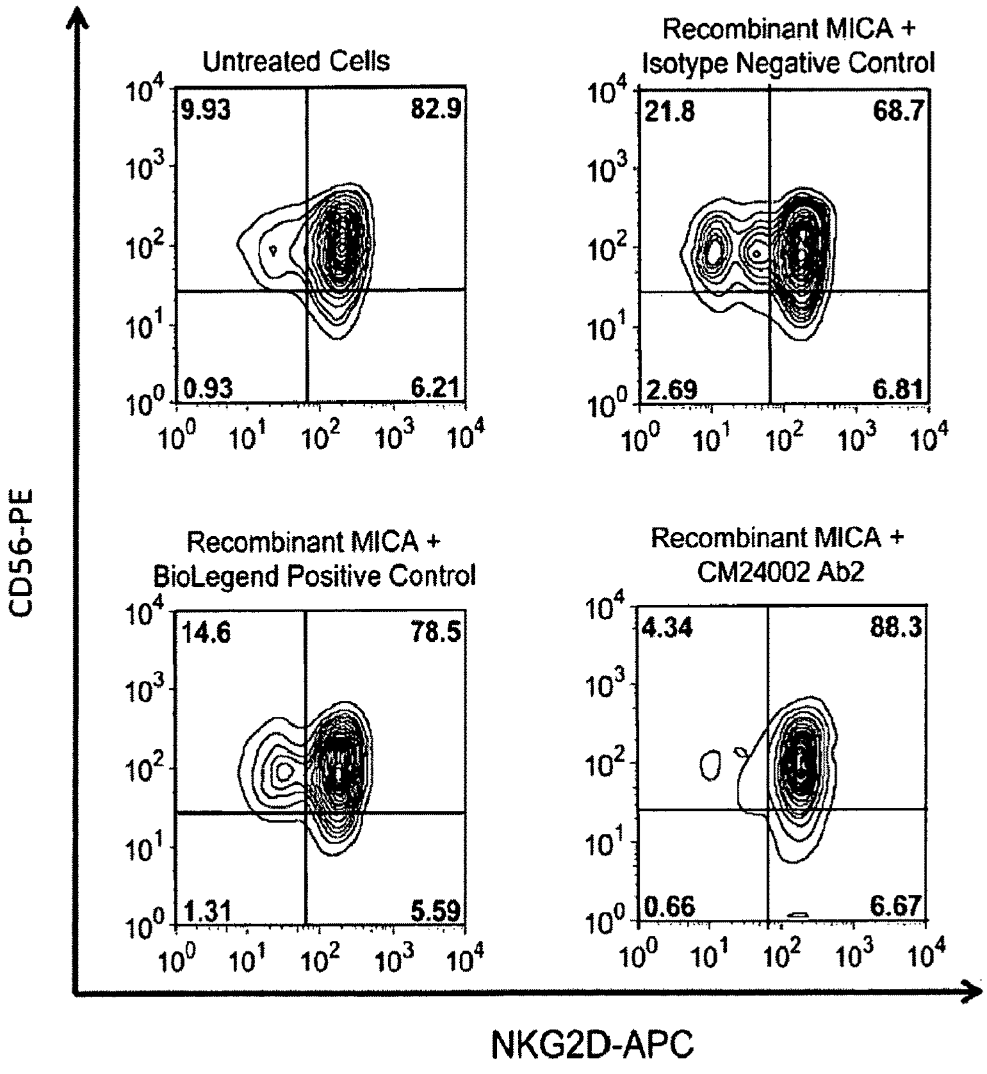
FIG. 29| A series of FACS plots showing regulation of NKG2D by recombinant MICA. Human NK cells were incubated with recombinant MICA at a concentration of 2 ng/ml for 48 hours. Indicated antibodies were added at the start of the incubation at a concentration of 10 μg/ml. After 48 hours, NKG2D expression was assessed on CD56+ NK cells by flow cytometry.

The ability of isolated anti-MICA antibody CM24002 Ab2 to prevent soluble MICA-mediated down-regulation of is cognate receptor, NKG2D was examined. Serum from patient CM24002 was used at a 1:10 dilution and incubated with human NK cells for a period of 48 hours. CM24002 Ab2 (concentration of 10 μg/ml), positive control commercial MICA antibody (BioLegend) or a negative control antibody (TTCF specific) were added to these cultures. NKG2D expression was assessed by flow cytometry at 48 hr (FIG. 28). Serum from patient CM24002 strongly down-regulated expression of NKG2D (thus disabling the function of this receptor). CM24002 Ab2 and the positive control MICA antibody partially restored NKG2D surface expression by NK cells. To demonstrate specificity, we repeated the above experiment by incubating cells with recombinant MICA at 2 ng/ml instead of patient serum (FIG. 29). CM24002 Ab2 completely prevented MICA-mediated down-regulation of NKG2D expression, while the negative control antibody (specific for TTCF) had no effect (FIG. 29). These data demonstrate that human MICA antibodies can prevent inhibition of the critical NKG2D receptor on human NK cells.

To further examine the ability of isolated anti-MICA antibodies to prevent soluble MICA-mediated down-regulation of NKG2D, the above experiment was repeated using multiple serum samples and additional isolated anti-MICA antibodies. As shown in FIG. 29, 15 out of 20 serum samples from patients with advanced melanoma contains significant levels of shed MICA. PBMCs were incubated with control serum or selected melanoma patient samples containing soluble MICA alone or in the presence of the indicated antibodies at 100 ug/ml for 48 hrs. At 48 hrs, NKG2D expression was determined on NK cells (CD3−, CD8−, CD56+) by flow cytometry (FIG. 40; data are presented as % of NK cells that are NKG2D positive). These data further demonstrate that human MICA antibodies blocked NKG2D down-regulation in the serum samples, restored NKG2D-mediated cytotoxicity in all of the serum samples tested, and can prevent inhibition of the critical NKG2D receptor on human NK cells.

Figure 59:
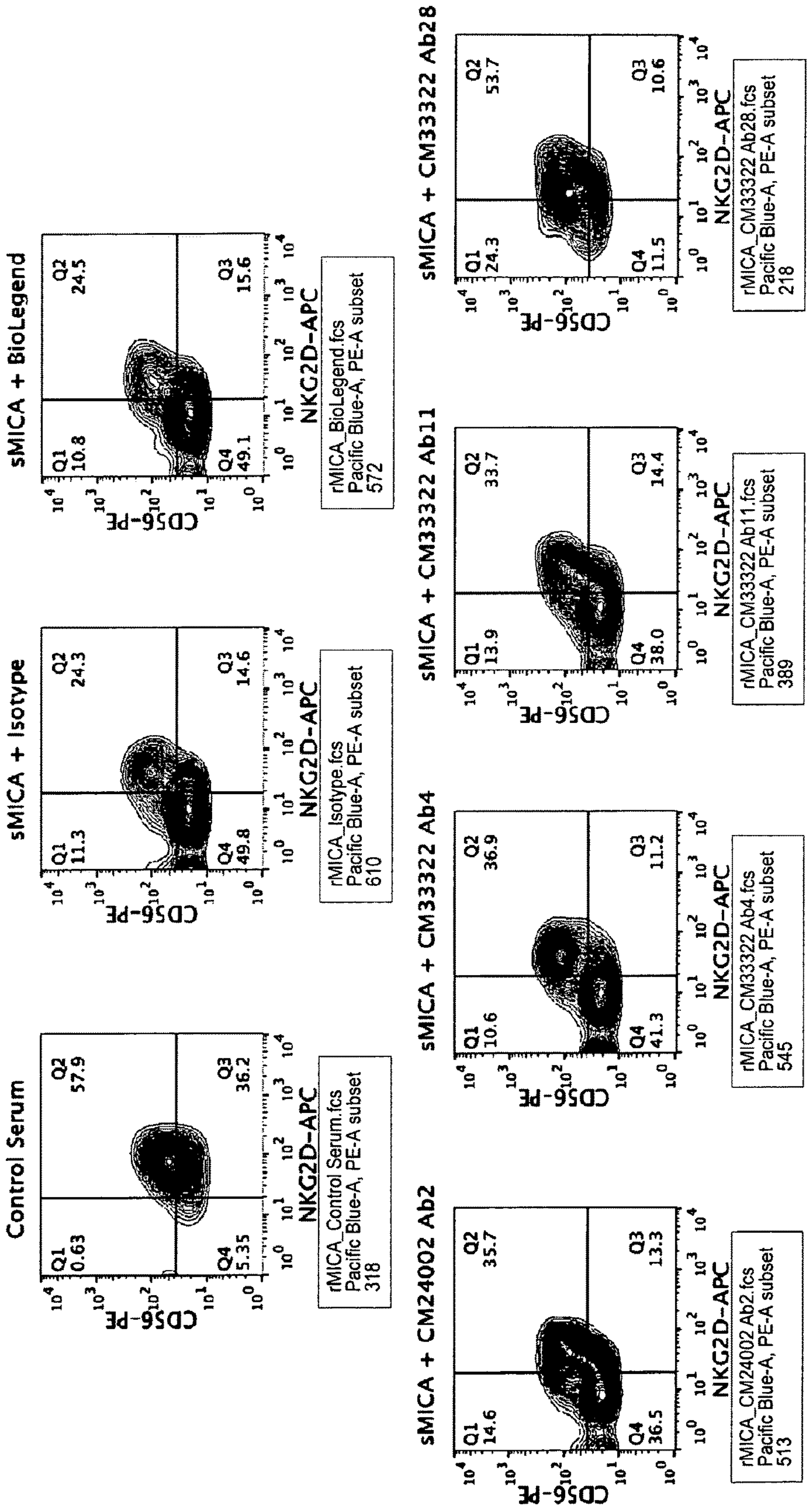
FIG. 59| A series of FACS plots showing regulation of NKG2D by recombinant MICA. Whole PBMCs were incubated with control serum or serum spiked with rMICA alone or in the presence of the indicated antibodies for 48 hrs. After 48 hrs, cells were washed and NKG2D surface expression was assessed by flow cytometry.

To further examine the ability of isolated anti-MICA antibodies to prevent soluble MICA-mediated down-regulation of NKG2D, the above experiment was repeated using additional isolated anti-MICA antibodies (e.g., CM24002 Ab2, CM33322 Ab4, CM33322 Ab11, or CM33322 Ab28). After 48 hrs, cells were washed and NKG2D surface expression was assessed by flow cytometry. As shown in FIG. 59, several anti-MICA antibodies block rMICA-induced NKG2D down-regulation.

Figure 57:
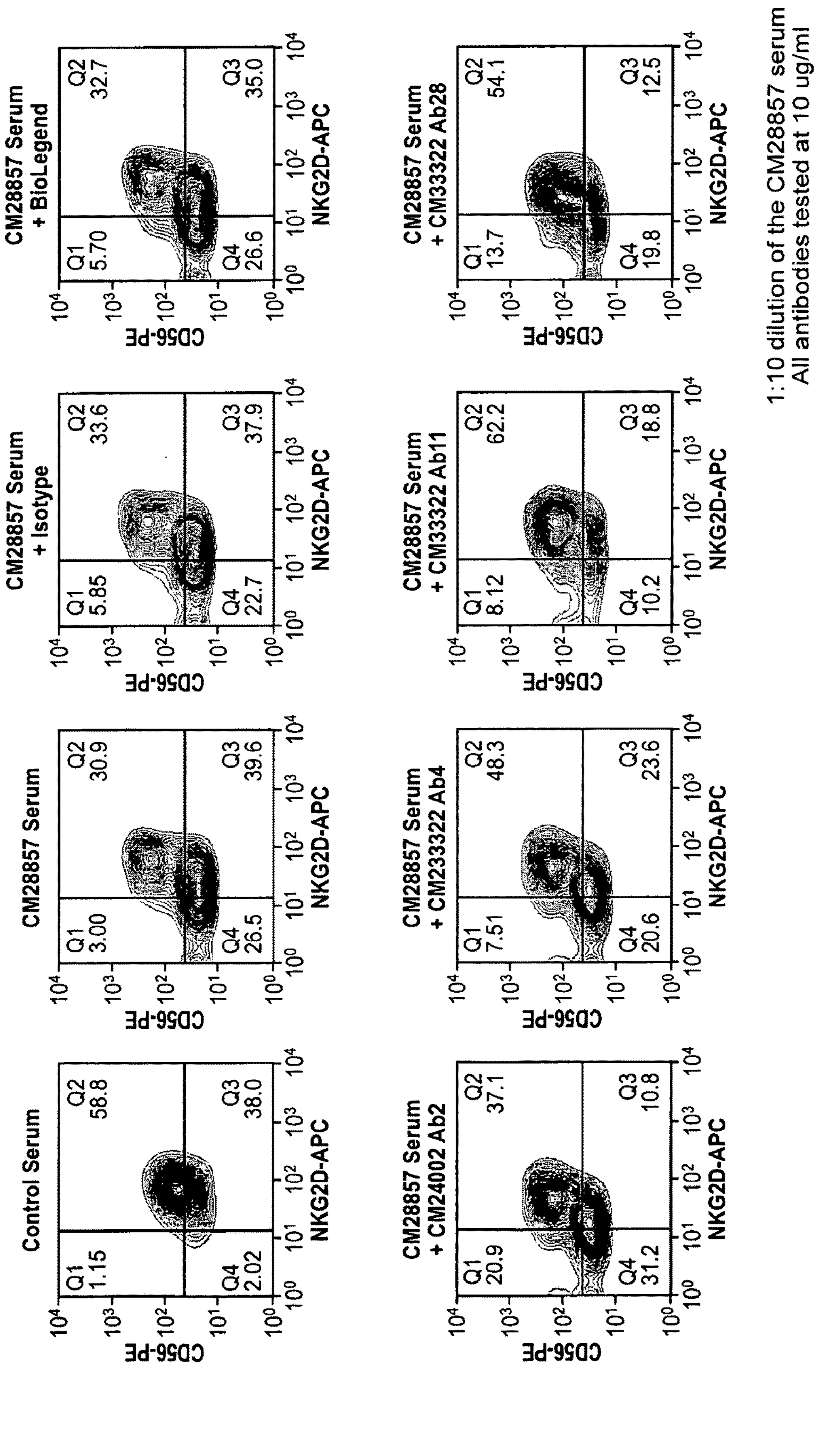
FIG. 57| A series of FACS plots showing regulation of NKG2D by serum MICA. Whole PBMCs were incubated with control serum or melanoma serum alone or in the presence of the indicated antibodies for 48 hrs. After 48 hrs, cells were washed and NKG2D surface expression was assessed by flow cytometry.

To examine the ability of isolated anti-MICA antibodies to prevent melanoma serum induced down-regulation of NKG2D, the above experiment was repeated using multiple serum samples and additional isolated anti-MICA antibodies. Whole PBMCs were incubated with control serum or melanoma serum alone or in the presence of the indicated antibodies for 48 hrs. After 48 hrs, cells were washed and NKG2D surface expression was assessed by flow cytometry. As shown in FIG. 57, several anti-MICA antibodies block melanoma serum induced NKG2D down-regulation.

Example 9

Anti-MICA Antibody Cell-Mediated Cytotoxicity

Figure 30:
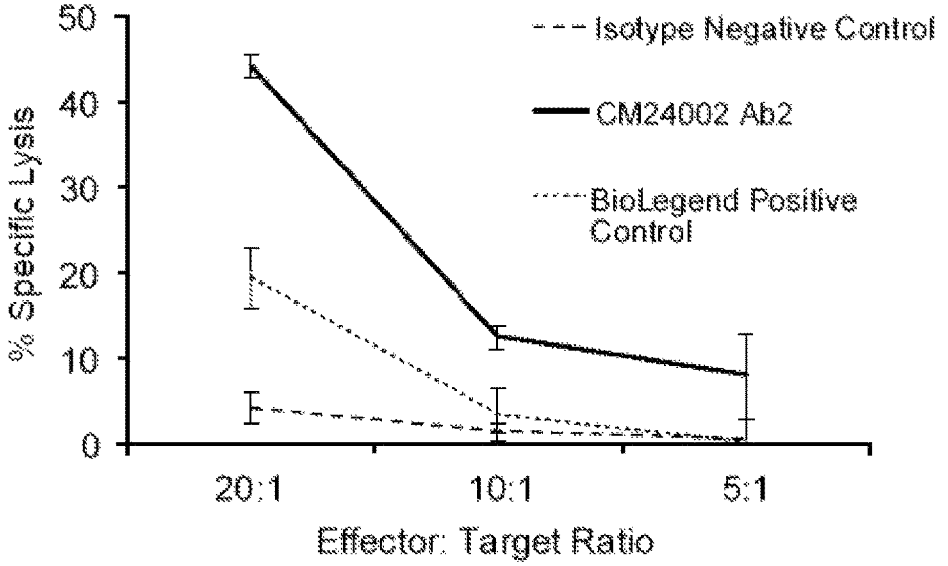
FIG. 30| Line graph demonstrating enhancement of cell-mediated toxicity by anti-MICA antibody CM24002 Ab2. Human NK cells were incubated with recombinant MICA (2 ng/ml) for 48 hours in the presence of indicated antibodies at 10 μg/ml. The ability of NK cells (effectors) to kill K562 target cells was assessed by measuring LDH release following 4 hour incubation at the indicated ratios.
Figure 31:
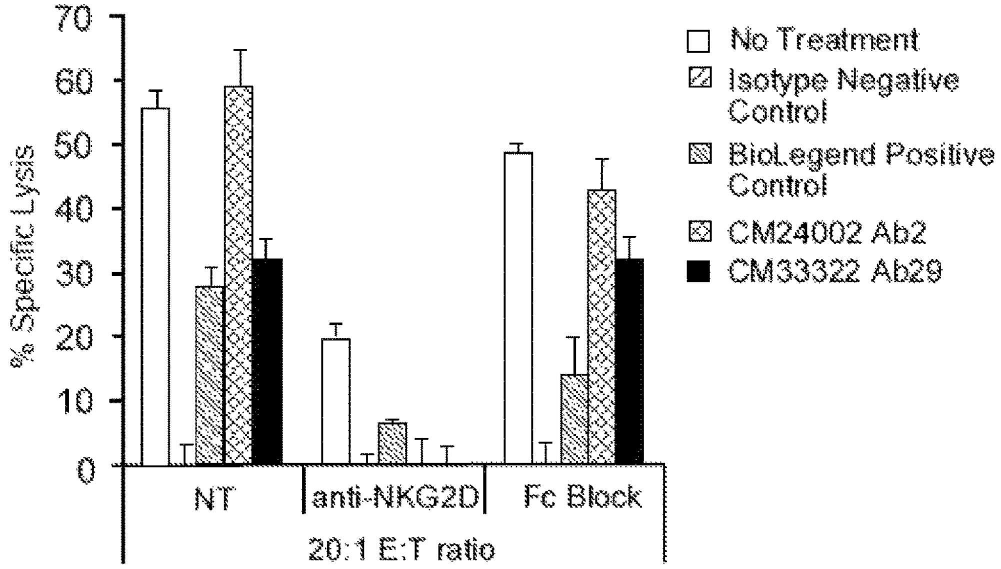
FIG. 31| Bar graph demonstrating cell-mediated toxicity by anti-MICA antibodies CM24002 Ab2 and CM33322 Ab29. Human NK cells were incubated with recombinant MICA (2 ng/ml) for 48 hours in the presence of the indicated antibodies at 10 μg/ml. The ability of NK cells (effectors) to kill K562 target cells was assessed by measuring LDH release following 4 hour incubation. NKG2D blocking antibody or Fc blocking antibody was added during the 4 hr incubation of effector and target cells to assess the contribution of Fc receptor and NKG2D to cell-mediated toxicity.

To determine if CM24002 Ab2 enables cell-mediated cytotoxicity, human NK cells (effector cells) were incubated for 48 hours with recombinant MICA (2 ng/ml) in the presence of CM24002 Ab2, a negative control antibody (TTCF specific) or a positive control antibody (BioLegend), all at 10 μg/ml. After 48 hours, cells were washed and incubated with K562 tumor cells at 20:1, 10:1, and 5:1 effector:target ratios for 4 hours. Specific lysis of target cells by NK cells was determined by release of a cytosolic protein (LDH) from K562 tumor cells. In the absence of MICA antibodies, there was no killing of K562 tumor cells by NK cells. However, CM24002 Ab2 greatly enhanced NK cell mediated lysis of K562 tumor cells and was more effective than the positive control murine MICA antibody at all effector:target ratios (FIG. 30). It was further demonstrated that killing of K562 tumor cells was indeed mediated by the NKG2D pathway (rather than Fc receptors). The above experiment was repeated, with the addition two experimental groups: a blocking antibody for NKG2D and human Fc block. In addition, CM33322 Ab29 was also tested. The data show that addition of CM24002 Ab2 and CM33322 Ab29 enabled NK cell mediated cytotoxicity. Killing of K562 cells did not occur when a blocking NKG2D antibody was added, while the Fc blocking reagent had little effect (FIG. 31). These data show that CM24002 Ab2 and CM33322 Ab29 restore the anti-tumor function of the NKG2D pathway.

Figure 58:
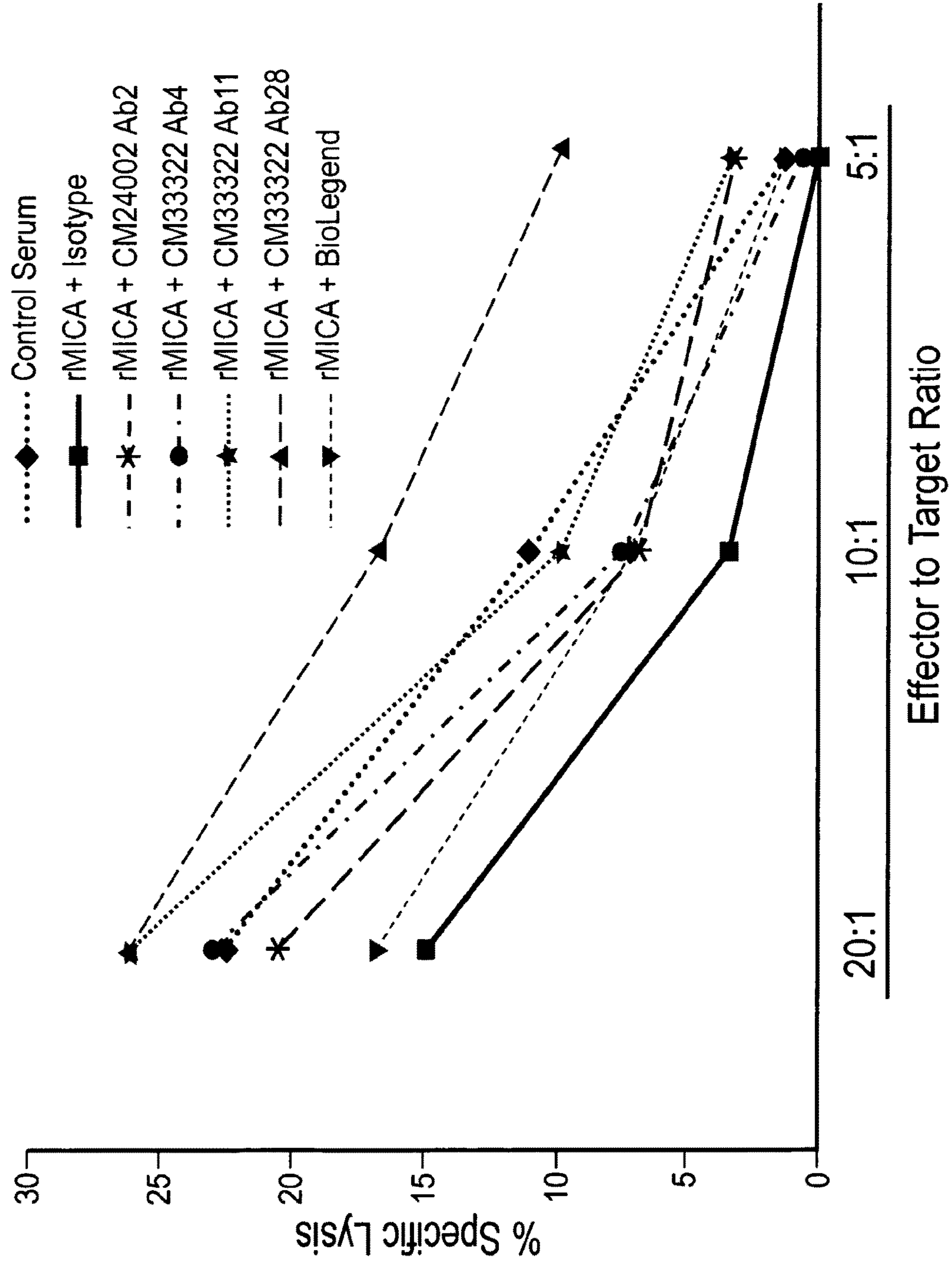
FIG. 58| A line graph showing cell-mediated toxicity by anti-MICA antibodies CM24002 Ab2, CM33322 Ab4, CM33322 Ab11, CM33322Ab28. Whole PBMCs were incubated for 48 hours with recombinant MICA (rMICA) in the presence of the indicated antibodies, a negative control antibody (TTCF specific) or a positive control antibody (BioLegend. Specific lysis was assessed by $^{51}$Cr release after 4 hours.

To determine if additional isolated anti-MICA enable cell-mediated cytotoxicity, whole PBMCs were incubated for 48 hours with recombinant MICA (rMICA) in the presence of CM24002 Ab2, CM33322 Ab4, CM33322 Ab11, CM33322 Ab28, a negative control antibody (TTCF specific) or a positive control antibody (BioLegend). After 48 hours, cells were washed and incubated with $^{51}$Cr labeled K562 target cells at 20:1, 10:1, and 5:1 effector:target ratios for 4 hours. Specific lysis was assessed by $^{51}$Cr release after 4 hours. As demonstrated in FIG. 58, NK cell killing activity is enhanced by anti-MICA antibodies in the presence of recombinant sMICA. To further determine if isolated anti-MICA antibodies enable cell-mediated cytotoxicity, human NK cells (effector cells) were incubated for 48 hours with incubated with melanoma patient serum. PBMCs were incubated with control serum or melanoma patient samples containing soluble MICA alone or in the presence of the indicated antibodies at 100 ug/ml for 48 hrs (negative isotype control antibody (TTCF specific) or a positive control antibody (BioLegend). At 48 hrs, cells were washed and incubated with $^{51}$Cr labeled K562 target cells at a 20:1 effector to target ratio. Specific lysis was assessed by scintillation counting after 4 hrs. (FIGS. 41-43 and 62) These data further show that CM24002 Ab2, CM33322 Ab29, CM33322 Ab4 and CM33322 Ab28 restore the anti-tumor function of the NKG2D pathway.

Figure 56:
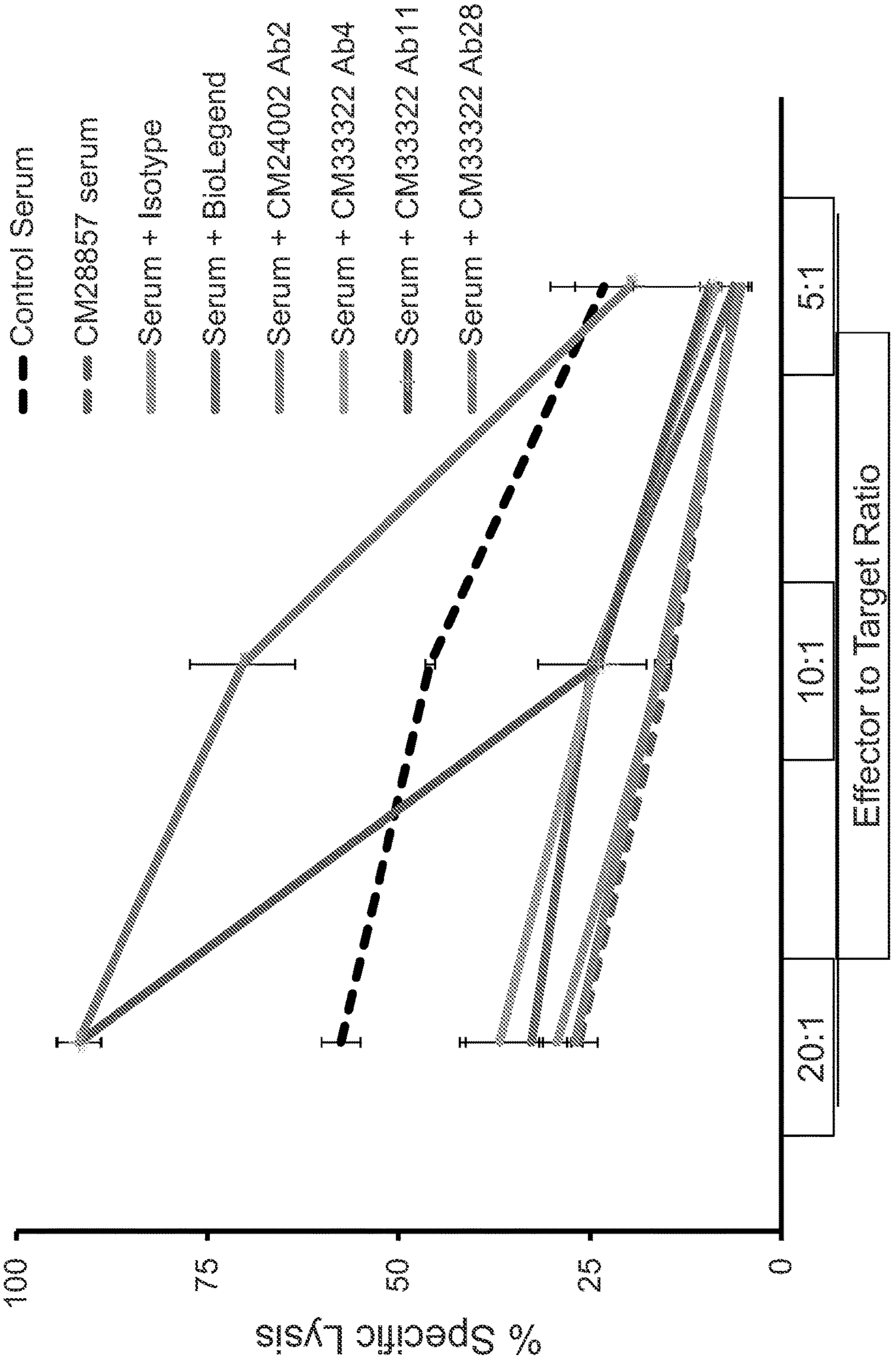
FIG. 56| A line graph showing anti-MICA antibodies enhance NKG2D-mediated cytotoxicity of K562 target cells by NK cells incubated with melanoma patient serum. PBMCs were incubated with control serum or melanoma patient samples containing soluble MICA alone or in the presence of the indicated antibodies for 48 hrs. At 48 hrs, cells were washed and incubated with $^{51}Cr$ labeled K562 target cells at a 20:1, 10:1 and 5:1 effector to target ratio. Specific lysis was assessed by scintillation counting after 4 hrs.

Whole PBMCs were incubated with control serum or melanoma serum alone or in the presence of CM24002 Ab2, CM33322 Ab4, CM33322 Ab11, and CM33322 Ab28 for 48 hrs. (FIG. 56) After 48 hrs, cells were washed and incubated with $^{51}Cr$ labeled K562 target cells at the indicated effector to target ratios. Specific lysis was assessed by $^{51}Cr$ release after 4 hrs. As demonstrated in FIG. 56, NK cell killing activity is enhanced by anti-MICA antibodies in the presence of melanoma serum.

Figure 54:
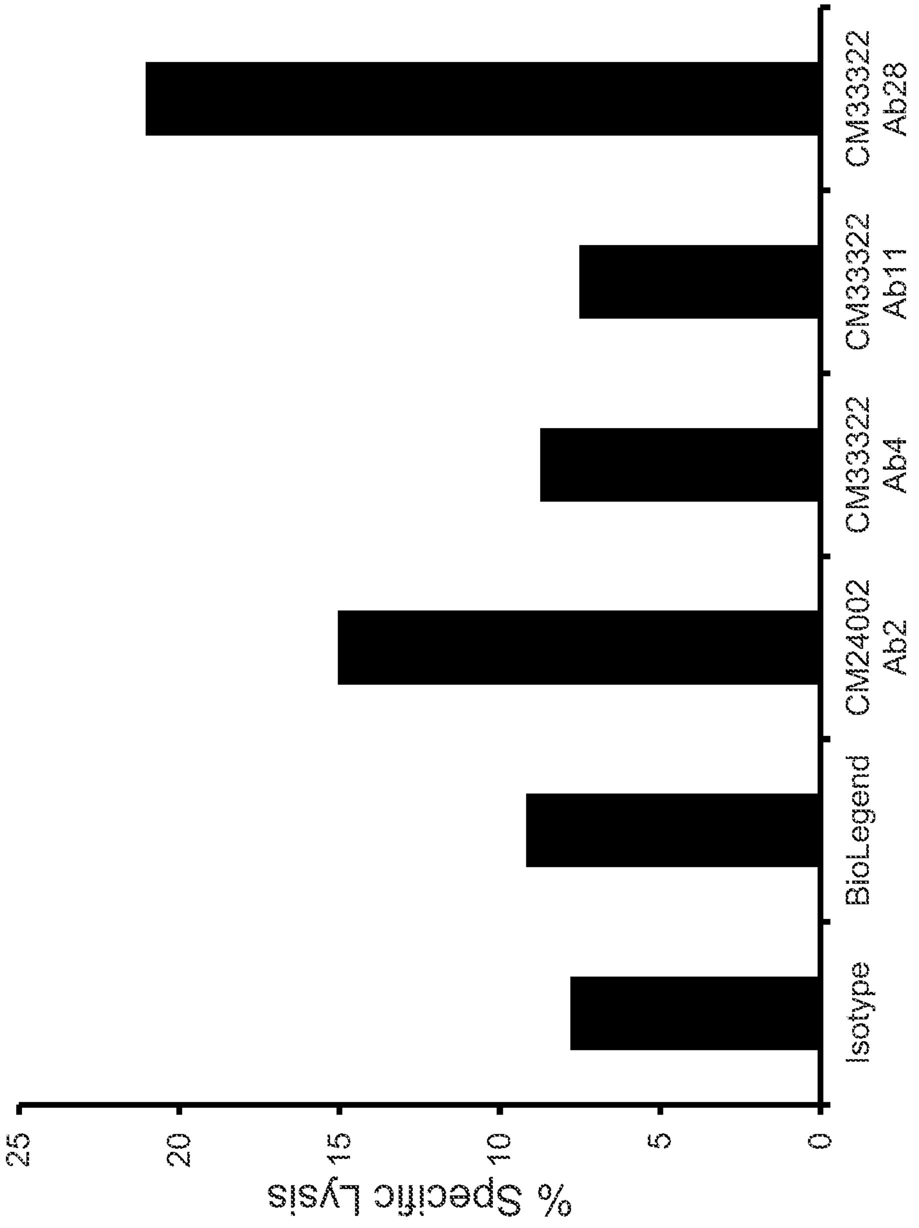
FIG. 54| Bar graph demonstrating cell-mediated toxicity by anti-MICA antibodies CM24002 Ab2, CM33322 Ab4, CM33322 Ab11 and CM33322 Ab28. $^{51}Cr$ labeled K562 cells were incubated in the presence of the indicated antibody for 30 minutes. At 30 minutes, whole PBMCs were added at a 20:1 effector to target ratio. Specific lysis was assessed by scintillation counting after 4 hrs.

In a further example, CM24002 Ab2 and CM33322 Ab28 greatly enhanced NK cell mediated lysis of K562 tumor cells and was more effective than the positive control murine MICA antibody at all effector:target ratios (FIG. 54).

In a further experiment, CM24002 Ab2, CM33322 Ab28 and CM33322 Ab29 prevented NKG2D receptor downregulation on NK cells and CD8 T cells during 48 hr incubation with sMICA patient serum (FIG. 62A-B). These MICA antibodies were also shown to prevent inhibition of CD8 T cell cytotoxicity by sMICA (clone specific for NY-ESO, $^{51}Cr$ labeled Mel375 cells, 20:1 E:T ratio) (FIG. 62C).

Example 10

Binding of Anti-MICA Antibody to Alpha 3 MICA Domain

Figure 32:
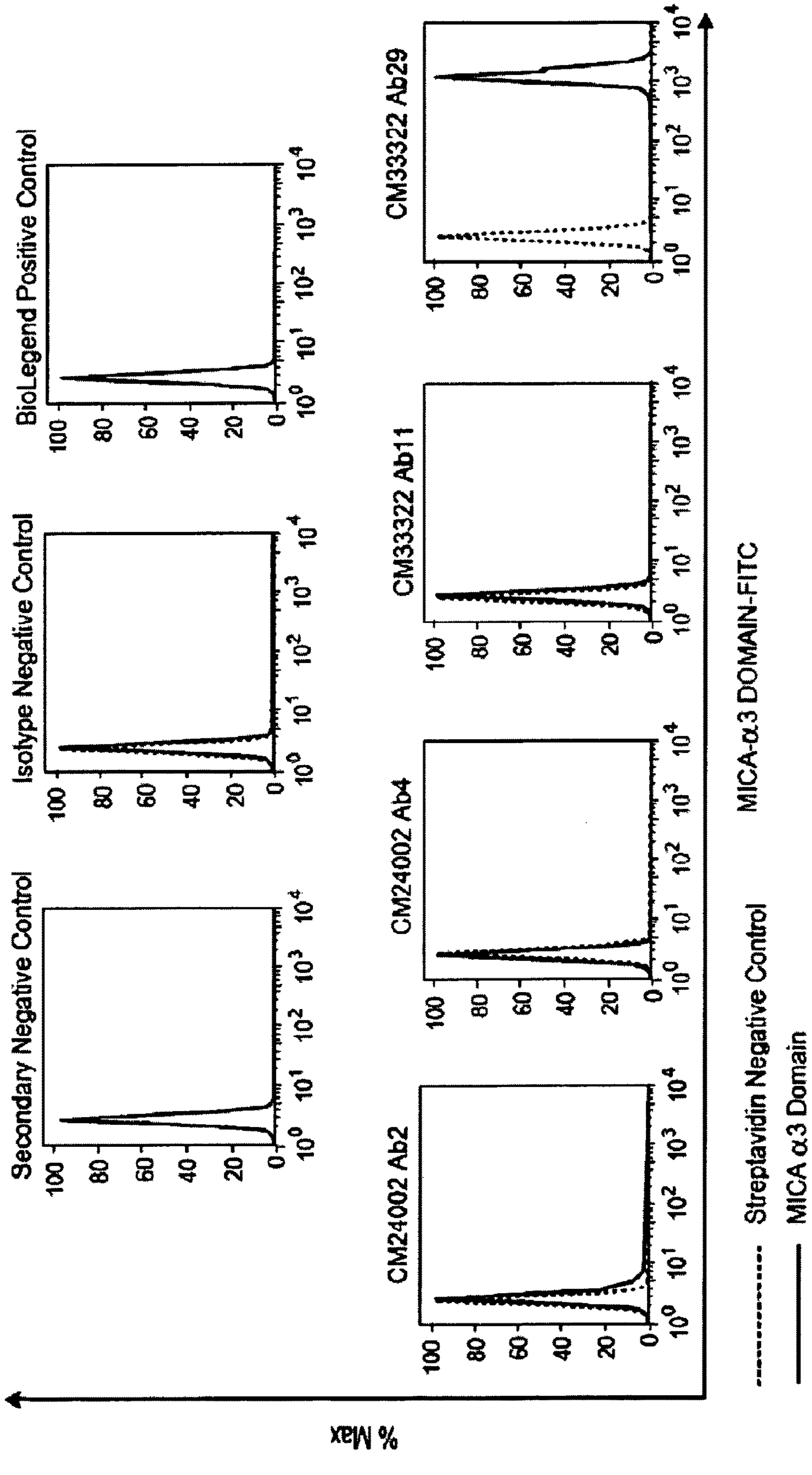
FIG. 32| A series of line graphs showing binding of MICA alpha 3 domain by recombinant anti-MICA antibodies. Recombinant MICA alpha 3 domains were biotinylated and captured on the surface of streptavidin-coated beads. Indicated antibodies were incubated at 10 μg/ml with the beads coated with the individual recombinant protein for 1 hr. Beads were subsequently washed and incubated with FITC-conjugated anti-human IgG secondary antibody. FITC fluorescence was quantified by flow cytometry.

The NKG2D receptor binds to the top alpha 1 and alpha 2 domains of MICA, and antibodies that bind to the same site may compete with the NKG2D receptor and thereby block killing of tumor cells by NK cells. Antibodies that bind to the alpha 3 domain are of particular interest because they cannot block NKG2D receptor binding. At the same time, such antibodies can interfere with proteolytic cleavage of MICA from the tumor cell surface. The ability of anti-MICA antibodies to the MICA alpha 3 domain was assessed using the previously described cytometric bead assay. The biotinylated recombinant protein was captured on streptavidin beads. Beads were then incubated with antibodies CM24002 Ab2, CM24002 Ab4, CM33322 Ab11, CM33322 Ab29, a negative control antibody (TTCF specific) or a positive control antibody (BioLegend), at 10 μg/ml followed by a FITC-labeled anti-human IgG secondary antibody and quantification of bead-bound FITC fluorescence by flow cytometry (FIG. 32). As shown in FIG. 32, CM33322 Ab29 bound to the MICA alpha 3 domain and is therefore of great interest for therapeutic applications.

Figure 63:
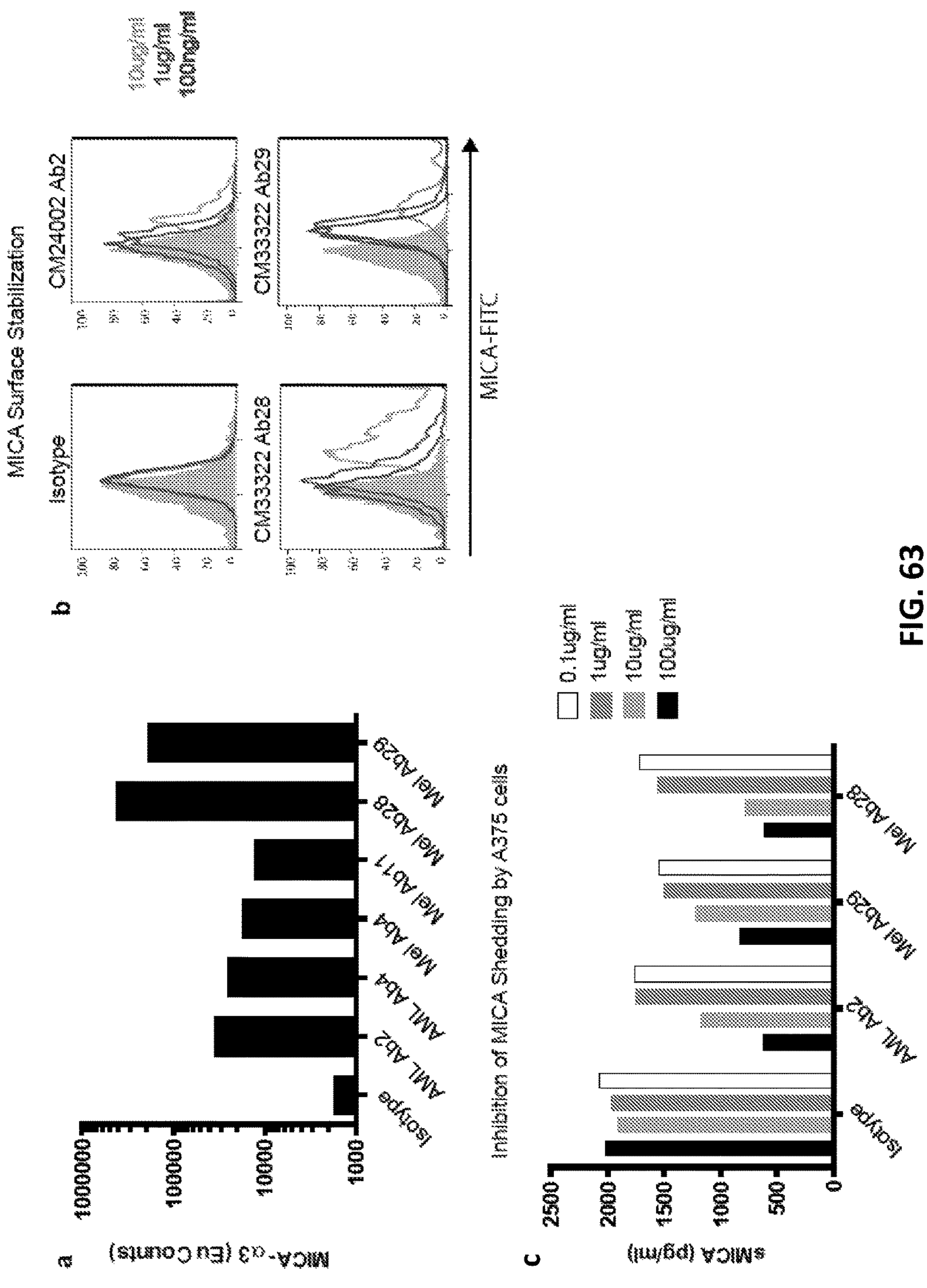
FIG. 63a-63c| A series of graphs showing (a) MICA antibodies bind to MICA α3 domain as measured by ELISA; (b) MICA α3 domain-specific antibodies increased MICA surface levels on RPMI-8226 cells during a 48 hour incubation; and (c) inhibited shedding of MICA by A375 cells during a 48 hour incubation (ELISA of supernatants for sMICA). Data are representative of at least three independent experiments.

In another experiment, CM24002 Ab2, CM24002 Ab4, CM33322 Ab11, CM33322 Ab29 and CM33322 Ab28 bound to recombinant MICA α3 domain as measured by ELISA (FIG. 63*a*). CM24002 Ab2, CM33322 Ab29 and CM33322 Ab28 were further shown to increase MICA surface levels on RPMI-8226 cells during 48 hour incubation.

Example 11

Binding of Anti-MICA Antibody to Tumor Cells

Figure 33:
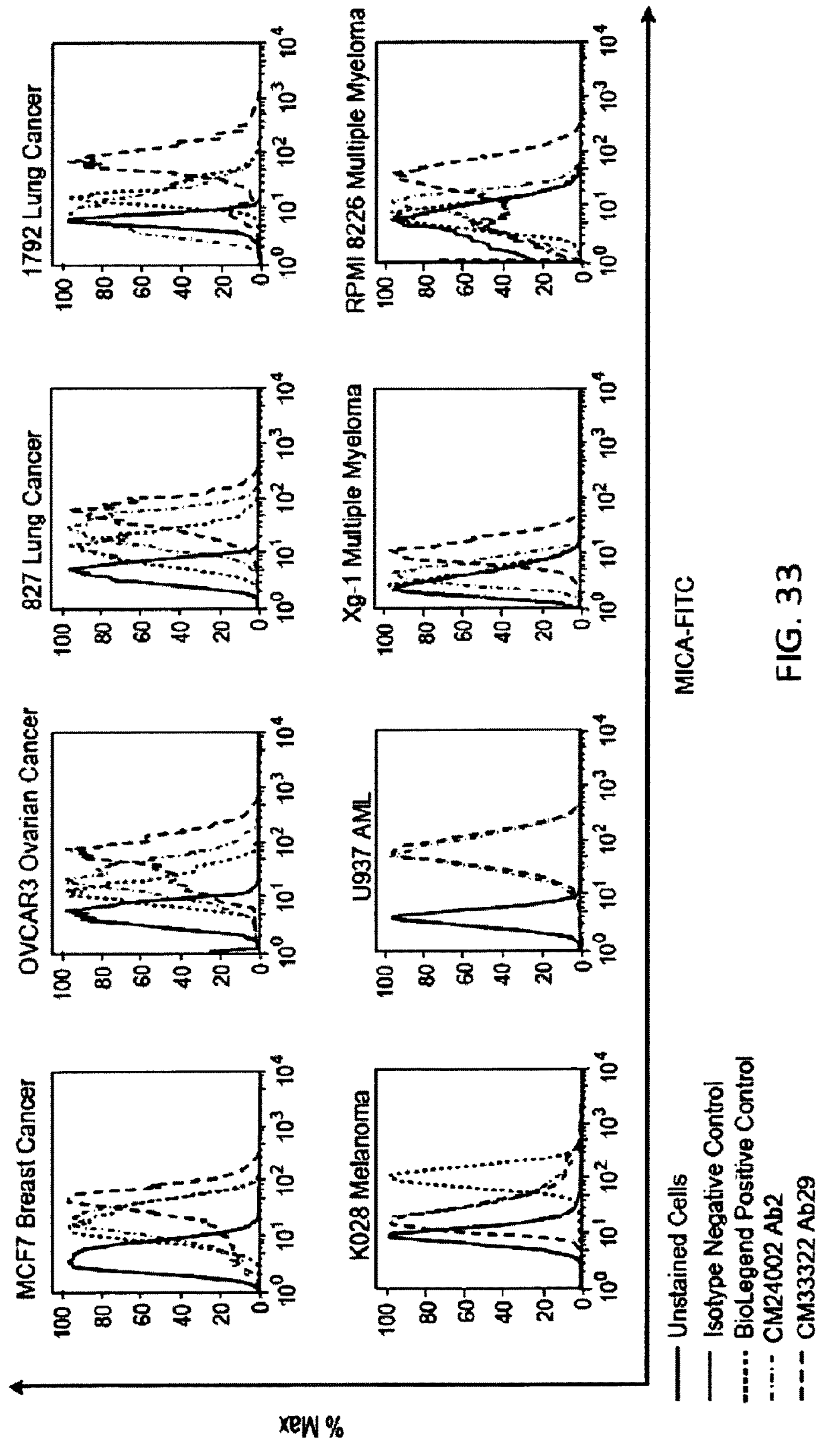
FIGS. 33| Line graphs demonstrating labeling of tumor cells by anti-MICA antibodies CM24002 Ab2 and CM33322 Ab29. Fluorescence was determined by flow cytometry.

The potential of CM24002 Ab2 and CM33322 Ab29 to be used to target a broad range of cancers was assessed. A panel of multiple myeloma (RPMI 8226 and Xg-1), ovarian cancer (OVCAR3), acute myeloid leukemia (U937), melanoma (K028), lung cancer (1792 and 827), and breast cancer (MCF7) cells were tested for labeling by CM24002 Ab2 and CM33322 Ab29. The tumor cells were resuspended at a concentration of $1\times10^6$ cells/ml in PBS with 1% BSA and stained with the CM24002 Ab2 and CM33322 Ab29, as well as positive and negative controls (murine MICA antibody and TTCF-specific antibody, respectively)(directly conjugated) at a concentration of 10 μg/ml for 1 hour at 4° C. Labeling was assessed by flow cytometry (FIG. 33). CM24002 Ab2 and CM33322 Ab29 both bound every tumor cell type tested, with labeling being greater than the commercial positive control for the majority of tested cell lines. When tested on Mel526, K029, RPMI-8226 and MCF-7 tumor cell lines, CM3332 Ab28 also demonstrated the ability to detect MICA on tumor cells.

Example 12

MICA Allele Specificity of Anti-MICA Antibody

Figure 34:
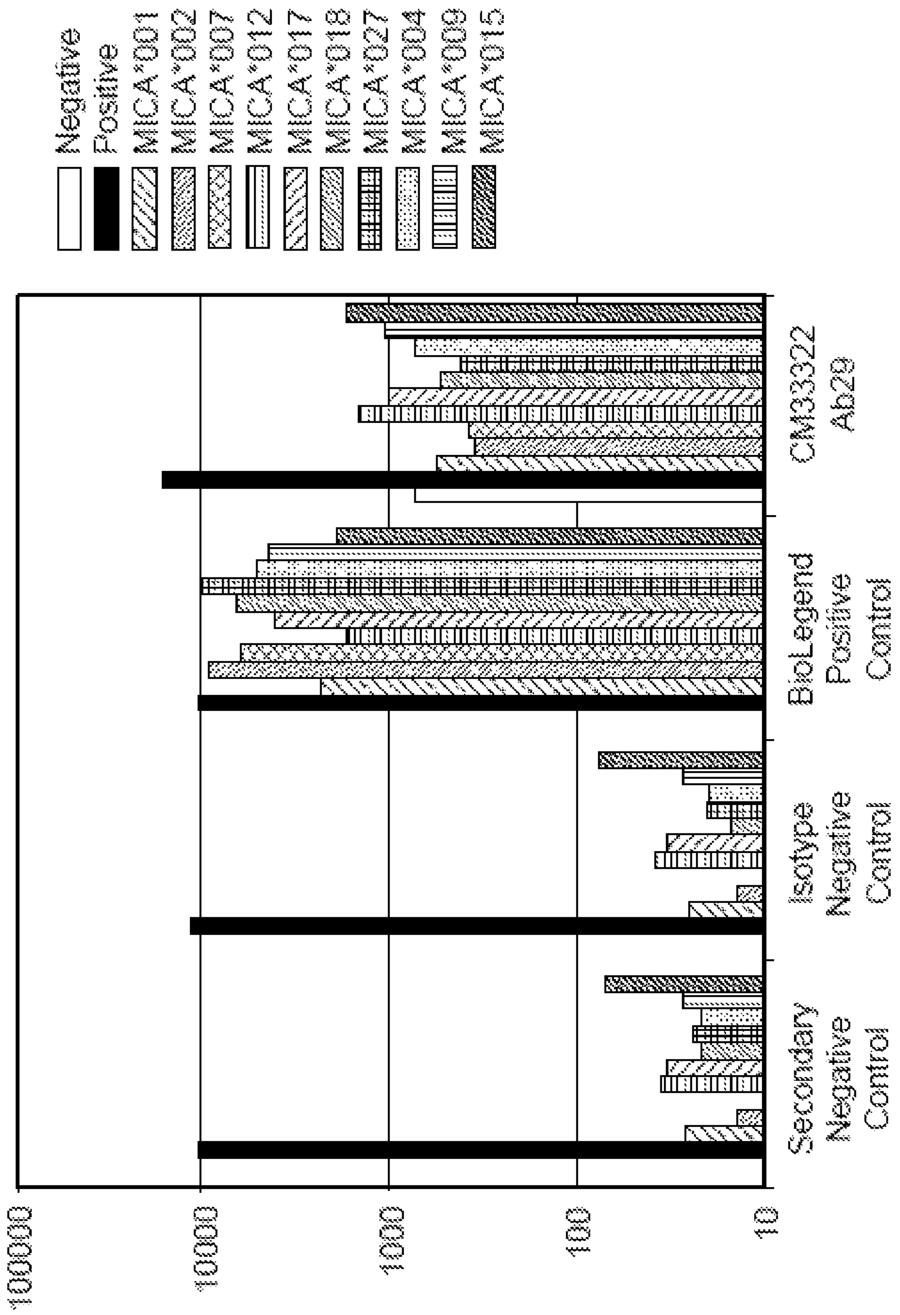
FIG. 34| Bar graph demonstrating MICA allelic specificity of anti-MICA antibody CM33322 Ab29 as determined by Luminex assay.
Figure 39:
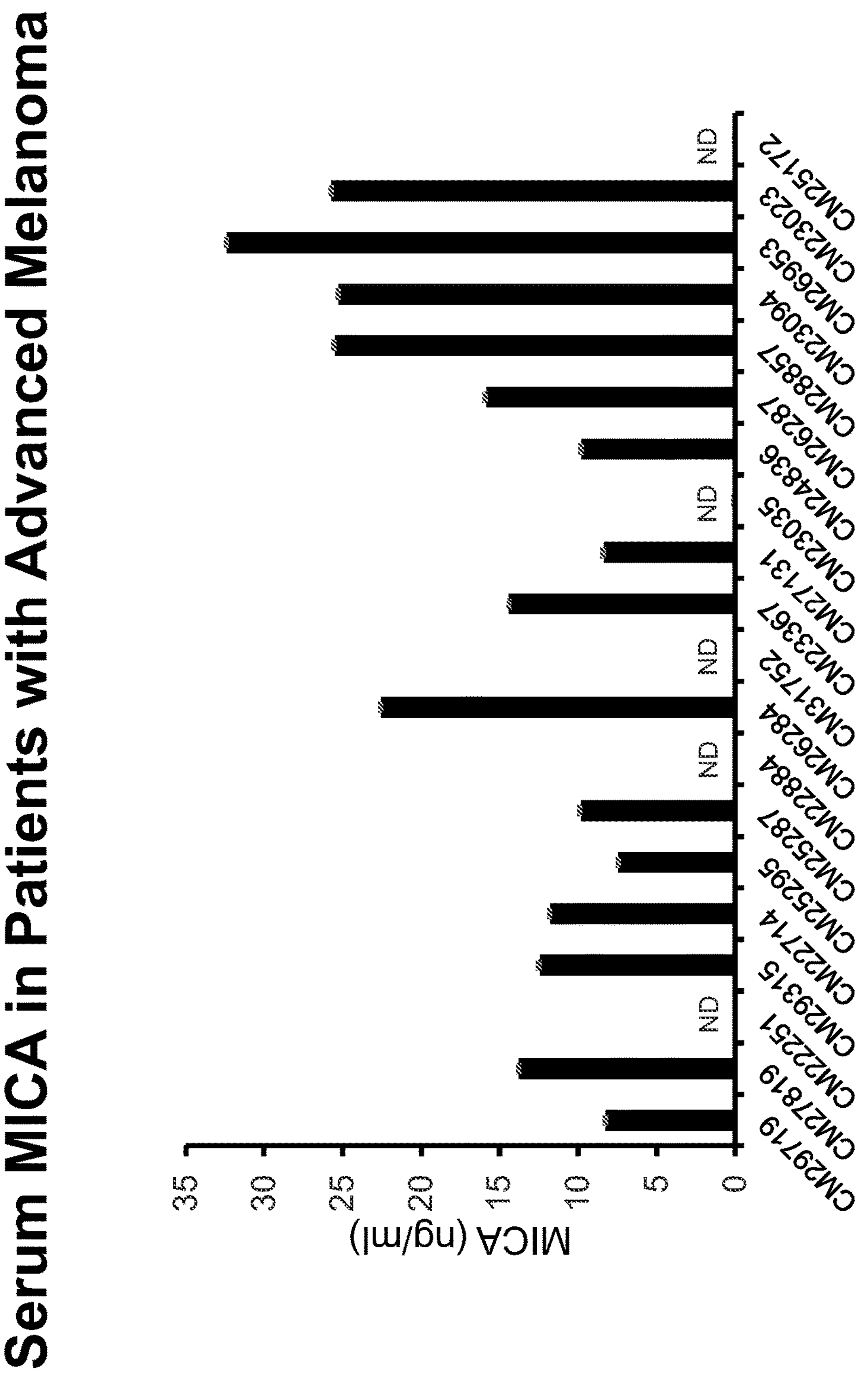
FIG. 39| Bar graph demonstration of serum MICA concentration in patients with advanced melanoma. Serum MICA was detected using a commercially available sandwich ELISA. Sera were tested at a 1:10 dilution.
Figure 41:
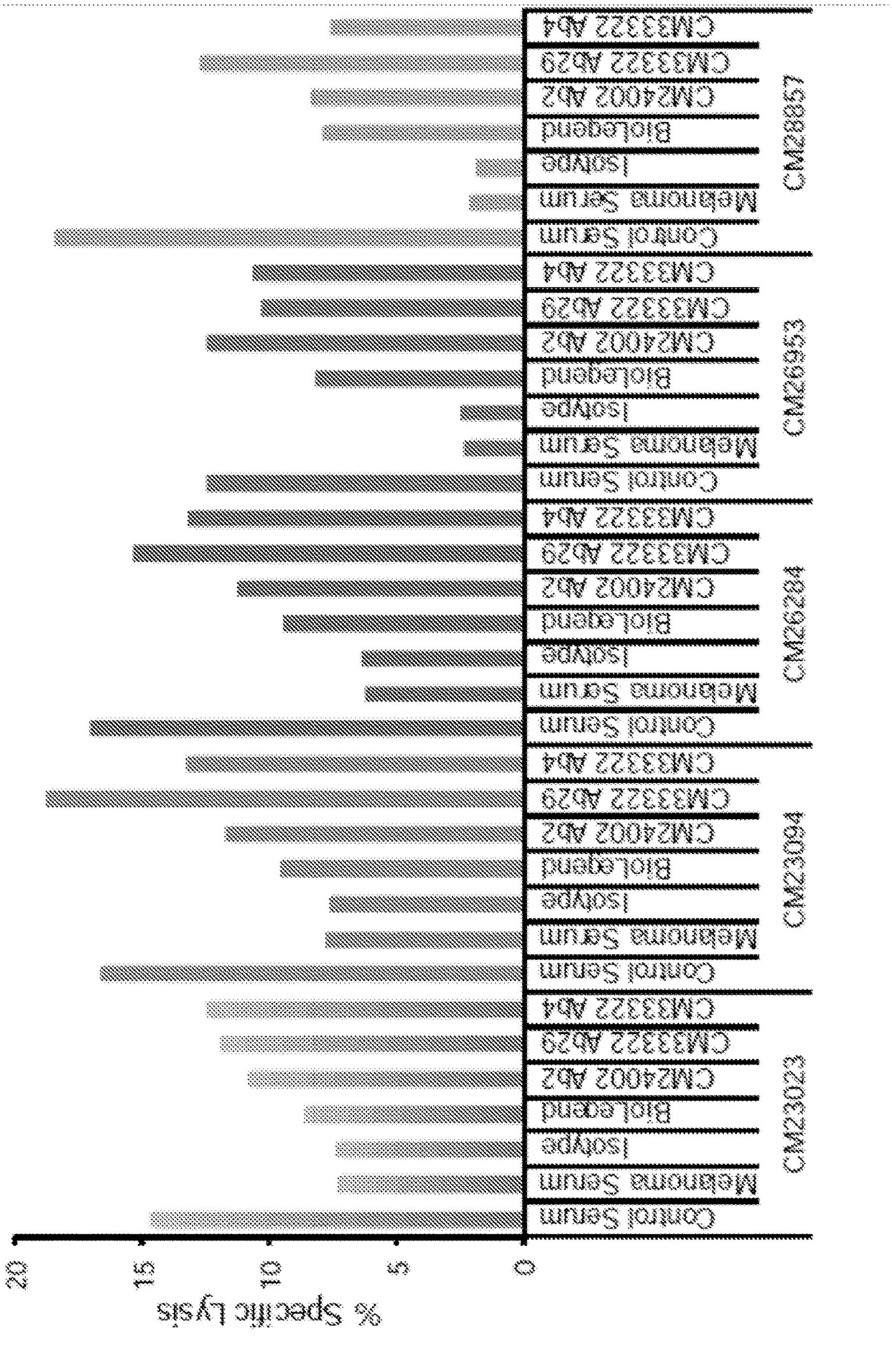
FIGS. 41-43| A series of graphs showing anti-MICA antibodies enhance NKG2D-mediated cytotoxicity of K562 target cells by NK cells incubated with melanoma patient serum. PBMCs were incubated with control serum or melanoma patient samples containing soluble MICA alone or in the presence of the indicated antibodies at 100 ug/ml for 48 hrs. At 48 hrs, cells were washed and incubated with $^{51}Cr$ labeled K562 target cells at a 20:1 effector to target ratio. Specific lysis was assessed by scintillation counting after 4 hrs.
Figure 42:
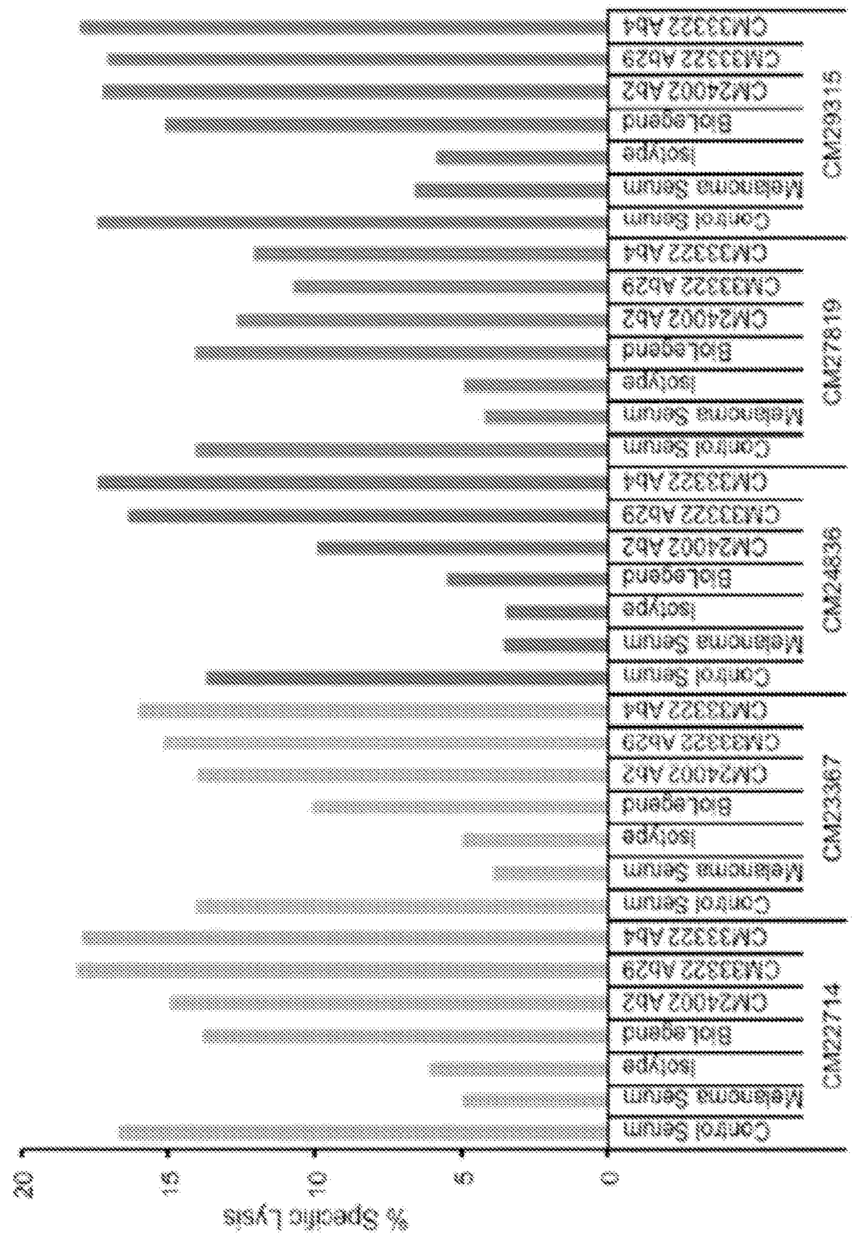
Figure 43:
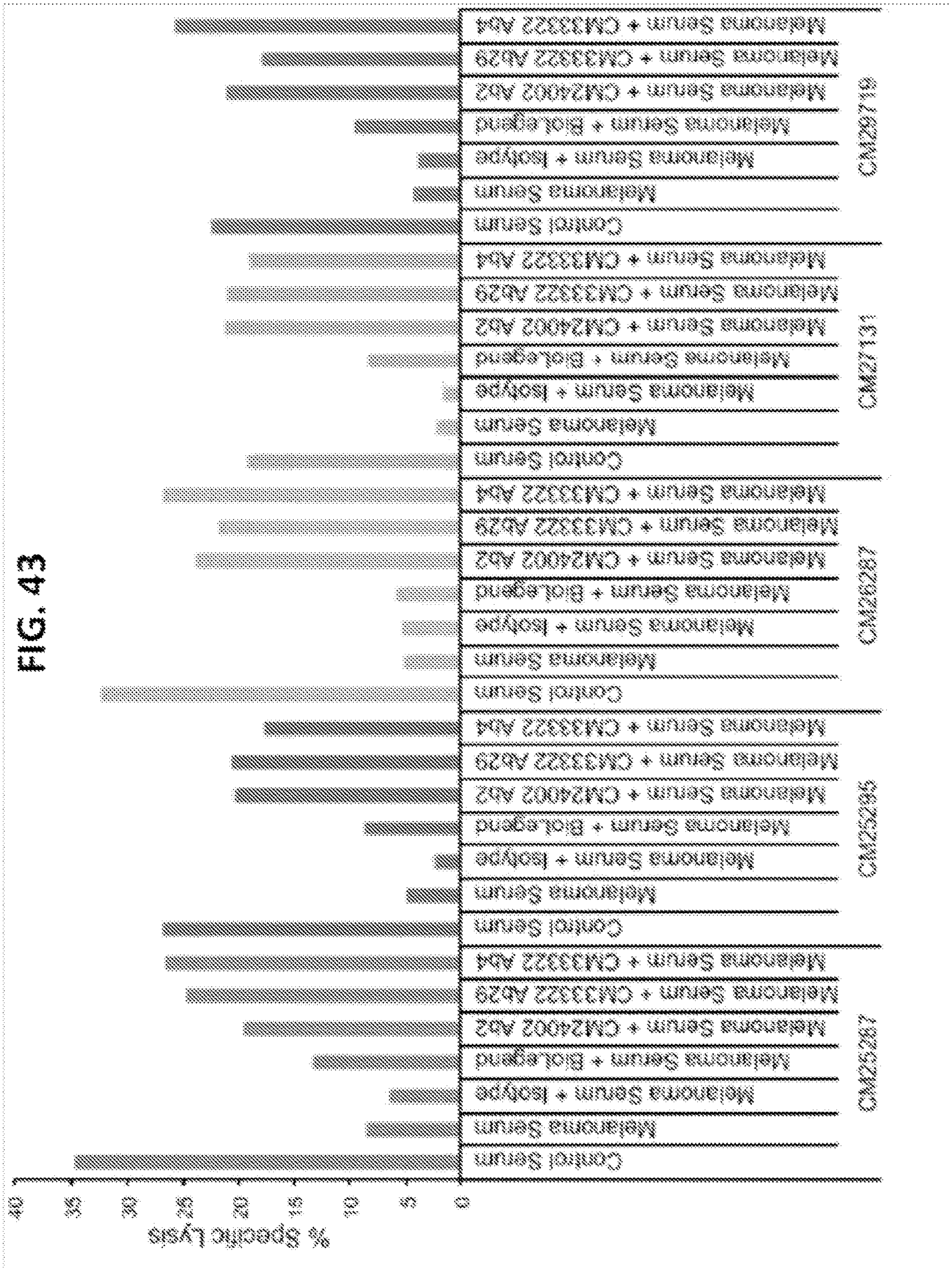

The allelic specificity of CM33322 Ab29 was assessed using a commercially available Luminex assay. The commercial test kit contains recombinant MICA alleles (MICA*001, *002, *007, *012, *017, *018, *027, *004, *009, and *015) directly conjugated to Luminex beads, each with intrinsic fluorescent properties enabling binding to be assessed in a single sample. Luminex beads coated with the indicated MICA alleles were incubated with CM33322 Ab29, BioLegend positive control, and the negative control (TTCF), at 10 μg/ml for 1 hr, with subsequent incubation with PE-conjugated anti-human IgG secondary antibody. Fluorescence was determined following incubation for 60 minutes with the indicated antibodies and subsequent incubation with anti-human PE-conjugated secondary antibody using a Luminex 200 instrument (FIG. 34). CM33322 Ab29 was able to bind to all alleles present in the commercial assay, indicating that it may be used in patients regardless of MICA genotype.

These data demonstrate the high biological activity of CM24002 Ab2 and CM33322 Ab29 and their ability to restore NK cell mediated lysis of tumor cells. These data demonstrate that cancer patients who responded to immunotherapies produced MICA antibodies that restored the anti-tumor activity of NK cells. Together, these results highlight the therapeutic potential of anti-MICA antibodies to overcome immune suppression and promote tumor destruction in cancer patients.

Example 13

In Vitro and In Vivo Biologic Activity of Anti-MICA Antibodies

Figure 44:
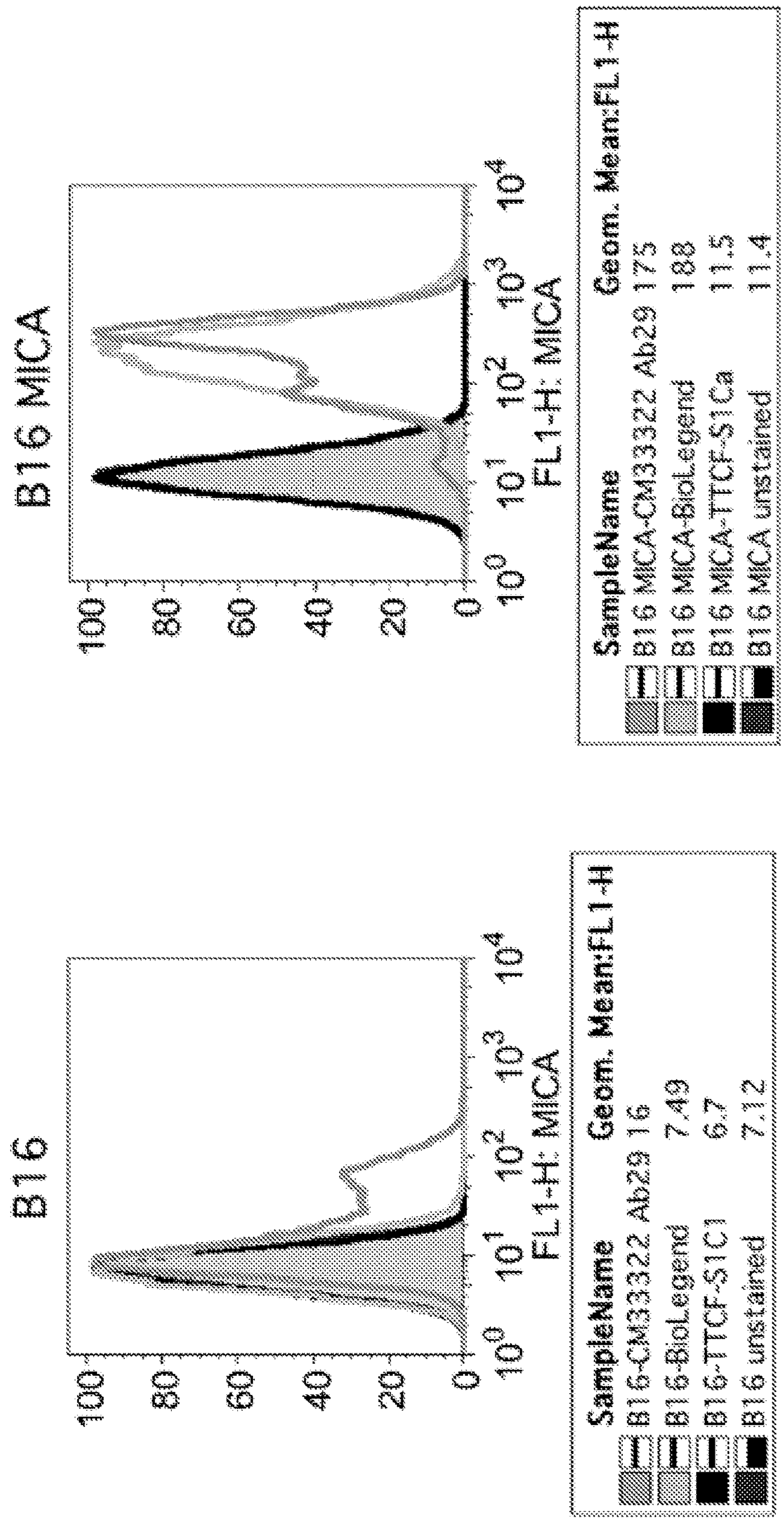
FIG. 44| Graphs showing binding of anti-MICA antibody CM33322 Ab29 to B16 melanoma cells that have been transduced to express human MICA. Indicated antibodies were incubated with B16 melanoma cells and B16 melanoma cells transduced to express human MICA at 10 ug/ml, and staining was analyzed by flow cytometry.

To examine directly the impact of anti-MICA antibodies on tumor growth, the in vitro and in vivo biologic activity of anti-MICA antibodies using a murine B16 was evaluated. For this study, B16 murine melanoma cells were transduced to express human MICA. Flow cytometry was used to detect cell B16 surface expression of MICA (FIG. 44).

Figure 45:
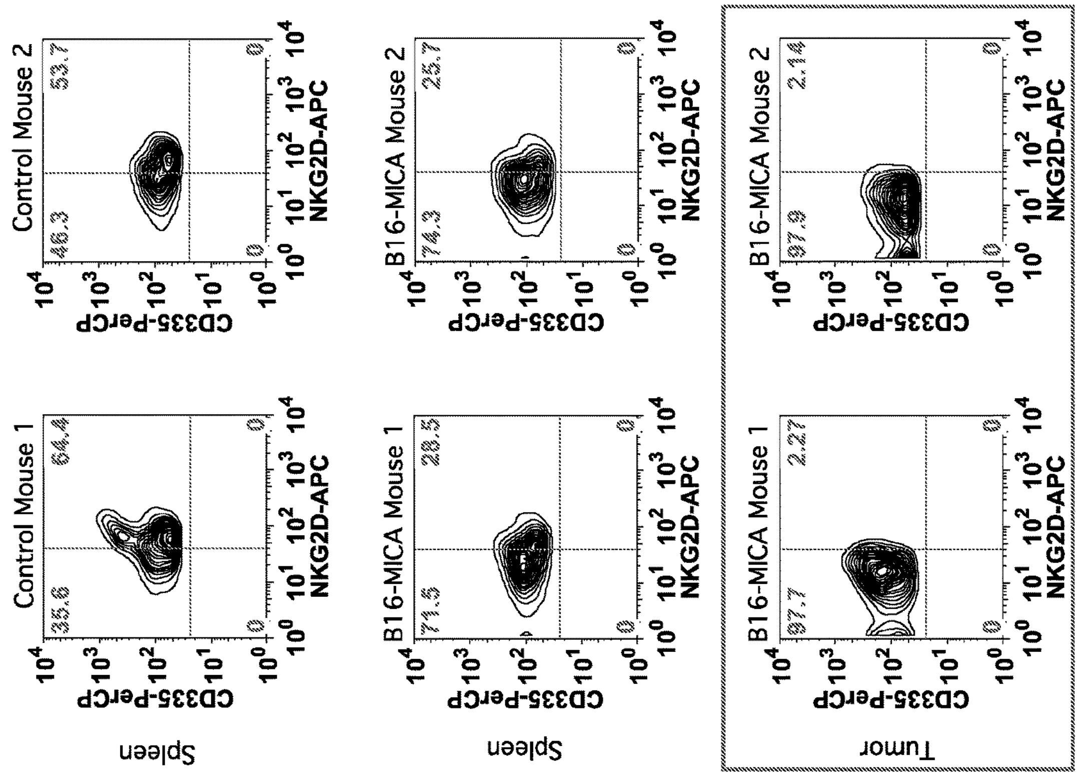
FIG. 45| A series of graphs demonstrating B16-MICA tumors down-regulate NKG2D expression on splenic NK cells and tumor-infiltrating NK cells. NKG2D expression was determined by flow cytometry on NK cells (CD3−, CD8−, CD335+) isolated from spleens of non-tumor mice or the spleen and tumor of tumor-bearing animals.

FIG. 45 provides a series of graphs demonstrating B16-MICA tumors down-regulate NKG2D expression on splenic NK cells and tumor-infiltrating NK cells. NKG2D expression was determined by flow cytometry on NK cells (CD3−, CD8−, CD335+) isolated from spleens of non-tumor mice or the spleen and tumor of tumor-bearing animals.

Figure 46:
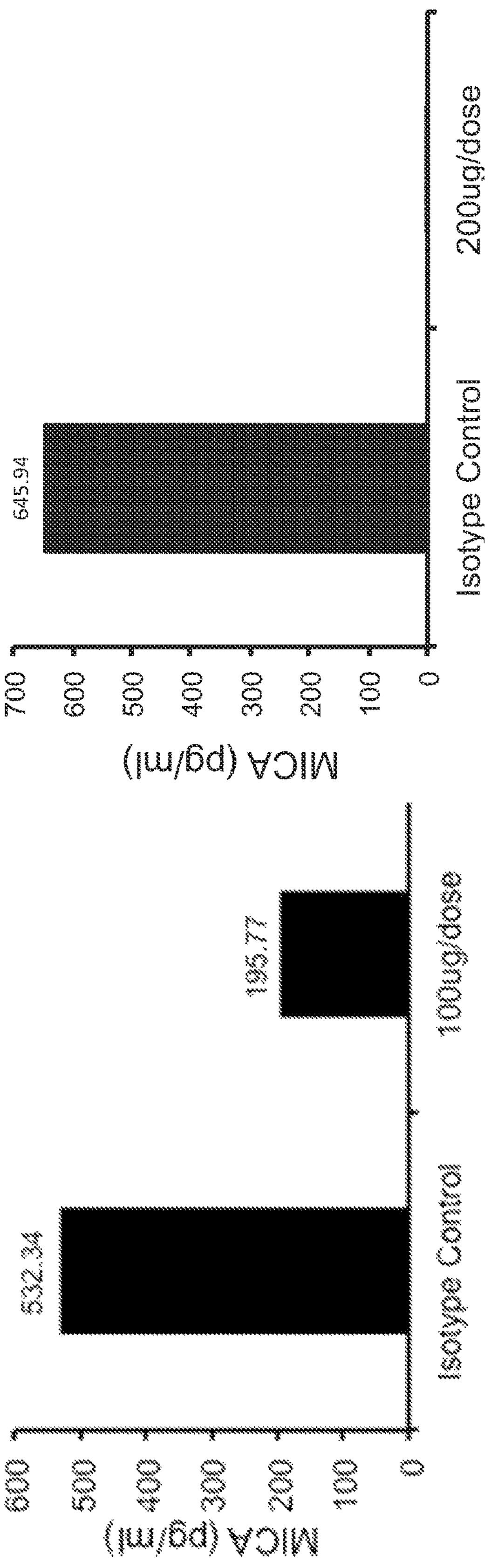
FIG. 46| A series of graphs demonstrating anti-MICA antibody treatment decreases serum-MICA levels in B16-MICA tumor bearing mice. B16-MICA tumor bearing B6 mice were treated with 100 ug or 200 ug/dose of CM33322 Ab29 via tail vein injection three times per week. At one week after the initial treatment, blood was collected, and serum MICA was measured by ELISA.
Figure 47:
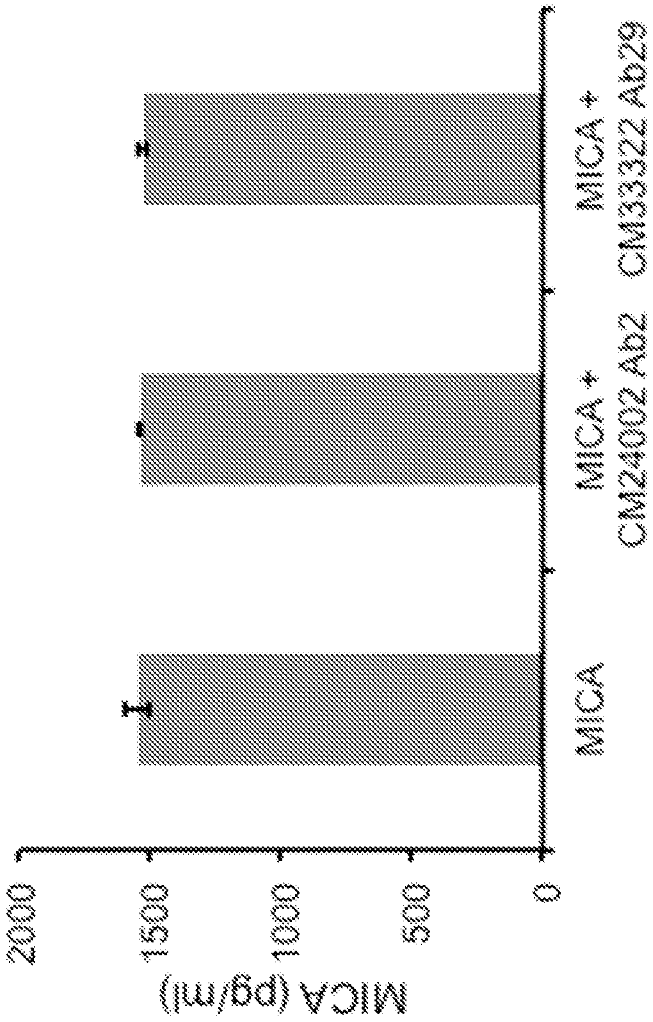
FIG. 47| A graph showing administration of anti-MICA antibodies does not interfere with MICA detection by sandwich ELISA. Recombinant MICA was incubated with a 1000-fold excess of antibody with rotation for 18 hrs. MICA concentration was determined by sandwich ELISA.

FIG. 46 shows anti-MICA antibody treatment decreases serum-MICA levels in B16-MICA tumor bearing mice. B16-MICA tumor bearing B6 mice were treated with 100 ug or 200 ug/dose of CM33322 Ab29 via tail vein injection three times per week. At one week after the initial treatment, blood was collected, and serum MICA was measured by ELISA. FIG. 47 shows that administration of anti-MICA antibodies does not interfere with MICA detection by sandwich ELISA. Recombinant MICA was incubated with a 1000-fold excess of antibody with rotation for 18 hrs. MICA concentration was determined by sandwich ELISA.

Figure 48:
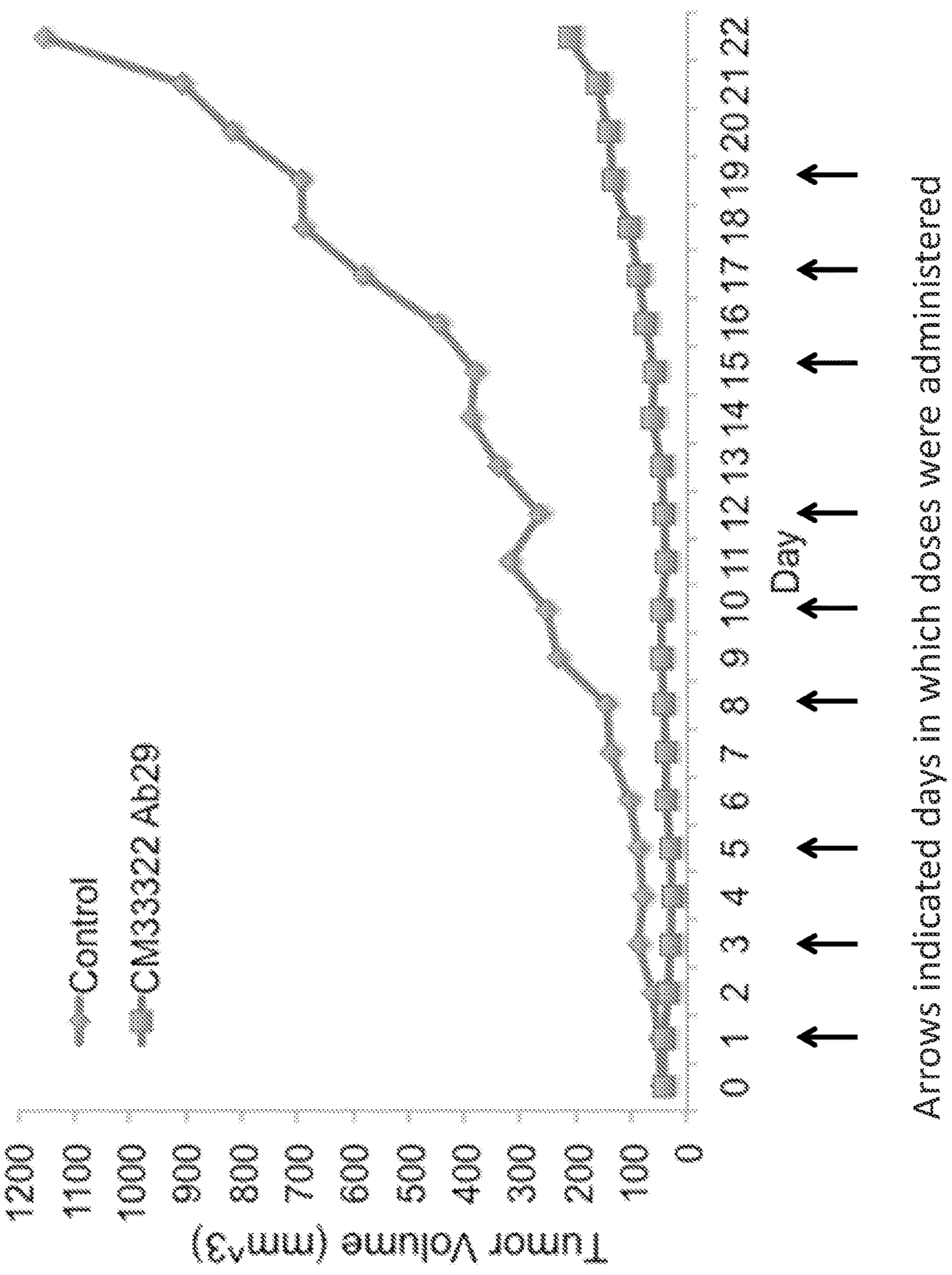
FIG. 48| A graph demonstrating treatment of B16-MICA tumor bearing mice with anti-MICA antibody CM33322 Ab29 halts tumor growth. B16-MICA tumor bearing mice were treated intravenously with 200 ug/dose of mouse IgG2a/κ isotype control or anti-MICA antibody CM33322 Ab29 beginning when tumors reached 5 mm in diameter. Doses were administered three times per week, and tumor volume was recorded daily. Arrows indicated dose administration.

To examine directly the impact of anti-MICA antibodies on tumor growth, the anti-MICA antibody CM33322 Ab29 was administered to B16-MICA tumor bearing mice. Mice were treated intravenously with 200 ug/dose of mouse IgG2a/K isotype control or anti-MICA antibody CM33322 Ab29 beginning when tumors reached 5 mm in diameter. Doses were administered three times per week, and tumor volume was recorded daily. As shown in FIG. 48, treatment of B16-MICA tumor bearing mice with anti-MICA antibody CM33322 AB29 halts tumor growth. These data showed growth inhibition of melanoma cells, both in vitro and in vivo, and show that anti-MICA antibody treatment may be a potential therapeutic strategy as consequence of modulation of host antitumor response and direct killing of tumor cells.

Example 14

Anti-MICA Antibodies Reduce MICA Shedding from Tumor Cells

Figure 49:
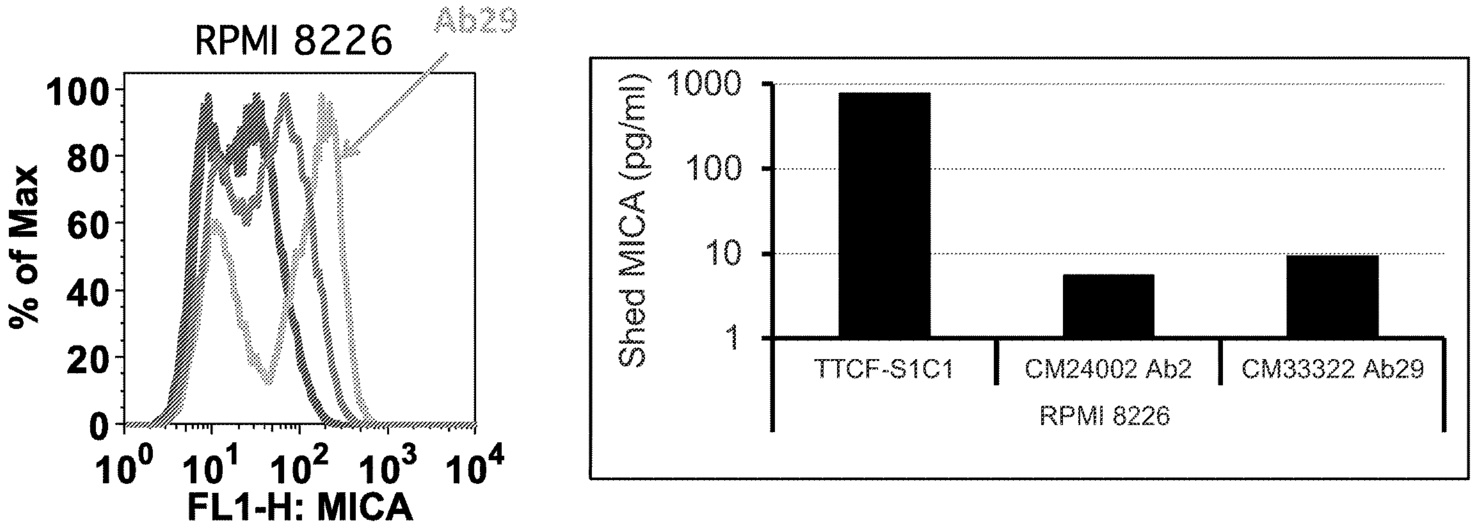
FIG. 49| A series of graphs demonstrating the ability of anti-MICA antibodies to reduce MICA shedding from tumor cells. RPMI-8226 cells were cultured in the presence of 10 ug/ml isotype control antibody, CM33322 Ab29, or CM24002 Ab2. After 48 hrs, cells were washed, and MICA surface expression was determined by flow cytometry, and shed MICA in conditioned media was assessed by sandwich ELISA.

The potential of CM24002 Ab2 and CM33322 Ab29 to reduce MICA shedding from tumor cells was examined. RPMI-8226 cells were cultured in the presence of 10 ug/ml isotype control antibody (TTCF-S1C1), CM33322 Ab29, or CM24002 Ab2. After 48 hrs, cells were washed, and MICA surface expression was determined by flow cytometry. As demonstrated in FIG. 49, CM24002 Ab2 and CM33322 Ab29 reduce MICA shedding RPMI-8226 cells.

Figure 55:
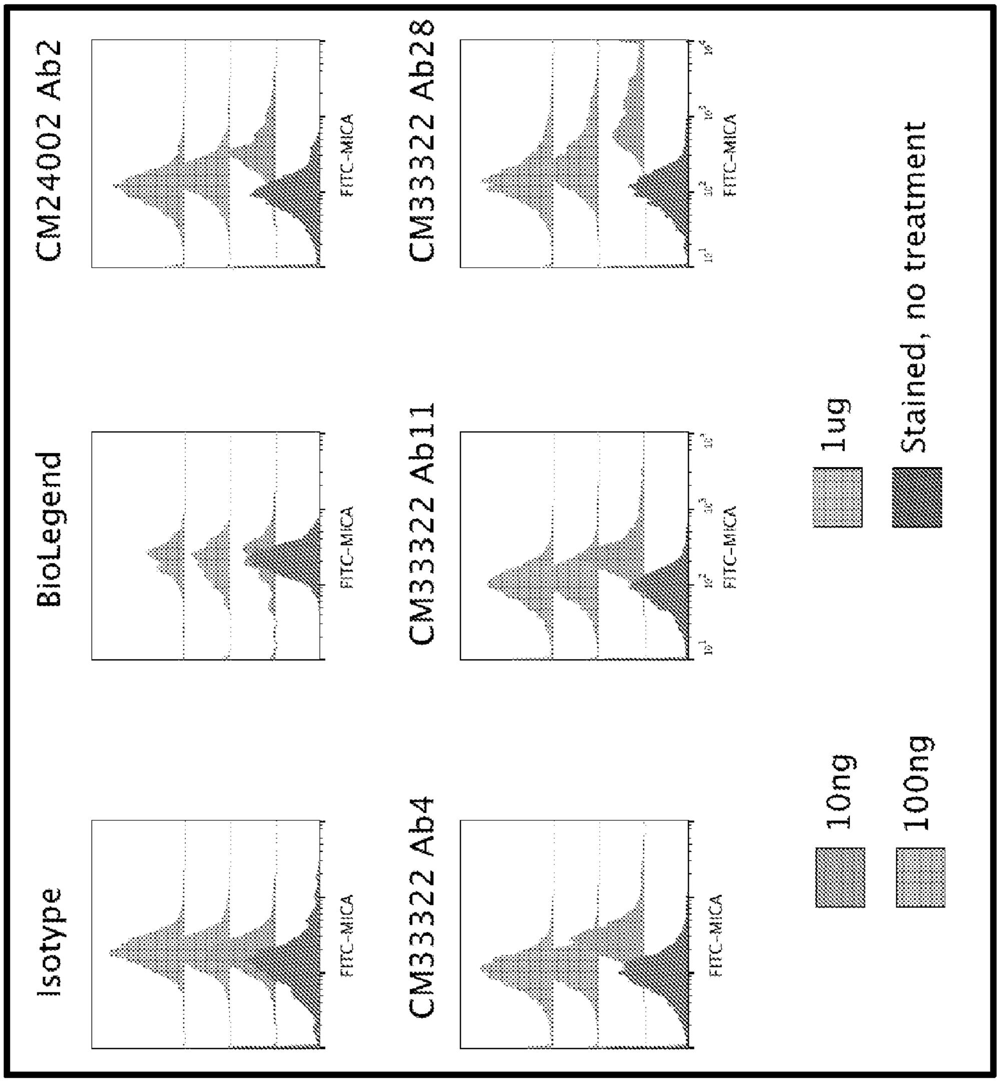
FIG. 55| A series of graphs demonstrating the ability of anti-MICA antibodies to reduce MICA shedding from tumor cells. RPMI-8226 cells were cultured in the presence of isotype control antibody, CM24002 Ab2, CM33322 Ab4, CM33322 Ab11, or CM33322 Ab28. After 48 hrs, cells were washed, and MICA surface expression was determined by flow cytometry, and shed MICA in conditioned media was assessed by sandwich ELISA.

In a further example, the potential of CM24002 Ab2, CM33322 Ab4, CM33322 Ab11 and CM33322 Ab28 to reduce MICA shedding from tumor cells was examined. RPMI-8226 cells were cultured in the presence of isotype control antibody (TTCF-S1C1) and CM24002 Ab2, CM33322 Ab4, CM33322 Ab11 or CM33322 Ab28. After 48 hrs, cells were washed, and MICA surface expression was determined by flow cytometry. As demonstrated in FIG. 55, CM24002 Ab2, CM33322 Ab4, CM33322 Ab11 and CM33322 Ab28 reduce MICA shedding RPMI-8226 cells.

In a further example, CM24002 Ab2, CM33322 Ab28 and CM33322 Ab29 inhibited shedding of MICA by A375 cells during a 48 hour incubation as measured by the presence of sMICA in tumor cell supernatants by ELISA (FIG. 63*c*).

Example 15

Therapeutic Activity of Human Anti-MICA Antibodies

Figure 64:
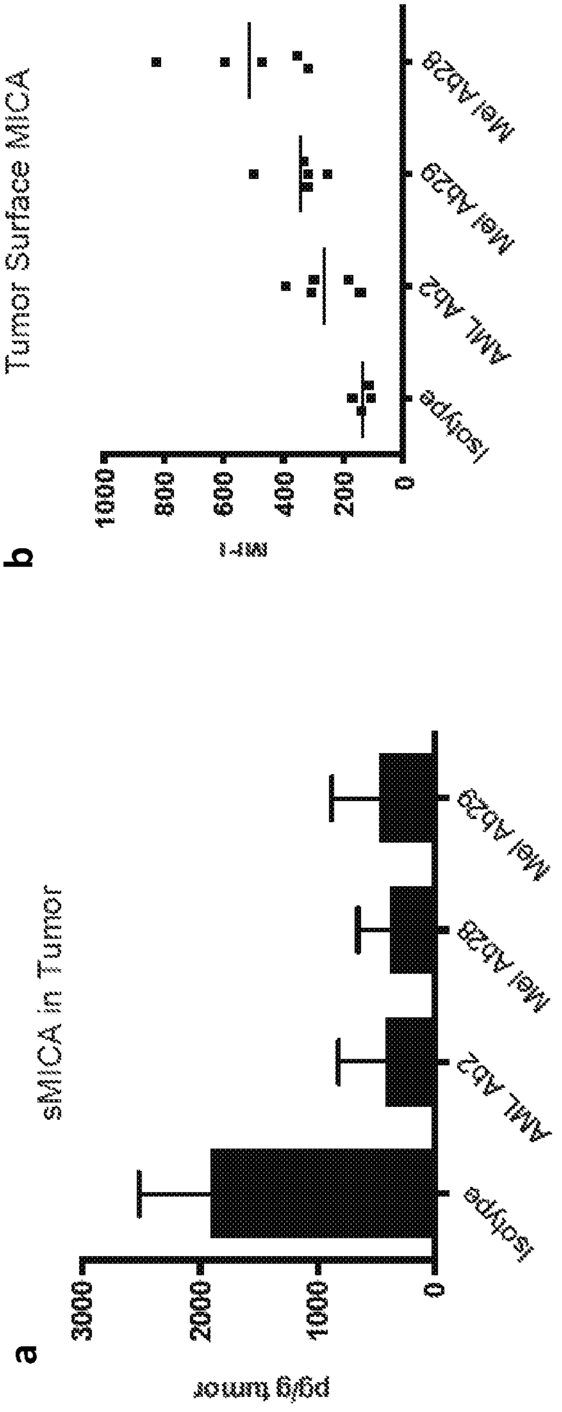
FIG. 64a-64b| A series of graphs showing that in SCID mice implanted with human U937 tumor cells, treatment with MICA antibodies for one week (3×100 μg Ab per week) (a) reduced sMICA in tumor homogenate (normalized to tumor mass); and (b) increased MICA expression on the surface of tumor cells (flow cytometry). Data represent a composite of three independent experiments (n=10 mice/group/experiment).

SCID mice implanted with human U937 tumor cells were treated with CM24002 Ab2, CM33322 Ab28 and CM33322 Ab29 (3×100 μg Ab per week). Following one week of treatment, all three antibodies significantly reduced sMICA in tumor homogenates (normalized to tumor mass) as measured by ELISA, and increased MICA expression on the surface of tumor cells in tumor homogenates as measured by flow cytometry (FIG. 64*a-b*).

Figure 65:
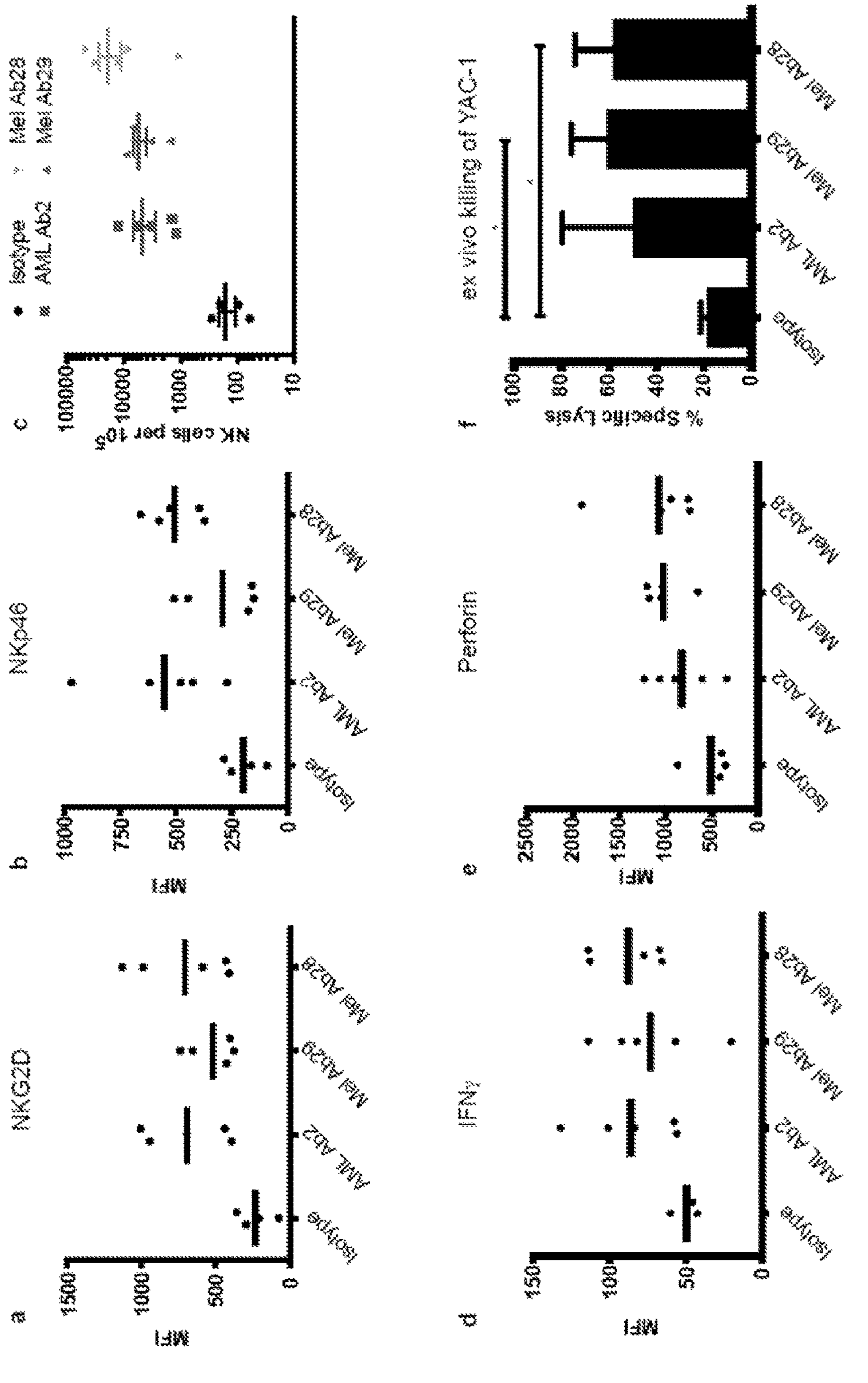
FIG. 65a-65f| A series of graphs showing the assessment of NK cell function in SCID mice bearing U937 tumors treated for one week with MICA mAbs (3×100 μg). Antibody treatment increased surface levels of NKG2D (a) and NKp46 (b) by tumor-infiltrating $CD45^+$ $NK1.1^+$ NK cells, and induced NK cell accumulation in tumors (c)(normalized to $1\times10^5$ $CD45^+$ cells). Treatment increased IFNγ (d) and perforin (e) expression by tumor infiltrating $CD45^+$ $NK1.1^+$ NK cells. (f) All three human MICA antibodies enhanced ex vivo killing of $^{51}$Cr labeled YAC-1 cells by splenocytes.

The NK cell function in the treated mice was also assessed. Treatment with CM24002 Ab2, CM33322 Ab28 or CM33322 Ab29 treatment increased surface levels of NKG2D and NKp46 by tumor-infiltrating $CD45^+$ $NK1.1^+$ NK cells, and induced NK cell accumulation in tumors (normalized to $1\times10^5$ $CD45^+$ cells). Treatment also increased IFNγ and perforin expression by tumor infiltrating $CD45^+$ $NK1.1^+$ NK cells. In addition, all three human MICA antibodies enhanced ex vivo killing of $^{51}Cr$ labeled YAC-1 cells by splenocytes. (FIG. 65 *a-f*).

Example 16

Epitope Mapping of Anti-MICA Antibodies

Experiments were conducted to determine the epitope sequences for CM33322 mAb 29, CM33322 11, CM33322 mAb4 and CM33322 mAb28. Briefly, epitope mapping was performed by peptide arrays containing a series of overlapping peptides spanning the full-length of MICA*009 extracellular domains. Each peptide in the arrays was a length of 20 amino acid linear sequence from the MICA*009 reference sequence (SEQ ID NO: 185), with each subsequent sequence overlapping by ten amino acids with the previous sequence (20 aa peptides with a 10 aa offset). These peptides were bound to glass slides through the use of flexible linkers. Antibodies were incubated with the slides, with antibody bound to peptide fragments detected with a Cy5 conjugated anti-human IgG antibody. Binding to array spots was assessed with a GenePix Microarray Scanner. The results indicate that mAbs CM33322 mAb 29, CM33322 11, CM33322 mAb4 and CM33322 mAb28 bind to a the alpha-3 region of human MICA or MICB.

Figure 61:
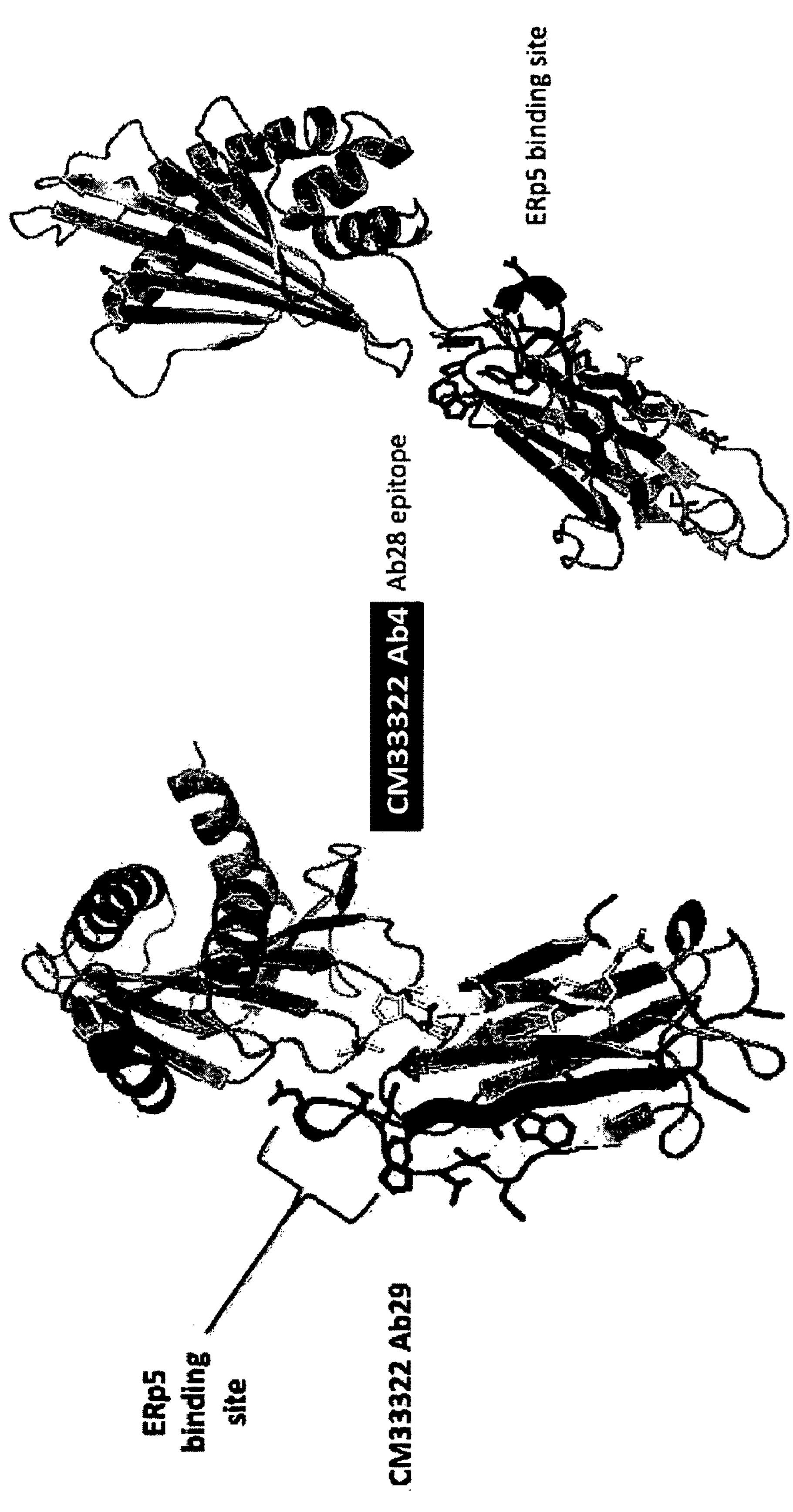
FIG. 61| Mapping of epitopes for CM33322Ab29, CM33322Ab4 and CM33322Ab28 on MICA*009 reference structure. Epitope mapping was performed using overlapping peptide arrays. Each peptide was a 20 amino acid linear sequence with 10 amino acid offset for each peptide.
Figure 62:
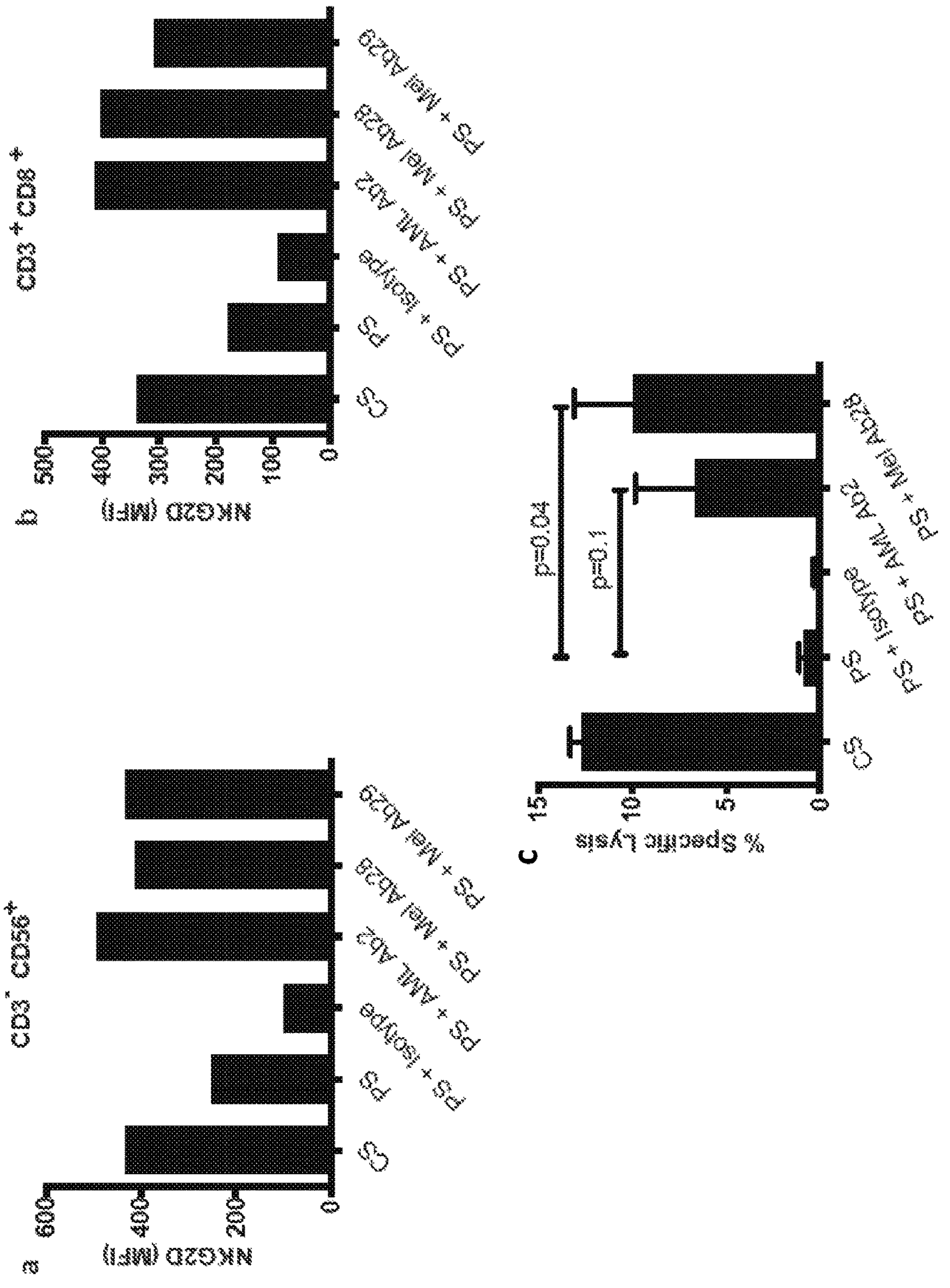
FIG. 62a-62c| A series of bar graphs showing antibodies CM24002 Ab2, CM33322Ab29 and CM33322Ab28 prevented NKGD receptor downregulation on human (a) NK cells and (b) CD8 T cells; and (c) CM24002 Ab2 and CM33322Ab28 antibodies prevented inhibition of CD8 T cell cytotoxicity by sMICA (clone specific for NY-ESO, $^{51}$Cr labeled Mel375 cells, 20:1 E:T ratio). Data are representative of at least three independent experiments.

The results indicate that all three antibodies interact with epitopes within the αF3 region of human MICA that include distinctly different continuous amino acid sequences. The amino acid sequence of the epitopes for CM33322 mAb 29, CM33322 11, CM33322 mAb4 and CM33322 mAb28 within the MICA*009 are shown in FIG. 60A-60D. The location of the epitopes for CM33322 mAb 29, CM33322 mAb4 and CM33322 mAb28 within the three-dimensional structure of MICA are also shown in FIG. 61.

The results indicated that the epitope recognized by antibody CM33322 mAb29 includes a contiguous amino acid sequence: GDVLPDGNGTYQTWVATRIC (SEQ ID NO: 186), which corresponds to amino acid residues 229 to 248 of human MICA SEQ ID NO: 185 (FIG. 60A). The epitope recognized by antibody CM33322 mAb11 includes a contiguous amino acid sequence: NVETEEWTP (SEQ ID NO: 187), which corresponds to amino acid residues 119 to 128 of human MICA SEQ ID NO: 185 (FIG. 60B). The epitope recognized by antibody CM33322 mAb 4 includes a contiguous amino acid sequence: TVPPMVNVTR (SEQ ID NO: 188), which corresponds to amino acid residues 179 to 188 of human MICA SEQ ID NO: 185 (FIG. 60C). The epitope recognized by antibody CM33322 mAb28 includes a contiguous amino acid sequence: TCRASSFYPR (SEQ ID NO: 189), which corresponds to amino acid residues 199 to 208 of human MICA (SEQ ID NO: 185).

EMBODIMENTS

1. A composition comprising a peptide that immunospecifically binds to MHC class I polypeptide-related sequence A (MICA), wherein the peptide comprises a $V_H$ complementarity determining region (CDR) 3 comprising the amino acid sequence shown in SEQ ID NO: 176 or a variant thereof having 5 or fewer conservative amino acid substitutions, and a $V_L$ CDR3 comprising the amino acid sequence shown in SEQ ID NO: 183 or a variant thereof having 5 or fewer conservative amino acid substitutions.

2. The composition of embodiment 1, wherein the peptide comprises a $V_H$ complementarity determining region (CDR) 3 comprising the amino acid sequence shown in SEQ ID NO: 176, and a $V_L$ CDR3 comprising the amino acid sequence shown in SEQ ID NO: 183.

3. The composition of embodiments 1 or 2, wherein the peptide comprises a $V_H$ CDR2 comprising the amino acid sequence shown in SEQ ID NO: 174 or a variant thereof having 5 or fewer conservative amino acid substitutions, or a $V_L$ CDR2 comprising the amino acid sequence shown in SEQ ID NO: 181 having 5 or fewer conservative amino acid substitutions, or both.

4. The composition of embodiment 3, wherein the peptide comprises a $V_H$ complementarity determining region CDR2 comprising the amino acid sequence shown in SEQ ID NO: 174, or a $V_L$ CDR2 comprising the amino acid sequence shown in SEQ ID NO: 181, or both.

5. The compositions of any one of embodiments 1-4, wherein the peptide comprises a $V_H$ CDR1 comprising the amino acid sequence shown in SEQ ID NO: 172 or a variant thereof having 5 or fewer conservative amino acid substitutions, or a $V_L$ CDR1 comprising the amino acid sequence shown in SEQ ID NO: 179 or a variant thereof having 5 or fewer conservative amino acid substitutions, or both.

6. The composition of embodiment 5, wherein the peptide comprises a $V_H$ complementarity determining region CDR1 comprising the amino acid sequence shown in SEQ ID NO: 172, or a $V_L$ CDR1 comprising the amino acid sequence shown in SEQ ID NO: 179, or both.

7. A chimeric antigen receptor (CAR) comprising a peptide that immunospecifically binds to MHC class I polypeptide-related sequence A (MICA), wherein the peptide comprises a $V_H$ complementarity determining region (CDR) 3 comprising the amino acid sequence shown in SEQ ID NO: 176 or a variant thereof having 5 or fewer conservative amino acid substitutions, and a $V_L$ CDR3 comprising the amino acid sequence shown in SEQ ID NO: 183 or a variant thereof having 5 or fewer conservative amino acid substitutions.

8. The chimeric antigen receptor (CAR) of embodiment 7, wherein the peptide comprises a $V_H$ complementarity determining region (CDR) 3 comprising the amino acid sequence shown in SEQ ID NO: 176, and a $V_L$ CDR3 comprising the amino acid sequence shown in SEQ ID NO: 183.

9. The chimeric antigen receptor (CAR) of embodiments 7 or 8, wherein the peptide comprises a $V_H$ CDR2 comprising the amino acid sequence shown in SEQ ID NO: 174 or a variant thereof having 5 or fewer conservative amino acid substitutions, or a $V_L$ CDR2 comprising the amino acid sequence shown in SEQ ID NO: 181 having 5 or fewer conservative amino acid substitutions, or both.

10. The chimeric antigen receptor (CAR) of embodiment 9, wherein the peptide comprises a $V_H$ complementarity determining region CDR2 comprising the amino acid sequence shown in SEQ ID NO: 174, or a $V_L$ CDR2 comprising the amino acid sequence shown in SEQ ID NO: 181, or both.

11. The chimeric antigen receptor (CAR) of any one of embodiments 8-10, wherein the peptide comprises a $V_H$ CDR1 comprising the amino acid sequence shown in SEQ ID NO: 172 or a variant thereof having 5 or fewer conservative amino acid substitutions, or a $V_L$ CDR1 comprising the amino acid sequence shown in SEQ ID NO: 179 or a variant thereof having 5 or fewer conservative amino acid substitutions, or both.

12. The chimeric antigen receptor (CAR) of embodiment 11, wherein the peptide comprises a $V_H$ complementarity determining region CDR1 comprising the amino acid sequence shown in SEQ ID NO: 172, or a $V_L$ CDR1 comprising the amino acid sequence shown in SEQ ID NO: 179, or both.

13. The chimeric antigen receptor (CAR) of any one of embodiments 7-12, wherein the peptide is an antibody or antibody fragment comprising:

a $V_H$ chain comprising the amino acid sequence shown in SEQ ID NO: 168, or a variant thereof having 5 or fewer conservative amino acid substitutions within the CDR1, CDR2, and CDR3 regions and FR1, FR2, FR3, FR4 regions comprising amino acid sequences with at least 80%, 85%, 90%, 95%, 96%, 97%, 98, 99%, or 100% identity to the corresponding FR1, FR2, FR3, FR4 regions of SEQ ID NO: 168; and a $V_L$ chain comprising the amino acid sequence shown in SEQ IDNO: 170, or a variant thereof having 5 or fewer conservative amino acid substitutions within the CDR1, CDR2, and CDR3 regions, and FR1, FR2, FR3, FR4, comprising amino acid sequences with at least 80%, 85%, 90%, 95%, 96%, 97%, 98, 99%, or 100% identity to the corresponding FR1, FR2, FR3, FR4 regions of SEQ ID NO: 170.

14. The chimeric antigen receptor (CAR) of embodiment 13, wherein the peptide is an antibody or antibody fragment comprising a $V_H$ chain comprising SEQ ID NO:168 and a $V_L$ chain comprising SEQ ID NO:170.

15. The chimeric antigen receptor (CAR) of any one of embodiments 7-14, further comprising an extracellular hinge domain, a T cell receptor transmembrane domain, and an intracellular T cell receptor signaling domain.

16. The chimeric antigen receptor (CAR) of any one of embodiments 7-15, wherein the peptide comprises a CD137 (4-IBB) signaling domain and a CD3-ζ chain.

17. A nucleic acid molecule encoding the chimeric antigen receptor (CAR) of any of embodiments 7-16.

18. A human T cell harboring the nucleic acid molecule of embodiment 18.

19. A method of treating cancer in a subject, the method comprising administering to a subject T cell of embodiment 18, wherein the T cell is an autologous T cell modified to express the chimeric antigen receptor (CAR).

20. A composition comprising a nucleic acid encoding a peptide that immunospecifically bind to MHC class I polypeptide-related sequence A (MICA), or an epitope thereon, wherein the nucleic acid comprises nucleotide sequence having at least about 75%, 80%, 90%, 95%, 99% or more, or complete (100%) sequence identity to SEQ ID NO: 167.

21. A composition comprising a nucleic acid encoding a peptide that immunospecifically bind to MHC class I polypeptide-related sequence A (MICA), or an epitope thereon, wherein the nucleic acid comprises nucleotide sequence having at least about 75%, 80%, 90%, 95%, 99% or more, or complete (100%) sequence identity to SEQ ID NO: 169.

22. A vector encoding a peptide that comprises a $V_H$ complementarity determining region (CDR) 3 comprising the amino acid sequence shown in SEQ ID NO: 176 or a variant thereof having 5 or fewer conservative amino acid substitutions, and a $V_L$ CDR3 comprising the amino acid sequence shown in SEQ ID NO: 183 or a variant thereof having 5 or fewer conservative amino acid substitutions.

23. The vector of embodiment 22, wherein the peptide comprises a $V_H$ complementarity determining region (CDR) 3 comprising the amino acid sequence shown in SEQ ID NO: 176, and a $V_L$ CDR3 comprising the amino acid sequence shown in SEQ ID NO: 183.

24. The vector of embodiments 22 or 23, wherein the peptide comprises a $V_H$ CDR2 comprising the amino acid sequence shown in SEQ ID NO: 174 or a variant thereof having 5 or fewer conservative amino acid substitutions, or a $V_L$ CDR2 comprising the amino acid sequence shown in SEQ ID NO: 181 having 5 or fewer conservative amino acid substitutions, or both.

25. The vector of embodiment 24, wherein the peptide comprises a $V_H$ complementarity determining region CDR2 comprising the amino acid sequence shown in SEQ ID NO: 174, or a $V_L$ CDR2 comprising the amino acid sequence shown in SEQ ID NO: 181, or both.

26. The vector of any one of embodiments 22-25, wherein the peptide comprises a $V_H$ CDR1 comprising the amino acid sequence shown in SEQ ID NO: 172 or a variant thereof having 5 or fewer conservative amino acid substitutions, or a $V_L$ CDR1 comprising the amino acid sequence shown in SEQ ID NO: 179 or a variant thereof having 5 or fewer conservative amino acid substitutions, or both.

27. The vector of embodiment 26, wherein the peptide comprises a $V_H$ complementarity determining region CDR1 comprising the amino acid sequence shown in SEQ ID NO: 172, or a $V_L$ CDR1 comprising the amino acid sequence shown in SEQ ID NO: 179, or both.

28. The vector of any one of embodiments 22-27, wherein the peptide is an antibody or antibody fragment comprising:

a $V_H$ chain comprising the amino acid sequence shown in SEQ ID NO: 168, or a variant thereof having 5 or fewer conservative amino acid substitutions within the CDR1, CDR2, and CDR3 regions and FR1, FR2, FR3, FR4 regions comprising amino acid sequences with at least 80%, 85%, 90%, 95%, 96%, 97%, 98, 99%, or 100% identity to the corresponding FR1, FR2, FR3, FR4 regions of SEQ ID NO: 168; and a $V_L$ chain comprising the amino acid sequence shown in SEQ IDNO: 170, or a variant thereof having 5 or fewer conservative amino acid substitutions within the CDR1, CDR2, and CDR3 regions, and FR1, FR2, FR3, FR4, comprising amino acid sequences with at least 80%, 85%, 90%, 95%, 96%, 97%, 98, 99%, or 100% identity to the corresponding FR1, FR2, FR3, FR4 regions of SEQ ID NO: 170.

29. The vector of embodiment 28, wherein the peptide is an antibody or antibody fragment comprising a $V_H$ chain comprising SEQ ID NO:168 and a $V_L$ chain comprising SEQ ID NO: 170.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An antibody or antibody fragment that immunospecifically binds to MEW class I polypeptide-related sequence A (MICA), wherein the antibody or antibody fragment comprises
(i) a heavy chain variable ($V_H$) region comprising $V_H$ CDR1, $V_H$ CDR2, and $V_H$ CDR3 as shown in the $V_H$ of sequence of SEQ ID NO: 168;
(ii) a light chain variable ($V_L$) region comprising $V_L$ CDR1, $V_L$ CDR2, and $V_L$ CDR3 as shown in the $V_L$ of sequence of SEQ ID NO: 170; and
(iii) a heterologous constant region or a heterologous $F_c$ region.

2. The antibody or antibody fragment of claim 1, wherein the antibody or antibody fragment comprises a $V_H$ region comprising an amino acid sequence that is at least 85%, 90%, 95%, 96%, 97%, 98% or 99% A identical to SEQ ID NO: 168.

3. The antibody or antibody fragment of claim 1, wherein the antibody or antibody fragment comprises a $V_L$ region comprising an amino acid sequence that is at least 85%, 90%, 95%, 96%, 97%, 98% or 99% A identical to SEQ ID NO: 170.

4. The antibody or antibody fragment of claim 1, wherein the $V_H$ region comprises
a $V_H$ CDR1 comprising SEQ ID NO: 172;
a $V_H$ CDR2 comprising SEQ ID NO: 174; and
a $V_H$ CDR3 comprising SEQ ID NO: 176.

5. The antibody or antibody fragment of claim 1, wherein the
a $V_L$ region comprises
a $V_L$ CDR1 comprising SEQ ID NO: 179,
a $V_L$ CDR2 comprising SEQ ID NO: 181, and
a $V_L$ CDR3 comprising SEQ ID NO: 183.

6. The antibody or antibody fragment of claim 1, wherein the $V_H$ region comprises the amino acid sequence shown in SEQ ID NO: 168 or a variant thereof with 5 or fewer conservative amino acid substitutions in residues that are not within a CDR.

7. The antibody or antibody fragment of claim 1, wherein the $V_L$ region comprises the amino acid sequence shown in SEQ ID NO: 170 or a variant thereof with 5 or fewer conservative amino acid substitutions in residues that are not within a CDR.

8. The antibody or antibody fragment of claim 1, wherein the antibody or antibody fragment binds to an epitope of human MHC class I polypeptide-related sequence A (MICA) comprising the amino acid sequence TCRASSFYPR (SEQ ID NO: 189).

9. The antibody or antibody fragment of claim 1, wherein the antibody or antibody fragment,
(a) binds to MICA α3 domain;
(b) reduces sMICA levels;
(c) inhibits shedding of MICA from tumor cells;
(d) inhibits sMICA mediated downregulation of the NKG2D receptor on NK cells;
(e) increases NK cell mediated lysis of tumor cells; or
(f) a combination of one or more of (a)-(e).

10. The antibody or antibody fragment of claim 1, wherein the $V_H$ region comprises the amino acid sequence of SEQ ID NO: 168; and the $V_L$ region comprises the amino acid sequence of SEQ ID NO: 170.

11. The antibody or antibody fragment of claim 1, wherein the antibody is human, humanized or chimeric.

12. A pharmaceutical composition comprising the antibody or antibody fragment of claim 1.

13. The pharmaceutical composition of claim 12, further comprising an anti-cancer therapeutic.

14. The pharmaceutical composition of claim 13, wherein the anti-cancer therapeutic is selected from the group consisting of,
(a) an histone deacetylase inhibitor (HDAC) selected from the group consisting of hydroxamic acid, vorinostat, suberoylanilide hydroxamic acid (SAHA), trichostatin A (TSA), LAQ824, panobinostat (LBH589), belinostat (PXD101), ITF2357 italfarmaco SpA, cyclic tetrapeptide, depsipeptide (romidepsin, FK228), benzamide; entinostat (SNDX-275/MS-275), MGCD0103, short-chain aliphatic acids, valproic acid, phenyl butyrate, AN-9, pivanex, CHR-3996, and CHR-2845;
(b) a proteasome inhibitor selected from the group consisting of bortezomib, NPI-0052, carfilzomib (PR-171), CEP 18770, and MLN9708;
(c) anti-CTLA-4 antibody or peptide, an anti-PD-1 antibody or peptide, an anti-PDL-1 antibody or peptide, an anti-OX40 antibody or peptide, an anti-GITR antibody or peptide, an anti-LAG-3 antibody or peptide, and an anti-TIM-3 antibody or peptide; and
(d) a combination (a), (b) and/or (c).

15. An isolated nucleic acid encoding the $V_H$ region of the antibody or antibody fragment of claim 1.

16. An isolated nucleic acid encoding the $V_L$ region of the antibody or antibody fragment of claim 1.

17. A method of treating cancer in a subject comprising administering to the subject a therapeutically effective amount of the antibody or antibody fragment of claim 1.

18. An antibody or antibody fragment that immunospecifically binds to MEW class I polypeptide-related sequence A (MICA), wherein the antibody or antibody fragment comprises
(i) a heavy chain variable ($V_H$) region comprising $V_H$ CDR1, $V_H$ CDR2, and $V_H$ CDR3 as shown in the $V_H$ of sequence of SEQ ID NO: 168;
(ii) a light chain variable (VL) region comprising $V_L$ CDR1, $V_L$ CDR2, and $V_L$ CDR3 as shown in the $V_L$ of sequence of SEQ ID NO: 170;
wherein the $V_H$ region comprises one or more amino acid residue modifications within one or more framework regions compared to the framework regions of SEQ ID NO: 168, and/or the $V_L$ region comprises one or more amino acid residue modifications within one or more framework regions compared to the framework regions of SEQ ID NO: 170.

19. The antibody or antibody fragment of claim 18, wherein the antibody or antibody fragment comprises
(i) a $V_H$ region comprising an amino acid sequence that is at least 85%, 90%, 95%, 96%, 97%, 98% or 99% identical to SEQ ID NO: 168; or
(ii) a $V_L$ region comprising an amino acid sequence that is at least 85%, 90%, 95%, 96%, 97%, 98% or 99% identical to SEQ ID NO: 170.

20. The antibody or antibody fragment of claim 18, wherein the antibody or antibody fragment binds to an epitope of human MHC class I polypeptide-related sequence A (MICA) comprising the amino acid sequence TCRASSFYPR (SEQ ID NO: 189).

21. The antibody or antibody fragment of claim 18, wherein the antibody or antibody fragment,
(a) binds to MICA α3 domain;
(b) reduces sMICA levels;
(c) inhibits shedding of MICA from tumor cells;
(d) inhibits sMICA mediated downregulation of the NKG2D receptor on NK cells;

(e) increases NK cell mediated lysis of tumor cells; or (f) a combination of one or more of (a)-(e).

22. The antibody or antibody fragment of claim 18, wherein the antibody is human, humanized or chimeric.

23. A pharmaceutical composition comprising the antibody or antibody fragment of claim 18.

24. The pharmaceutical composition of claim 23, further comprising an anti-cancer therapeutic.

25. An isolated nucleic acid encoding the $V_H$ region of the antibody or antibody fragment of claim 18.

26. An isolated nucleic acid encoding the $V_L$ region of the antibody or antibody fragment of claim 18.

27. A method of treating cancer in a subject comprising administering to the subject a therapeutically effective amount of the antibody or antibody fragment of claim 18.

28. An antibody fragment that immunospecifically binds to MHC class I polypeptide-related sequence A (MICA), wherein the antibody fragment comprises (i) a heavy chain variable ($V_H$) region comprising $V_H$ CDR1, $V_H$ CDR2, and $V_H$ CDR3 as shown in the $V_H$ of sequence of SEQ ID NO: 168; and (ii) a light chain variable ($V_L$) region comprising $V_L$ CDR1, $V_L$ CDR2, and $V_L$ CDR3 as shown in the $V_L$ of sequence of SEQ ID NO: 170.

29. The antibody fragment of claim 28, wherein the antibody fragment is a Fab fragment, a F(ab')$_2$ fragment, a $F_V$ fragment, a sc$F_V$ fragment, a diabody or a linear antibody.

30. The antibody fragment of claim 28, wherein the antibody fragment comprises (i) a $V_H$ region comprising an amino acid sequence that is at least 85%, 90%, 95%, 96%, 97%, 98% or 99% identical to SEQ ID NO: 168; or (ii) a $V_L$ region comprising an amino acid sequence that is at least 85%, 90%, 95%, 96%, 97%, 98% or 99% identical to SEQ ID NO: 170.

31. The antibody fragment of claim 28, wherein the antibody fragment binds to an epitope of human MHC class I polypeptide-related sequence A (MICA) comprising the amino acid sequence TCRASSFYPR (SEQ ID NO: 189).

32. The antibody fragment of claim 28, wherein the antibody fragment, (a) binds to MICA α3 domain;

(b) reduces sMiCA levels;

(c) ihibits shedding of MICA from tumor cells;

(d) inhibits sMICA mediated downregulation of the NKG2D receptor on NK cells;

(e) increases NK cell mediated lysis of tumor cells; or (f) a combination of one or more of (a)-(e).

33. The antibody fragment of claim 28, wherein the $V_H$ region comprises the amino acid sequence of SEQ ID NO: 168; and the $V_L$ region comprises the amino acid sequence of SEQ ID NO: 170.

34. A pharmaceutical composition comprising the antibody fragment of claim 28.

35. The pharmaceutical composition of claim 34, further comprising an anti-cancer therapeutic.

36. A method of treating cancer in a subject comprising administering to the subject a therapeutically effective amount of the antibody fragment of claim 28.

* * * * *

UNITED STATES PATENT AND TRADEMARK OFFICE

CERTIFICATE OF CORRECTION

PATENT NO. : 10,106,611 B2
APPLICATION NO. : 15/100060
DATED : October 23, 2018
INVENTOR(S) : Kai W. Wucherpfennig et al.

It is certified that error appears in the above-identified patent and that said Letters Patent is hereby corrected as shown below:

In the Claims

At Column 165, Claim number 1, Line number 3:
"cally binds to MEW class I polypeptide-related sequence A"
Should read:
-- cally binds to MHC class I polypeptide-related sequence A --

At Column 165, Claim number 2, Line number 18:
"90%, 95%, 96%, 97%, 98% or 99% A identical to SEQ ID"
Should read:
-- 90%, 95%, 96%, 97%, 98% or 99% identical to SEQ ID --

At Column 165, Claim number 3, Line number 23:
"90%, 95%, 96%, 97%, 98% or 99% A identical to SEQ ID"
Should read:
-- 90%, 95%, 96%, 97%, 98% or 99% identical to SEQ ID --

At Column 166, Claim number 8, Line number 32:
"cifically binds to MEW class I polypeptide-related sequence"
Should read:
-- cifically binds to MHC class I polypeptide-related sequence --

At Column 166, Claim number 18, Line number 38:
"(ii) a light chain variable (VL) region comprising $V_L$"
Should read:
-- (ii) a light chain variable ($V_L$) region comprising $V_L$ --

Signed and Sealed this
Fifth Day of February, 2019

Andrei Iancu
*Director of the United States Patent and Trademark Office*